(12) United States Patent
Player et al.

(10) Patent No.: US 8,232,409 B2
(45) Date of Patent: Jul. 31, 2012

(54) HETEROCYCLIC BENZIMIDAZOLES AS TRPM8 MODULATORS

(75) Inventors: Mark R. Player, Phoenixville, PA (US); Daniel J. Parks, Downingtown, PA (US); William Parsons, Belle Mead, NJ (US); Sanath K. Meegalla, Boothwyn, PA (US); Carl R. Illig, Phoenixville, PA (US); Shelley K. Ballentine, Lansdale, PA (US)

(73) Assignee: Janssen Pharmaceutica N.V., Beerse (BE)

( * ) Notice: Subject to any disclaimer, the term of this patent is extended or adjusted under 35 U.S.C. 154(b) by 336 days.

(21) Appl. No.: 12/576,283

(22) Filed: Oct. 9, 2009

(65) Prior Publication Data
US 2010/0093788 A1  Apr. 15, 2010

Related U.S. Application Data

(60) Provisional application No. 61/105,449, filed on Oct. 15, 2008.

(51) Int. Cl.
*A61K 31/4188* (2006.01)
*A61K 31/4184* (2006.01)
*A61K 31/422* (2006.01)
*A61K 31/437* (2006.01)
*C07D 405/00* (2006.01)
*C07D 413/04* (2006.01)
*C07D 413/14* (2006.01)

(52) U.S. Cl. ........ 548/300.7; 548/240; 546/17; 514/278; 514/378; 514/394

(58) Field of Classification Search ................ 548/300.7
See application file for complete search history.

(56) References Cited

FOREIGN PATENT DOCUMENTS

| DE | 10215321 A1 | 4/2002 |
|---|---|---|
| WO | WO 2005/037197 A2 | 4/2005 |
| WO | WO 2006/028545 A2 | 3/2006 |
| WO | WO 2006/040103 A1 | 4/2006 |
| WO | WO 2006/040136 A1 | 4/2006 |
| WO | WO 2006/136245 A1 | 12/2006 |
| WO | WO 2007/017092 A1 | 2/2007 |
| WO | WO 2007/017093 A1 | 2/2007 |
| WO | WO 2007/017094 A1 | 2/2007 |
| WO | WO 2007/130780 A2 | 11/2007 |
| WO | WO 2007/134107 A2 | 11/2007 |

OTHER PUBLICATIONS

International Search Report mailed Jan. 4, 2010 for corresponding Application No. PCT/US2009/060407.
Abe, J., et al. "Ca$^{2+}$-Dependent PKC Activation Mediates Menthol-induced Desensitization of Transient Receptor Potential M8", Neuroscience Letters 397 (2006) pp. 140-144.
Acikel, M., et al. "The Effect of Pulmonary Hypertension on Left Atrial Mechanical Functions in Chronic Obstructive Lung Disease", International Journal of Cardiology 97 (2004) p. 187-192.
Barnett, A., et al. Cold Periods and Coronary Events; An Analysis of Populations Worldwide, J. Epidermiol Community Health (2005) vol. 59, pp. 551-557.
Behrendt, H., et al, "Characterization of the Mouse Cold-Menthol Receptor TRPM8 and Vannilloid Receptor Type-1 VR1 Using a Fluormetric Imaging Plate Reader (FLIPR) Assay", British Journal of Pharmacology (2004) vol. 141, pp. 737-745.
Bennett, G., et al. "A Peripheral Mononeuropathy in Rat That Produces Disorders of Pain Sensation Like Those Seen in Man", Pain, vol. 33 (1988) pp. 87-107.
Bhatnagar, S., et al. "Tramadol for Postoperative Shivering: A Double-Blind Comparison With Pethidine", Anaesth Intensive Care, vol. 29 (2001) pp. 149-154.
Bolser, D., et al. Pharmacological Studies of Allergic Cough in the Guinea Pig, European Journal of Pharmacology, vol. 277 (1995) pp. 159-164.
Braga, P., et al. Dextrorphan and Dextromethethophran: Comparative Antitussie Effects on Guinea Pigs, Drugs Exptl. Clin. Res. (5) (1994) pp. 199-203.
Braw, Y., et al. Anxiety-Like Behaviors in Pre-Pubertal Rats of the Flinders Sensitive Line (FLS) and Winstar-Kyoto (WKY) Animal Models of Depression, Behavioral Brain research, vol. 167 (2006) pp. 261-269.
Butler, S. et al. "A Limited Arthritic Model for Chronic Pain Studies in the Rat", Pain, vol. 48 (1992) pp. 73-81.
Cankar, K., et al. "Microvascular Sin Response to Local Cooling and Body Tilt Early After Digital Replantation", The Journal of Hand Surgery vol. 25A (May 2000) pp. 552-558.
Collier, H., et al. "The Abdominal Constriction Response and Its Suppression by Analgesic Drugs in the Mouse", Br. J. Pharmac. Chemother. (1968) vol. 32 pp. 295-310.
Cryan, J., et al. "The Ascent of Mouse: Advances in Modeling Human Depression and Anxiety", Nature Reviews, vol. 4 (Sep. 2005) pp. 775-790.
Defrin, R., et al. "Characterization of Chronic Pain and Somatosensory Function in Spinal Cord Injury Subjects", Pain, vol. 89 (2001) pp. 253-263.
Defrin, R., et al. "Sensory Determinants of Thermal Pain", Brain (2002) vol. 125,pp. 501-510.
Desmeules, J., et al. "Neurophysiologic Evidence for a Central Sensitization in Patients With Fibromyalgia", Arthritis 7 Rheumatism, vol. 48, No. 5 (May 2003) pp. 1420-1429.

(Continued)

*Primary Examiner* — Laura L. Stockton
(74) *Attorney, Agent, or Firm* — Thomas J. Dodd

(57) ABSTRACT

Disclosed are compounds, compositions and methods for treating various diseases, syndromes, conditions and disorders, including pain. Such compounds are represented by Formula I as follows:

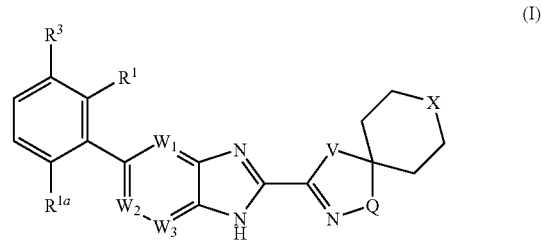

(I)

wherein $W_1$, $W_2$, $W_3$, $R^1$, $R^{1a}$, $R^2$, $R^{2a}$, $R^3$, V, Q, and X are defined herein.

40 Claims, No Drawings

OTHER PUBLICATIONS

Eccles, R., et al. Menthol: Effects on Nasal Sensation of Airflow and the Drive to Breathe, Current Allergy and Asthma reports (2003) vol. 3, pp. 210-214.

El Mouedden, M., et al. "Evaluation of Pain-Related Behavior, Bone Destruction and Effectiveness of Fentanyl, Sufentanil, and Morphine in a Murine Model of Cancer Pain", Pharmacology, Biochemistry and Behavior, vol. 82 (2005 pp. 109-119.

Erichsen, H., et al. "Comparative Actions of the Opioid Analgesics Morphine, Methadone and Codeine in Rat Models of Peripheral and Central Neurophatic Pain", Pain, vol. 116 (2005) pp. 347-358.

Farina, V., and Krishnamurthy, V., "The Stille Reaction", Table of Contents, Supplied by The British Library, 1997, Organic Reactions, vol. 50.

Finnerup, N., et al. "Intravenous Lidocaine Relieves Spinal Cord Injury Pain", Anesthesiology (2005) vol. 102 pp. 1023-1030.

Forst, T., et al. Skin Microcirculation in Patients with Type 1 Diabetes With and Without Neuropathy After Neurovascular Stimulation, Clinical Science (1998) vol. 94, pp. 255-261.

Fox, A., et al. "Critical Evaluation of the Streptozotocin Model of Painful Diabetic Neuropathy in the Rat", Pain, vol. 81 (1999) pp. 307-316.

Gherghel, D., et al. "Abnormal Systemic and Ocular Vascular Response to Temperature Provocation in Primary Open-Angle Glaucoma Patients A Case for Autonomic Failure?" Investigative Ophthalmology & Visual Science (Oct. 2004) vol. 45, No. 10 pp. 3546-3554.

Ghilardi, J., et al. "Selective Blockade of the Capsaicin Receptor TRPV1 Attenuates Bone Cancer Pain", Journal of Neuroscience (Mar. 2005) vol. 25(12) pp. 3126-3131.

Grahn, D., et al. "Appropriate Thermal Manipulations Eliminate Tremors in Rats Recovering From Halothane Anesthesia", Journal for Applied Physiol. vol. 81 (1996) pp. 2547-2554.

Greenlee, W., et al. Addition of Trimethylsilyn Cyanide to α-Substituted Ketones: Catalyst Efficiency, Tetrahedron Letters, vol. 24, No. 42 (1983) pp. 4559-4560.

Greenspan, J., et al. "Allodynia in Patients with Post-Stroke Central Pain (CPSP) Studied by Statistical quantitative Sensory Testing Within Individuals", Pain, vol. 109 (2004) pp. 357-366.

Gregory, R., et al. "Cyanohydrins in Nature and the Laboratory: Biology< preparations, and Synthetic Applications", Chem. Review, vol. 99 (1999) pp. 3649-3682.

Hall, E., et al. "Time-Course of Infection and Responses in a Coughing Rat Model of Pertussis", M. Med. Microbiol. vol. 48 (1999) pp. 95-98.

Hallas, B., et al. "Establishment of Behavioral Parameters for the Evaluation of Osteopathic Treatment Principles in a Rat Model of Arthritis", JAOA, vol. 97, No. 4 (Apr. 1997) pp. 207-214.

Hirayama, T., et al. "Effect of FK3657, a Non-Peptide Bradykinin $B_2$ Receptor Antagonist, on Allergic Airway Disease Models", European Journal of Pharmacology, vol. 467 (2003) pp. 197-203.

Hord, A., et al. "Changes in Rat paw Perfusion After Experimental Mononeuropathy: Assessment by Laser Doppler Fluxmetry", Anesth. Analg. (1999) vol. 88 pp. 103-108.

Huff, B., et al. "Synthesis of Unsymmetrical Biaryls Using a Modified Suzuke Cross-Coupling: 4-Biphenylcarboxaldehyde ([1,1'-Biphenyl]-4-Carboxyaldehyde", Organic Syntheses, vol. 75 (1998) pp. 53-60.

Hunter, J., et al. "The Effect of Novel Anti-Epileptic Drugs in Rat Experimental Models of Acute and Chronic Pain", European Journal of Pharmacology vol. 324 (1997) pp. 153-160.

Iyengar, S., et al. Efficacy of Duloxetine, a Potent and Balanced Serotonin-Norepinephrine Reuptake Inhibitor in Persistent Pain Models in Rats, Journal of Pharmacology and Experimental Therapeutics, vol. 311, No. 2 (2004) pp. 576-584.

Jorum, E., et al. "Cold Allodynia and Hyperalgesia in Neurophathic Pain: The Effect of N-Methyl-D-Aspartate (NMDA) Receptor Antagonist Ketamine—a Double-Blind, Cross-Over Comparison with Alfentanil and Placebo", Pain, vol. 101 (2003) pp. 229-235.

Kobayashi, K., et al. "Distinct Expression of TRPM8, TRPA1, and TRPV1 mRNAs in Rat Primary Afferent Neurons with A /C-Fibers and Colocalization with Trk Receptors" The Journal of Comparative Neurology (2005) vol. 493 pp. 596-606.

Kozak, W., et al. "Non-Prostaglandin Eicostanoids in Fever and Anapyrexia", Frontiers in Bioscience vol. 9 (Sep. 2004) pp. 3339-3355.

Lamah, M., et al. "In Vivo Microscopic Study of Microcirculatory Perfusion of the Skin of the Foot in Peripheral Vascular Disease", European J. Vasc. Endovas. Surgery, vol. 18 (1999) pp. 48-51.

Laude, E., et al. "The Antitussive Effects of Menthol, Camphor and Cineole n Conscious Guinea-Pigs", Pulmonary Pharmacology (1994) vol. 7, pp. 179-184.

Lee, B., et al. "Behavioral Characteristics of a Mouse Model of Cancer Pain", Yonsei Medical Journal, vol. 46, No. 2 (2005) pp. 252-259.

Luger, N., et al. "Efficacy of Systemic Morphine Suggests a Fundamental Difference in the Mechanisms that Generate Bone Cancer vs. Inflammatory Pain", Pain (2002) vol. 99 pp. 397-406.

Lutolf, O., et al. "Influence of Local Finger Cooling on Laser Doppler flux and Nailfold Capillary Blood Flow Velocity in Normal Subjects and in Patients With Raynaud's Phenomenon", Microvascular Research vol. 46 (1993) pp. 374-382.

Margot, C., et al. "1,2-Elimination of Alcohol From Homoallyl Ethers Under the Influence of Mixed Metal Bases", Tetrahedron, vol. 46, No. 7 (1990) pp. 2411-2424.

Magyar, T., et al, "Evaluation of Vaccines for Atrophic Rhinitis-A Comparison of Three Challenge Models", Vaccine, vol. 20 (2002) pp. 1797-1802.

Marno, P., "How Different Measures of Cold Weather Affect Chronic Obstructive Pulmonary Disease (COPD)", European Respi. (2006) vol. 15(101) pp. 185-186.

Maryanoff, B., et al. "The Wittig Olefination Reaction and Modifications Involving Phosphoryl-Stablized Carbanions. Stereochemistry, Mechanism, and Selected Synthetic Aspects", Chem. Reviews (1989) vol. 89, pp. 863-927.

McKemy, D., et al. "Identification of a Cold Receptor Reveals a General Role for TRP Channels in Thermosensation", Nature, vol. 416 (Mar. 2002) pp. 52-58.

McMurray, G., et al. "Animal Models in Urological Disease and Sexual Dysfunction", British Journal of Pharmacology (2006) vol. 147 pp. 562-579.

Miyaura, N., et al. "Palladium-Catalyzed Cross-Coupling Reactions of Organoboron Compound", Chem. Rev. (1995) vol. 95 pp. 2457-2463.

Morice, A., "Effect of Inhaled Menthol on Citric Acid Induced Cough in Normal Subjects", Thorax (1994) vol. 49 pp. 1024-1026.

Morin, C., et al. "Disruption of Thermal Perception in a Multiple Sclerosis Patient With Central Pain", The Clinical Journal of Pain vol. 18 (2002) pp. 191-195.

Motta, A., et al. "The Antiociceptive Effect of Iontophoretic Direct Application of Diclofenac to Arthritic Knee-joints of Rats", Life Sciences 73 (2001) pp. 1995-2004.

Mukerji, G., et al. "Pain During Ice Water Test Distinguishes Clinical Bladder Hypersensitivity from Overactivity Disorders", BMC urology (2006) vol. 6, p. 1-7.

Mundla, S, et al. "Regioselective synthesis of 4-Hala Ortho-Dinitrobenzene Derivatives", Tetrahedron Letters, vol. 41 (2000) pp. 4277-4279.

Nagakura, Y., et al. "Allodynia and Hyperalgesia in Adjuvant-Induced Arthritic Rats Time Course of Progression and Efficacy of Analgesics", The Journal of Pharmacology and Experimental Therapeutics, vol. 306, No. 2 pp. 490-497, 2003.

Nakao, Y., et al. "Alkenyl- and Aryl[2-Hydrdoxymethyl)Phenyl]Dimethylsilanes: An Entry to Tetraoganosilicon Reagents for the Silicon-Based Cross-Coupling Reaction", JACS (2005) vol. 127 pp. 6952-6953.

Nikki, P., et al. "Halothane-Induced Heat Loss and Shivering in Rats", Acta Anaesth. Scandinav. (1968) vol. 12, pp. 125-134.

Pomonis, J., et al. "N-(4-Tertiarybutylphenyl)-4-(3-Chlorophyridin-2- y)tetrahydropyrazine-2(2H)-carbox-amide (BCTC), a Novel, Orally Effective Vanilloid Receptor 1 Antagonists with Analgesic Properties: II. In Vivo Characterization in Rat Models of Inflammatory and Neuropathic Pain", Journal of Pharmacology and Experimental Therapeutics, vol. 306 No. 1 (2003) pp. 387-398.

Premkumar, L., et al. "Downregulation of Transient Receptor Potential Melastatin 89 by Protein Kinase C-Mediated Dephosphorylation", Journal of Neuroscience (2005) vol. 25(49) p. 11322-11329.

Ribeiro, R., et al. "Involvement of Resident Macrophages and Mast Cells in the Writhing Nociceptive Response Induced by Zymosan and Acetic Acid in Mice", European Journal of Pharmacology (2000) vol. 387 p. 111-118.

Roza, C., et al. "Cold Sensitivity in Axotomized Fibers of Experimental Neuromas in Mice", Pain, vol. 120 (2006) pp. 24-35.

Rupniak, N., et al. "Effects of the Bradykinin $B_1$ Receptor Antagonist de-sArg$^9$ [Leu$^8$]Bradykinin and Genetic Disruption of the $B_2$ Receptor on Nociception in Rats and mice", Pain, vol. 71 (1997) pp. 89-97.

Sabino, M., et al. "Simultaneous Reduction in Cancer Pain, Bone Destruction, and Tumor Growth by Selective Inhibitor of Cyclooxygenase-2$^1$", Cancer Research, Col. 62 (2002) pp. 7343-7349.

Sahoo, A., et al. "Cross-Coupling of Triallyl(arly)Silanes with Aryl Bromides and Chlorides: An Alternative Convenient Biaryl synthesis", Advanced Synth. Catal. (2004) vol. 346 pp. 1715-1727.

Saint-Mezard, P., et al. "Allergic Contact Dermatitis", European J. of Dermatology (2004) vol. 14 p. 284-295.

Siegel, J., et al. "Synthesis of 4,4'-bisbenzimidazoles as Building Blocks for Supramolecular Structure", Organic Letters (2006) vol. 8, No. 22 p. 4989-4992.

Sluka, K., et al. "Behavioral and Immunohistochemical Changes in an Experimental Arthritis Model in Rats", Pain vol. 55 (1993) pp. 367-377.

Soulard, C., eta I. "Pharmacological Evaluation JO 1870:Relation to the Potential Treatment of Urinary Bladder Incontinence", Journal of Pharmacology and Experimental Therapeutics (1992) vol. 260, No. 3 pp. 1152-1158.

Stein, R., et al. "Cool (TRPMS8) and Hot (TRPV1) Receptors in the Bladder and Male Genital Tract", Journal of Urology, vol. 172 (2004) pp. 1175-1178.

Suzuki, R., et al. "The Effectiveness of Spinal and Systemic Morphine on Rat dorsal Horn Neuronal Responses in the Spinal Nerve Ligation Model of Neuropathic Pain", Pain, vol. 80 (1999) pp. 215-228.

Svendsen, K., et al. Sensory Function and Quality of Life in Patients with Multiple Sclerosis and Pain, pain, vol. 114 (2005) pp. 473-481.

Tanaka, M., et al. "Mechanisms of Capsaicin- and Citric-Acid-Induced Cough reflexes in Guinea Pigs", J. Pharmacology. Science, vol. 99 (2005) pp. 77-82.

Thomsen, J., et al. "The Effect of Topically Applied Salicylic Compounds on Serotonin-Induced Scratching Behaviour in Hairless Rats", Experimental Dermatology, vol. 11 (2002) pp. 370-375.

Tiniakov, R., et al., "Canine Model of Nasal Congestion and Allergic Rhinitis", J. Applied Physiol. vol. 94 (2003) pp. 1821-1828.

Tomazetti, J., et al. "Baker Yeast-Induced Fever in Young Rats: Characterization and Validation of an Animal Model for Antipyretics Screening", Journal of Neuroscience Methods, vol. 147 (2005) pp. 29-35.

Trevisani, M., et al. "Antitussive Activity of Iodo-Resiniferatoxin in Guinea Pigs", Thorax, vol. 59 (2004) pp. 769-772.

Tsai, Y., et al. "A Comparison of Tramadol, Amitriptyline, and Meperidine for Postepidural Anesthetic Shivering in Parturients", Obstetric Anesthesia, vol. 93 (2001) pp. 1288-1292.

Tsukimi, Y., et al. "Cold Response of the Bladder in Guinea Pig: Involvement of Transient Receptor Potential Channel, TRPM8", Urology, vol. 65 (2005) pp. 406-410.

Van Miert, A., et al. "The Antipyretic Effect of Flurbiprofen", European Journal of Pharmacology, vol. 44 (1977) pp. 197-204.

Venable, J., et al. "Preparation and Biological Evaluation of Indole, Benzimidazole, and Thienopyrolle Piperazine Carboxamides: Potent Human Histamine $H_4$ Antagonists", J. Med. Chem., vol. 48 (2005) pp. 8289-8298.

Wei, E., et al. "AG-3-5:A Chemical Producing Sensations of Cold", J. Pharm. Pharmacol., vol. 35 (1983) pp. 110-112.

Weisshaar, E., et al. "Systemic Drugs With Antipruritic Potency", Skin Therapy Letter, vol. 5, No. 5 (2000) pp. 106.

Weisshaar, E., et al. "Effect of Topical Capsaicin on the Cutaneous Reactions and Itching to Histamine in Atopic Eczema Compared to Healthy Skin", Arch Dermatology. Res, vol. 290 (1998) pp. 306-311.

Wille, J., et al. Cis-Urocanic Acid induces Mast Cell Degranulation and Release of Preformed TNF-α: A Possible Mechanism Linking UBV and cis-Urocanic Acid to Immunosuppression of Contact Hypersensitivity, Skin Pharmacol. Applied Skin Physiol. vol. 12 (1999) pp. 18-27.

Woods, M., et al. "Efficacy of the βe-Adrenergic Receptor Agonist CL-316243 on Experimental Bladder Hyperreflexia and Detrusor Instability in the Rat", The Journal of Urology, vol. 66 (2001) pp. 1142-1147.

Xing, H., et al. "Chemical and Cold Sensitivity of Two Distinct Populations of TRPM8-Expressing Somatosensory Neurons", J. Neurophysiol. vol. 95 (2006) pp. 1221-1230.

Xue, Y., et al. "Crystal Structure of the PXR-T1317 Complex Provides a Scaffold to Examine the Potential for Receptor Antagonism", Bioorganic & Medicinal Chemistry, vol. 15 (2007) pp. 2156-2166.

Youngblood, W., "Synthesis of a New *trans-$A_2B_2$* Phthalocyanine Motif as Building Block for Rodlike Phthalocyanine Polymers", J. Organic Chemistry, vol. 71 (2006) pp. 3345-3356.

HETEROCYCLIC BENZIMIDAZOLES AS TRPM8 MODULATORS

CROSS-REFERENCE TO RELATED APPLICATIONS

The present application claims the benefits of the filing of U.S. Provisional Application No. 61/105,449 filed Oct. 15, 2008. The complete disclosures of the aforementioned related patent applications are hereby incorporated herein by reference for all purposes.

FIELD OF THE INVENTION

The present invention relates to heterocyclic benzimidazoles that act as modulators of the TRPM8 receptor. The present invention also relates to processes for the preparation of heterocyclic benzimidazoles and to their use in treating various diseases, syndromes, and disorders, including those that cause inflammatory pain, neuropathic pain, cold intolerance or cold allodynia, peripheral vascular pain, itch, urinary incontinence, chronic obstructive pulmonary disease, pulmonary hypertension and anxiety, including other stress-related disorders, and combinations thereof.

BACKGROUND OF THE INVENTION

Transient receptor potential (TRP) channels are non-selective cation channels that are activated by a variety of stimuli. Numerous members of the ion channel family have been identified to date, including the cold-menthol receptor, also called TRPM8 (McKemy, D. D. et al. *Nature* 2002, 416 (6876), 52-58). Collectively, the TRP channels and related TRP-like receptors connote sensory responsivity to the entire continuum of thermal exposure, selectively responding to threshold temperatures ranging from noxious hot through noxious cold as well as to certain chemicals that mimic these sensations. Specifically, TRPM8 is known to be stimulated by cool to cold temperatures as well as by menthol and icilin, which may be responsible for the therapeutic cooling sensation that these agents provoke.

TRPM8 is located on primary nociceptive neurons (A-delta and C fibers) and is also modulated by inflammation-mediated second messenger signals (Abe, J. et al. *Neurosci. Lett.* 2006, 397(1-2), 140-144; Premkumar, L. S. et al. *J. Neurosci.* 2005; 25(49), 11322-11329). The localization of TRPM8 on both A-delta and C-fibers may provide a basis for abnormal cold sensitivity in pathologic conditions wherein these neurons are altered, resulting in pain, often of a burning nature (Kobayashi, K. et al. *J. Comp. Neurol.* 2005, 493(4), 596-606; Roza, C. et al. *Pain* 2006, 120(1-2), 24-35; and Xing, H. et al. *J. Neurophysiol.* 2006, 95, 1221-30). Cold intolerance and paradoxical burning sensations induced by chemical or thermal cooling closely parallel symptoms seen in a wide range of clinical disorders and thus provide a strong rationale for the development of TRPM8 modulators as novel antihyperalgesic or antiallodynic agents. TRPM8 is also known to be expressed in the brain, lung, bladder, gastrointestinal tract, blood vessels, prostate and immune cells, thereby providing the possibility for therapeutic modulation in a wide range of maladies.

In International patent application WO 2006/040136A1 from Bayer Healthcare AG, Lampe, T. et al. purportedly describes substituted 4-benzyloxy-phenylmethylamide derivatives as cold menthol receptor-1 (CMR-1) antagonists for the treatment of urological disorders. International patent application WO 2006/040103A1 from Bayer Healthcare AG purportedly describes methods and pharmaceutical compositions for treatment and/or prophylaxis of respiratory diseases or disorders. International patent applications WO 2007/017092A1, WO 2007/017093A1 and WO 2007/017094A1, from Bayer Healthcare AG, purportedly describe benzyloxyphenylmethyl carbamate, substituted 2-benzyloxybenzoic acid amide and substituted 4-benzyloxybenzoic acid amide derivatives for the treatment of diseases associated with the Cold Menthol Receptor (CMR), a.k.a. TRPM8.

There is a need in the art for TRPM8 antagonists that can be used to treat a disease, syndrome, or condition in a mammal in which the disease, syndrome, or condition is affected by the modulation of TRPM8 receptors, such as pain, the diseases that lead to such pain, and pulmonary or vascular dysfunction.

SUMMARY OF THE INVENTION

The present invention is directed to compounds of Formula (I)

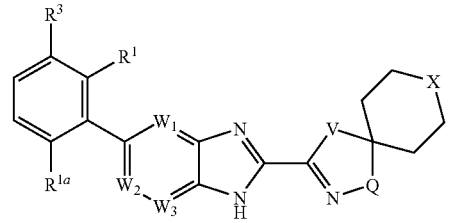

Formula (I)

wherein $W_1$ is $C(R^{2a})$ or N;
$W_2$ is CH or N;
$W_3$ is $C(R^2)$ or N;
such that no more than one of $W_1$, $W_2$, and $W_3$ is N; and when one of $W_1$, $W_2$, and $W_3$ is N, then $R^2$ and $R^{2a}$ are hydrogen;
$R^1$ is fluoro, chloro, trifluoromethyl, (1-hydroxy-1-methyl) ethyl, 2,2,2-trifluoroethyl, trifluoromethoxy, or difluoromethoxy; or $R^1$ and $R^3$ are taken together to form a single fused —$OCF_2O$— moiety;
$R^{1a}$ is hydrogen, fluoro, chloro, or bromo;
$R^2$ is hydrogen, $C_{1-4}$alkyl, fluoro, chloro, bromo, cyano, trifluoromethyl, hydroxy($C_{1-6}$)alkyl, $C_{1-3}$alkoxy($C_{1-6}$)alkyl, cyclopropyl, —CH=$CHCH_2OH$, or $C_{2-4}$alkenyl bound via an unsaturated carbon atom;
$R^{2a}$ is hydrogen or methyl;
$R^3$ is hydrogen, fluoro, or taken with $R^1$ to form —$OCF_2O$—;
V and Q are selected from the group consisting of
V is $CH(R^4)$ and Q is O;
V is NH and Q is $CH_2$; and
V is O and Q is $CH_2$;
$R^4$ is hydrogen or $C_{1-4}$alkyl;
X is $CH_2$, $C(CH_3)_2$, $CF_2$, or O;
with the proviso that when V is NH, X is other than O;
and enantiomers, diastereomers, solvates, and pharmaceutically acceptable salts thereof.

The present invention is also directed to a pharmaceutical composition comprising, consisting of and/or consisting essentially of a pharmaceutically acceptable carrier, a pharmaceutically acceptable excipient, and/or a pharmaceutically acceptable diluent and a compound of Formula (I) or a pharmaceutically acceptable salt form thereof.

Also provided are processes for making a pharmaceutical composition comprising, consisting of, and/or consisting essentially of admixing a compound of Formula (I) and a pharmaceutically acceptable carrier, a pharmaceutically acceptable excipient, and/or a pharmaceutically acceptable diluent.

The present invention is further directed to methods for treating or ameliorating a TRPM8-modulated disorder in a subject, including a mammal and/or human, in which the disease, syndrome, or condition is affected by the modulation of TRPM8 receptors, such as pain, the diseases that lead to such pain, and pulmonary or vascular dysfunction using a compound of Formula (I). In particular, the methods of the present invention are directed to treating or ameliorating a TRPM8 receptor-modulated disorder including inflammatory pain, cold-intolerance or cold allodynia, peripheral vascular pain, itch, urinary incontinence, chronic obstructive pulmonary disease, pulmonary hypertension and anxiety, including other stress-related disorders, using a compound of Formula (I).

The present invention is also directed to methods for producing the instant compounds and pharmaceutical compositions and medicaments thereof.

DETAILED DESCRIPTION OF THE INVENTION

The term "independently" means that when more than one of such substituent is possible, such substituents may be the same or different from each other.

The term "alkyl" whether used alone or as part of a substituent group refers to straight and branched carbon chains having 1 to 8 carbon atoms or any number within this range. Therefore, designated numbers of carbon atoms (e.g. $C_{1-8}$) shall refer independently to the number of carbon atoms in an alkyl moiety or to the alkyl portion of a larger alkyl-containing substituent. In substituent groups with multiple alkyl groups such as $(C_{1-6}alkyl)_2$ amino- the $C_{1-6}$alkyl groups of the dialkylamino may be the same or different.

The term "alkoxy" refers to an O-alkyl substituent group, wherein alkyl is as defined supra. To the extent substituted, an alkyl and alkoxy chain may be substituted on a carbon atom.

The terms "alkenyl" and "alkynyl" refer to straight and branched carbon chains having 2 or more carbon atoms, wherein an alkenyl chain has at least one double bond in the chain and an alkynyl chain has at least one triple bond in the chain.

The term "cycloalkyl" refers to saturated or partially unsaturated, monocyclic or polycyclic hydrocarbon rings of from 3 to 14 carbon atom members. Examples of such rings include, and are not limited to cyclopropyl, cyclobutyl, cyclopentyl, cyclohexyl, cycloheptyl and adamantyl. Similarly, "cycloalkenyl" refers to a cycloalkyl that contains at least one double bond in the ring. Additionally, a "benzofused cycloalkyl" is a cycloalkyl ring that is fused to a benzene ring. A "heteroaryl-fused cycloalkyl" is a cycloalkyl ring that is fused to a 5 or 6-membered heteroaryl ring (containing one of O, S or N and, optionally, one additional nitrogen).

The term "heterocyclyl" refers to a nonaromatic cyclic ring of 5 to 7 members in which 1 to 2 members are nitrogen, or a nonaromatic cyclic ring of 5 to 7 members in which zero, one or two members are nitrogen and up to two members are oxygen or sulfur; wherein, optionally, the ring contains zero to one unsaturated bonds, and, optionally, when the ring is of 6 or 7 members, it contains up to two unsaturated bonds. As used herein, "benzofused heterocyclyl" includes a 5 to 7 membered monocyclic heterocyclic ring fused to a benzene ring. As used herein, "heteroaryl-fused heterocyclyl" refers to 5 to 7 membered monocyclic heterocyclic ring fused to a 5 or 6 membered heteroaryl ring (containing one of O, S or N and, optionally, one additional nitrogen). As used herein, "cycloalkyl-fused heterocyclyl" refers to a 5 to 7 membered monocyclic heterocyclic ring fused to a 5 to 7 membered cycloalkyl or cycloalkenyl ring. Furthermore, as used herein, "heterocyclyl-fused heterocycyl" refers to a 5 to 7 membered monocyclic heterocyclic ring fused to a 5 to 7 membered heterocyclyl ring (of the same definition as above but absent the option of a further fused ring).

For instant compounds of the invention, the carbon atom ring members that form the heterocyclyl ring are fully saturated. Other compounds of the invention may have a partially saturated heterocyclyl ring. As used herein, "heterocyclyl" also includes a 5 to 7 membered monocyclic heterocycle bridged to form bicyclic rings. Such compounds are not considered to be fully aromatic and are not referred to as heteroaryl compounds. Examples of heterocyclyl groups include, and are not limited to, pyrrolinyl (including 2H-pyrrole, 2-pyrrolinyl or 3-pyrrolinyl), pyrrolidinyl, 2-imidazolinyl, imidazolidinyl, 2-pyrazolinyl, pyrazolidinyl, piperidinyl, morpholinyl, thiomorpholinyl and piperazinyl.

The term "aryl" refers to an unsaturated, aromatic monocyclic ring of 6 carbon members or to an unsaturated, aromatic polycyclic ring of from 10 to 14 carbon members. Examples of such aryl rings include, and are not limited to, phenyl, naphthalenyl or anthracenyl. Preferred aryl groups for the practice of this invention are phenyl and naphthalenyl.

The term "heteroaryl" refers to an aromatic ring of 5 or 6 members wherein the ring consists of carbon atoms and has at least one heteroatom member. Suitable heteroatoms include nitrogen, oxygen or sulfur. In the case of 5 membered rings, the heteroaryl ring contains one member of nitrogen, oxygen or sulfur and, in addition, may contain up to three additional nitrogens. In the case of 6 membered rings, the heteroaryl ring may contain from one to three nitrogen atoms. For the case wherein the 6 membered ring has three nitrogens, at most two nitrogen atoms are adjacent.

Optionally, the heteroaryl ring is fused to a benzene ring to form a "benzo fused heteroaryl"; similarly, the heteroaryl ring is optionally fused to a 5 or 6 membered heteroaryl ring (containing one of O, S or N and, optionally, one additional nitrogen) to form a "heteroaryl-fused heteroaryl"; similarly, the heteroaryl ring is optionally fused to a 5 to 7 membered cycloalkyl ring or a 5 to 7 membered heterocyclo ring (as defined supra but absent the option of a further fused ring) to form a "cycloalkyl-fused heteroaryl". Examples of heteroaryl groups include, and are not limited to, furyl, thienyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl or pyrazinyl; examples of heteroaryl groups with the optionally fused benzene rings include indolyl, isoindolyl, indolinyl, benzofuryl, benzothienyl, indazolyl, benzimidazolyl, benzthiazolyl, benzoxazolyl, benzisoxazolyl, benzothiadiazolyl, benzotriazolyl, quinolizinyl, quinolinyl, isoquinolinyl or quinazolinyl.

The term "arylalkyl" means an alkyl group substituted with an aryl group (e.g., benzyl, phenethyl). Similarly, "arylalkoxy" indicates an alkoxy group substituted with an aryl group (e.g., benzyloxy).

The term "halogen" refers to fluorine, chlorine, bromine and iodine. Substituents that are substituted with multiple halogens are substituted in a manner that provides compounds that are stable.

Whenever the terms "alkyl" or "aryl" or either of their prefix roots appear in a name of a substituent (e.g., arylalkyl, alkylamino) the name is to be interpreted as including those limitations given above for "alkyl" and "aryl." Designated numbers of carbon atoms (e.g., $C_1$-$C_6$) refer independently to the number of carbon atoms in an alkyl moiety, an aryl moiety, or in the alkyl portion of a larger substituent in which alkyl appears as its prefix root. For alkyl and alkoxy substituents, the designated number of carbon atoms includes all of the independent members included within a given range specified. For example $C_{1-6}$alkyl would include methyl, ethyl, propyl, butyl, pentyl and hexyl individually as well as sub-combinations thereof (e.g. $C_{1-2}$, $C_{1-3}$, $C_{1-4}$, $C_{1-5}$, $C_{2-6}$, $C_{3-6}$, $C_{4-6}$, $C_{5-6}$, $C_{2-5}$, etc.).

In general, under standard nomenclature rules used throughout this disclosure, the terminal portion of the designated side chain is described first followed by the adjacent functionality toward the point of attachment. Thus, for example, a "phenyl$C_1$-$C_6$ alkylamido$C_1$-$C_6$ alkyl" substituent refers to a group of the formula:

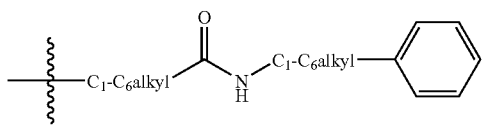

Unless otherwise noted, it is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

The term "subject" as used herein, refers to an animal, preferably a mammal, most preferably a human, who has been the object of treatment, observation or experiment.

The term "therapeutically effective amount" means that amount of active compound or pharmaceutical agent that elicits the biological or medicinal response in a tissue system, animal or human that is being sought by a researcher, veterinarian, medical doctor or other clinician, which includes alleviation or partial alleviation of the symptoms of the disease, syndrome, condition or disorder being treated.

The term "composition" is intended to encompass a product comprising the specified ingredients in therapeutically effective amounts, as well as any product that results, directly or indirectly, from combinations of the specified ingredients in the specified amounts.

The term "antagonist" is used to refer to a compound capable of producing, depending on the circumstance, a functional antagonism of the TRPM8 ion channel, including, but not limited to, competitive antagonists, non-competitive antagonists, desensitizing agonists, and partial agonists.

As used herein, "inflammatory hypersensitivity" is used to refer to a condition that is characterized by one or more hallmarks of inflammation, including edema, erythema, hyperthermia and pain, and/or by an exaggerated physiologic or pathophysiologic response to one or more than one type of stimulation, including thermal, mechanical, and/or chemical stimulation.

The term "TRPM8-modulated" is used to refer to the condition of being affected by the modulation of the TRPM8 receptor, including the state of being mediated by the TRPM8 receptor.

An embodiment of the invention is a method of treating or preventing at least one of the following diseases, syndromes, and conditions selected from the group consisting of migraine, post herpetic neuralgia, post traumatic neuralgia, post chemotherapy neuralgia, complex regional pain syndrome I and II (CRPS I/II), fibromyalgia, inflammatory bowel disease, pruritis, asthma, chronic obstructive pulmonary disease, toothache, bone pain and pyresis in a subject, which method comprises, consists of, and/or consists essentially of administering to the subject, including an animal, a mammal, and a human in need of such treatment or prevention, a therapeutically effective amount of a TRPM8 antagonist that is a compound of Formula (I).

Another embodiment of the invention is a method of treating or preventing at least one of the following diseases, syndromes, and conditions selected from hypertension, peripheral vascular disease, Raynaud's disease, reperfusion injury or frostbite in a subject, which method comprises administering to the subject, including an animal, a mammal, and a human in need of such treatment or prevention a therapeutically effective amount of a TRPM8 antagonist that is a compound of Formula (I).

A further embodiment of the invention is a method of accelerating post-anesthetic recovery or post-hypothermia recovery in a subject, including an animal, a mammal, and a human, which method comprises administering to the subject, including an animal, a mammal, and a human in need of such accelerated recovery, a therapeutically effective amount of a TRPM8 antagonist that is a compound of Formula (I).

An embodiment of the present invention is directed to compounds of Formula (I)

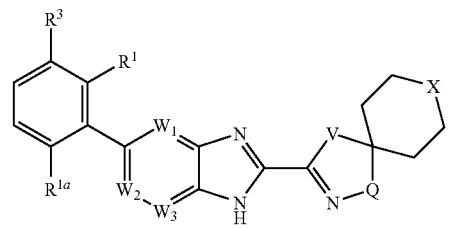

Formula (I)

wherein a) $W_1$ is $C(R^{2a})$ or N; $W_2$ is CH or N; $W_3$ is $C(R^2)$ or N; such that no more than one of $W_1$, $W_2$, and $W_3$ is N; and when one of $W_1$, $W_2$, and $W_3$ is N, then $R^2$ and $R^{2a}$ are hydrogen;

b) $R^1$ is fluoro, trifluoromethyl, (1-hydroxy-1-methyl) ethyl, 2,2,2-trifluoroethyl, trifluoromethoxy, or difluoromethoxy; or $R^1$ and $R^3$ are taken together to form a single fused —OCF$_2$O— moiety;

c) $R^1$ is fluoro, trifluoromethyl, (1-hydroxy-1-methyl) ethyl, 2,2,2-trifluoroethyl, trifluoromethoxy, or difluoromethoxy;

d) $R^{1a}$ is hydrogen or fluoro;

e) $R^2$ is hydrogen, $C_{1-4}$alkyl, fluoro, chloro, bromo, cyano, trifluoromethyl, hydroxy($C_{1-6}$)alkyl, $C_{1-3}$alkoxy($C_{1-6}$) alkyl, or —CH=CHCH$_2$OH;

f) $R^2$ is $C_{1-4}$alkyl, fluoro, chloro, bromo, cyano, trifluoromethyl, hydroxy($C_{1-6}$)alkyl, or —CH=CHCH$_2$OH;

g) $R^2$ is methyl, fluoro, chloro, bromo, trifluoromethyl, or hydroxy($C_{1-6}$)alkyl;

h) $R^{2a}$ is hydrogen or methyl;

i) $R^3$ is hydrogen or taken with $R^1$ to form —OCF$_2$O—;

j) $R^3$ is hydrogen;

k) V and Q are selected from the group consisting of

V is CH(R$^4$) and Q is O;
V is NH and Q is CH$_2$; and
V is O and Q is CH$_2$;
l) V and Q are selected from the group consisting of
V is CH(R$^4$) and Q is O; and
V is O and Q is CH$_2$;
m) R$^4$ is hydrogen or methyl;
n) X is CH$_2$, CF$_2$, or O;
o) X is CH$_2$ or O;
with the proviso that when V is NH, X is other than O;
and enantiomers, diastereomers, solvates, and pharmaceutically acceptable salts thereof;
and any combination of embodiments a) through o) above, provided that it is understood that combinations in which different embodiments of the same substituent would be combined are excluded.

An embodiment of the present invention is directed to compounds of Formula (I)

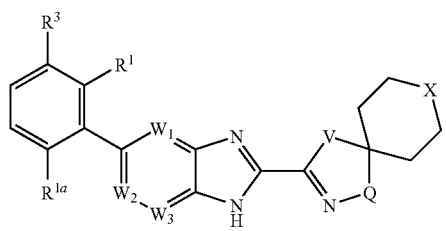

Formula (I)

wherein
W$_1$ is C(R$^{2a}$) or N;
W$_2$ is CH or N;
W$_3$ is C(R$^2$) or N;
such that no more than one of W$_1$, W$_2$, and W$_3$ is N; and when one of W$_1$, W$_2$, and W$_3$ is N, then R$^2$ and R$^{2a}$ are hydrogen;
R$^1$ is fluoro, trifluoromethyl, (1-hydroxy-1-methyl)ethyl, 2,2,2-trifluoroethyl, trifluoromethoxy, or difluoromethoxy; or R$^1$ and R$^3$ are taken together to form a single fused —OCF$_2$O— moiety;
R$^{1a}$ is hydrogen or fluoro;
R$^2$ is hydrogen, C$_{1-4}$alkyl, fluoro, chloro, bromo, cyano, trifluoromethyl, hydroxy(C$_{1-6}$)alkyl, C$_{1-3}$alkoxy(C$_{1-6}$)alkyl, or —CH=CHCH$_2$OH;
R$^{2a}$ is hydrogen or methyl;
R$^3$ is hydrogen or taken with R$^1$ to form —OCF$_2$O—;
V and Q are selected from the group consisting of
V is CH(R$^4$) and Q is O;
V is NH and Q is CH$_2$; and
V is O and Q is CH$_2$;
R$^4$ is hydrogen or methyl;
X is CH$_2$, CF$_2$, or O;
with the proviso that when V is NH, X is other than O;
and enantiomers, diastereomers, solvates, and pharmaceutically acceptable salts thereof.

An embodiment of the present invention is directed to compounds of Formula (I)

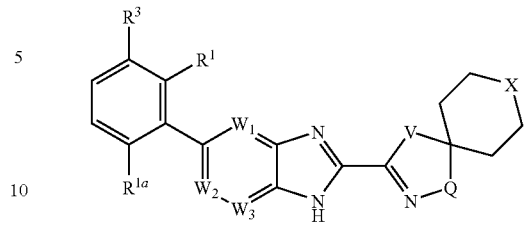

Formula (I)

wherein
W$_1$ is C(R$^{2a}$) or N;
W$_2$ is CH or N;
W$_3$ is C(R$^2$) or N;
such that no more than one of W$_1$, W$_2$, and W$_3$ is N; and when one of W$_1$, W$_2$, and W$_3$ is N, then R$^2$ and R$^{2a}$ are hydrogen;
R$^1$ is fluoro, trifluoromethyl, (1-hydroxy-1-methyl)ethyl, 2,2,2-trifluoroethyl, trifluoromethoxy, or difluoromethoxy;
R$^{1a}$ is hydrogen or fluoro;
R$^2$ is hydrogen, C$_{1-4}$alkyl, fluoro, chloro, bromo, cyano, trifluoromethyl, hydroxy(C$_{1-6}$)alkyl, C$_{1-3}$alkoxy(C$_{1-6}$)alkyl, or —CH=CHCH$_2$OH;
R$^{2a}$ is hydrogen or methyl;
R$^3$ is hydrogen;
V and Q are selected from the group consisting of
V is CH(R$^4$) and Q is O; and V is O and Q is CH$_2$;
R$^4$ is hydrogen or methyl;
X is CH$_2$, CF$_2$, or O;
and enantiomers, diastereomers, solvates, and pharmaceutically acceptable salts thereof.

An embodiment of the present invention is directed to compounds of Formula (I)

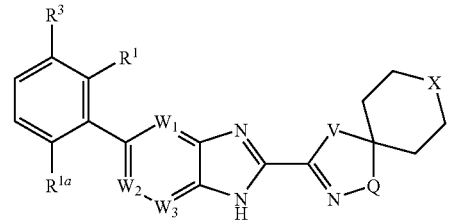

Formula (I)

wherein
W$_1$ is C(R$^{2a}$) or N;
W$_2$ is CH or N;
W$_3$ is C(R$^2$) or N;
such that no more than one of W$_1$, W$_2$, and W$_3$ is N; and when one of W$_1$, W$_2$, and W$_3$ is N, then R$^2$ and R$^{2a}$ are hydrogen;
R$^1$ is fluoro, trifluoromethyl, (1-hydroxy-1-methyl)ethyl, 2,2,2-trifluoroethyl, trifluoromethoxy, or difluoromethoxy;
R$^{1a}$ is hydrogen or fluoro;
R$^2$ is C$_{1-4}$alkyl, fluoro, chloro, bromo, cyano, trifluoromethyl, hydroxy(C$_{1-6}$)alkyl, C$_{1-3}$ alkoxy(C$_{1-6}$)alkyl, or —CH=CHCH$_2$OH;
R$^{2a}$ is hydrogen or methyl;
R$^3$ is hydrogen;
V and Q are selected from the group consisting of
V is CH(R$^4$) and Q is O; and V is O and Q is CH$_2$;

$R^4$ is hydrogen or methyl;
X is $CH_2$, $CF_2$, or O;
and enantiomers, diastereomers, solvates, and pharmaceutically acceptable salts thereof.

An embodiment of the present invention is directed to compounds of Formula (I)

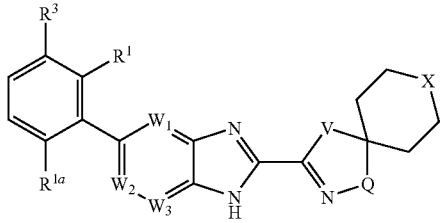

Formula (I)

wherein
$W_1$ is $C(R^{2a})$ or N;
$W_2$ is CH or N;
$W_3$ is $C(R^2)$ or N;
 such that no more than one of $W_1$, $W_2$, and $W_3$ is N; and when one of $W_1$, $W_2$, and $W_3$ is N, then $R^2$ and $R^{2a}$ are hydrogen;
$R^1$ is fluoro, trifluoromethyl, (1-hydroxy-1-methyl)ethyl, 2,2,2-trifluoroethyl, trifluoromethoxy, or difluoromethoxy;
$R^{1a}$ is hydrogen or fluoro;
$R^2$ is methyl, fluoro, chloro, bromo, cyano, trifluoromethyl, hydroxy($C_{1-6}$)alkyl, $C_{1-3}$alkoxy($C_{1-6}$)alkyl, or —CH=CHCH$_2$OH;
$R^{2a}$ is hydrogen or methyl;
$R^3$ is hydrogen;
V and Q are selected from the group consisting of
 V is $CH(R^4)$ and Q is O; and V is O and Q is $CH_2$;
$R^4$ is hydrogen or methyl;
X is $CH_2$ or O;
and enantiomers, diastereomers, solvates, and pharmaceutically acceptable salts thereof.

A further embodiment of the present invention is directed to a compound of Formula (I)

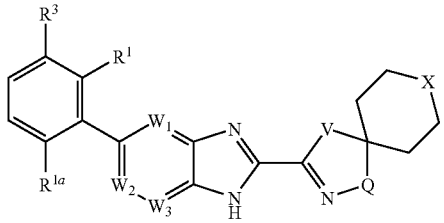

Formula (I)

selected from the group consisting of:
a compound wherein $W_1$ is $C(R^{2a})$, $W_2$ is CH, $W_3$ is $C(R^2)$, $R^1$ is trifluoromethyl, $R^{1a}$, $R^2$, $R^{2a}$, and $R^3$ are hydrogen, V is $CH(R^4)$, Q is O, $R^4$ is hydrogen, and X is $CH_2$;
a compound wherein $W_1$ is $C(R^{2a})$, $W_2$ is CH, $W_3$ is $C(R^2)$, $R^1$ is trifluoromethoxy, $R^{1a}$, $R^2$, $R^{2a}$, and $R^3$ are hydrogen, V is O, Q is $CH_2$, and X is $CH_2$;
a compound wherein $W_1$ is $C(R^{2a})$, $W_2$ is CH, $W_3$ is $C(R^2)$, $R^1$ is trifluoromethoxy, $R^{1a}$, $R^2$, $R^{2a}$, and $R^3$ are hydrogen, V is O, Q is $CH_2$, and X is $CH_2$;
a compound wherein $W_1$ is $C(R^{2a})$, $W_2$ is CH, $W_3$ is $C(R^2)$, $R^1$ is trifluoromethyl, $R^{1a}$, $R^2$, $R^{2a}$, and $R^3$ are hydrogen, V is O, Q is $CH_2$, and X is $CH_2$;
a compound wherein $W_1$ is $C(R^{2a})$, $W_2$ is CH, $W_3$ is $C(R^2)$, $R^1$ is trifluoromethyl, $R^{1a}$, $R^2$, $R^{2a}$, and $R^3$ are hydrogen, V is O, Q is $CH_2$, and X is $CH_2$;
a compound wherein $W_1$ is $C(R^{2a})$, $W_2$ is CH, $W_3$ is $C(R^2)$, $R^1$ is trifluoromethyl, $R^{1a}$ is fluoro, $R^2$, $R^{2a}$, and $R^3$ are hydrogen, V is $CH(R^4)$, Q is O, $R^4$ is hydrogen, and X is $CH_2$;
a compound wherein $W_1$ is $C(R^{2a})$, $W_2$ is CH, $W_3$ is $C(R^2)$, $R^1$ is trifluoromethoxy, $R^{1a}$, $R^2$, $R^{2a}$, and $R^3$ are hydrogen, V is $CH(R^4)$, Q is O, $R^4$ is hydrogen, and X is $CH_2$;
a compound wherein $W_1$ is $C(R^{2a})$, $W_2$ is CH, $W_3$ is $C(R^2)$, $R^1$ is trifluoromethoxy, $R^{1a}$, is fluoro, $R^2$, $R^{2a}$, and $R^3$ are hydrogen, V is $CH(R^4)$, Q is O, $R^4$ is hydrogen, and X is $CH_2$;
a compound wherein $W_1$ is $C(R^{2a})$, $W_2$ is CH, $W_3$ is $C(R^2)$, $R^1$ is trifluoromethyl, $R^{1a}$, $R^2$, $R^{2a}$, and $R^3$ are hydrogen, V is $CH(R^4)$, Q is O, $R^4$ is hydrogen, and X is O;
a compound wherein $W_1$ is $C(R^{2a})$, $W_2$ is CH, $W_3$ is $C(R^2)$, $R^1$ is trifluoromethyl, $R^{1a}$, $R^2$, $R^{2a}$, and $R^3$ are hydrogen, V is $CH(R^4)$, Q is O, $R^4$ is hydrogen, and X is $CF_2$;
a compound wherein $W_1$ is $C(R^{2a})$, $W_2$ is CH, $W_3$ is $C(R^2)$, $R^1$ is 2,2,2-trifluoroethyl, $R^{1a}$, $R^2$, $R^{2a}$, and $R^3$ are hydrogen, V is $CH(R^4)$, Q is O, $R^4$ is hydrogen, and X is $CH_2$;
a compound wherein $W_1$ is $C(R^{2a})$, $W_2$ is CH, $W_3$ is $C(R^2)$, $R^1$ is taken with $R^3$ to form —$OCF_2O$—, $R^{1a}$, $R^2$, and $R^{2a}$ are hydrogen, V is $CH(R^4)$, Q is O, $R^4$ is hydrogen, and X is $CH_2$;
a compound wherein $W_1$ is $C(R^{2a})$, $W_2$ is CH, $W_3$ is $C(R^2)$, $R^1$ is difluoromethoxy, $R^1$, $R^2$, $R^{2a}$, and $R^3$ are hydrogen, V is $CH(R^4)$, Q is O, $R^4$ is hydrogen, and X is $CH_2$;
a compound wherein $W_1$ is $C(R^{2a})$, $W_2$ is CH, $W_3$ is $C(R^2)$, $R^1$ is trifluoromethyl, $R^{1a}$ is hydrogen, $R^2$ is fluoro, $R^{2a}$ is hydrogen, $R^3$ is hydrogen, V is $CH(R^4)$, Q is O, $R^4$ is hydrogen, and X is $CH_2$;
a compound wherein $W_1$ is $C(R^{2a})$, $W_2$ is CH, $W_3$ is $C(R^2)$, $R^1$ is trifluoromethyl, $R^{1a}$, $R^2$, $R^{2a}$, and $R^3$ are hydrogen, V is $CH(R^4)$, Q is O, $R^4$ is methyl, and X is $CH_2$;
a compound wherein $W_1$ is $C(R^{2a})$, $W_2$ is CH, $W_3$ is $C(R^2)$, $R^1$ is trifluoromethyl, $R^{1a}$ is hydrogen, $R^2$ is chloro, $R^{2a}$ is hydrogen, $R^3$ is hydrogen, V is $CH(R^4)$, Q is O, $R^4$ is hydrogen, and X is $CH_2$;
a compound wherein $W_1$ is $C(R^{2a})$, $W_2$ is CH, $W_3$ is $C(R^2)$, $R^1$ is trifluoromethyl, $R^{1a}$ is hydrogen, $R^2$ is bromo, $R^{2a}$ is hydrogen, $R^3$ is hydrogen, V is $CH(R^4)$, Q is O, $R^4$ is hydrogen, and X is $CH_2$;
a compound wherein $W_1$ is $C(R^{2a})$, $W_2$ is CH, $W_3$ is $C(R^2)$, $R^1$ is (1-hydroxy-1-methyl)ethyl, $R^{1a}$, $R^2$, $R^{2a}$, and $R^3$ are hydrogen, V is $CH(R^4)$, Q is O, $R^4$ is hydrogen, and X is $CH_2$;
a compound wherein $W_1$ is $C(R^{2a})$, $W_2$ is CH, $W_3$ is $C(R^2)$, $R^1$ is trifluoromethyl, $R^1$, $R^2$, $R^{2a}$, and $R^3$ are hydrogen, V is NH, Q is $CH_2$, and X is $CH_2$;
a compound wherein $W_1$ is $C(R^{2a})$, $W_2$ is CH, $W_3$ is $C(R^2)$, $R^1$ is difluoromethoxy, $R^{1a}$ is hydrogen, $R^2$ is methyl, $R^{2a}$ is hydrogen, $R^3$ is hydrogen, V is $CH(R^4)$, Q is O, $R^4$ is hydrogen, and X is $CH_2$;
a compound wherein $W_1$ is $C(R^{2a})$, $W_2$ is CH, $W_3$ is $C(R^2)$, $R^1$ is trifluoromethyl, $R^{1a}$ is hydrogen, $R^2$ is cyano, $R^{2a}$ is hydrogen, $R^3$ is hydrogen, V is $CH(R^4)$, Q is O, $R^4$ is hydrogen, and X is $CH_2$;
a compound wherein $W_1$ is $C(R^{2a})$, $W_2$ is CH, $W_3$ is $C(R^2)$, $R^1$ is trifluoromethyl, $R^{1a}$ is hydrogen, $R^2$ is 3-hydroxypropyl, $R^{2a}$ is hydrogen, $R^3$ is hydrogen, V is $CH(R^4)$, Q is O, $R^4$ is hydrogen, and X is $CH_2$;

a compound wherein $W_1$ is $C(R^{2a})$, $W_2$ is CH, $W_3$ is $C(R^2)$, $R^1$ is fluoro, $R^{1a}$, $R^2$, $R^{2a}$, and $R^3$ are hydrogen, V is $CH(R^4)$, Q is O, $R^4$ is hydrogen, and X is $CH_2$;

a compound wherein $W_1$ is $C(R^{2a})$, $W_2$ is CH, $W_3$ is $C(R^2)$, $R^1$ is trifluoromethyl, $R^{1a}$ is hydrogen, $R^2$ is hydrogen, $R^{2a}$ is methyl, $R^3$ is hydrogen, V is $CH(R^4)$, Q is O, $R^4$ is hydrogen, and X is $CH_2$;

a compound wherein $W_1$ is $C(R^{2a})$, $W_2$ is CH, $W_3$ is $C(R^2)$, $R^1$ is trifluoromethyl, $R^{1a}$ is hydrogen, $R^2$ is 1-hydroxy-prop-2-en-3-yl, $R^{2a}$ is hydrogen, $R^3$ is hydrogen, V is $CH(R^4)$, Q is O, $R^4$ is hydrogen, and X is $CH_2$;

a compound wherein $W_1$ is $C(R^{2a})$, $W_2$ is CH, $W_3$ is $C(R^2)$, $R^1$ is fluoro, $R^{1a}$ is fluoro, $R^2$, $R^{2a}$, and $R^3$ are hydrogen, V is $CH(R^4)$, Q is O, $R^4$ is hydrogen, and X is $CH_2$;

a compound wherein $W_1$ is $C(R^{2a})$, $W_2$ is CH, $W_3$ is $C(R^2)$, $R^1$ is trifluoromethyl, $R^{1a}$ is hydrogen, $R^2$ is trifluoromethyl, $R^{2a}$ is hydrogen, $R^3$ is hydrogen, V is $CH(R^4)$, Q is O, $R^4$ is hydrogen, and X is $CH_2$;

a compound wherein $W_1$ is $C(R^{2a})$, $W_2$ is CH, $W_3$ is $C(R^2)$, $R^1$ is trifluoromethyl, $R^{1a}$ is hydrogen, $R^2$ is trifluoromethyl, $R^{2a}$ is hydrogen, $R^3$ is hydrogen, V is $CH(R^4)$, Q is O, $R^4$ is methyl, and X is $CH_2$;

a compound wherein $W_1$ is $C(R^{2a})$, $W_2$ is CH, $W_3$ is $C(R^2)$, $R^1$ is trifluoromethyl, $R^{1a}$, $R^2$, $R^{2a}$, and $R^3$ are hydrogen, V is O, Q is $CH_2$, and X is O;

a compound wherein $W_1$ is $C(R^{2a})$, $W_2$ is CH, $W_3$ is $C(R^2)$, $R^1$ is chloro, $R^{1a}$ is hydrogen, $R^2$ is trifluoromethyl, $R^{2a}$ is hydrogen, $R^3$ is hydrogen, V is $CH(R^4)$, Q is O, $R^4$ is hydrogen, and X is $CH_2$;

a compound wherein $W_1$ is $C(R^{2a})$, $W_2$ is CH, $W_3$ is $C(R^2)$, $R^1$ is fluoro, $R^{1a}$, $R^2$, $R^{2a}$, and $R^3$ are hydrogen, V is $CH(R^4)$, Q is O, $R^4$ is hydrogen, and X is O;

a compound wherein $W_1$ is $C(R^{2a})$, $W_2$ is CH, $W_3$ is $C(R^2)$, $R^1$ is trifluoromethyl, $R^{1a}$ is hydrogen, $R^2$ is methyl, $R^{2a}$ is hydrogen, $R^3$ is hydrogen, V is $CH(R^4)$, Q is O, $R^4$ is hydrogen, and X is O;

a compound wherein $W_1$ is $C(R^{2a})$, $W_2$ is CH, $W_3$ is $C(R^2)$, $R^1$ is trifluoromethyl, $R^{1a}$ is hydrogen, $R^2$ is bromo, $R^{2a}$ is hydrogen, $R^3$ is hydrogen, V is $CH(R^4)$, Q is O, $R^4$ is hydrogen, and X is O;

a compound wherein $W_1$ is $C(R^{2a})$, $W_2$ is CH, $W_3$ is $C(R^2)$, $R^1$ is trifluoromethyl, $R^{1a}$ is hydrogen, $R^2$ is chloro, $R^{2a}$ is hydrogen, $R^3$ is hydrogen, V is $CH(R^4)$, Q is O, $R^4$ is hydrogen, and X is O;

a compound wherein $W_1$ is $C(R^{2a})$, $W_2$ is CH, $W_3$ is $C(R^2)$, $R^1$ is trifluoromethyl, $R^{1a}$ is hydrogen, $R^2$ is cyano, $R^{2a}$ is hydrogen, $R^3$ is hydrogen, V is $CH(R^4)$, Q is O, $R^4$ is hydrogen, and X is O;

a compound wherein $W_1$ is $C(R^{2a})$, $W_2$ is CH, $W_3$ is $C(R^2)$, $R^1$ is trifluoromethyl, $R^{1a}$, $R^2$, $R^{2a}$, and $R^3$ are hydrogen, V is $CH(R^4)$, Q is O, $R^4$ is hydrogen, and X is $C(CH_3)_2$;

a compound wherein $W_1$ is $C(R^{2a})$, $W_2$ is CH, $W_3$ is $C(R^2)$, $R^1$ is chloro, $R^{1a}$, $R^2$, $R^{2a}$, and $R^3$ are hydrogen, V is $CH(R^4)$, Q is O, $R^4$ is hydrogen, and X is $C(CH_3)_2$;

a compound wherein $W_1$ is $C(R^{2a})$, $W_2$ is CH, $W_3$ is $C(R^2)$, $R^1$ is fluoro, $R^{1a}$ is fluoro, $R^2$ is hydrogen, $R^{2a}$ is hydrogen, $R^3$ is hydrogen, V is $CH(R^4)$, Q is O, $R^4$ is hydrogen, and X is O;

a compound wherein $W_1$ is $C(R^{2a})$, $W_2$ is CH, $W_3$ is $C(R^2)$, $R^1$ is trifluoromethyl, $R^{1a}$ is hydrogen, $R^2$ is trifluoromethyl, $R^{2a}$ is hydrogen, $R^3$ is hydrogen, V is $CH(R^4)$, Q is O, $R^4$ is hydrogen, and X is $C(CH_3)_2$;

a compound wherein $W_1$ is $C(R^{2a})$, $W_2$ is CH, $W_3$ is $C(R^2)$, $R^1$ is chloro, $R^{1a}$, $R^2$, $R^{2a}$, and $R^3$ are hydrogen, V is $CH(R^4)$, Q is O, $R^4$ is hydrogen, and X is O;

a compound wherein $W_1$ is $C(R^{2a})$, $W_2$ is CH, $W_3$ is $C(R^2)$, $R^1$ is trifluoromethyl, $R^{1a}$ is hydrogen, $R^2$ is chloro, $R^{2a}$ is hydrogen, $R^3$ is hydrogen, V is $CH(R^4)$, Q is O, $R^4$ is hydrogen, and X is $C(CH_3)_2$;

a compound wherein $W_1$ is $C(R^{2a})$, $W_2$ is CH, $W_3$ is $C(R^2)$, $R^1$ is trifluoromethyl, $R^{1a}$ is hydrogen, $R^2$ is trifluoromethyl, $R^{2a}$ is hydrogen, $R^3$ is hydrogen, V is $CH(R^4)$, Q is O, $R^4$ is hydrogen, and X is O;

a compound wherein $W_1$ is $C(R^{2a})$, $W_2$ is CH, $W_3$ is $C(R^2)$, $R^1$ is trifluoromethyl, $R^{1a}$ is hydrogen, $R^2$ is $CH_2CH_2C(CH_3)_2OH$, $R^{2a}$ is hydrogen, $R^3$ is hydrogen, V is $CH(R^4)$, Q is O, $R^4$ is hydrogen, and X is $CH_2$;

a compound wherein $W_1$ is $C(R^{2a})$, $W_2$ is CH, $W_3$ is $C(R^2)$, $R^1$ is fluoro, $R^{1a}$ is fluoro, $R^2$ is chloro, $R^{2a}$ is hydrogen, $R^3$ is hydrogen, V is $CH(R^4)$, Q is O, $R^4$ is hydrogen, and X is $CH_2$;

a compound wherein $W_1$ is $C(R^{2a})$, $W_2$ is CH, $W_3$ is $C(R^2)$, $R^1$ is chloro, $R^{1a}$, $R^2$, $R^{2a}$, and $R^3$ are hydrogen, V is $CH(R^4)$, Q is O, $R^4$ is hydrogen, and X is $CH_2$;

a compound wherein $W_1$ is $C(R^{2a})$, $W_2$ is CH, $W_3$ is $C(R^2)$, $R^1$ is trifluoromethyl, $R^{1a}$ is hydrogen, $R^2$ is methyl, $R^{2a}$ is hydrogen, $R^3$ is hydrogen, V is $CH(R^4)$, Q is O, $R^4$ is hydrogen, and X is $CH_2$;

a compound wherein $W_1$ is $C(R^{2a})$, $W_2$ is CH, $W_3$ is $C(R^2)$, $R^1$ is fluoro, $R^{1a}$ is hydrogen, $R^2$ is methyl, $R^{2a}$ is hydrogen, $R^3$ is hydrogen, V is $CH(R^4)$, Q is O, $R^4$ is hydrogen, and X is $CH_2$;

a compound wherein $W_1$ is $C(R^{2a})$, $W_2$ is CH, $W_3$ is $C(R^2)$, $R^1$ is fluoro, $R^{1a}$ is fluoro, $R^2$ is methyl, $R^{2a}$ is hydrogen, $R^3$ is hydrogen, V is $CH(R^4)$, Q is O, $R^4$ is hydrogen, and X is $CH_2$;

a compound wherein $W_1$ is $C(R^{2a})$, $W_2$ is CH, $W_3$ is $C(R^2)$, $R^1$ is fluoro, $R^{1a}$ is hydrogen, $R^2$ is chloro, $R^{2a}$ is hydrogen, $R^3$ is hydrogen, V is $CH(R^4)$, Q is O, $R^4$ is hydrogen, and X is $CH_2$;

a compound wherein $W_1$ is $C(R^{2a})$, $W_2$ is CH, $W_3$ is $C(R^2)$, $R^1$ is trifluoromethoxy, $R^{1a}$ is hydrogen, $R^2$ is chloro, $R^{2a}$ is hydrogen, $R^3$ is hydrogen, V is $CH(R^4)$, Q is O, $R^4$ is hydrogen, and X is $CH_2$;

a compound wherein $W_1$ is $C(R^{2a})$, $W_2$ is CH, $W_3$ is $C(R^2)$, $R^1$ is trifluoromethoxy, $R^{1a}$ is hydrogen, $R^2$ is trifluoromethyl, $R^{2a}$ is hydrogen, $R^3$ is hydrogen, V is $CH(R^4)$, Q is O, $R^4$ is hydrogen, and X is $CH_2$;

a compound wherein $W_1$ is $C(R^{2a})$, $W_2$ is CH, $W_3$ is $C(R^2)$, $R^1$ is trifluoromethyl, $R^{1a}$ is hydrogen, $R^2$ is $CH_2CH_2CH_2OCH_3$, $R^{2a}$ is hydrogen, $R^3$ is hydrogen, V is $CH(R^4)$, Q is O, $R^4$ is hydrogen, and X is $CH_2$;

a compound wherein $W_1$ is $C(R^{2a})$, $W_2$ is CH, $W_3$ is $C(R^2)$, $R^1$ is fluoro, $R^{1a}$ is hydrogen, $R^2$ is trifluoromethyl, $R^{2a}$ is hydrogen, $R^3$ is hydrogen, V is $CH(R^4)$, Q is O, $R^4$ is hydrogen, and X is $CH_2$;

a compound wherein $W_1$ is $C(R^{2a})$, $W_2$ is CH, $W_3$ is $C(R^2)$, $R^1$ is trifluoromethyl, $R^{1a}$ is hydrogen, $R^2$ is methyl, $R^{2a}$ is methyl, $R^3$ is hydrogen, V is $CH(R^4)$, Q is O, $R^4$ is hydrogen, and X is $CH_2$;

a compound wherein $W_1$ is $C(R^{2a})$, $W_2$ is CH, $W_3$ is $C(R^2)$, $R^1$ is trifluoromethyl, $R^{1a}$ is hydrogen, $R^2$ is chloro, $R^{2a}$ is methyl, $R^3$ is hydrogen, V is $CH(R^4)$, Q is O, $R^4$ is hydrogen, and X is $CH_2$;

a compound wherein $W_1$ is N, $W_2$ is CH, $W_3$ is $C(R^2)$, $R^1$ is trifluoromethyl, $R^{1a}$ is hydrogen, $R^2$ is hydrogen, $R^3$ is hydrogen, V is $CH(R^4)$, Q is O, $R^4$ is hydrogen, and X is $CH_2$;

a compound wherein $W_1$ is $C(R^{2a})$, $W_2$ is N, $W_3$ is $C(R^2)$, $R^1$ is trifluoromethyl, $R^{1a}$, $R^2$, $R^{2a}$, and $R^3$ are hydrogen, V is $CH(R^4)$, Q is O, $R^4$ is hydrogen, and X is $CH_2$;

a compound wherein $W_1$ is $C(R^{2a})$, $W_2$ is CH, $W_3$ is N, $R^1$ is trifluoromethyl, $R^{1a}$, $R^{2a}$, and $R^3$ are hydrogen, V is $CH(R^4)$, Q is O, $R^4$ is hydrogen, and X is $CH_2$;

and enantiomers, diastereomers, solvates, and pharmaceutically acceptable salts thereof.
A further embodiment of the present invention is directed to compounds 1-58, pictured below in Table 1.
TABLE 1
| Cpd No. | Structure |
|---|---|
| 1 | 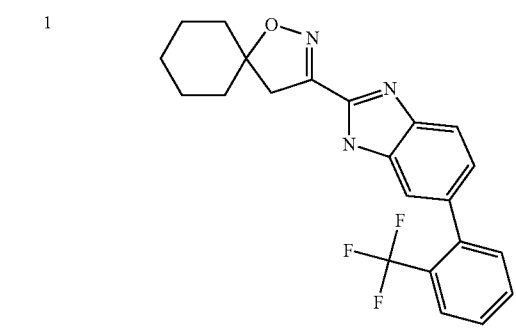 |
| 2 | 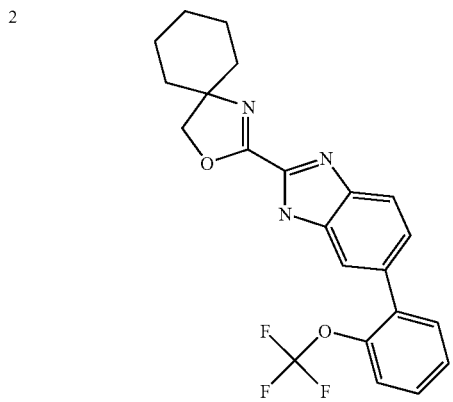 |
| 3 | 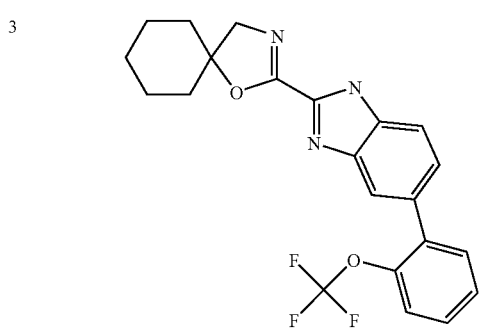 |
| 4 | 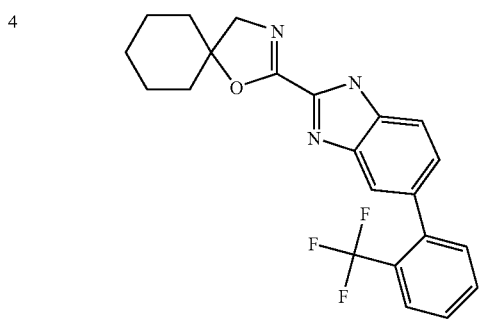 |
TABLE 1-continued
| Cpd No. | Structure |
|---|---|
| 5 | 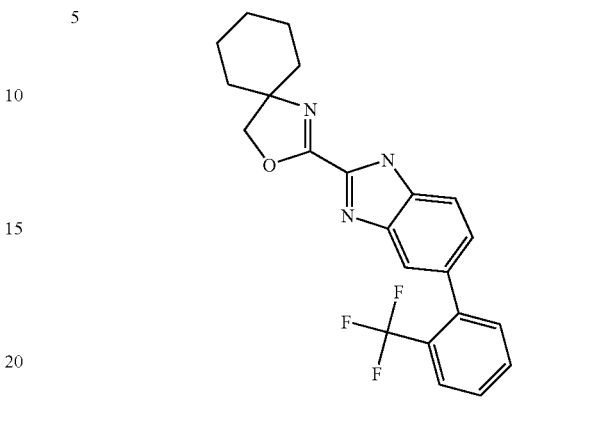 |
| 6 | 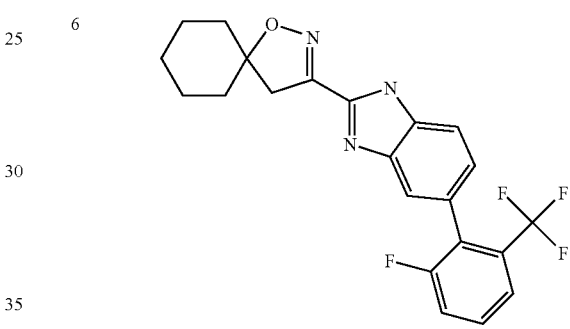 |
| 7 | 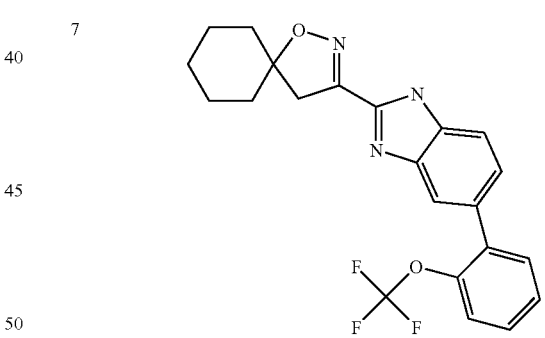 |
| 8 | 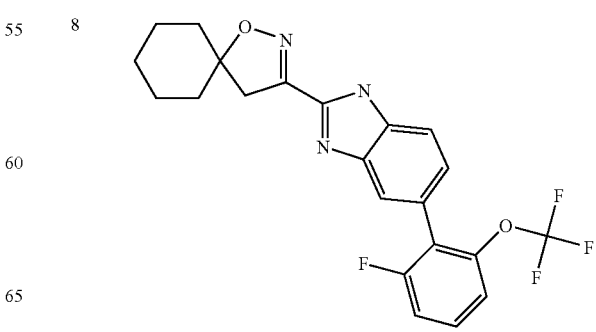 |

TABLE 1-continued

| Cpd No. | Structure |
|---|---|
| 9 | (structure) |
| 10 | (structure) |
| 11 | (structure) |
| 12 | (structure) |
| 13 | (structure) |
| 14 | (structure) |
| 15 | (structure) |
| 16 | (structure) |
| 17 | (structure) |

TABLE 1-continued

| Cpd No. | Structure |
|---|---|
| 18 | 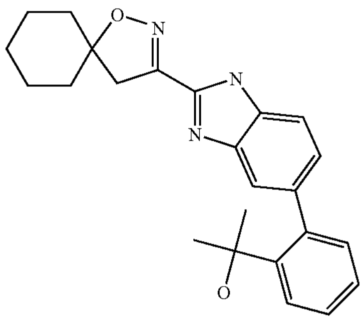 |
| 19 | 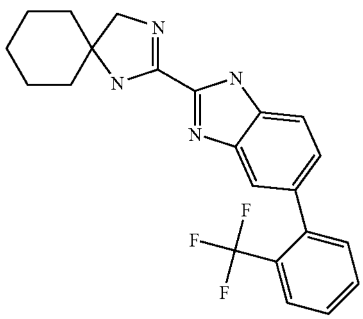 |
| 20 | 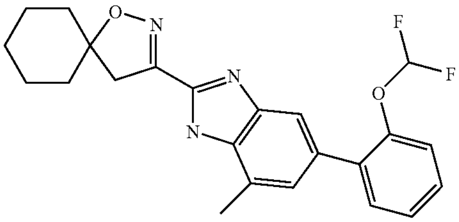 |
| 21 | 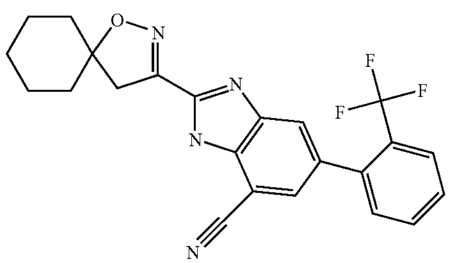 |
| 22 | 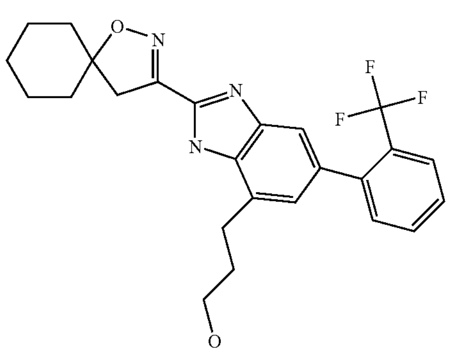 |
| 23 | |
| 24 | |
| 25 | |
| 26 | |
| 27 | |

TABLE 1-continued

| Cpd No. | Structure |
|---|---|
| 28 | |
| 29 | |
| 30 | |
| 31 | |
| 32 | |
| 33 | 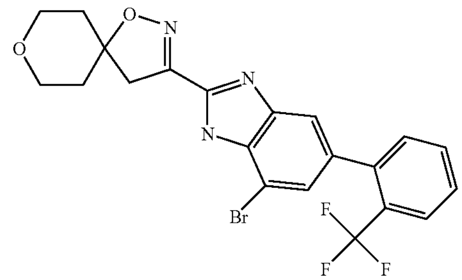 |
| 34 | 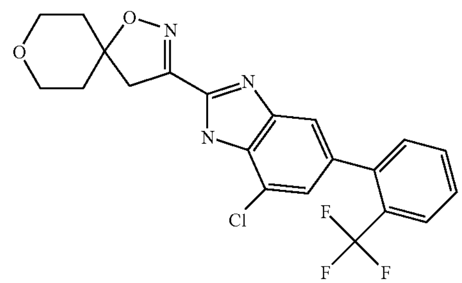 |
| 35 | 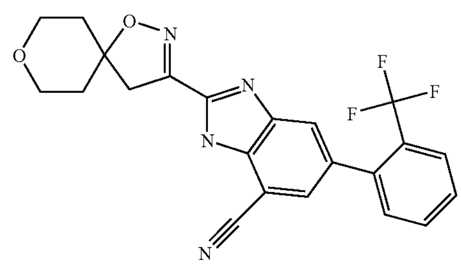 |
| 36 | 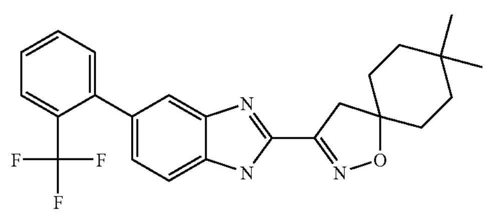 |
| 37 | 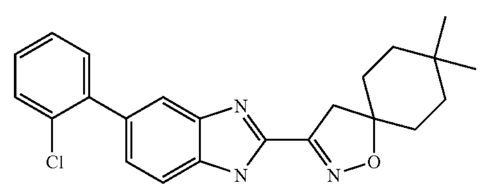 |
| 38 | 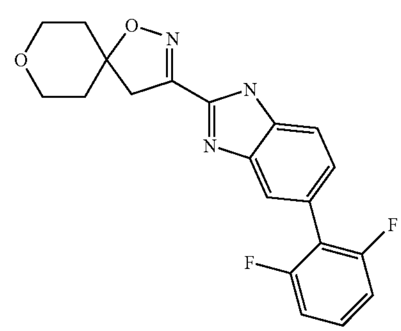 |

TABLE 1-continued

| Cpd No. | Structure |
|---|---|
| 39 | |
| 40 | |
| 41 | |
| 42 | |
| 43 | |
| 44 | 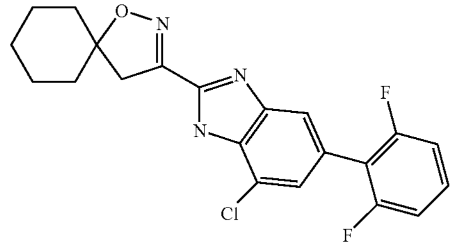 |
| 45 | 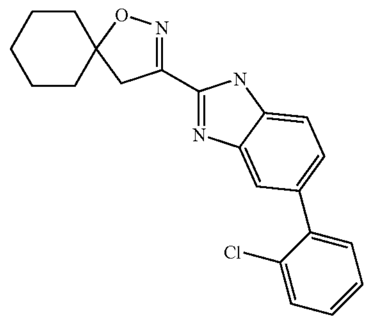 |
| 46 | 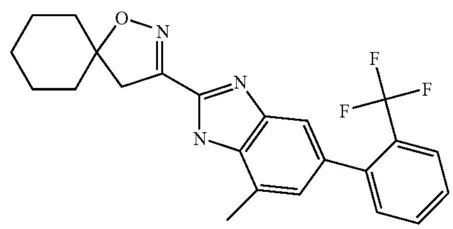 |
| 47 | 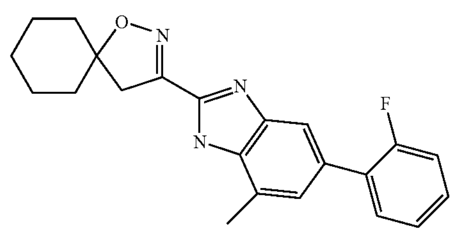 |
| 48 | 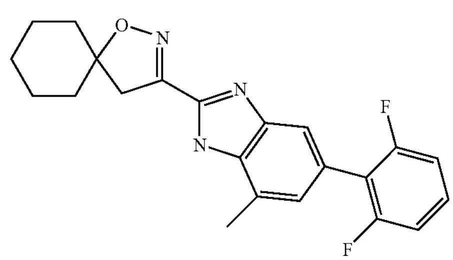 |
| 49 | 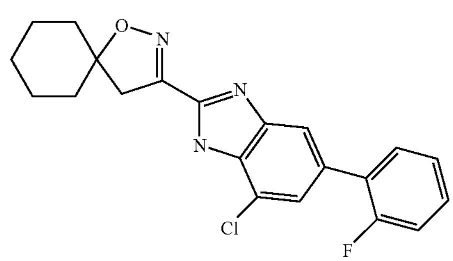 |

TABLE 1-continued
| Cpd No. | Structure |
|---|---|
| 50 | 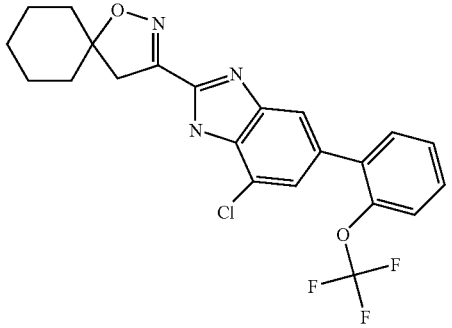 |
| 51 | 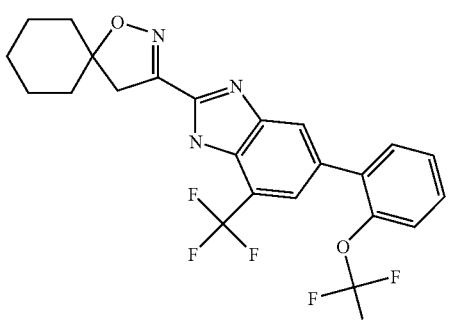 |
| 52 | 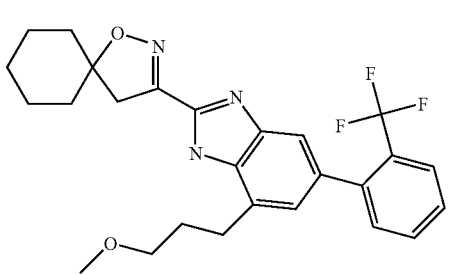 |
| 53 | 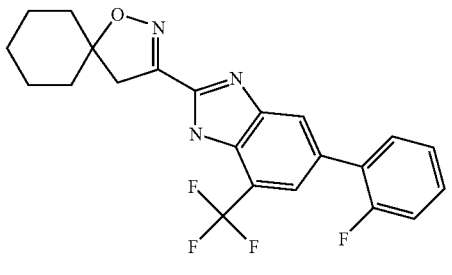 |
| 54 | 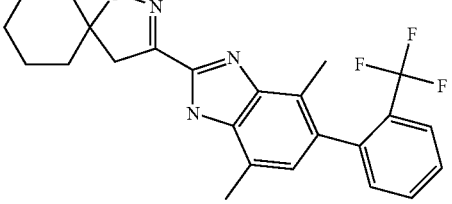 |
| 55 | 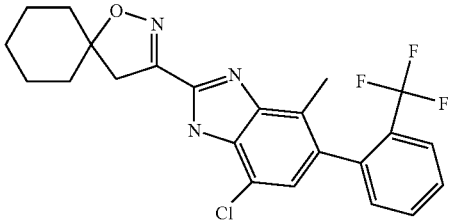 |
| 56 | 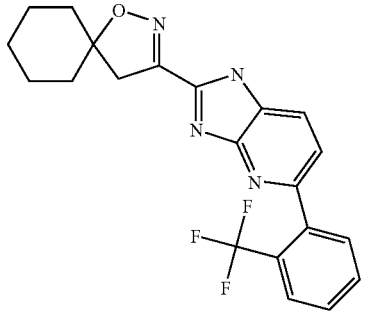 |
| 57 | 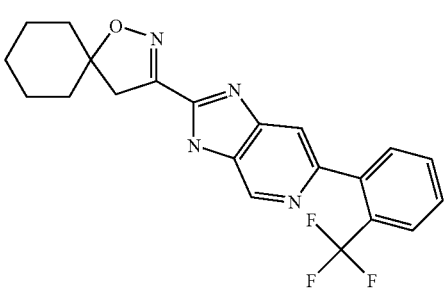 |
| 58 | 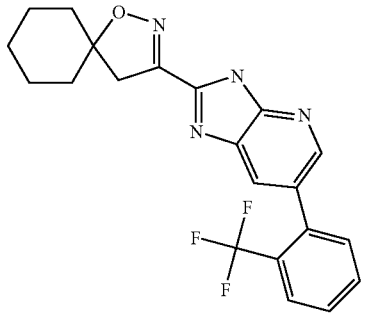 |
An even further embodiment of the present invention is directed to compounds of Formula (I) wherein the compounds have a formula selected from the group consisting of a) Cpd 27

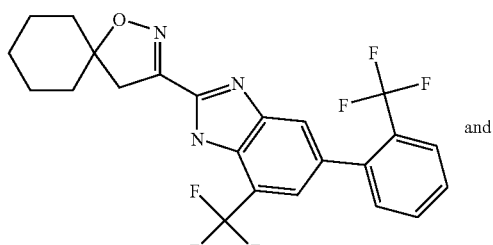

and b) Cpd 16

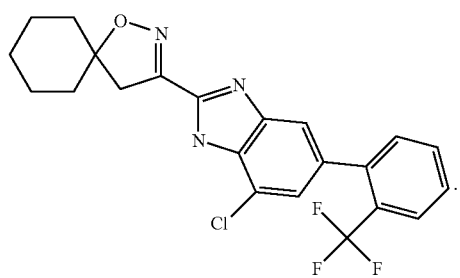

For use in medicine, salts of compounds of Formula (I) refer to non-toxic "pharmaceutically acceptable salts." Other salts may, however, be useful in the preparation of compounds of Formula (I) or of their pharmaceutically acceptable salts thereof. Suitable pharmaceutically acceptable salts of compounds of Formula (I) include acid addition salts which can, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of Formula (I) carry an acidic moiety, suitable pharmaceutically acceptable salts thereof may include alkali metal salts, such as sodium or potassium salts; alkaline earth metal salts, such as calcium or magnesium salts; and salts formed with suitable organic ligands, such as quaternary ammonium salts. Thus, representative pharmaceutically acceptable salts include acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids and bases that may be used in the preparation of pharmaceutically acceptable salts include acids including acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxoglutaric acid, glycolic acid, hippuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, phosphoric acid, L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid and undecylenic acid; and bases including ammonia, L-arginine, benethamine, benzathine, calcium hydroxide, choline, deanol, diethanolamine, diethylamine, 2-(diethylamino)-ethanol, ethanolamine, ethylenediamine, N-methylglucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

Embodiments of the present invention include prodrugs of compounds of Formula (I). In general, such prodrugs will be functional derivatives of the compounds that are readily convertible in vivo into the required compound. Thus, in the methods of treating or preventing embodiments of the present invention, the term "administering" encompasses the treatment or prevention of the various diseases, conditions, syndromes and disorders described with the compound specifically disclosed or with a compound that may not be specifically disclosed, but which converts to the specified compound in vivo after administration to a patient. Conventional procedures for the selection and preparation of suitable prodrug derivatives are described, for example, in "Design of Prodrugs", ed. H. Bundgaard, Elsevier, 1985.

Where the compounds according to embodiments of this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention. The skilled artisan will understand that the term compound as used herein, is meant to include solvated compounds of Formula I.

Where the processes for the preparation of the compounds according to certain embodiments of the invention give rise to a mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

One embodiment of the present invention is directed to a composition, including a pharmaceutical composition, comprising, consisting of, and/or consisting essentially of the (+)-enantiomer of a compound of Formula (I) wherein said composition is substantially free from the (−)-isomer of said compound. In the present context, substantially free means less than about 25%, preferably less than about 10%, more preferably less than about 5%, even more preferably less than about 2% and even more preferably less than about 1% of the (−)-isomer calculated as $$\% \ (+)\text{-enantiomer} = \frac{(\text{mass}(+)\text{-enantiomer})}{(\text{mass}(+)\text{-enantiomer}) + (\text{mass}(-)\text{-enantiomer})} \times 100.$$

Another embodiment of the present invention is a composition, including a pharmaceutical composition, comprising, consisting of, and consisting essentially of the (−)-enantiomer of a compound of Formula (I) wherein said composition is substantially free from the (+)-isomer of said compound. In the present context, substantially free from means less than about 25%, preferably less than about 10%, more preferably less than about 5%, even more preferably less than about 2% and even more preferably less than about 1% of the (+)-isomer calculated as $$\% \ (-)\text{-enantiomer} = \frac{(\text{mass}(-)\text{-enantiomer})}{(\text{mass}(+)\text{-enantiomer}) + (\text{mass}(-)\text{-enantiomer})} \times 100.$$

During any of the processes for preparation of the compounds of the various embodiments of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1999. The protecting groups may be removed at a convenient subsequent stage using methods known from the art.

Even though the compounds of embodiments of the present invention (including their pharmaceutically acceptable salts and pharmaceutically acceptable solvates) can be administered alone, they will generally be administered in admixture with a pharmaceutically acceptable carrier, a pharmaceutically acceptable excipient, and/or a pharmaceutically acceptable diluent selected with regard to the intended route of administration and standard pharmaceutical or veterinary practice. Thus, particular embodiments of the present invention are directed to pharmaceutical and veterinary compositions comprising compounds of Formula (I) and at least one pharmaceutically acceptable carrier, pharmaceutically acceptable excipient, and/or pharmaceutically acceptable diluent By way of example, in the pharmaceutical compositions of embodiments of the present invention, the compounds of Formula (I) may be admixed with any suitable binder(s), lubricant(s), suspending agent(s), coating agent(s), solubilizing agent(s), and combinations thereof.

Solid oral dosage forms, such as tablets or capsules, containing the compounds of the present invention may be administered in at least one dosage form at a time, as appropriate. It is also possible to administer the compounds in sustained release formulations.

Additional oral forms in which the present inventive compounds may be administered include elixirs, solutions, syrups, and suspensions; each optionally containing flavoring agents and coloring agents.

Alternatively, compounds of Formula (I) can be administered by inhalation (intratracheal or intranasal) or in the form of a suppository or pessary, or they may be applied topically in the form of a lotion, solution, cream, ointment or dusting powder. For example, they can be incorporated into a cream comprising, consisting of, and/or consisting essentially of an aqueous emulsion of polyethylene glycols or liquid paraffin. They can also be incorporated, at a concentration of between about 1% and about 10% by weight of the cream, into an ointment comprising, consisting of, and/or consisting essentially of a white wax or white soft paraffin base together with any stabilizers and preservatives as may be required. An alternative means of administration includes transdermal administration by using a skin or transdermal patch.

The pharmaceutical compositions of the present invention (as well as the compounds of the present invention alone) can also be injected parenterally, for example intracavernosally, intravenously, intramuscularly, subcutaneously, intradermally or intrathecally. In this case, the compositions will also include at least one of a suitable carrier, a suitable excipient, and a suitable diluent.

For parenteral administration, the pharmaceutical compositions of the present invention are best used in the form of a sterile aqueous solution that may contain other substances, for example, enough salts and monosaccharides to make the solution isotonic with blood.

For buccal or sublingual administration, the pharmaceutical compositions of the present invention may be administered in the form of tablets or lozenges, which can be formulated in a conventional manner.

By way of further example, pharmaceutical compositions containing at least one of the compounds of Formula (I) as the active ingredient can be prepared by mixing the compound(s) with a pharmaceutically acceptable carrier, a pharmaceutically acceptable diluent, and/or a pharmaceutically acceptable excipient according to conventional pharmaceutical compounding techniques. The carrier, excipient, and diluent may take a wide variety of forms depending upon the desired route of administration (e.g., oral, parenteral, etc.). Thus for liquid oral preparations, such as suspensions, syrups, elixirs and solutions, suitable carriers, excipients and diluents include water, glycols, oils, alcohols, flavoring agents, preservatives, stabilizers, coloring agents and the like; for solid oral preparations, such as powders, capsules and tablets, suitable carriers, excipients and diluents include starches, sugars, diluents, granulating agents, lubricants, binders, disintegrating agents and the like. Solid oral preparations also may be optionally coated with substances, such as sugars, or be enterically-coated so as to modulate the major site of absorption and disintegration. For parenteral administration, the carrier, excipient and diluent will usually include sterile water, and other ingredients may be added to increase solubility and preservation of the composition. Injectable suspensions or solutions may also be prepared utilizing aqueous carriers along with appropriate additives, such as solubilizers and preservatives.

A therapeutically effective amount of a compound of Formula (I) or a pharmaceutical composition thereof includes a dose range from about 0.1 mg to about 3000 mg, in particular from about 1 mg to about 1000 mg or, more particularly, from about 10 mg to about 500 mg of active ingredient in a regimen of about 1 to 4 times per day for an average (70 kg) human; although, it is apparent to one skilled in the art that the therapeutically effective amount for active compounds of the invention will vary as will the diseases, syndromes, conditions, and disorders being treated.

For oral administration, a pharmaceutical composition is preferably provided in the form of tablets containing about 0.01, about 10, about 50, about 100, about 150, about 200, about 250, and about 500 milligrams of the inventive compound as the active ingredient.

Advantageously, a compound of Formula (I) may be administered in a single daily dose, or the total daily dosage may be administered in divided doses of two, three and four times daily.

Optimal dosages of a compound of Formula (I) to be administered may be readily determined and will vary with the particular compound used, the mode of administration, the strength of the preparation, and the advancement of the disease, syndrome, condition, or disorder. In addition, factors associated with the particular subject being treated, including subject age, weight, diet and time of administration, will result in the need to adjust the dose to achieve an appropriate therapeutic level. The above dosages are thus exemplary of the average case. There can be, of course, individual instances wherein higher or lower dosage ranges are merited, and such are within the scope of this invention.

Compounds of Formula (I) may be administered in any of the foregoing compositions and dosage regimens or by means of those compositions and dosage regimens established in the art whenever use of a compound of Formula (I) is required for a subject in need thereof.

As antagonists of the TRPM8 ion channel, the compounds of Formula (I) are useful in methods for treating and preventing a disease, a syndrome, a condition, or a disorder in a subject, including an animal, a mammal and a human in which the disease, the syndrome, the condition, or the disorder is affected by the modulation of TRPM8 receptors. Such methods comprise, consist of, and consist essentially of administering to a subject, including an animal, a mammal, and a human in need of such treatment or prevention a therapeutically effective amount of a compound, salt, or solvate of Formula (I). In particular, the compounds of Formula (I) are useful for preventing or treating pain, or diseases, syndromes, conditions, or disorders causing such pain, or pulmonary or vascular dysfunction. More particularly, the compounds of Formula (I) are useful for preventing or treating inflammatory pain, inflammatory hypersensitivity conditions, neuropathic pain, anxiety, depression, and cardiovascular disease aggravated by cold, including peripheral vascular disease, vascular hypertension, pulmonary hypertension, Raynaud's disease, and coronary artery disease, by administering to a subject in need thereof a therapeutically effective amount of a compound of Formula (I).

Examples of inflammatory pain include pain due to a disease, condition, syndrome, disorder, or a pain state including inflammatory bowel disease, visceral pain, migraine, post-operative pain, osteoarthritis, rheumatoid arthritis, back pain, lower back pain, joint pain, abdominal pain, chest pain, labor, musculoskeletal diseases, skin diseases, toothache, pyresis, burn, sunburn, snake bite, venomous snake bite, spider bite, insect sting, neurogenic bladder, interstitial cystitis, urinary tract infection, rhinitis, contact dermatitis/hypersensitivity, itch, eczema, pharyngitis, mucositis, enteritis, irritable bowel syndrome, cholecystitis, pancreatitis, postmastectomy pain syndrome, menstrual pain, endometriosis, sinus headache, tension headache, or arachnoiditis.

One type of inflammatory pain is inflammatory hyperalgesia, which can be further distinguished as inflammatory somatic hyperalgesia or inflammatory visceral hyperalgesia. Inflammatory somatic hyperalgesia can be characterized by the presence of an inflammatory hyperalgesic state in which a hypersensitivity to thermal, mechanical and/or chemical stimuli exists. Inflammatory visceral hyperalgesia can also be characterized by the presence of an inflammatory hyperalgesic state, in which an enhanced visceral irritability exists.

Examples of inflammatory hyperalgesia include a disease, syndrome, condition, disorder, or pain state including inflammation, osteoarthritis, rheumatoid arthritis, back pain, joint pain, abdominal pain, musculoskeletal diseases, skin diseases, post operative pain, headaches, toothache, burn, sunburn, insect sting, neurogenic bladder, urinary incontinence, interstitial cystitis, urinary tract infection, cough, asthma, chronic obstructive pulmonary disease, rhinitis, contact dermatitis/hypersensitivity, itch, eczema, pharyngitis, enteritis, irritable bowel syndrome, inflammatory bowel diseases including Crohn's Disease or ulcerative colitis.

One embodiment of the present invention is directed to a method for treating inflammatory somatic hyperalgesia in which a hypersensitivity to thermal, mechanical and/or chemical stimuli exists, comprising the step of administering to a subject in need of such treatment a therapeutically effective amount of a compound, salt or solvate of Formula (I).

A further embodiment of the present invention is directed to a method for treating inflammatory visceral hyperalgesia in which a enhanced visceral irritability exists, comprising, consisting of, and/or consisting essentially of the step of administering to a subject in need of such treatment a therapeutically effective amount of a compound, salt or solvate of Formula (I).

A further embodiment of the present invention is directed to a method for treating neuropathic cold allodynia in which a hypersensitivity to a cooling stimuli exists, comprising, consisting of, and/or consisting essentially of the step of administering to a subject in need of such treatment a therapeutically effective amount of a compound, salt or solvate of Formula (I).

Examples of an inflammatory hypersensitivity condition include urinary incontinence, benign prostatic hypertrophy, cough, asthma, rhinitis and nasal hypersensitivity, itch, contact dermatitis and/or dermal allergy, and chronic obstructive pulmonary disease.

Examples of a neuropathic pain include pain due to a disease, syndrome, condition, disorder, or pain state including cancer, neurological disorders, spine and peripheral nerve surgery, brain tumor, traumatic brain injury (TBI), spinal cord trauma, chronic pain syndrome, fibromyalgia, chronic fatigue syndrome, neuralgias (trigeminal neuralgia, glossopharyngeal neuralgia, postherpetic neuralgia and causalgia), lupus, sarcoidosis, peripheral neuropathy, bilateral peripheral neuropathy, diabetic neuropathy, central pain, neuropathies associated with spinal cord injury, stroke, amyotrophic lateral sclerosis (ALS), Parkinson's disease, multiple sclerosis, sciatic neuritis, mandibular joint neuralgia, peripheral neuritis, polyneuritis, stump pain, phantom limb pain, bony fractures, oral neuropathic pain, Charcot's pain, complex regional pain syndrome I and II (CRPS I/II), radiculopathy, Guillain-Barre syndrome, meralgia paresthetica, burning-mouth syndrome, optic neuritis, postfebrile neuritis, migrating neuritis, segmental neuritis, Gombault's neuritis, neuronitis, cervicobrachial neuralgia, cranial neuralgia, geniculate neuralgia, glossopharyngial neuralgia, migrainous neuralgia, idiopathic neuralgia, intercostals neuralgia, mammary neuralgia, Morton's neuralgia, nasociliary neuralgia, occipital neuralgia, red neuralgia, Sluder's neuralgia, splenopalatine neuralgia, supraorbital neuralgia, vulvodynia, or vidian neuralgia.

One type of neuropathic pain is neuropathic cold allodynia, which can be characterized by the presence of a neuropathy-associated allodynic state in which a hypersensitivity to cooling stimuli exists. Examples of neuropathic cold allodynia include allodynia due to a disease, condition, syndrome, disorder or pain state including neuropathic pain (neuralgia), pain arising from spine and peripheral nerve surgery or trauma, traumatic brain injury (TBI), trigeminal neuralgia, postherpetic neuralgia, causalgia, peripheral neuropathy, diabetic neuropathy, central pain, stroke, peripheral neuritis, polyneuritis, complex regional pain syndrome I and II (CRPS I/II) and radiculopathy.

Examples of anxiety include social anxiety, post-traumatic stress disorder, phobias, social phobia, special phobias, panic disorder, obsessive-compulsive disorder, acute stress disorder, separation anxiety disorder, and generalized anxiety disorder.

Examples of depression include major depression, bipolar disorder, seasonal affective disorder, post-natal depression, manic depression, and bipolar depression.

General Synthetic Methods

Representative compounds of the present invention can be synthesized in accordance with the general synthetic methods described below and illustrated in the schemes that follow. Since the schemes are an illustration, the invention should not be construed as being limited by the specific chemical reactions and specific conditions described in the schemes and examples. The various starting materials used in the schemes are commercially available or may be prepared by methods well within the skill of persons versed in the art. The variables are as defined herein and within the skill of persons versed in the art.

Abbreviations used in the instant specification, particularly the schemes and examples, are as follows:

| Abbreviation | Meaning |
| --- | --- |
| AcOH | acetic acid |
| AIBN | azobisisobutyronitrile |
| aq | aqueous |
| atm | atmosphere |

| Abbreviation | Meaning |
| --- | --- |
| BOC | tert-butyloxycarbonyl |
| Cpd | compound |
| CSA | camphorsulfonic acid |
| DCC | N,N-dicyclohexylcarbodiimide |
| DCE | 1,2-dichloroethane |
| DCM | dichloromethane |
| DIPEA | diisopropylethylamine |
| DMA | N,N-dimethylacetamide |
| DME | 1,2-dimethoxyethane |
| DMF | N,N-dimethylformamide |
| DMSO | dimethyl sulfoxide |
| dppf | 1,1'-bis-(diphenylphosphino)ferrocene |
| EDCI | 1-(3-dimethylaminopropyl)-3-ethylcarbodiimide hydrochloride |
| EtOAc | ethyl acetate |
| EtOH | ethanol |
| h | hour(s) |
| HCl | hydrochloric acid |
| HOBt | 1-hydroxybenzotriazole |
| MeOH | methanol |
| min | minute(s) |
| NCS | N-chlorosuccinimide |
| PHMS | polymethylhydrosiloxane |
| PyBroP | bromotripyrrolidinophosphonium hexafluorophosphate |
| rt | room temperature |
| S-Phos | 2-dicyclohexylphosphino-2',6'-dimethoxybiphenyl |
| satd | saturated |
| TBSCl | tert-butyldimethylsilyl chloride |
| TEA | triethylamine |
| THF | tetrahydrofuran |
| TLC | thin layer chromatography |

The following describes the general methodology that can be used to produce isoxazolinyl benzimidazoles of Formula (I).

Scheme I

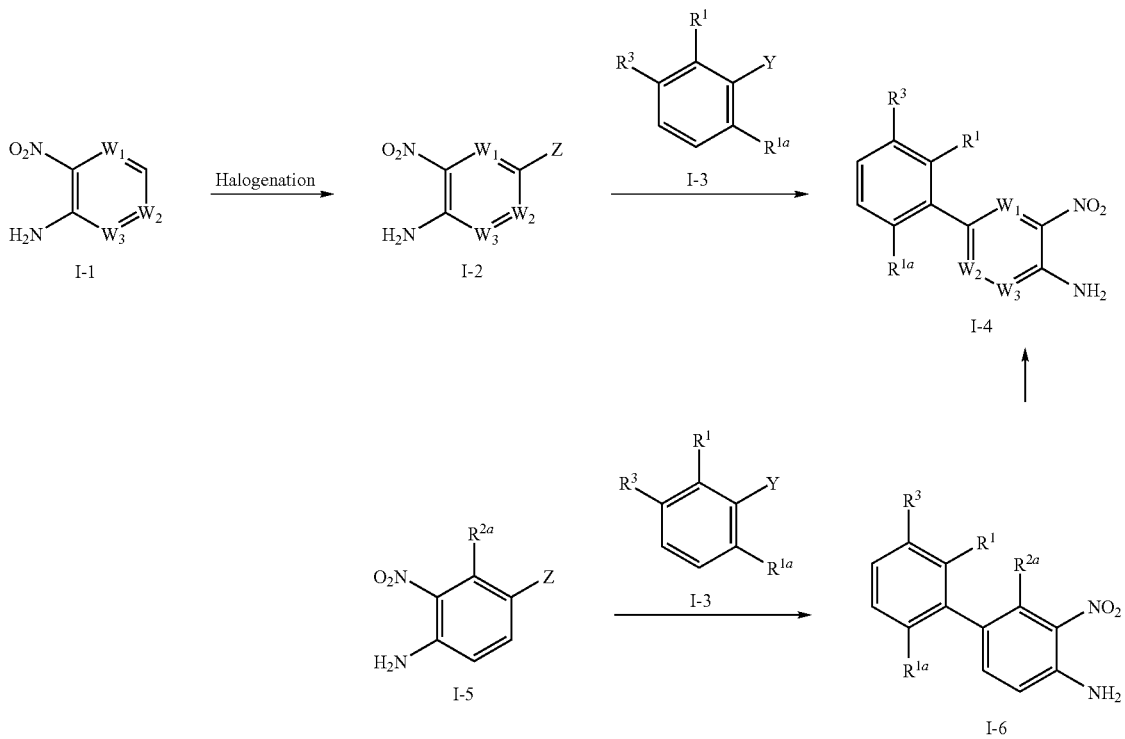

A suitably substituted compound of the Formula I-2 wherein Z is chloro, bromo, or iodo and $R^2$ is other than chloro or bromo, can serve as a useful intermediate for the construction of the biaryl portion of the compounds of the present invention as shown in Scheme I. When not commercially available, a compound of the Formula I-2 wherein $W_1$ is $C(R^{2a})$, $W_2$ is CH and $W_3$ is $C(R^2)$ can be prepared by the halogenation of a suitably substituted corresponding compound of the Formula I-1 using a variety of reagents. (For a review, see: Coombes, R. G. "Organic Reaction Mechanisms (Electrophilic Aromatic Substitution)"; John Wiley & Sons, Ltd. (New York), 2003; p 287-295.) A preferred reagent for bromination is bromine in a suitable solvent such as DCM, tetrachloromethane or preferably acetic acid. A preferred reagent for chlorination is sulfuryl chloride in a suitable solvent such as DCM or tetrachloromethane. Preferred reagents for iodination include iodine in a suitable solvent such as DCM or tetrachloromethane or, more preferably, iodine and a silver salt such as silver sulfate in a suitable solvent such as ethanol.

A compound of the Formula I-2 can then be coupled with a suitably substituted aryl boronic acid, trialkyltin reagent, trialkylsilane, and the like, of the Formula I-3 (wherein Y is the reactive coupling functionality) by a variety of coupling reactions (e.g. Suzuki, Stille, and Hiyama reactions) that are well known to those versed in the art. (For a review of Suzuki reactions, see: Miyaura; N.; Suzuki, A. Chem. Rev. 1995, 95, 2457. For a review of Stille reactions, see: Farina, V.; Krishnamurthy, V.; Scott, W. J. "The Stille Reaction"; Organic Reactions 1997, 50, 1-652. For references to Hiyama chemistry, see: Sahoo, A. K.; Oda, T.; Nakao, and Y. Hiyama Adv. Synth. Catal. 2004, 346, 1715-1727 and T. Nakao, Y, et al. J. Amer. Chem. Soc. 2005, 127, 6952-6953). A particularly useful method is the palladium-catalyzed Suzuki cross-coupling reaction (see also, Huff, B. et al. Org. Syn. 1997, 75, 53-60, and Goodson, F. E. et al. Org. Syn. 1997, 75, 61-68). Suitable palladium catalysts for this reaction include palladium (II) acetate, palladium (II) chloride, bis(acetonitrile)-dichloropalladium(II), dichloro-bis(di-tert-butylphenylphosphine)-palladium (II) and the like; or preferably [1,1'-bis-(diphenylphosphino)-ferrocene]-palladium (II) dichloride dichloromethane adduct ((dppf)PdCl$_2$.DCM) and tetrakis-(triphenylphosphine)-palladium(0) (Pd(PPh$_3$)$_4$). The reactions also may be carried out in the presence or absence of added ligands for palladium which, when used, include one or more than one of triphenylphosphine, tri-o-tolylphosphine, tri(tert-butyl)-phosphine, 1,1'-bis(diphenylphosphino)-ferrocene, bis[2-(diphenyl-phosphino)phenyl]ether, 2-dicyclohexylphosphino-2',6'-dimethoxybiphenyl, 1-butyl-3-methylimidazolium hexafluorophosphate, and the like. Suitable bases for this transformation include cesium carbonate, potassium carbonate, sodium carbonate, cesium fluoride, potassium fluoride, potassium tert-butoxide, sodium tert-butoxide, aqueous sodium hydroxide, aqueous sodium bicarbonate or preferably potassium phosphate or aqueous sodium carbonate. Useful solvents include ethanol, THF, DMF, toluene, benzene or preferably DME or dioxane.

In this instance, a mixture of a compound of the Formula I-2 and a compound of the Formula I-3 (wherein Y is a boronic acid or ester) in a mixture of DME and water containing sodium carbonate and a catalytic amount of a preferred palladium catalyst can be heated to about 90° C. to give the intermediate of the Formula I-4.

When $R^2$ is fluoro, chloro, or bromo, $R^2$ can be introduced after the biaryl coupling as described herein by starting with a suitably substituted compound of the Formula I-5 to give a biaryl intermediate of the Formula I-6, followed by halogenation using the conditions described herein to produce a compound of the Formula I-4.

Alternatively when $W_1$ is $C(R^{2a})$, $W_2$ is CH, and $W_3$ is $C(R^2)$, the biaryl coupling partners can be reversed as shown in Scheme II such that a halo group is on the aryl ring in a compound of the Formula II-2 (Z=iodo, bromo, or chloro) and a boronic acid or ester moiety (Y=B(OH)$_2$ or B(OR)$_2$ where B(OR)$_2$ is, for example, pinacolatoboryl or neopentylglycolatoboryl) is on a compound of the Formula II-1, employing the catalysts, optional ligands, bases and solvents described for Scheme I. In this instance, a mixture of a compound of the Formula II-1 and a compound of the Formula II-2; in a solvent mixture of DME and water; in the presence of a base such as sodium carbonate; and a catalytic amount of a preferred palladium catalyst; can be heated to 90° C. to give the intermediate of the Formula I-4.

When not readily available, boronic esters of the Formula II-1 can be synthesized from the corresponding halo derivatives of the Formula I-2, wherein $W_1$ is $C(R^{2a})$, $W_2$ is CH, and $W_3$ is $C(R^2)$, by a palladium-catalyzed boronation reaction (see, for example, Ishiyama, T. et al. J. Org. Chem. 1995, 60, 7508-10 and Murata, M. et al. J. Org. Chem. 2000, 65, 164-8). Preferred conditions include treatment with a diboron reagent such as bis(pinacolato)diboron, a palladium catalyst such as (dppf)PdCl$_2$, and a base, preferably potassium acetate, in a suitable solvent such as DMSO, DMF or preferably dioxane.

Scheme II

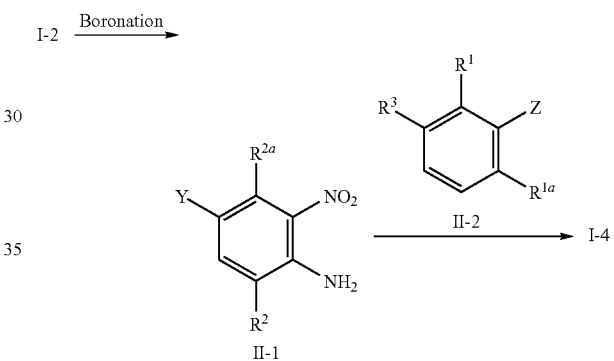

The nitro group of a compound of the Formula I-4 can be reduced to an amino group as shown in Scheme III to afford a compound of the Formula III-1 by a variety of standard methods (see: M. Hudlicky, "Reductions in Organic Chemistry"; Ellis Horwood, Ltd.: Chichester, UK, 1984). These include, where appropriate, catalytic hydrogenation using palladium metal as a catalyst in a suitable solvent such as methanol or ethanol, or, reduction with iron or zinc metal in the presence of a suitable acidic reagent or solvent such as hydrochloric acid or acetic acid, or by using iron and ammonium chloride in ethanol and water. One preferred method is with iron powder as the reducing agent in a mixture of ethanol and acetic or hydrochloric acid and heating at 50-80° C.

Scheme III

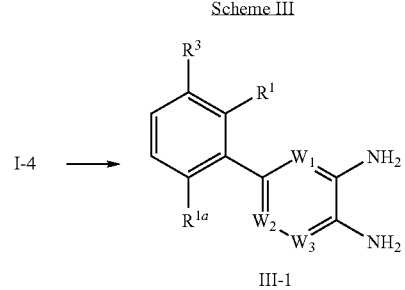

As illustrated in Scheme IV, an intermediate of the Formula IV-3 (wherein V is C(R⁴) and Q is O) can be produced through the [3+2]cycloaddition reaction of an in situ-generated nitrile oxide and an appropriately substituted alkene of the Formula IV-2. (For a review of this chemistry, see: Jaeger, Volker; Colinas, Pedro A., Eds. "Chemistry of Heterocyclic Compounds (Synthetic Applications of 1,3-Dipolar Cycloaddition Chemistry toward Heterocycles and Natural Products)"; John Wiley & Sons, Ltd. (New York), 2002; Chapter 59, p 361-472.) Preferred conditions for this reaction include generation of the nitrile oxide from ethyl chlorohydroxyiminoacetate (Cpd IV-1) in an appropriate solvent, preferably DCM, in the presence of the alkene of the Formula IV-2 with a trialkylamine, such as diisopropylethylamine, as a base.

Scheme IV

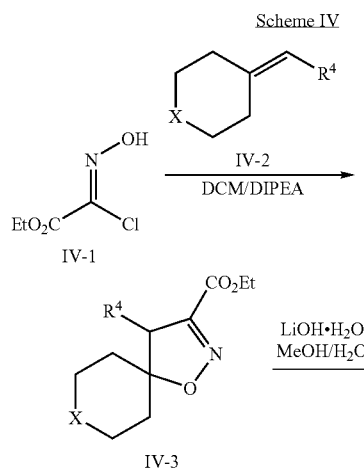

The resulting ester of the Formula IV-3 can be saponified by a number of common methods to produce the corresponding carboxylic acid; for example, by the action of lithium hydroxide in a water and methanol solvent mixture to give the carboxylic acid of the Formula IV-4.

The acid chloride of a compound of the Formula IV-4 can be prepared using any of a number of standard known chlorinating agents such as thionyl chloride or preferably oxalyl chloride as shown in Scheme V with DCM as the solvent and preferably with DMF added as a catalyst. The acid chloride thus produced can be added to a compound of the Formula III-1 in the presence of an acid scavenger and in an appropriate solvent, such as triethylamine in DCM, to give a mixture of the mono-acylated biphenyl intermediates of the Formula V-1. A di-acylated biphenyl product may also be generated during the course of the reaction and can be separated from the mono-acylated mixture through conventional chromatographic methods.

Scheme V

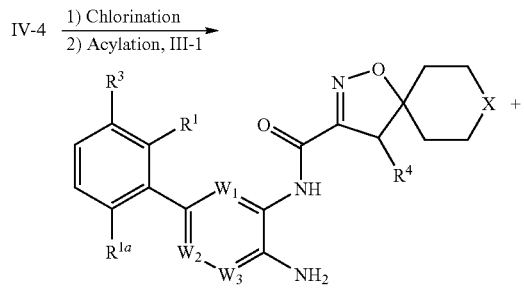

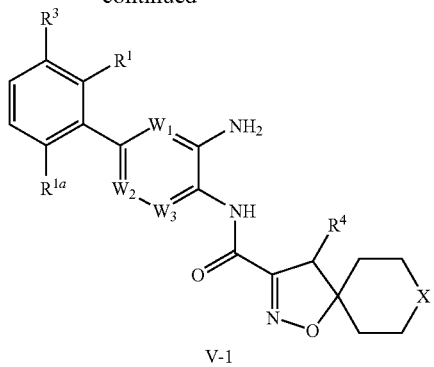

The compound mixture of the Formula V-1 may be cyclized to a benzimidazole of the Formula VI-1 (Scheme VI) by the action of an acid catalyst while heating to about 100° C. in an appropriate solvent. One preferred acid catalyst is (1S)-(+)-10-camphorsulfonic acid and a preferred solvent is dioxane. Other suitable acid catalysts include toluenesulfonic acid and acetic acid. Other suitable solvents include toluene and acetic acid.

Scheme VI

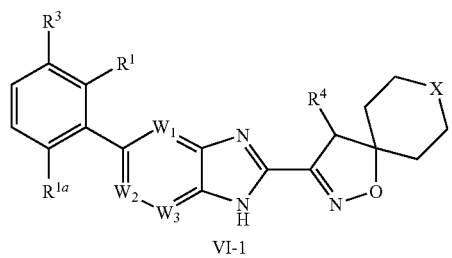

Scheme VII describes the general methodology that can be used to produce benzimidazoles of Formula (I) containing the corresponding heterocyclic moieties of oxazoline (wherein V is O and Q is CH₂); and imidazoline (wherein V is NH and Q is CH₂).

Scheme VII

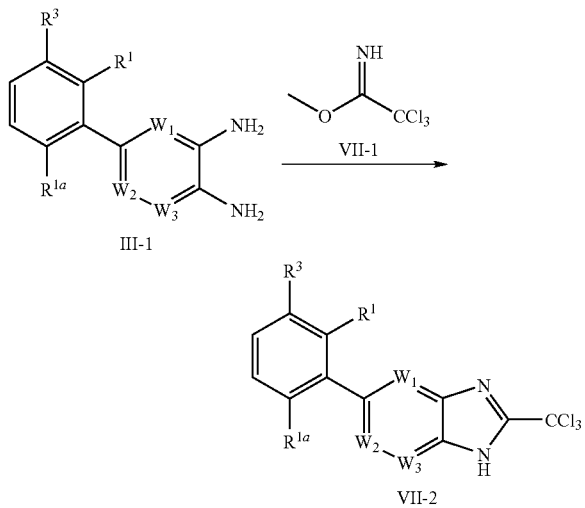

In this approach, a compound of the Formula VII-2 may be a useful common precursor. A compound of the Formula VII-2 can be produced by the reaction of a diamine of the Formula III-1 with an appropriately reactive trichloromethyl-substituted compound of the Formula VII-1 such as methyl 2,2,2-trichloroacetamidate, in the presence of an acid catalyst such as acetic acid and in a suitable solvent such as DCM or methanol; and more preferably in the presence of acetic acid as both catalyst and solvent (Venable, J. D. et al. *J. Med. Chem.* 2005, 48, 8289-98).

Scheme VIII illustrates the reaction of various dinucleophiles of the Formula VIII-1 with a compound of the Formula VII-2, in a suitable solvent, and in the presence or absence of a base to afford heterocycles of the Formula VIII-2. Preferred conditions include the use of TEA or DIPEA as a base in DMF, DCM or preferably THF as a solvent.

Scheme VIII

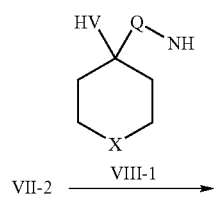

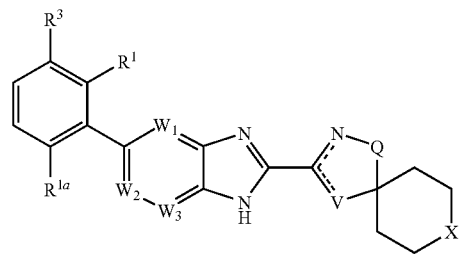

VIII-2

Scheme IX illustrates a route for the preparation of various derivatives of the Formula VIII-1, namely those of Formulae VIII-1a, VIII-1b, and VIII-1c, that are useful for the preparation of compounds of the Formula (I).

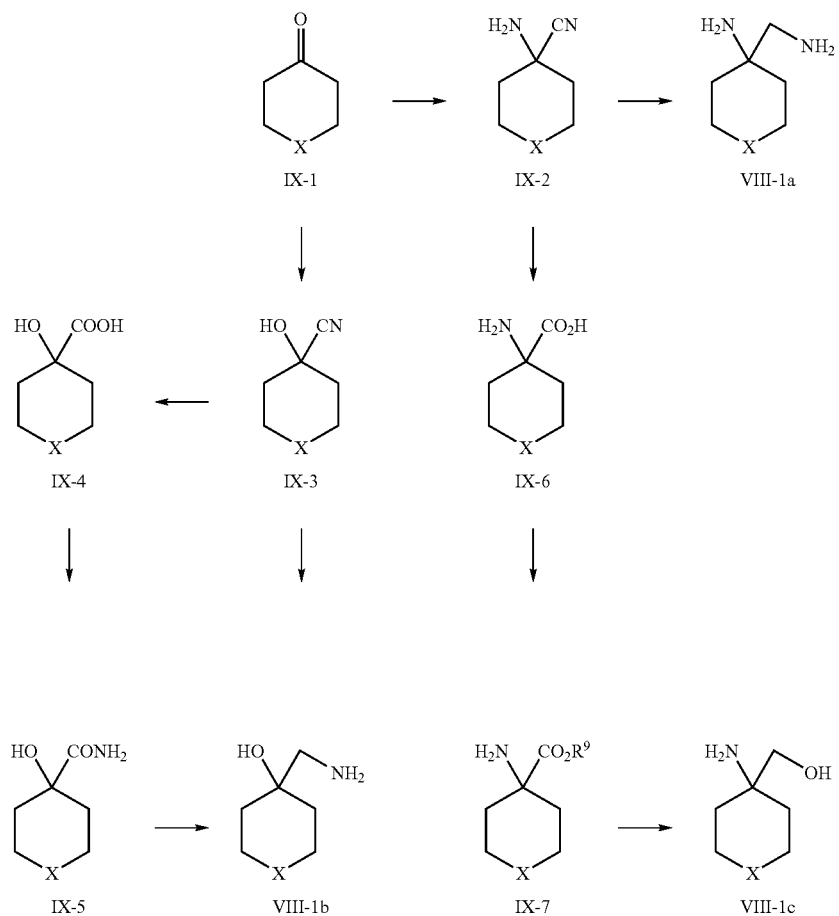

A diamine of the Formula VIII-1a (wherein V is NH, and Q is CH$_2$) can be prepared by an initial Strecker-type reaction (see, for example, patent application WO 2006/028545) by reacting an appropriately substituted ketone of the Formula IX-1 with an amine and a cyanide derivative such as cyanotrimethylsilane, or sodium or potassium cyanide, in the presence of an acid such as acetic acid or hydrochloric acid, to give an aminonitrile of the Formula IX-2. Subsequent reduction of the cyano group of a compound of the Formula IX-2 to give a compound of the Formula VIII-1a may be effected by a number of methods. Reducing agents such as lithium aluminum hydride, alane, lithium trimethoxyaluminum hydride or borane in a suitable solvent such as THF or diethyl ether may be used. (For a review and preferred conditions, see: Hudlicky, M. "Reductions in Organic Chemistry"; Ellis Horwood, Ltd.: Chichester, UK, 1984.) An alternative reduction method is by hydrogenation over a metal catalyst in an alcoholic solvent such as methanol or ethanol, at pressures of about 0 to about 100 psi, and, more particularly, at a pressure of about 30 to about 50 psi. Useful catalysts include Raney nickel, rhodium, palladium and platinum. An acid catalyst such as acetic acid, perchloric acid, sulfuric acid or hydrochloric acid may be employed during the hydrogenation reaction. When an acid catalyst is not present, ammonia optionally may be added to the reaction to suppress formation of possible side products.

Cyanohydrin formation may be employed to give a compound of the Formula IX-3 by treatment of a ketone of the Formula IX-1 with a cyanide derivative in the presence of a catalyst (for a review, see: Gregory, R. J. Chem. Rev. 1999, 99, 3649). Reaction conditions may include the use of cyanotrimethylsilane (TMSCN), potassium cyanide and 18-crown-6 in DCM (see: Greenlee, W. J.; Hangauer, D. G. Tetrahedron Lett. 1983, 24, 4559). Subsequent reduction of the nitrile using the methods described above for the formation of a compound of the Formula VIII-1a may then be employed to provide an amino alcohol of the Formula VIII-1b (wherein V is O and Q is CH$_2$).

Hydrolysis of a compound of the Formula IX-3 may be used to give the corresponding hydroxy acid of the Formula IX-4 by treatment with a strong acid such as concentrated sulfuric acid or concentrated hydrochloric acid in a suitable solvent such as water, with or without an added co-solvent such as dioxane, ethanol or acetic acid. The coupling of ammonia in a suitable form such as an ammonium salt, for example NH$_4$Cl, with an acid of the Formula IX-4 using conventional amide bond formation may afford a compound of the Formula IX-5 (for a review, see: M. Bodansky and A. Bodansky, The Practice of Peptide Synthesis, Springer-Verlag, NY (1984)). Preferred methods include the use of bromotripyrrolidinophosphonium hexafluorophosphate (PyBroP), N,N-dicyclohexylcarbodiimide (DCC) or more preferably 1-(3-dimethylaminopropyl)-3-ethylcarbodiimide hydrochloride (EDCI) in the presence of 1-hydroxybenzotriazole (HOBt), with a base such as DIPEA, TEA or preferably 4-methylmorpholine and in a solvent such as DCM, THF, dioxane or preferably DMF. Amide reduction of a compound of the Formula IX-5 using reduction methods such as with borane, complexed with THF or dimethyl sulfide, in a suitable solvent such as THF at reflux temperature, provides an alternative route to a compound of the Formula VIII-1b.

The conversion of a compound of the Formula IX-6 to the corresponding amino ester of the Formula IX-7 (wherein R$^9$ is C$_{1-2}$alkyl) may be carried out by a number of standard procedures used for ester formation on amino acids and peptides (for a review, see: Bodansky; M.; Bodansky, A. "The Practice of Peptide Synthesis"; Springer-Verlag: NY, 1984) such as by the action of thionyl chloride in methanol or ethanol at about 0° C., or by the action of trimethylsilyldiazomethane (when R$^9$ is methyl) in a suitable solvent such as methanol or ethanol. Subsequent reduction of the ester using standard methods (see: Hudlicky, M. "Reductions in Organic Chemistry"; Ellis Horwood, Ltd.: Chichester, UK, 1984) may afford a compound of the Formula VIII-1c (wherein V is O and Q is CH$_2$). When not commercially available, a compound of the Formula IX-6 may be derived from the previously described aminonitrile of Formula IX-2 by hydrolysis of the cyano group using concentrated sulfuric acid or preferably 6-12 M hydrochloric acid at temperatures of 50-100° C., with or without an added solvent such as dioxane.

Scheme X describes an alternate route to compounds of Formula VI-1.

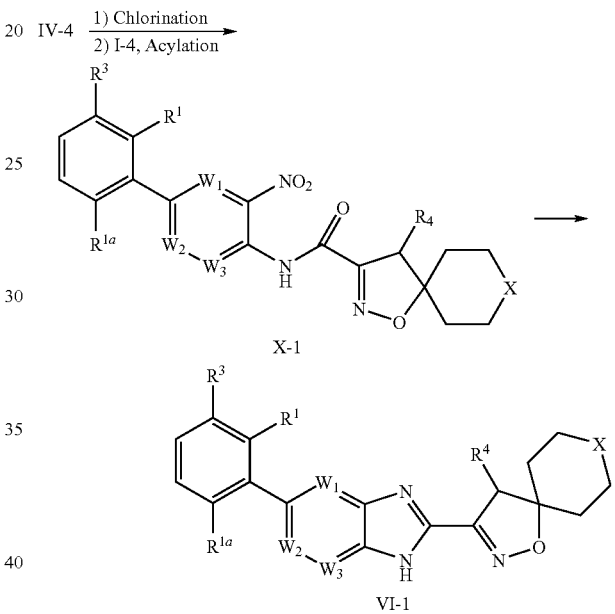

The amino group of a compound of the Formula I-4 may be acylated by an acid chloride derivative of a carboxylic acid of the Formula IV-4. The acid chloride may be prepared from a compound of Formula IV-4 using a conventional chlorinating agent as described in Scheme V. One equivalent of acid chloride may be added to a compound of the Formula I-4, in the presence of a base, in an appropriate solvent, such as sodium hydride in THF, to give a mono-acylated biphenyl intermediate of the Formula X-1. When more than 1 equivalent of acid chloride is used, N,N-diacylated compounds may also be generated during the course of the reaction and may be separated from the mono-acylated compound X-1 through conventional chromatographic methods. A compound of Formula X-1 may be cyclized to a benzimidazole of the Formula VI-1 by the action of an acid catalyst and an appropriate reducing agent while heating to about 100° C. in an appropriate solvent. A preferred reducing agent is iron powder, a preferred solvent is acetic acid, and a preferred acid catalyst is acetic acid. Other suitable acid catalysts include (1S)-(+)-10-camphorsulfonic acid and toluenesulfonic acid. Other suitable solvents include toluene.

Scheme XI illustrates an alternate synthesis of compounds of the Formula VI-1 utilizing intermediates of the Formula XI-3 (wherein V is CH(R$^4$), and Q is O).

Scheme XI

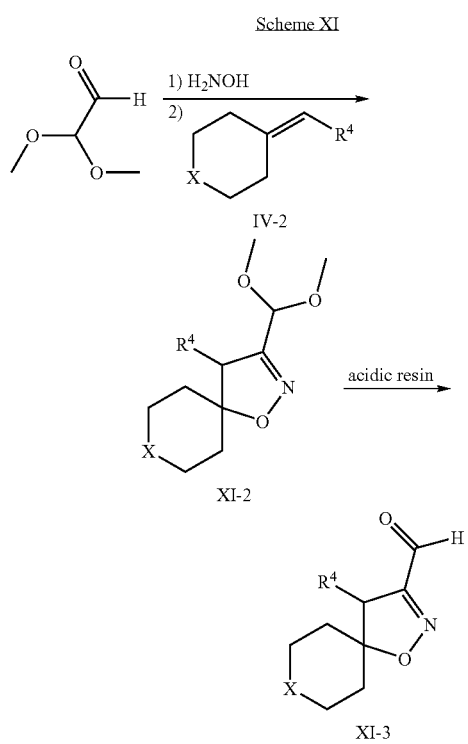

Compounds of the Formula XI-2 may be prepared by the reaction of dimethoxy-acetaldehyde with aqueous hydroxylamine in an appropriate solvent, such as DMF, and the in-situ generated chlorooxime may then be added to a solution of an alkene of the Formula IV-2 and an acid scavenger in an appropriate solvent such as DIPEA in DCM using a procedure similar to that of Liu, K., et al; *J. Org. Chem.* 1980 45, 3916-3918. Where compounds of Formula XI-1 are not commercially available, they may be produced from the corresponding ketone by a Wittig olefination reaction. (For example, see: March, J. "Advanced Organic Chemistry"; John Wiley and Sons, Inc.: NY, 1992 and Maryanoff; Reitz *Chem. Rev.* 1989, 89, 863-927.) The resulting dimethylketal of compounds of Formula XI-2 may be hydrolyzed by a number of common methods to produce the corresponding aldehyde, for example, by the addition of a strongly acidic cationic exchange resin such as Amberlyst-15 resin or Dowex 50 resin in acetone (see, Coppola, G. M.; *Synthesis* 1984, 1021-1023), to give aldehydes of the Formula XI-3. Reaction of diamines of Formula III-1 with aldehydes of the Formula XI-3 in the presence of $Na_2S_2O_5$ in an appropriate solvent such as DMF provides compounds of the Formula VI-1.

One skilled in the art will recognize that protecting groups may be necessary at certain stages of the synthesis depending upon the substituents and functional groups present on the reactants, and those skilled in the art will recognize where appropriate groups can be employed. (For lists of suitable protecting groups, conditions for protection and deprotection and a review of the chemistry, see: Greene, T. W.; G. M. Wuts, P. G. M. "Protective Groups in Organic Synthesis"; John Wiley and Sons, Inc.: NY, 1999.) Microwave accelerated reactions also can be performed using commercial microwave units designed for this purpose, for example the Personal Chemistry Smith Synthesizer instrument.

The product of each process step may be separated from the reaction mixture and purified before use as a starting material in a subsequent step. Separation techniques typically include evaporation, extraction, precipitation and filtration. Purification techniques typically include column chromatography (Still, W. C. et al. *J. Org. Chem.* 1978, 43, 2921), thin-layer chromatography, preparative HPLC, crystallization, trituration, and distillation.

The starting materials and product of each process step are confirmed by spectroscopic, spectrometric and analytical methods including nuclear magnetic resonance (NMR), mass spectrometry (MS) and liquid chromatography (HPLC).

For preparing compounds of the present invention, common solvents known to those skilled in the art were used such as, but not necessarily limited to, ethyl ether, THF, dioxane, methanol, ethanol, isopropanol, DMF, benzene, toluene, hexanes, cyclohexane, DCM, DME, and DCE. Compounds of the present invention may be isolated as the acid addition salt and may contain one or more equivalents of the acid. The free base also may be obtained by techniques known to those skilled in the art.

SPECIFIC EXAMPLES

Reagents were purchased from commercial sources. Microanalyses were performed at Quantitative Technologies, Inc., Whitehouse, N.J. and are expressed in percentage by weight of each element per total molecular weight. Nuclear magnetic resonance (NMR) spectra for hydrogen atoms were measured in the indicated solvent with (TMS) as the internal standard on a Bruker Avance or Varian (300 or 400, or 500 MHz) spectrometer. The values are expressed in parts per million downfield from TMS. The mass spectra (MS) were determined on an Agilent spectrometer as (ESI) m/z (M+H$^+$) using an electrospray technique. Optical rotations were obtained on a Perkin-Elmer polarimeter using the sodium D line as wavelength of light. Unless otherwise noted, the materials used in the examples were obtained from readily available commercial suppliers or synthesized by standard methods known to one skilled in the art of chemical synthesis. The substituent groups, which vary between examples, are hydrogen unless otherwise noted.

Example 1

3-[7-Trifluoromethyl-5-(2-trifluoromethyl-phenyl)-1H-benzimidazol-2-yl]-1-oxa-2-aza-spiro[4.5]dec-2-ene hydrochloride (Cpd 27) JNJ41876666

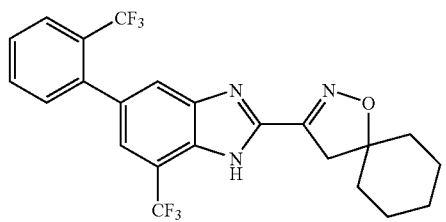

A. Ethyl 1-oxa-2-aza-spiro[4.5]dec-2-ene-3-carboxylate

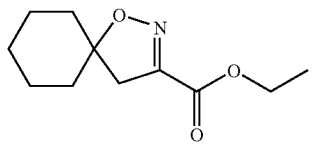

To a 300 mL pressure vessel equipped with a magnetic stir bar was added methylenecyclohexane (5.83 g, 60.6 mmol) and EtOH (150 mL). Nitro-acetic acid ethyl ester (16.8 mL, 152 mmol) and DABCO (680 mg, 6.06 mmol) were then added. Additional EtOH (30 mL) was added to rinse the sides of the vessel, which was tightly capped. The mixture was heated to 80° C. for 42 h and then cooled to RT. The solvent was removed under reduced pressure, and the residue was divided into three equal portions. Each portion was purified by column chromatography using an 80-g $SiO_2$ pre-packed column eluting with EtOAc/hexanes, 0:1 to 1:4, v/v over 30 min, yielding 8.12 g (64%) of the desired ester. $^1$H-NMR (400 MHz, $CDCl_3$) δ: 4.34 (q, J=7.2 Hz, 2H), 2.91 (s, 2H), 1.71-1.88 (m, 4H), 1.60-1.71 (m, 2H), 1.39-1.53 (m, 4H), 1.37 (t, J=7.1 Hz, 3H).

B. 1-Oxa-2-aza-spiro[4.5]dec-2-ene-3-carboxylic acid

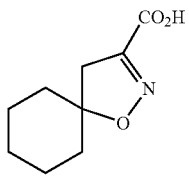

Ethyl 1-oxa-2-aza-spiro[4.5]dec-2-ene-3-carboxylate (8.12 g, 38.5 mmol, as prepared in the previous step) was placed in a 200 mL round-bottom flask equipped with a magnetic stir bar, and MeOH (75 mL) and water (25 mL) were added. Lithium hydroxide monohydrate (1.77 g, 42.3 mmol) was added as a solid. The reaction was stirred at RT for 20 h, and the solvents were removed under reduced pressure. The resulting solid was triturated with ether and collected by filtration. The solid was then dissolved in water (200 mL) and acidified to pH 2 with 3 M aq HCl. The precipitate was isolated by filtration, washed well with water, air dried, and dried under vacuum. The filtrate was extracted three times with DCM (50 mL). The combined organic extracts were dried over anhydrous $MgSO_4$, filtered, and the solvent was removed under reduced pressure. The initial precipitate and the material from the extraction were combined, giving 5.81 g (83%) of the title compound. $^1$H-NMR (400 MHz, $CDCl_3$) δ: 2.93 (s, 2H), 1.72-1.89 (m, 4H), 1.60-1.72 (m, 2H), 1.37-1.54 (m, 4H).

C. 4-Bromo-2-nitro-6-trifluoromethyl-phenylamine

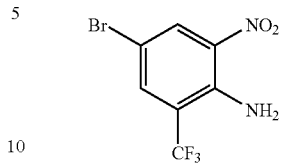

2-Nitro-6-trifluoromethyl-phenylamine (10.0 g, 48.5 mmol) was placed in a 200 mL round-bottom flask equipped with a magnetic stir bar. Glacial acetic acid (100 mL) and bromine (3.24 mL, 63.1 mmol) were added, and the mixture was stirred at RT for 18 h. The mixture was poured into ice (200 mL), and the excess bromine was quenched with 10% aq $Na_2S_2O_3$ (25 mL). The precipitate was isolated by filtration and washed with water. The solid was air-dried and then dried under vacuum to yield 13.8 g (100%) of the title compound. $^1$H-NMR (400 MHz, $CDCl_3$) δ: 8.49 (d, J=2.3 Hz, 1H), 7.83 (d, J=1.8 Hz, 1H).

D. 5-Nitro-3,2'-bis-trifluoromethyl-biphenyl-4-ylamine

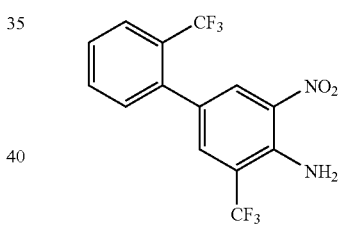

4-Bromo-2-nitro-6-trifluoromethyl-phenylamine (10.0 g, 35.2 mmol, as prepared in the previous step), 2-trifluoromethylphenylboronic acid (8.70 g, 45.8 mmol), and (dppf) $PdCl_2$ DCM (1.44 g, 1.76 mmol) were placed in a 500 mL round-bottom flask equipped with a magnetic stir bar and reflux condenser. The flask was evacuated and backflushed with Ar. DME (150 mL) and 2M aq $Na_2CO_3$ (50.0 mL, 100 mmol) were added via cannula. The mixture was stirred at 90° C. for 18 h. The mixture was cooled to RT, diluted with EtOAc (100 mL), then washed with water (100 mL) and brine (100 mL). The combined aqueous layers were extracted twice with EtOAc (50 mL). The combined organic extracts were dried over $MgSO_4$, filtered, and the solvent was removed under reduced pressure. The residue was purified on an 80-g pre-packed $SiO_2$ column eluting with EtOAc/hexanes, 0:1 to 1:4, v/v over 30 min, yielding 11.3 g (92%) of the title compound. $^1$H-NMR (400 MHz, $CDCl_3$) δ: 8.35 (d, J=2.0 Hz, 1H), 7.78 (d, J=7.8 Hz, 1H), 7.74 (s, 1H), 7.61 (t, J=7.2 Hz, 1H), 7.53 (t, J=7.6 Hz, 1H), 7.33 (d, J=7.6 Hz, 1H), 6.75 (br. s., 2H).

E. 5,2'-Bistrifluoromethyl-biphenyl-3,4-diamine

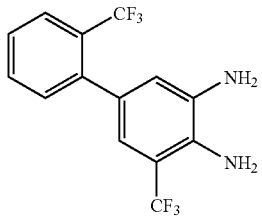

5-Nitro-3,2'-bis-trifluoromethyl-biphenyl-4-ylamine (11.3 g, 32.5 mmol, as prepared in the previous step) was placed in a 500 mL round-bottom flask equipped with a magnetic stir bar. Anhydrous EtOH (150 mL) and 3M aq HCl (30 mL) were added via syringe. Iron powder (9.07 g, 162 mmol) was added, and the mixture was stirred at 80° C. for 6 h. The reaction was cooled to RT and filtered through a pad of Celite. The filter cake was washed with MeOH (300 mL). The solvent was removed under reduced pressure. The residue was dissolved in EtOAc (150 mL) and washed with water (150 mL). The aqueous layer was diluted with brine (100 mL) and extracted twice with EtOAc (50 mL). The combined organic extracts were washed with satd aq $NaHCO_3$, dried over $MgSO_4$, filtered, and the solvent was removed under reduced pressure. The material was used directly in the next step without further purification.

F. 1-Oxa-2-aza-spiro[4.5]dec-2-ene-3-carboxylic acid (4-amino-5,2'-bis-trifluoromethyl-biphenyl-3-yl)-amide

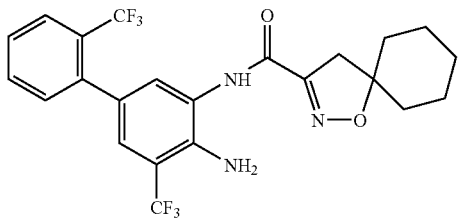

1-Oxa-2-aza-spiro[4.5]dec-2-ene-3-carboxylic acid (4.17 g, 22.8 mmol, as prepared in step B of this Example) was placed in a 100 mL round-bottom flask equipped with a magnetic stir bar. DCM (45 mL) and DMF (50 μL) were added via syringe. To the stirred solution was added oxalyl chloride (2.60 mL, 29.6 mmol) dropwise via syringe. After completion of the addition, the reaction was stirred at RT for 2 h. The solvent was removed under reduced pressure, the resulting residue was dissolved in DCM (230 mL), and this acid chloride solution was placed in a dropping funnel.

5,2'-Bistrifluoromethyl-biphenyl-3,4-diamine (10.4 g, 32.5 mmol, as prepared in step E of this Example) was placed in a 1000 mL round-bottom flask equipped with a magnetic stir bar, and DCM (300 mL) and TEA (9.53 mL, 68.4 mmol) were added. The above-prepared acid chloride solution was added dropwise over a period of 4 h to the stirred reaction mixture. After completion of the addition, the solution was stirred at RT for 1 h, and the solvent was removed under reduced pressure. The crude product was purified by column chromatography using an 80-g $SiO_2$ pre-packed column eluting with EtOAc/hexanes 0:1 to 3:7, v/v over 30 min, yielding 9.22 g (83%) of the title compound. Mass Spectrum (LCMS, APCI pos.): Calcd. for $C_{23}H_{21}F_6N_3O_2$: 486.2 (M+H). found: 486.1.

G. 3-[7-Trifluoromethyl-5-(2-trifluoromethyl-phenyl)-1H-benzimidazol-2-yl]-1-oxa-2-aza-spiro[4.5]dec-2-ene

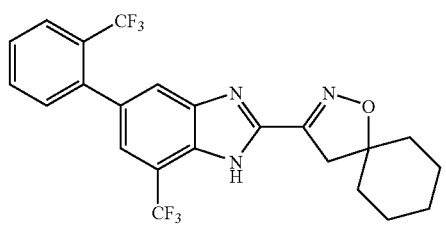

1-Oxa-2-aza-spiro[4.5]dec-2-ene-3-carboxylic acid (4-amino-5,2'-bis-trifluoromethyl-biphenyl-3-yl)-amide (9.22 g, 19.0 mmol, as prepared in the previous step) was placed in a 250 mL round-bottom flask equipped with a magnetic stir bar. Dry dioxane (200 mL) and CSA (883 mg, 3.80 mmol) were added. The flask was fitted with a reflux condenser, and the mixture was stirred at 100° C. for 7.5 h. The reaction was cooled to RT, and the solvent was removed under reduced pressure. The residue was dissolved in EtOAc (100 mL) and washed twice with satd aq $NaHCO_3$ (50 mL). The organic extract was dried over $MgSO_4$, filtered, and the solvent was removed under reduced pressure. The residue was dissolved in a minimum amount of MeOH (50 mL) and placed in a freezer for 1 h. The resulting precipitate was isolated by filtration and washed with MeOH. The precipitate was purified by recrystallization from hot MeOH (30 mL), giving a pale yellow solid, which was dried under high vacuum. The filtrate was concentrated under reduced pressure and purified by column chromatography using an 80-g $SiO_2$ pre-packed column eluting with EtOAc/hexanes, 0:1 to 3:7, v/v over 30 min. The solid precipitate and column-purified material were combined, yielding 8.12 g (91%) of the title compound. $^1$H-NMR (400 MHz, $CDCl_3$) δ: $^1$H-NMR (400 MHz, DMSO-$d_6$) δ: 7.89 (d, J=7.6 Hz, 1H), 7.77 (t, J=7.3 Hz, 1H), 7.68 (t, J=7.6 Hz, 2H), 7.55 (d, J=7.6 Hz, 1H), 7.48 (s, 1H), 3.33 (s, 2H), 1.63-1.82 (m, 6H), 1.35-1.58 (m, 4H).

H. 3-[7-Trifluoromethyl-5-(2-trifluoromethyl-phenyl)-1H-benzimidazol-2-yl]-1-oxa-2-aza-spiro[4.5]dec-2-ene hydrochloride 3-[7-Trifluoromethyl-5-(2-trifluoromethyl-phenyl)-1H-benzimidazol-2-yl]-1-oxa-2-aza-spiro[4.5]dec-2-ene (524 mg, 1.12 mmol, as prepared in the previous step) was placed in an 8 mL vial, dry MeOH (2 mL) was added, and the mixture was warmed until the solid dissolved. This mixture was added to a mL vial containing ether (20 mL) and 1 M HCl in ether (1.12 mL, 1.12 mmol), resulting in a homogeneous solution. The solution was transferred to a 100 mL round-bottom flask, the solvent was removed under reduced pressure, and the solid was dried under vacuum, giving 469 mg (83%) of the desired HCl salt. $^1$H-NMR (400 MHz, $d_6$-DMSO) δ: 7.89 (d, J=7.6 Hz, 1H), 7.73-7.81 (m, 1H), 7.71 (s, 1H), 7.63-7.70 (m, 1H), 7.55 (d, J=7.3 Hz, 1H), 7.48 (s, 1H), 3.33 (s, 2H), 1.62-1.83 (m, 6H), 1.33-1.59 (m, 4H). Mass Spectrum (LCMS, ESI pos.): Calcd. for $C_{23}H_{19}F_6N_3O$: 468.1 (M+H). found: 468.3. Elemental Analysis Calcd. for $C_{23}H_{19}F_6N_3O$: C, 59.10; H, 4.10; F, 24.39; N, 8.99. Found C, 59.06; H, 4.04; F, 24.30; N, 9.04 (% $H_2O$ 0.39, Pd <1 ppm).

Using the procedures described in Example 1, and reagents, starting materials and conditions known to those skilled in the art, the following compounds representative of the present invention were prepared:

| Cpd | Data |
|---|---|
| 1 | 3-[5-(2-Trifluoromethyl-phenyl)-1H-benzimidazol-2-yl]-1-oxa-2-aza-spiro[4.5]dec-2-ene<br>$^1$H-NMR (400 MHz, $d_4$-MeOH) δ: 7.79 (d, J = 7.8 Hz, 1H), 7.65 (td, J = 7.6, 0.8 Hz, 1H), 7.64 (br s, 1H), 7.56 (t, J = 7.6 Hz, 1H), 7.54 (br s, 1H), 7.43 (d, J = 7.6 Hz, 1H), 7.25 (d, J = 8.1 Hz, 1H), 3.29 (s, 2H), 1.71-1.91 (m, 6H), 1.48-1.64 (m, 4H). Mass Spectrum (LCMS, ESI pos.): Calcd. for $C_{22}H_{20}F_3N_3O$: 400.2 (M + H); found: 400.2. |
| 7 | 3-[5-(2-Trifluoromethoxy-phenyl)-1H-benzimidazol-2-yl]-1-oxa-2-aza-spiro[4.5]dec-2-ene hydrochloride<br>$^1$H-NMR (400 MHz, $d_6$-DMSO) δ: 7.72 (d, J = 8.6 Hz, 1H), 7.70 (s, 1H), 7.57-7.63 (m, 1H), 7.47-7.56 (m, 3H), 7.42 (dd, J = 8.3, 1.3 Hz, 1H), 3.31 (s, 2H), 1.62-1.80 (m, 6H), 1.34-1.57 (m, 4H). Mass Spectrum (LCMS, ESI pos.): Calcd. for $C_{22}H_{20}F_3N_3O_2$: 416.2 (M + H); found: 416.2. |
| 14 | 3-[7-Fluoro-5-(2-trifluoromethyl-phenyl)-1H-benzimidazol-2-yl]-1-oxa-2-aza-spiro[4.5]dec-2-ene hydrochloride<br>$^1$H-NMR (400 MHz, $d_6$-DMSO) δ: 7.86 (d, J = 7.8 Hz, 1H), 7.74 (t, J = 7.6 Hz, 1H), 7.65 (t, J = 7.6 Hz, 1H), 7.50 (d, J = 7.6 Hz, 1H), 7.26 (s, 1H), 7.03 (d, J = 11.4 Hz, 1H), 3.31 (s, 2H), 1.60-1.81 (m, 6H), 1.29-1.58 (m, 4H). Mass Spectrum (LCMS, ESI pos.): Calcd. for $C_{22}H_{19}F_4N_3O$: 418.2 (M + H); found: 418.4. |
| 15 | 4-Methyl-3-[5-(2-trifluoromethyl-phenyl)-1H-benzimidazol-2-yl]-1-oxa-2-aza-spiro[4.5]dec-2-ene hydrochloride<br>$^1$H-NMR (400 MHz, $d_6$-DMSO) δ: 7.86 (d, J = 7.6 Hz, 1H), 7.72-7.78 (m, 1H), 7.70 (d, J = 8.3 Hz, 1H), 7.59-7.68 (m, 1H), 7.56 (s, 1H), 7.47 (d, J = 7.6 Hz, 1H), 7.28 (d, J = 8.3 Hz, 1H), 3.51 (q, J = 7.2 Hz, 1H), 1.33-1.90 (m, 10H), 1.27 (d, J = 7.3 Hz, 3H). Mass Spectrum (LCMS, ESI pos.): Calcd. for $C_{23}H_{22}F_3N_3O$: 414.2 (M + H); found: 414.4. |
| 23 | 3-[5-(2-Fluoro-phenyl)-1H-benzimidazol-2-yl]-1-oxa-2-aza-spiro[4.5]dec-2-ene trifluoroacetic acid salt<br>$^1$H-NMR (400 MHz, $d_6$-DMSO) δ: 7.76 (s, 1H), 7.71 (d, J = 8.3 Hz, 1H), 7.59 (td, J = 8.0, 1.5 Hz, 1H), 7.47-7.51 (m, 1H), 7.38-7.47 (m, 1H), 7.27-7.38 (m, 2H), 3.30 (s, 2H), 1.63-1.80 (m, 6H), 1.34-1.56 (m, 4H). |
| 28 | 4-Methyl-3-[7-trifluormethyl-5-(2-trifluoromethyl-phenyl)-1H-benzimidazol-2-yl]-1-oxa-2-aza-spiro[4.5]dec-2-ene hydrochloride<br>$^1$H-NMR (400 MHz, $d_6$-DMSO) δ: 7.89 (d, J = 7.6 Hz, 1H), 7.73-7.81 (m, 1H), 7.70 (s, 1H), 7.63-7.70 (m, 1H), 7.54 (d, J = 7.6 Hz, 1H), 7.48 (s, 1H), 3.50 (q, J = 7.2 Hz, 1H), 1.76-1.87 (m, 1H), 1.48-1.76 (m, 8H), 1.32-1.44 (m, 1H), 1.30 (d, J = 7.3 Hz, 3H). Mass Spectrum (LCMS, ESI pos.): Calcd. for $C_{23}H_{19}F_6N_3O$: 482.2 (M + H); found: 482.3. |
| 51 | 3-[5-(2-Trifluoromethoxyphenyl)-7-trifluoromethyl-1H-benzimidazol-2-yl]-1-oxa-2-aza-spiro[4.5]dec-2-ene hydrochloride<br>$^1$H-NMR (400 MHz, $d_6$-DMSO) δ: 7.86 (s, 1H), 7.66-7.73 (m, 1H), 7.64 (s, 1H), 7.50-7.62 (m, 3H), 3.33 (s, 2H), 1.62-1.83 (m, 6H), 1.34-1.61 (m, 4H). Mass Spectrum (LCMS, ESI pos.): Calcd. for $C_{23}H_{19}F_6N_3O_2$: 484.1 (M + H); found: 484.2. |
| 53 | 3-[5-(2-Fluorophenyl)-7-trifluoromethyl-1H-benzimidazol-2-yl]-1-oxa-2-aza-spiro[4.5]dec-2-ene hydrochloride<br>$^1$H-NMR (400 MHz, $d_6$-DMSO) δ: 7.92 (s, 1H), 7.71 (s, 1H), 7.62-7.70 (m, 1H), 7.44-7.52 (m, 1H), 7.32-7.41 (m, 2H), 3.33 (s, 2H), 1.61-1.83 (m, 6H), 1.35-1.59 (m, 4H). Mass Spectrum (LCMS, ESI pos.): Calcd. for $C_{22}H_{19}F_4N_3O$: 418.2 (M + H); found: 418.2. |
| 54 | 3-[4,7-Dimethyl-5-(2-trifluoromethylphenyl)-1H-benzimidazol-2-yl]-1-oxa-2-aza-spiro[4.5]dec-2-ene hydrochloride<br>$^1$H-NMR (400 MHz, $d_6$-DMSO) δ: 7.86 (d, J = 7.6 Hz, 1H), 7.73 (t, J = 7.5 Hz, 1H), 7.64 (t, J = 7.7 Hz, 1H), 7.35 (d, J = 7.6 Hz, 1H), 6.92 (s, 1H), 3.37 (s, 2H), 2.53 (s, 3H), 2.18 (s, 3H), 1.62-1.85 (m, 6H), 1.31-1.55 (m, 4H). Mass Spectrum (LCMS, ESI pos.): Calcd. for $C_{24}H_{24}F_3N_3O$: 428.2 (M + H); found: 428.3. |

Example 2

3-[5-(2-Trifluoromethylphenyl)-1H-benzimidazol-2-yl]-1,8-dioxa-2-aza-spiro[4.5]dec-2-ene (Cpd 9)

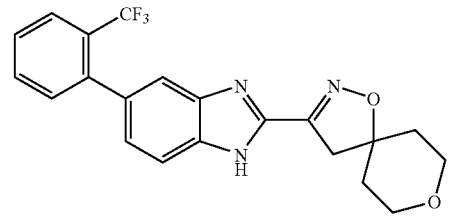

A. Ethyl 1,8-dioxa-2-aza-spiro[4.5]dec-2-ene-3-carboxylate

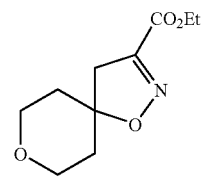

The method of Schlosser, M. et al. (*Tetrahedron* 1990, 46, 2411-2424) was used. The methyltriphenylphosphonium bromide/sodium amide "instant ylide" mixture (Aldrich) (1.2 eq., 2.5 g, 6.0 mmol) was placed in a 40 mL vial equipped with a magnetic stir bar, and the vessel was evacuated and backflushed with Ar. Dry ether (10 mL) was added via syringe, and the reaction was stirred at RT for 2 h. Tetrahydropyran-4-one (0.46 mL, 5.0 mmol) was added dropwise via syringe, and the reaction was stirred at RT for 16 h. The reaction was quenched with water, and the aqueous layer was extracted twice with ether (5 mL). The combined organic extracts were washed with brine, dried over anhydrous $MgSO_4$, and filtered.

The ether solution was transferred to a 100 mL round-bottom flask equipped with a magnetic stir bar, and DIPEA (1.1 eq., 0.96 mL, 5.5 mmol) was added via syringe. Ethyl 2-chloro-2-(hydroxyimino)acetate (1 eq., 758 mg, 5.00 mmol) was dissolved in DCM (50 mL) and placed in a dropping funnel. The DCM solution was added dropwise to the vigorously stirred ether reaction mixture over a period of 2 h. The resulting solution was stirred at RT for 3 days. The solvent was removed under reduced pressure, and the residue was purified by column chromatography using a 24-g $SiO_2$ pre-packed column eluting with EtOAc/hexanes, 0:1 to 2:3, v/v over 30 min, yielding 264 mg (25%) of the desired ester. $^1$H-NMR (400 MHz, $CDCl_3$) δ: 4.35 (q, J=7.2 Hz, 2H), 3.89 (ddd, J=11.7, 8.6, 3.4 Hz, 2H), 3.63-3.76 (m, 2H), 2.99 (s, 2H), 1.87-1.98 (m, 2H), 1.74-1.87 (m, 2H), 1.37 (t, J=7.2 Hz, 3H).

B. 3-[5-(2-Trifluoromethyl-phenyl)-1H-benzimidazol-2-yl]-1,8-dioxa-2-aza-spiro[4.5]dec-2-ene

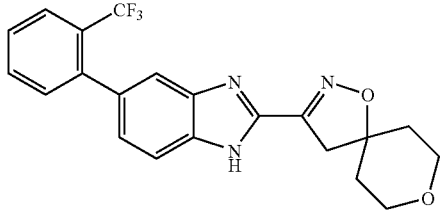

The title compound was prepared according to steps D through H of Example 1. $^1$H-NMR (400 MHz, d$_6$-DMSO+ d$_1$-TFA) δ: 7.86 (d, J=7.6 Hz, 1H), 7.71-7.78 (m, 1H), 7.68 (d, J=8.3 Hz, 1H), 7.60-7.67 (m, 1H), 7.55 (s, 1H), 7.48 (d, J=7.3 Hz, 1H), 7.26 (d, J=9.1 Hz, 1H), 3.75-3.87 (m, 2H), 3.54-3.68 (m, 2H), 3.42 (s, 2H), 1.79-1.94 (m, 4H). Mass Spectrum (LCMS, ESI pos.): Calcd. for C$_{22}$H$_{18}$F$_5$N$_3$O: 402.1 (M+H). found: 402.2.

Using the procedures described in Example 2, and reagents, starting materials and conditions known to those skilled in the art, the following compounds representative of the present invention were prepared:

| Cpd | Data |
|---|---|
| 10 | 8,8,-Difluoro-3-[5-(2-trifluoromethyl-phenyl)-1H-benzimidazol-2-yl]-1-oxa-2-aza-spiro[4.5]dec-2-ene JNJ41658110 $^1$H-NMR (400 MHz, d$_6$-DMSO + d$_1$-TFA) δ: 7.85 (d, J = 7.8 Hz, 1H), 7.71-7.78 (m, 1H), 7.69 (d, J = 8.3 Hz, 1H), 7.59-7.67 (m, 1H), 7.56 (s, 1H), 7.48 (d, J = 7.6 Hz, 1H), 7.27 (d, J = 8.3 Hz, 1H), 3.45 (s, 2H), 1.85-2.23 (m, 8H). Mass Spectrum (LCMS, ESI pos.): Calcd. for C$_{22}$H$_{18}$F$_5$N$_3$O: 436.1 (M + H); found: 436.2. |

Example 3

3-[4-Methyl-5-(2-trifluoromethyl-phenyl)-1H-benzimidazol-2-yl]-1-oxa-2-aza-spiro[4.5]dec-2-ene hydrochloride (Cpd 24)

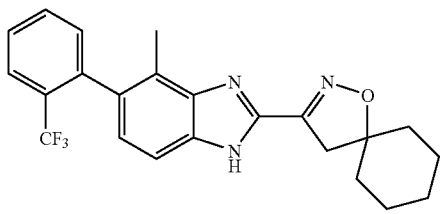

A. 1-Bromo-2-methyl-3,4-dinitro-benzene

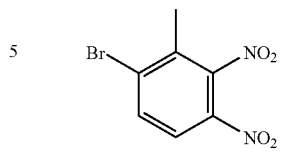

The title compound was prepared by an adaptation of the procedure described by Mundla, S. R. (*Tetrahedron Lett.* 2000, 41, 4277-4279). 2-Bromo-6-nitrotoluene (1.09 g, 5.05 mmol) was placed in a 50 mL round-bottom flask equipped with a magnetic stir bar. Conc. H$_2$SO$_4$ (10 mL) was added, and the solid was allowed to dissolve. The reaction was cooled in an ice bath, and fuming nitric acid (1.5 eq., 0.340 mL, 7.57 mmol) was added dropwise via syringe at a rate such that the temperature of the mixture remained below 10° C. After completion of the addition, the reaction was allowed to warm to RT and stir for 2 h. The reaction mixture was poured into crushed ice, and the precipitate was isolated by filtration. The solid was washed with water (30 mL) and allowed to air dry. The crude product was purified by column chromatography using a 40-g SiO$_2$ pre-packed column eluting with EtOAc/hexanes, 0:1 to 1:4, v/v over 30 min, yielding 879 mg (67%) of the title compound. $^1$H-NMR (400 MHz, CDCl$_3$) δ: 7.97 (d, J=8.8 Hz, 1H), 7.91 (d, J=8.8 Hz, 1H), 2.45 (s, 3H).

B. 3-[4-Methyl-5-(2-trifluoromethyl-phenyl)-1H-benzimidazol-2-yl]-1-oxa-2-aza-spiro[4.5]dec-2-ene hydrochloride

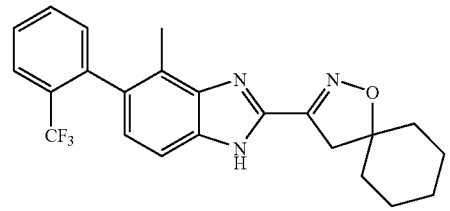

The title compound was prepared according to steps D through H of Example 1. $^1$H-NMR (400 MHz, d$_6$-DMSO) δ: 7.87 (d, J=7.6 Hz, 1H), 7.75 (t, J=7.3 Hz, 1H), 7.66 (t, J=7.6 Hz, 1H), 7.52 (d, J=8.3 Hz, 1H), 7.38 (d, J=7.3 Hz, 1H), 7.16 (d, J=8.3 Hz, 1H), 3.38 (s, 2H), 2.25 (s, 3H), 1.64-1.83 (m, 6H), 1.34-1.56 (m, 4H). Mass Spectrum (LCMS, ESI pos.): Calcd. for C$_{23}$H$_{22}$F$_3$N$_3$O: 414.2 (M+H). found: 414.3.

Example 4

3-[5-(2-Fluoro-6-trifluoromethoxy-phenyl)-1H-benzimidazol-2-yl]-1-oxa-2-aza-spiro[4.5]dec-2-ene hydrochloride (Cpd 8)

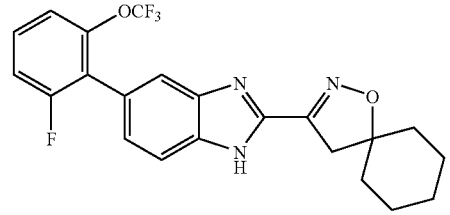

A. 2'-Fluoro-3-nitro-6'-trifluoromethoxy-biphenyl-4-ylamine

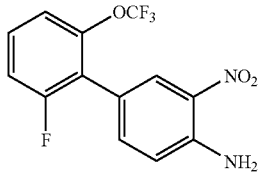

2-Fluoro-1-iodo-6-trifluoromethoxybenzene (612 mg, 2.00 mmol, prepared as described in WO2005/097136), 4-amino-3-nitrophenylboronic acid pinacol ester (1.3 eq., 687 mg, 2.60 mmol), and (dppf)PdCl$_2$.DCM (0.05 eq., 81.6 mg, 0.100 mmol) were placed in a 40 mL vial equipped with a magnetic stir bar. The vial was evacuated and backflushed with Ar, and DME (10 mL) and 2M aq Na$_2$CO$_3$ (4 mL) were added via syringe. The vial was capped tightly and placed in a heating block where the reaction was stirred at 90° C. for 24 h. The reaction was cooled to room temperature, diluted with EtOAc, and washed sequentially with water and brine. The organic extract was dried over anhydrous MgSO$_4$, filtered, and the solvent was removed under reduced pressure. The crude product was purified by column chromatography using an 80-g SiO$_2$ pre-packed column eluting with EtOAc/hexanes, 0:1 to 2:3, v/v over 30 min, yielding 548 mg (87%) of the desired compound. $^1$H-NMR (400 MHz, CDCl$_3$) δ: 8.21 (s, 1H), 7.30-7.47 (m, 2H), 7.18 (d, J=8.1 Hz, 1H), 7.14 (t, J=8.6 Hz, 1H), 6.91 (d, J=6.6 Hz, 1H), 5.37 (br. s., 2H).

B. 3-[5-(2-Fluoro-6-trifluoromethoxyphenyl)-1H-benzimidazol-2-yl]-1-oxa-2-aza-spiro[4.5]dec-2-ene hydrochloride The title compound was prepared according to Example 1, steps E through H. $^1$H-NMR (400 MHz, d$_6$-DMSO) δ: 7.72 (d, J=8.3 Hz, 1H), 7.63 (s, 1H), 7.55-7.62 (m, 1H), 7.45 (t, J=8.8 Hz, 1H), 7.40 (d, J=8.3 Hz, 1H), 7.30 (d, J=8.3 Hz, 1H), 3.31 (s, 2H), 1.63-1.80 (m, 6H), 1.33-1.57 (m, 4H). Mass Spectrum (LCMS, ESI pos.): Calcd. for C$_{22}$H$_{19}$F$_4$N$_3$O$_2$: 434.1 (M+H). found: 434.2.

Using the procedures described in Example 4, and reagents, starting materials and conditions known to those skilled in the art, the following compounds representative of the present invention were prepared:

| Cpd | Data |
|---|---|
| 12 | 3-[5-(2,2-Difluoro-benzo[1,3]dioxol-4-yl)-1H-benzimidazol-2-yl]-1-oxa-2-aza-spiro[4.5]dec-2-ene hydrochloride<br>$^1$H-NMR (400 MHz, d$_6$-DMSO) δ: 7.95 (d, J = 1.0 Hz, 1H), 7.76 (d, J = 8.6 Hz, 1H), 7.67 (dd, J = 8.5, 1.6 Hz, 1H), 7.55 (dd, J = 8.0, 1.1 Hz, 1H), 7.41 (dd, J = 8.1, 1.3 Hz, 1H), 7.34 (t, J = 8.1 Hz, 1H), 1.63-1.82 (m, 6H), 1.37-1.55 (m, 4H). Mass Spectrum (LCMS, ESI pos.): Calcd. for C$_{22}$H$_{19}$F$_2$N$_3$O$_3$: 412.1 (M + H); found: 412.4. |
| 13 | 3-[5-(2-Difluoromethoxy-phenyl)-1H-benzimidazol-2-yl]-1-oxa-2-aza-spiro[4.5]dec-2-ene hydrochloride<br>$^1$H-NMR (400 MHz, d$_6$-DMSO) δ: 7.72 (d, J = 1.0 Hz, 1H), 7.71 (d, J = 5.3 Hz, 1H), 7.48-7.55 (m, 1H), 7.47 (dd, J = 5.6, 1.8 Hz, 1H), 7.45 (dd, J = 6.1, 1.5 Hz, 1H), 7.37-7.41 (m, 1H), 7.33 (d, J = 8.3 Hz, 1H), 7.16 (t, J = 74 Hz, 1H), 3.32 (s, 2H), 1.63-1.83 (m, 6H), 1.37-1.56 (m, 4H). Mass Spectrum (LCMS, ESI pos.): Calcd. for C$_{22}$H$_{21}$F$_2$N$_3$O$_2$: 398.2 (M + H); found: 398.4. |
| 26 | 3-[5-(2,6-Difluoro-phenyl)-1H-benzimidazol-2-yl]-1-oxa-2-aza-spiro[4.5]dec-2-ene trifluoroacetic acid salt<br>$^1$H-NMR (400 MHz, d$_6$-DMSO) δ: 7.70 (d, J = 8.3 Hz, 1H), 7.66 (s, 1H), 7.43-7.54 (m, 1H), 7.33 (dd, J = 8.6, 1.3 Hz, 1H), 7.19-7.29 (m, 2H), 3.30 (s, 2H), 1.63-1.79 (m, 6H), 1.35-1.55 (m, 4H). Mass Spectrum (LCMS, ESI pos.): Calcd. for C$_{21}$H$_{19}$F$_2$N$_3$O: 368.2 (M + H); found: 368.2. |

Example 5

3-{5-[2-(2,2,2-Trifluoroethyl)-phenyl]-1H-benzimidazol-2-yl}-1-oxa-2-aza-spiro[4.5]dec-2-ene (Cpd 11)

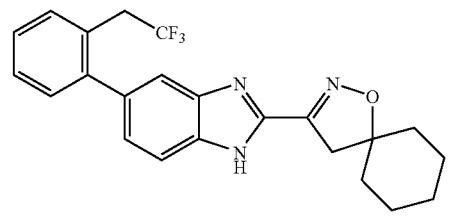

A. 1-(2-Bromo-phenyl)-2,2,2-trifluoro-ethanol

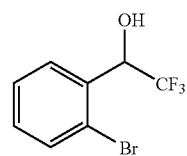

The title compound was prepared by an adaptation of the method described in Xue, Y. et al. (*Bioorg. Med. Chem.* 2007, 15, 2156-2166). Tetrabutylammonium fluoride hydrate (0.05 eq., 131 mg, 0.050 mmol) was placed in a 40 mL vial equipped with a magnetic stir bar, and the vial was evacuated and backflushed with Ar. Dry THF (25 mL) was added via syringe, and 2-bromobenzaldehyde (1.16 mL, 10.0 mmol) and trimethylsilyltrifluoromethane (1.3 eq., 1.90 mL, 13.0 mmol) were sequentially added via syringe. The reaction was stirred at RT for 16 h, and additional CF$_3$TMS (1 mL) was added. After stirring for 2 h, the reaction was poured into 3 M aq HCl (30 mL) and stirred at RT for 2 h. The reaction mixture was extracted three times with DCM (30 mL), and the combined organic extracts were dried over anhydrous MgSO$_4$, filtered, and the solvent removed under reduced pressure, yielding 1.83 g (72%) of the title compound. $^1$H-NMR (400 MHz, CDCl$_3$) δ: 7.69 (d, J=7.8 Hz, 1H), 7.60 (dd, J=8.1, 1.3 Hz, 1H), 7.40 (td, J=7.6, 1.1 Hz, 1H), 7.27 (td, J=7.7, 1.8 Hz, 1H), 5.56-5.68 (m, 1H), 2.77 (d, J=4.8 Hz, 1H).

B. Thiocarbonic acid O-[1-(2-bromo-phenyl)-2,2,2-trifluoro-ethyl]ester O-phenyl ester

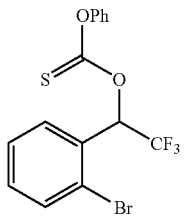

The title compound was prepared by an adaptation of the method described in Robins, M. J. et al. (*J. Am. Chem. Soc.* 1983, 105, 4059-4065). 1-(2-Bromo-phenyl)-2,2,2-trifluoroethanol (615 mg, 2.41 mmol, as prepared in the previous step) was placed in an 8 mL vial equipped with a magnetic stir bar. DCM (4 mL) and TEA (1.2 eq., 0.403 mL, 2.89 mmol) were added via syringe. Phenyl chlorothionoformate (1.1 eq., 0.367 mL, 2.65 mmol) was added dropwise via syringe to the water-cooled solution. After completion of the addition, the reaction was stirred at RT for 16 h, poured into water, and extracted three times with DCM (10 mL). The combined organic extracts were dried over anhydrous $MgSO_4$ filtered, and the solvent was removed under reduced pressure. The crude product was purified by column chromatography using a 12-g $SiO_2$ pre-packed column eluting with EtOAc/hexanes, 0:1 to 1:4, v/v over 30 min, yielding 695 mg (74%) of the title compound. $^1$H-NMR (400 MHz, $CDCl_3$) δ: 7.58-7.68 (m, 2H), 7.36-7.48 (m, 3H), 7.27-7.36 (m, 2H), 7.04-7.15 (m, 3H).

C. 1-Bromo-2-(2,2,2-trifluoro-ethyl)-benzene

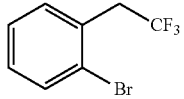

The method of Fu, G. C. et al. (*J. Am. Chem. Soc.* 1997, 119, 6949-6950) was used. Thiocarbonic acid O-[1-(2-bromo-phenyl)-2,2,2-trifluoro-ethyl]ester O-phenyl ester (353 mg, 0.902 mmol, as prepared in the previous step) was placed in an 8 mL vial equipped with a magnetic stir bar. Polymethylhydrosiloxane (PMHS) (5 eq., 300 mg, 4.51 mmol) was added via pipette, and toluene (0.9 mL) and n-butanol (5.5 eq., 0.454 mL, 4.96 mmol) were added via syringe. $(Bu_3Sn)_2O$ (0.038 eq., 17 µL, 0.034 mmol) was added via microsyringe, and AIBN (0.15 eq., 22.2 mg, 0.135 mmol) was added as a solid. The reaction was capped tightly, placed in a heating block, and stirred at 80° C. for 14 h.

Additional $(Bu_3Sn)_2O$ (17 µL) and AIBN (22 mg) were added, and the reaction was stirred an additional 14 h at 80° C. The reaction was cooled to RT, diluted with THF (4 mL), and quenched with 2M aq NaOH (1 mL). The reaction was stirred at RT for 12 h and extracted three times with ether (10 mL). The combined organic extracts were washed with 1M HCl and brine, dried over anhydrous $MgSO_4$, filtered, and the solvent was removed under reduced pressure. The crude product was purified by column chromatography using a 12 g $SiO_2$ pre-packed column eluting with EtOAc/hexanes, 0:1 to 3:17, v/v over 30 min, yielding 70 mg (34%) of the title compound. $^1$H-NMR (400 MHz, $CDCl_3$) δ: 7.61 (dd, J=8.0, 1.1 Hz, 1H), 7.35-7.40 (m, 1H), 7.31 (td, J=7.5, 1.1 Hz, 1H), 7.19 (td, J=7.7, 1.8 Hz, 1H), 3.63 (q, J=10.6 Hz, 2H).

D. 3-{5-[2-(2,2,2-Trifluoroethyl)-phenyl]-1H-benzimidazol-2-yl}-1-oxa-2-aza-spiro[4.5]dec-2-ene

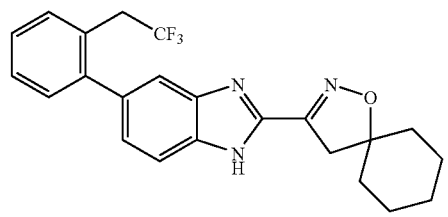

The procedures described in Example 4, steps A and B were used to prepare the title compound. $^1$H-NMR (400 MHz, $d_4$-MeOH) δ: 7.64-7.82 (m, 1H), 7.52-7.64 (m, 1H), 7.45-7.52 (m, 1H), 7.36-7.43 (m, 2H), 7.28-7.36 (m, 1H), 7.13-7.27 (m, 1H), 3.48 (q, J=11.1 Hz, 1H), 3.29 (s, 2H), 1.69-1.91 (m, 6H), 1.46-1.63 (m, 4H). Mass Spectrum (LCMS, ESI pos.): Calcd. for $C_{23}H_{22}F_3N_3O$: 414.2 (M+H). found: 414.3.

Example 6

3-[7-Chloro-5-(2-trifluoromethylphenyl)-1H-benzimidazol-2-yl]-1-oxa-2-aza-spiro[4.5]dec-2-ene hydrochloride (Cpd 16)

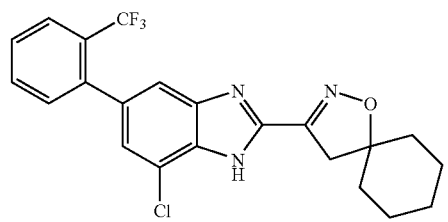

A. 3-Nitro-2'-trifluoromethyl-biphenyl-4-ylamine

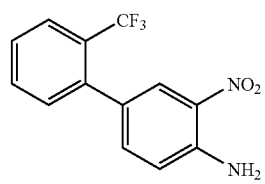

4-Bromo-2-nitroaniline (10.1 g, 46.7 mmol), 2-trifluoromethylphenylboronic acid (1.3 eq., 11.5 g, 60.7 mmol), and $(dppf)PdCl_2 \cdot DCM$ (0.05 eq., 1.91 g, 2.34 mmol) were placed in a 500 mL round-bottom flask equipped with a magnetic stir bar. The vial was evacuated and backflushed with Ar, and DME (180 mL) and 2M aq $Na_2CO_3$ (60 mL) were added via syringe. The flask was capped tightly, and the reaction was stirred at 90° C. for 16 h. The reaction was cooled to RT, diluted with EtOAc, and washed sequentially with water and brine. The organic extract was dried over anhydrous $MgSO_4$, filtered, and the solvent was removed under reduced pressure. The crude product was dry-loaded onto 25 g of $SiO_2$ and purified by column chromatography using an 80-g SiO$_2$ pre-packed column eluting with EtOAc/hexanes, 0:1 to 3:7, v/v over 20 min, yielding 12.8 g (97%) of the desired compound. $^1$H-NMR (400 MHz, CDCl$_3$) δ: 8.11 (d, J=2.0 Hz, 1H), 7.75 (d, J=7.8 Hz, 1H), 7.54-7.62 (m, J=7.6 Hz, 1H), 7.44-7.53 (m, J=7.8 Hz, 1H), 7.36 (dd, J=8.6, 1.3 Hz, 1H), 7.33 (d, J=7.6 Hz, 1H), 6.84 (d, J=8.6 Hz, 1H).

B. 3-Chloro-5-nitro-2'-trifluoromethyl-biphenyl-4-ylamine

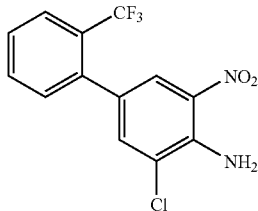

The procedure of Nickson, T. E. et al. (*Synthesis* 1985, 669-670) was used. 3-Nitro-2'-trifluoromethyl-biphenyl-4-ylamine (12.7 g, 45.0 mmol, as prepared in the previous step) was placed in a 250 mL round-bottom flask equipped with a magnetic stir bar and a reflux condenser, and dry acetonitrile (150 mL) was added. The solid was allowed to dissolve, and NCS (1.5 eq., 9.02 g, 67.5 mmol) was added as a solid. The reaction was heated at 80° C. for 3 days. The reaction was cooled to RT, diluted with EtOAc, then washed twice with water (20 mL) and once with brine (30 mL). The combined organic extracts were dried over MgSO$_4$, filtered, and the solvent was removed under reduced pressure. The crude material was chromatographed on an 80-g SiO$_2$ pre-packed column eluting with EtOAc/hexanes, 0:1 to 3:7, v/v over 30 min, yielding 6.96 g (49%) of the title compound. $^1$H-NMR (400 MHz, CDCl$_3$) δ: 8.10 (d, J=2.0 Hz, 1H), 7.76 (d, J=7.6 Hz, 1H), 7.57-7.62 (m, 1H), 7.56 (d, J=1.8 Hz, 1H), 7.44-7.54 (m, 1H), 7.32 (d, J=7.3 Hz, 1H), 6.64 (br. s., 2H).

C. 3-[7-Chloro-5-(2-trifluoromethylphenyl)-1H-benzimidazol-2-yl]-1-oxa-2-aza-spiro[4.5]dec-2-ene

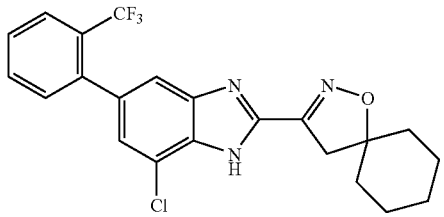

1-Oxa-2-aza-spiro[4.5]dec-2-ene-3-carboxylic acid (4.02 g, 21.9 mmol, as prepared in Example 1, step B) was placed in a round-bottom flask equipped with a magnetic stir bar. DCM (40 mL) and DMF (50 μL) were added. Oxalyl chloride (2.5 mL, 28.5 mmol) was added dropwise via syringe, and the mixture was stirred at RT for 1 h. The solvent was removed under reduced pressure. 3-Chloro-5-nitro-2'-trifluoromethyl-biphenyl-4-ylamine (6.96 g. 21.9 mmol) was placed in a round-bottom flask equipped with a magnetic stir bar. The flask was evacuated and backflushed with argon, and dry THF (50 mL) was added. The mixture was cooled to 0° C. in an ice bath, then NaH (2.64 g, 65.8 mmol, 60% dispersion in oil) was added in small portions. The above-prepared acid chloride was taken up in dry THF (20 mL) and added dropwise to the 3-chloro-5-nitro-2'-trifluoromethyl-biphenyl-4-ylamine solution at 0° C. over 10 min. After the addition was complete, the mixture was allowed to stir an additional 30 min at 0° C. then warm to RT and stir at that temperature for 16 h. The mixture was quenched with water, diluted with brine, and extracted three times with EtOAc. The combined organic extracts were dried over MgSO$_4$, filtered, and the solvent was removed under reduced pressure. The residue was dissolved in AcOH and placed in a round-bottom flask equipped with a magnetic stir bar. Fe powder (6.14 g, 110 mmol) was added. The flask was tightly capped, and the mixture was heated to 80° C. for 1 h. The mixture was cooled to RT and poured into ice. The resulting precipitate was filtered and washed with water. The filtrate was extracted with EtOAc. The combined organic extracts were dried over MgSO$_4$, filtered, and the solvent was removed under reduced pressure. The crude material was chromatographed on an 80-g SiO$_2$ pre-packed column eluting with EtOAc/hexanes, 0:1 to 3:7, v/v over 30 min. The resulting material was recrystallized from MeOH and isolated by filtration, yielding 5.12 g (54%) of the title compound. $^1$H NMR (400 MHz, DMSO-d$_6$) δ: 13.52 (br. s., 1H), 7.86 (d, J=7.6 Hz, 1H), 7.75 (t, J=7.5 Hz, 1H), 7.65 (t, J=7.6 Hz, 1H), 7.51 (d, J=7.6 Hz, 1H), 7.35 (s, 1H), 7.25 (s, 1H), 1.63-1.82 (m, 6H), 1.34-1.60 (m, 4H).

D. 3-[7-Chloro-5-(2-trifluoromethylphenyl)-1H-benzimidazol-2-yl]-1-oxa-2-aza-spiro[4.5]dec-2-ene hydrochloride 3-[7-Chloro-5-(2-trifluoromethylphenyl)-1H-benzimidazol-2-yl]-1-oxa-2-aza-spiro[4.5]dec-2-ene (2.39 g, 5.52 mmol) was placed in a 100 mL round-bottom flask. EtOAc (10 mL) was added, and the solid was allowed to dissolve. HCl (5.52 mL, 5.52 mmol, 1 M in ether) was added dropwise via syringe with swirling to ensure sufficient mixing. The mixture was sonicated for 2 min, resulting in a white precipitate, which was isolated by filtration and washed twice with EtOAc (10 mL) then once with ether (20 mL). The solid was dried under high vacuum, yielding the title compound (2.43 g, 94%). $^1$H-NMR (400 MHz, d$_6$-DMSO) δ: 7.86 (d, J=7.8 Hz, 1H), 7.75 (t, J=7.5 Hz, 1H), 7.65 (t, J=7.6 Hz, 1H), 7.51 (d, J=7.6 Hz, 1H), 7.38 (s, 1H), 7.26 (s, 1H), 3.33 (s, 2H), 1.63-1.81 (m, 6H), 1.32-1.58 (m, 4H). Mass Spectrum (LCMS, ESI pos.): Calcd. for C$_{22}$H$_{19}$ClF$_3$N$_3$O: 434.1 (M+H). found: 434.4.

Example 7

3-[7-Bromo-5-(2-trifluoromethylphenyl)-1H-benzimidazol-2-yl]-1-oxa-2-aza-spiro[4.5]dec-2-ene hydrochloride (Cpd 17)

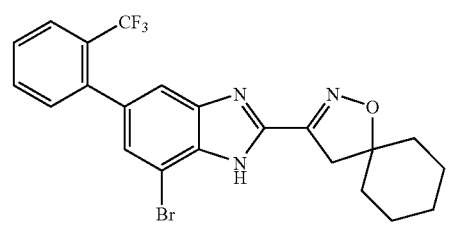

A. 3-Bromo-5-nitro-2'-trifluoromethyl-biphenyl-4-ylamine

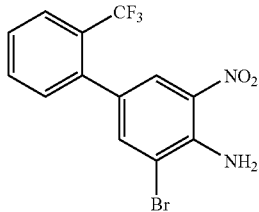

The method of Siegel, J. S. et al. (*Org. Lett.,* 2006, 8, 4989-4992) was used. 3-Nitro-2'-trifluoromethyl-biphenyl-4-ylamine (302 mg, 1.07 mmol, as prepared in Example 6, step A) was placed in an 8 mL vial equipped with a magnetic stir bar, and glacial acetic acid (2 mL) was added via pipette. The solid was allowed to dissolve, and bromine (1.07 eq., 59.0 µL, 1.14 mmol) was added dropwise via microsyringe. The reaction was tightly capped and stirred at RT for 30 min, during which time a precipitate formed. The reaction was poured into crushed ice, and the precipitate was isolated by filtration. The precipitate was washed with water (50 mL), dissolved in DCM (40 mL), dried over anhydrous MgSO$_4$, filtered, and the solvent removed under reduced pressure. The crude material was chromatographed on a 24-g SiO$_2$ pre-packed column eluting with EtOAc/hexanes, 0:1 to 1:4, v/v over 20 min, yielding 341 mg (88%) of the title compound. $^1$H-NMR (400 MHz, CDCl$_3$) δ: 8.14 (d, J=2.0 Hz, 1H), 7.76 (d, J=7.8 Hz, 1H), 7.72 (d, J=2.0 Hz, 1H), 7.59 (t, J=7.5 Hz, 1H), 7.51 (t, J=7.7 Hz, 1H), 7.32 (d, J=7.6 Hz, 1H), 6.70 (br. s., 2H).

B. 3-[7-Bromo-5-(2-trifluoromethylphenyl)-1H-benzimidazol-2-yl]-1-oxa-2-aza-spiro[4.5]dec-2-ene hydrochloride The title compound was prepared according to Example 1, steps E through H. $^1$H-NMR (400 MHz, d$_6$-DMSO) δ: 7.86 (d, J=7.1 Hz, 1H), 7.75 (t, J=7.3 Hz, 1H), 7.65 (t, J=7.7 Hz, 1H), 7.51 (d, J=7.6 Hz, 1H), 7.41 (s, 1H), 7.39 (s, 1H), 3.33 (s, 2H), 1.62-1.81 (m, 6H), 1.32-1.59 (m, 4H). Mass Spectrum (LCMS, ESI pos.): Calcd. for C$_{22}$H$_{19}$BrF$_3$N$_3$O: 478.1 (M+H). found: 478.3.

Example 8

3-[5-(2-Difluoromethoxyphenyl)-7-methyl-1H-benzimidazol-2-yl]-1-oxa-2-aza-spiro[4.5]dec-2-ene hydrochloride (Cpd 20)

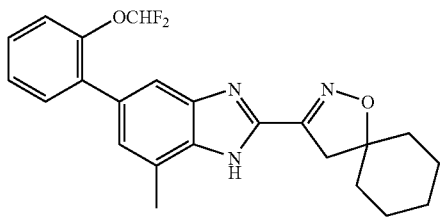

A. 4-Amino-5-methyl-3-nitrophenylboronic acid pinacol ester

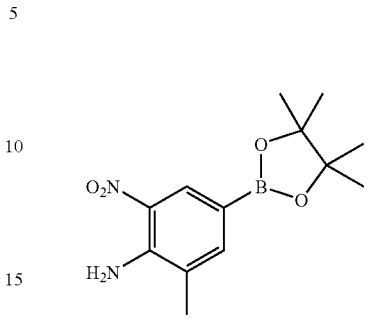

The title compound was prepared by an adaptation of the method described by Lee, Y.-K. et al. (*J. Med. Chem.* 2008, 51, 282-297). 4-Bromo-6-methyl-2-nitroaniline (1.16 g, 5.02 mmol), bis-(pinacolato)-diboron (3.0 eq., 3.81 g, 15.0 mmol), (dppf)PdCl$_2$.DCM (0.1 eq., 420 mg, 0.514 mmol), and potassium acetate (4.0 eq., 1.96 g, 20.0 mmol) were placed in a 100 mL round-bottom flask equipped with a magnetic stir bar. The flask was fitted with a reflux condenser, and the apparatus was evacuated and backflushed with Ar. Dry dioxane (50 mL) was added via syringe, and the reaction was heated to reflux for 18 h. The reaction was cooled to RT, diluted with EtOAc (50 mL), and filtered. The filtrate was concentrated under reduced pressure and purified by column chromatography on a 40-g SiO$_2$ pre-packed column eluting with EtOAc/hexanes, 0:1 to 3:7, v/v over 30 min, yielding 1.09 g (78%) of the title compound. $^1$H-NMR (400 MHz, CDCl$_3$) δ: 8.48 (s, 1H), 7.65 (s, 1H), 6.33 (br. s., 2H), 2.23 (s, 3H), 1.34 (s, 12H).

B. 3-[5-(2-Difluoromethoxyphenyl)-7-methyl-1H-benzimidazol-2-yl]-1-oxa-2-aza-spiro[4.5]dec-2-ene hydrochloride

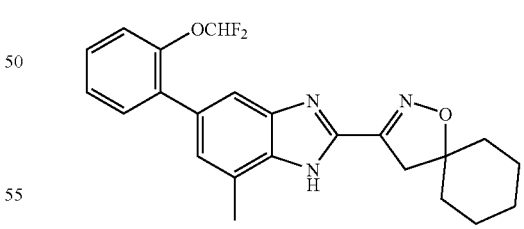

The title compound was prepared according to Example 4, steps A and B. $^1$H-NMR (400 MHz, d$_6$-DMSO) δ: 7.55 (s, 1H), 7.51 (dd, J=7.6, 1.8 Hz, 1H), 7.43-7.49 (m, 1H), 7.37 (dd, J=7.6, 1.0 Hz, 1H), 7.32 (d, J=8.1 Hz, 1H), 7.29 (s, 1H), 7.16 (t, J=74 Hz, 2H), 3.37 (s, 2H), 2.63 (s, 3H), 1.65-1.83 (m, 6H), 1.34-1.57 (m, 4H). Mass Spectrum (LCMS, ESI pos.): Calcd. for C$_{23}$H$_{23}$F$_2$N$_3$O$_2$: 412.2 (M+H). found: 412.3.

Example 9

2-(1-Oxa-2-aza-spiro[4.5]dec-2-en-3-yl)-6-(2-trifluoromethyl-phenyl)-3H-benzimidazole-4-carbonitrile hydrochloride (Cpd 21)

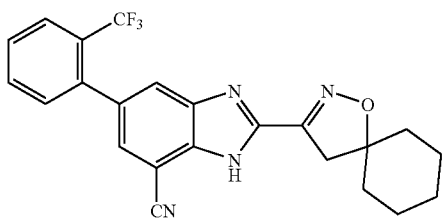

A. 3-Iodo-5-nitro-2'-trifluoromethyl-biphenyl-4-ylamine

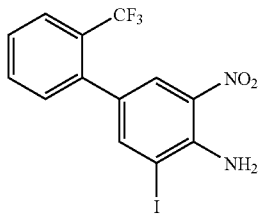

The method of Koradin, C. et al. (*Tetrahedron* 2003, 59, 1571-1587) was used. 3-Nitro-2'-trifluoromethyl-biphenyl-4-ylamine (752 mg, 2.66 mmol, as prepared in Example 6, step A) was placed in a 40 mL vial equipped with a magnetic stir bar, and anhydrous EtOH (27 mL) was added. Iodine (1.4 eq., 945 mg, 3.72 mmol) was added as a solid to the stirred solution. Silver sulfate (1.4 eq., 1.16 g, 3.72 mmol) was added in one portion as a solid, and the reaction was stirred at RT for 24 h. The reaction was filtered, and the solvent was removed under reduced pressure. The residue was dissolved in DCM (30 mL), washed with 10% aq Na$_2$S$_2$O$_3$ (10 mL), dried over anhydrous MgSO$_4$, filtered, and the solvent was removed under reduced pressure. The crude product was purified by column chromatography using a 40-g SiO$_2$ pre-packed column eluting with EtOAc/hexanes, 0:1 to 1:4, v/v, yielding 902 mg (83%) of the title compound. $^1$H-NMR (400 MHz, CDCl$_3$) δ: 8.17 (d, J=2.0 Hz, 1H), 7.94 (d, J=2.0 Hz, 1H), 7.76 (d, J=7.3 Hz, 1H), 7.58 (t, J=7.6 Hz, 1H), 7.50 (t, J=7.7 Hz, 1H), 7.32 (d, J=7.6 Hz, 1H), 6.74 (br. s., 2H).

B. 3-Cyano-5-nitro-2'-trifluoromethyl-biphenyl-4-ylamine

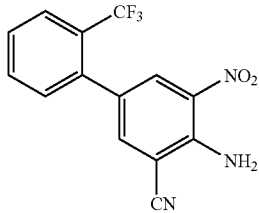

The title compound was prepared by an adaptation of the method described by Youngblood, W. J. (*J. Org. Chem.* 2006, 71, 3345-3356). 3-Iodo-5-nitro-2'-trifluoromethyl-biphenyl-4-ylamine (230 mg, 0.564 mmol, as prepared in the previous step) and Cu(I)CN (1.5 eq., 7.57 mg, 0.845 mmol) were placed in an 8 mL vial equipped with a magnetic stir bar. Dry DMA (2.5 mL) was added via syringe, and the vial was tightly capped and placed in a heating block. The reaction was stirred at 140° C. for 14 h, cooled to RT, and poured into water. The precipitate was isolated by filtration and washed with water (10 mL). The precipitate was dissolved in EtOAc (25 mL), dried over anhydrous MgSO$_4$, filtered, and the solvent was removed under reduced pressure. The crude product was purified by preparative TLC on a 2000 μm SiO$_2$ plate developed with EtOAc/hexanes, 1:9 v/v, yielding 86 mg (50%) of the title compound. $^1$H-NMR (400 MHz, CDCl$_3$) δ: 8.37 (d, J=1.8 Hz, 1H), 7.79 (d, J=7.8 Hz, 1H), 7.71 (d, J=1.5 Hz, 1H), 7.62 (t, J=7.3 Hz, 1H), 7.55 (t, J=7.7 Hz, 1H), 7.31 (d, J=7.6 Hz, 1H), 6.84 (br. s., 2H).

C. 2-(1-Oxa-2-aza-spiro[4.5]dec-2-en-3-yl)-6-(2-trifluoromethyl-phenyl)-3H-benzimidazole-4-carbonitrile hydrochloride

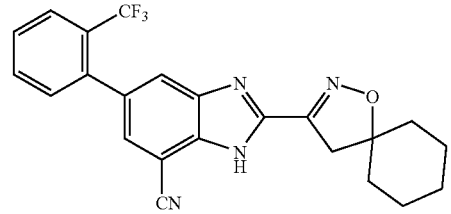

The title compound was prepared according to Example 1, steps E through H. $^1$H-NMR (400 MHz, d$_6$-DMSO) δ: 7.88 (d, J=7.6 Hz, 1H), 7.74-7.81 (m, 1H), 7.71 (s, 2H), 7.64-7.70 (m, 1H), 7.53 (d, J=7.6 Hz, 1H), 3.35 (s, 2H), 1.63-1.82 (m, 6H), 1.31-1.59 (m, 4H). Mass Spectrum (LCMS, ESI pos.): Calcd. for C$_{23}$H$_{19}$F$_3$N$_4$O: 425.2 (M+H). found: 425.2.

Example 10

3-[2-(1-Oxa-2-aza-spiro[4.5]dec-2-en-3-yl)-6-(2-trifluoromethylphenyl)-3H-benzimidazol-4-yl]-propan-1-ol hydrochloride (Cpd 22)

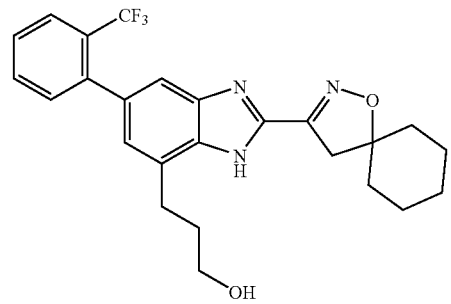

A. 3-(4-Amino-5-nitro-2'-trifluoromethyl-biphenyl-3-yl)-prop-2-yn-1-ol

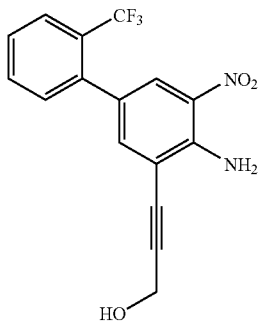

3-Iodo-5-nitro-2'-trifluoromethyl-biphenyl-4-ylamine (466 mg, 1.14 mmol, as prepared in Example 9, step A), $(Ph_3P)_2PdCl_2$ (0.05 eq., 40.1 mg, 0.057 mmol), and CuI (0.05 eq., 10.2 mg, 0.054 mmol) were placed in a 40 mL vial equipped with a magnetic stir bar. The vial was evacuated and backflushed with Ar, and anhydrous THF (6 mL) and TEA (4.0 eq., 0.64 mL, 4.56 mmol) were added via syringe. Propargyl alcohol (4 eq., 0.270 mL, 4.56 mmol) was added via syringe, and the reaction was stirred at RT for 16 h. The solution was diluted with EtOAc (20 mL) and filtered. The solvent was removed under reduced pressure, and the crude product was purified by column chromatography on a 24-g $SiO_2$ pre-packed column eluting with EtOAc/hexanes, 0:1 to 3:2, v/v over 20 min, yielding 279 mg (73%) of the title compound. $^1$H-NMR (400 MHz, $CDCl_3$) δ: 8.10 (d, J=2.0 Hz, 1H), 7.73 (d, J=7.6 Hz, 1H), 7.53-7.59 (m, 1H), 7.53 (d, J=1.8 Hz, 1H), 7.43-7.51 (m, 1H), 7.29 (d, J=7.6 Hz, 1H), 6.82 (br. s., 2H), 4.59 (s, 2H).

B. 3-(4,5-Diamino-2'-trifluoromethyl-biphenyl-3-yl)-propan-1-ol

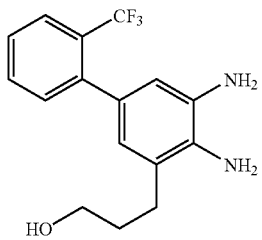

3-(4-Amino-5-nitro-2'-trifluoromethyl-biphenyl-3-yl)-prop-2-yn-1-ol (148 mg, 0.440 mmol, as prepared in the previous step) was placed in an 8 mL vial equipped with a magnetic stir bar, and dry EtOH (2 mL) was added via syringe. To the ethanol solution was added 10% Pd on activated carbon (27 mg), and the vial was capped with a rubber septum. Hydrogen gas was bubbled through the stirred solution for 3 min, and the reaction was stirred under an atmosphere of $H_2$ at 1 atm for 16 h. The vial was vented, the reaction was filtered, and the filter was washed three times with MeOH (5 mL). The solvent was removed under reduced pressure to give 101 mg (73%) of the desired compound. $^1$H-NMR (400 MHz, $CDCl_3$) δ: 7.68 (d, J=7.6 Hz, 1H), 7.48 (t, J=7.3 Hz, 1H), 7.38 (t, J=7.6 Hz, 1H), 7.30 (d, J=7.6 Hz, 1H), 6.61 (s, 1H), 6.60 (s, 1H), 3.65 (t, J=5.9 Hz, 2H), 3.48 (br. s., 4H), 2.66 (t, J=7.3 Hz, 2H), 1.86 (quin, J=6.6 Hz, 2H).

C. 5-[3-(tert-Butyl-dimethyl-silanoxy)-propyl]-2'-trifluoromethyl-biphenyl-3,4-diamine

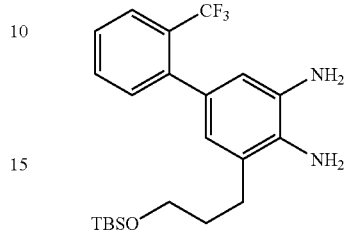

3-(4,5-Diamino-2'-trifluoromethyl-biphenyl-3-yl)-propan-1-ol (101 mg, 0.324 mmol, as prepared in the previous step) was placed in an 8 mL vial equipped with a magnetic stir bar, and DCM (2 mL) was added via pipette. Imidazole (1.1 eq., 24.5 mg, 0.356 mmol) and TBSCl (1.1 eq., 53.7 mg, 0.356 mmol) were added sequentially as solids, and the reaction was stirred at RT for 2 h. The reaction was filtered, the precipitate was washed once with DCM (5 mL), and the filtrate was concentrated under reduced pressure. The crude product was purified by column chromatography on a 24-g $SiO_2$ pre-packed column eluting with EtOAc/hexanes, 0:1 to 1:1, v/v over 30 min, yielding 93.2 mg (68%) of the title compound. $^1$H-NMR (400 MHz, $CDCl_3$) δ: 7.69 (d, J=7.8 Hz, 1H), 7.49 (t, J=7.5 Hz, 1H), 7.38 (t, J=7.6 Hz, 1H), 7.32 (d, J=7.6 Hz, 1H), 6.61 (s, 1H), 6.59 (s, 1H), 3.66 (t, J=5.9 Hz, 2H), 3.52 (br. s., 4H), 2.65 (t, J=7.3 Hz, 2H), 1.75-1.87 (m, 2H), 0.91 (s, 9H), 0.07 (s, 6H).

D. 3-[2-(1-Oxa-2-aza-spiro[4.5]dec-2-en-3-yl)-6-(2-trifluoromethylphenyl)-3H-benzimidazol-4-yl]-propan-1-ol hydrochloride

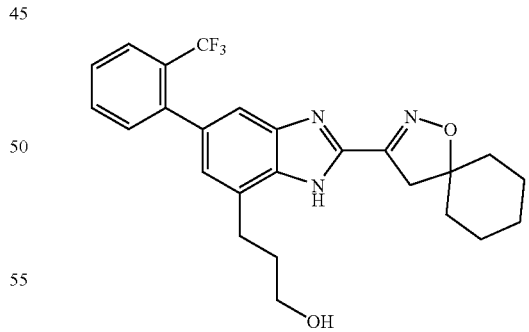

The title compound was prepared according to Example 1, steps F through H. $^1$H-NMR (400 MHz, $d_6$-DMSO) δ: 7.85 (d, J=7.6 Hz, 1H), 7.73 (t, J=7.5 Hz, 1H), 7.63 (t, J=7.6 Hz, 1H), 7.48 (d, J=7.3 Hz, 1H), 7.37 (s, 1H), 7.08 (s, 1H), 3.45 (t, J=6.6 Hz, 2H), 3.33 (s, 2H), 3.01 (t, J=7.5 Hz, 2H), 1.79-1.90 (m, 2H), 1.61-1.79 (m, 6H), 1.31-1.57 (m, 4H). Mass Spectrum (LCMS, ESI pos.): Calcd. for $C_{25}H_{26}F_3N_3O_2$: 458.2 (M+H). found: 458.3.

Example 11

3-[2-(1-Oxa-2-aza-spiro[4.5]dec-2-en-3-yl)-6-(2-trifluoromethylphenyl)-3H-benzimidazol-4-yl]-prop-2-en-1-ol (Cpd 25)

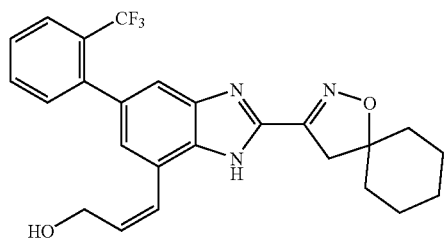

A. 3-(4,5-Diamino-2'-trifluoromethyl-biphenyl-3-yl)-prop-2-en-1-ol

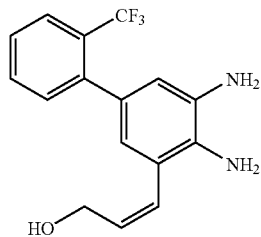

3-(4-Amino-5-nitro-2'-trifluoromethyl-biphenyl-3-yl)-prop-2-yn-1-ol (131 mg, 0.390 mmol, as prepared in Example 10, step A) was placed in an 8 mL vial equipped with a magnetic stir bar, and EtOH (4 mL) was added via syringe followed by water (1 mL). Ammonium chloride (10 eq., 209 mg, 3.90 mmol) and Fe powder (5 eq., 109 mg, 1.95 mmol) were added as solids. The vial was tightly capped, placed in a heated block, and stirred at 80° C. for 16 h. The reaction was cooled to RT, filtered, and the solids were washed three times with MeOH (5 mL). The filtrate was concentrated under reduced pressure, the residue was dissolved in EtOAc (20 mL) and washed with water (20 mL), and the aqueous layer was extracted three times with EtOAc (10 mL). The combined organic extracts were washed with brine (20 mL), dried over anhydrous MgSO$_4$, filtered, and the solvent was removed under reduced pressure, yielding 95 mg of the title compound as a 1:1 mixture with 3-(4,5-diamino-2'-trifluoromethylbiphenyl-3-yl)-prop-2-yn-1-ol. The mixture was carried through to the next step.

B. 5-[3-(tert-Butyldimethylsilanoxy)-propenyl]-2'-trifluoromethylbiphenyl-3,4-diamine

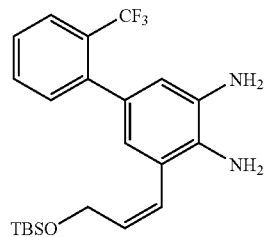

The procedure described in Example 10, step C was used with the crude mixture of 3-(4,5-diamino-2'-trifluoromethyl-biphenyl-3-yl)-prop-2-en-1-ol and 3-(4,5-diamino-2'-trifluoromethylbiphenyl-3-yl)-prop-2-yn-1-ol. The crude product was purified by preparative TLC on a 2000 μm SiO$_2$ plate developed with EtOAc/hexanes, 1:4 v/v, yielding 55.6 mg (43% over two steps) of the title compound. $^1$H-NMR (400 MHz, CDCl$_3$) δ: 7.72 (d, J=7.8 Hz, 1H), 7.51 (t, J=7.6 Hz, 1H), 7.41 (t, J=7.7 Hz, 1H), 7.32 (d, J=7.6 Hz, 1H), 6.65 (s, 1H), 6.52 (s, 1H), 6.45 (d, J=11.4 Hz, 1H), 5.95 (dt, J=11.6, 6.1 Hz, 1H), 4.31 (dd, J=6.3, 1.0 Hz, 2H), 0.87 (s, 9H), 0.02 (s, 6H).

C. 3-[2-(1-Oxa-2-aza-spiro[4.5]dec-2-en-3-yl)-6-(2-trifluoromethylphenyl)-3H-benzimidazol-4-yl]-prop-2-en-1-ol

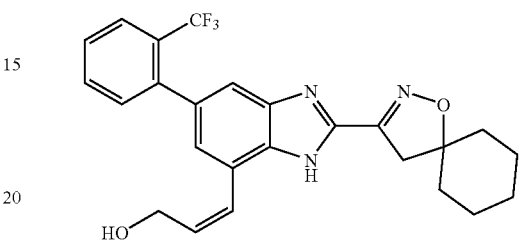

The title compound was prepared according to Example 1, steps F and G. $^1$H-NMR (400 MHz, d$_4$-MeOH) δ: 7.80 (d, J=7.8 Hz, 1H), 7.66 (t, J=7.2 Hz, 1H), 7.56 (t, J=7.6 Hz, 1H), 7.44 (d, J=7.6 Hz, 1H), 7.58-7.35 (br. m, 1H), 6.77-7.16 (m, 2H), 6.08 (dt, J=11.7, 6.7 Hz, 1H), 4.32 (d, J=6.6 Hz, 2H), 1.67-1.91 (m, 6H), 1.43-1.65 (m, 4H). Mass Spectrum (LCMS, ESI pos.): Calcd. for C$_{25}$H$_{24}$F$_3$N$_3$O$_2$: 456.2 (M+H). found: 456.1.

Example 12

3-[5-(2-Fluoro-6-trifluoromethyl-phenyl)-1H-benzimidazol-2-yl]-1-oxa-2-aza-spiro[4.5]dec-2-ene (Cpd 6)

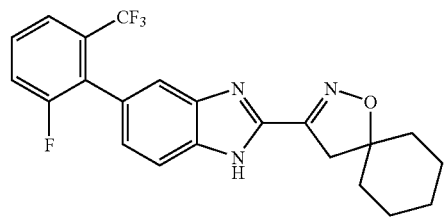

A. 2'-Fluoro-3-nitro-6'-trifluoromethyl-biphenyl-4-ylamine

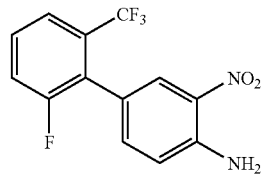

Using the procedure for step A in Example 4, the title compound was prepared from 1-bromo-2-fluoro-6-trifluoromethylbenzene (0.850 mL, 6.09 mmol) and 4-amino-3-nitrophenylboronic acid pinacol ester (1.3 eq., 2.09 g, 7.92 mmol) in 89% yield (1.62 g). $^1$H-NMR (400 MHz, CDCl$_3$) δ: 8.10 (s, 1H), 7.53-7.61 (m, 1H), 7.43-7.53 (m, 1H), 7.35 (t, J=8.5 Hz, 1H), 7.30 (d, J=7.3 Hz, 1H), 6.89 (d, J=8.3 Hz, 1H), 5.47 (br. s., 2H).

B. 2'-Fluoro-6'-trifluoromethyl-biphenyl-3,4-diamine

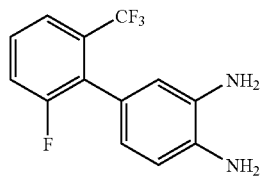

2'-Fluoro-3-nitro-6'-trifluoromethyl-biphenyl-4-ylamine (754 mg, 2.51 mmol, as prepared in the previous step) was placed in a 40 mL vial equipped with a magnetic stir bar, then EtOH (20 mL) and water (5 mL) were added. Ammonium chloride (10 eq., 1.34 g, 25.1 mmol) was added as a solid, and then iron powder (5 eq., 701 mg, 12.6 mmol) was added. The vial was tightly capped and placed in a heating block where the reaction was stirred at 80° C. for 14 h. The reaction was cooled to rt, poured into water, and extracted three times with EtOAc (40 mL). The combined organic extracts were dried over anhydrous $MgSO_4$, filtered, and the solvent was removed under reduced pressure to give 662 mg (98%) of the title compound. $^1$H-NMR (400 MHz, $CDCl_3$) δ: 7.52 (d, J=7.8 Hz, 1H), 7.39 (td, J=7.9, 5.7 Hz, 1H), 7.25-7.32 (m, 1H), 6.71-6.77 (m, 1H), 6.60-6.67 (m, 2H), 3.45 (br. s., 4H).

C. 3-[5-(2-Fluoro-6-trifluoromethyl-phenyl)-1H-benzimidazol-2-yl]-1-oxa-2-aza-spiro[4.5]dec-2-ene

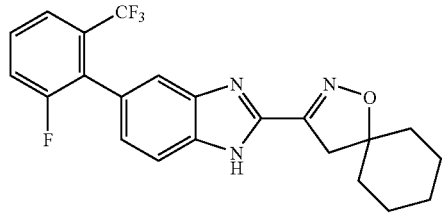

The procedures described in Example 1, steps F and G were used to prepare the title compound. $^1$H-NMR (400 MHz, $d_6$-DMSO+$d_1$-TFA) δ: 7.63-7.77 (m, 4H), 7.57 (s, 1H), 7.23 (d, J=8.3 Hz, 1H), 3.31 (s, 2H), 1.63-1.85 (m, 6H), 1.34-1.59 (m, 4H). Mass Spectrum (LCMS, ESI pos.): Calcd. for $C_{22}H_{19}F_4N_3O$: 418.2 (M+H). found: 418.2.

Example 13

2-{2-[2-(1-Oxa-2-aza-spiro[4.5]dec-2-en-3-yl)-1H-benzimidazol-5-yl]-phenyl}-propan-2-ol (Cpd 18)

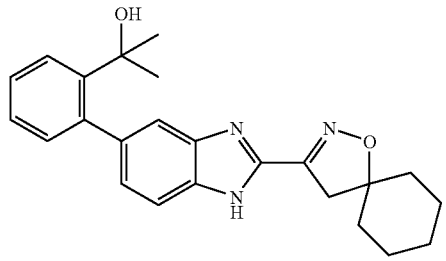

A. 3-(5-Bromo-1H-benzimidazol-2-yl)-1-oxa-2-aza-spiro[4.5]dec-2-ene

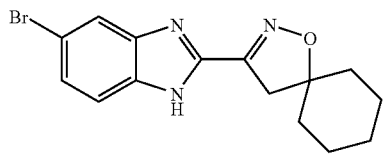

The title compound was prepared from 1-oxa-2-aza-spiro[4.5]dec-2-ene-3-carboxylic acid (283 mg, 1.55 mmol, as prepared in Example 1, step B) and 4-bromobenzene-1,2-diamine (1.3 eq., 377 mg, 2.02 mmol) in 68% overall yield (299 mg) according to the procedures described in Example 1, steps F and G. $^1$H-NMR (400 MHz, $d_4$-MeOH) δ: 7.74 (s, 1H), 7.51 (d, J=8.6 Hz, 1H), 7.40 (dd, J=8.6, 1.8 Hz, 1H), 3.25 (s, 2H), 1.69-1.88 (m, 6H), 1.43-1.63 (m, 4H).

B. 2-{2-[2-(1-Oxa-2-aza-spiro[4.5]dec-2-en-3-yl)-1H-benzimidazol-5-yl]-phenyl}-propan-2-ol

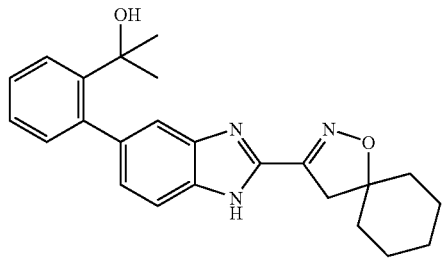

Using the procedure for step D in Example 1, the title compound was prepared from 3-(5-bromo-1H-benzimidazol-2-yl)-1-oxa-2-aza-spiro[4.5]dec-2-ene (150 mg, 0.449 mmol, as prepared in the previous step) and 3,3-dimethyl-3H-benzo[c][1,2]oxaborol-1-ol (2.0 eq., 145 mg, 0.898 mmol, prepared as described in US2007/259936) and (dppf)$PdCl_2$.DCM (0.10 eq., 36.6 mg, 0.045 mmol) in 9% yield (16.4 mg). $^1$H-NMR (400 MHz, $d_4$-MeOH) δ: 7.82 (dd, J=8.1, 1.3 Hz, 1H), 7.53-7.68 (m, 1H), 7.47 (br. s., 1H), 7.35 (td, J=7.6, 1.6 Hz, 1H), 7.19-7.24 (m, 2H), 7.05 (dd, J=7.6, 1.3 Hz, 1H), 3.28 (s, 2H), 1.69-1.90 (m, 6H), 1.46-1.65 (m, 4H), 1.33 (s, 6H). Mass Spectrum (LCMS, ESI pos.): Calcd. for $C_{24}H_{27}N_3O_2$: 390.2 (M+H). found: 390.4.

Example 14

2-[5-(2-Trifluoromethoxy-phenyl)-1H-benzimidazol-2-yl]-3-oxa-1-aza-spiro[4.5]dec-1-ene (Cpd 2)

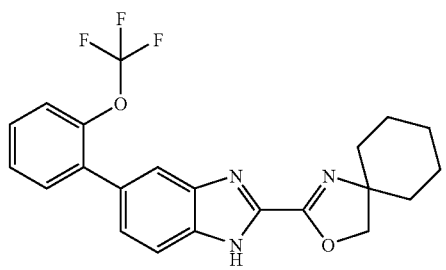

A. (4-Bromo-2-tert-butoxycarbonylamino-phenyl)-carbamic acid tert-butyl ester

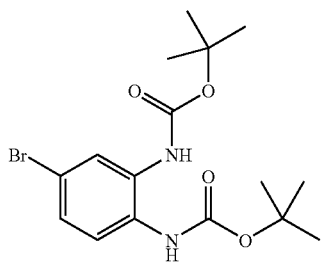

4-Bromo-benzene-1,2-diamine (1.87 g, 10.0 mmol) was placed in a 100 mL round-bottom flask equipped with a magnetic stir bar. DCM (50 mL), solid BOC-anhydride (5.46 g, 25.0 mmol) and 2.5 M aqueous NaOH (10 mL) were added. The mixture was stirred at rt for 3 d. The mixture was diluted with water and extracted three times with DCM (20 mL). The combined organic extracts were dried over $MgSO_4$, filtered, and the solvent was removed under reduced pressure. The residue was chromatographed on a 50-g pre-packed $SiO_2$ column, eluting with EtOAc/hexanes, 1:9, v/v to afford 3.40 g (88%) of the title compound.

B. (3-tert-Butoxycarbonylamino-2'-trifluoromethoxy-biphenyl-4-yl)-carbamic acid tert-butyl ester

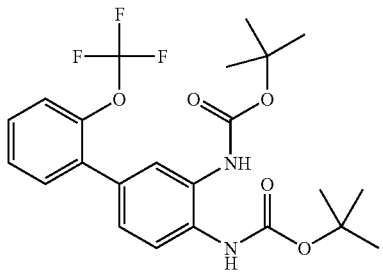

The title compound was prepared from (4-bromo-2-tert-butoxycarbonylamino-phenyl)-carbamic acid tert-butyl ester (as prepared in the previous step) and 2-trifluoromethoxyphenylboronic acid according to the procedure described in Example 1, step D. $^1$H-NMR (400 MHz, $CDCl_3$) δ: 7.59 (br. s., 2H), 7.37-7.42 (m, 1H), 7.26-7.34 (m, 3H), 7.24 (dd, J=8.3, 2.0 Hz, 1H), 7.00 (br. s., 1H), 6.94 (br. s., 1H), 1.52 (s, 9H), 1.50 (s, 9H).

C. 2-Trichloromethyl-5-(2-trifluoromethoxy-phenyl)-1H-benzimidazole

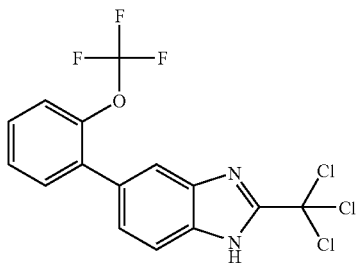

(3-tert-Butoxycarbonylamino-2'-trifluoromethoxy-biphenyl-4-yl)-carbamic acid tert-butyl ester (573 mg, 1.22 mmol, as prepared in the previous step) was placed in a mL vial equipped with a magnetic stir bar. DCM (10 mL) and TFA (5 mL) were added, and the mixture stirred at rt for 12 h. The solvent was removed under reduced pressure, and the residue was dissolved in DCM and washed with 2M aq NaOH. The organic extract was dried over $MgSO_4$ and concentrated in vacuo. The residue was dissolved in AcOH (5 mL) and placed in an 8 mL vial equipped with a magnetic stir bar. The mixture was cooled to 0° C., treated with methyl-2,2,2-trichloroacetimidate (0.167 mL, 1.35 mmol) via syringe, and stirred at rt for 3 days. The solvent was removed under reduced pressure. The crude product was purified by column chromatography using a 12-g $SiO_2$ pre-packed column eluting with EtOAc/hexanes, 0:1 to 2:5, v/v over 30 min, yielding 409 mg (85%) of the desired compound. $^1$H-NMR (400 MHz, $d_4$-MeOH) δ: 7.71-7.77 (m, 2H), 7.52-7.57 (m, 1H), 7.39-7.51 (m, 4H).

D. (1-Amino-cyclohexyl)-methanol

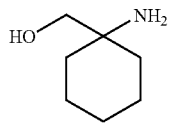

$LiAlH_4$ powder (2.28 g, 60.0 mmol) was placed in a 200 mL round-bottom flask equipped with a magnetic stir bar. The flask was evacuated and backflushed with Ar, cooled to 0° C., and charged with dry THF (10 mL) via cannula. 1-Aminocyclohexylcarboxylic acid (2.86 g, 20.0 mmol) was added in small portions as a solid. Upon completion of the addition, the mixture was heated to reflux for 12 h. The mixture was cooled to 0° C., treated slowly with satd aq $Na_2CO_3$ (50 mL), warmed to rt, and stirred for 2 h. A white precipitate formed, which was separated by filtration, washed with THF (75 mL), and washed twice with EtOAc (100 mL). The filtrate was concentrated in vacuo. The residue was dissolved in DCM (50 mL), dried over $Na_2SO_4$, and concentrated in vacuo to afford 2.80 g (97%) of the title compound. $^1$H-NMR (400 MHz, $CDCl_3$) δ: 3.33 (s, 2H), 1.45-1.56 (m, 6H), 1.31-1.45 (m, 4H).

E. 2-[5-(2-Trifluoromethoxy-phenyl)-1H-benzimidazol-2-yl]-3-oxa-1-aza-spiro[4.5]dec-1-ene 2-Trichloromethyl-5-(2-trifluoromethoxy-phenyl)-1H-benzimidazole (241 mg, 0.610 mmol, as prepared in step B of this Example) and (1-amino-cyclohexyl)-methanol (315 mg, 2.44 mmol, as prepared in the previous step) were placed in a 40 mL vial equipped with a magnetic stir bar. Water (8 mL) was added, and the mixture was cooled to 0° C. and stirred at that temperature for 1 h. Complete dissolution of starting materials did not occur, so the mixture was warmed to rt, treated with dioxane (8 mL), and stirred at rt for 14 h. The mixture was extracted three times with EtOAc (20 mL). The combined organic extracts were dried over $MgSO_4$ and concentrated in vacuo. The crude product was purified by column chromatography using a 12-g $SiO_2$ pre-packed column eluting with EtOAc/hexanes, 0:1 to 2:5, v/v over 30 min. The column was repeated under these conditions, yielding 24.6 mg (10%) of the desired compound. $^1$H-NMR (400 MHz, $d_6$-DMSO) δ: 7.78 (br. s., 1H), 7.46-7.64 (m, 5H), 7.27-7.46 (m, 1H), 4.27 (s, 2H), 1.60-1.82 (m, 6H), 1.47-1.58 (m, 1H), 1.33-1.46 (m, 3H).

Using the procedures described in Example 14, and reagents, starting materials and conditions known to those skilled in the art, the following compounds representative of the present invention were prepared:

| Cpd | Data |
|---|---|
| 3 | 2-[5-(2-Trifluoromethoxy-phenyl)-1H-benzimidazol-2-yl]-1-oxa-3-aza-spiro[4.5]dec-2-ene<br>$^1$H-NMR (400 MHz, d$_4$-MeOH) δ: 7.74 (br. s., 2H), 7.50-7.56 (m, 1H), 7.37-7.48 (m, 4H), 3.82 (s, 2H), 1.78-1.96 (m, 4H), 1.66-1.77 (m, 2H), 1.47-1.62 (m, 4H). Mass Spectrum (LCMS, ESI pos.): Calcd. for C$_{22}$H$_{20}$F$_3$N$_3$O$_2$: 416.2 (M + H); found: 416.1. |
| 4 | 2-[5-(2-Trifluoromethyl-phenyl)-1H-benzimidazol-2-yl]-1-oxa-3-aza-spiro[4.5]dec-2-ene<br>$^1$H-NMR (400 MHz, d$_4$-MeOH) δ: 7.79 (d, J = 7.8 Hz, 1H), 7.73 (br. s, 1H), 7.65 (t, J = 7.2 Hz, 1H), 7.60 (br. s, 1H), 7.56 (t, J = 7.6 Hz, 1H), 7.43 (d, J = 7.6 Hz, 1H), 7.29 (br. d, J = 6.8 Hz, 1H), 3.84 (s, 2H), 1.80-1.98 (m, 4H), 1.69-1.79 (m, 2H), 1.43-1.65 (m, 4H).<br>Mass Spectrum (LCMS, ESI pos.): Calcd. for C$_{22}$H$_{20}$F$_3$N$_3$O: 400.2 (M + H); found: 400.1. |
| 5 | 2-[5-(2-Trifluoromethyl-phenyl)-1H-benzimidazol-2-yl]-3-oxa-1-aza-spiro[4.5]dec-1-ene<br>$^1$H-NMR (400 MHz, d$_4$-MeOH) δ: 7.79 (d, J = 7.8 Hz, 1H), 7.71 (br. s, 1H), 7.65 (t, J = 7.2 Hz, 1H), 7.62 (br. s, 1H), 7.56 (t, J = 7.7 Hz, 1H), 7.42 (d, J = 7.6 Hz, 1H), 7.29 (d, J = 6.6 Hz, 1H), 4.32 (s, 2H), 1.75-1.94 (m, 4H), 1.65-1.75 (m, 2H), 1.41-1.65 (m, 4H). Mass Spectrum (LCMS, ESI pos.): Calcd. for C$_{22}$H$_{20}$F$_3$N$_3$O: 400.2 (M + H); found: 400.2. |
| 19 | 2-(1,3-Diaza-spiro[4.5]dec-2-en-2-yl)-5-(2-trifluoromethyl-phenyl)-1H-benzimidazole<br>$^1$H-NMR (400 MHz, d$_4$-MeOH) δ (ppm): 7.80-7.84 (m, 2H), 7.71 (s, 1H), 7.69 (t, J = 7.3 Hz, 1H), 7.60 (t, J = 7.8 Hz, 1H), 7.39-7.47 (m, 2H), 3.99 (s, 2H), 1.76-2.03 (m, 6H), 1.45-1.69 (m, 4H).<br>Mass Spectrum (LCMS, ESI pos.) Calcd. for C$_{22}$H$_{21}$F$_3$N$_4$: 399.2 (M + H), Found 399.2. |
| 29 | 2-[5-(2-Trifluoromethyl-phenyl)-1H-benzimidazol-2-yl]-3,8-dioxa-1-aza-spiro[4.5]dec-1-ene<br>$^1$H-NMR (400 MHz, CDCl$_3$) δ (ppm): 7.79 (d, J = 7.8 Hz, 1H), 7.48-7.79 (m, 4H), 7.42 (d, J = 7.6 Hz, 1H), 7.23-7.35 (m, 1H), 4.36 (s, 2H), 3.97-4.09 (m, 2H), 3.65-3.78 (m, 2H), 1.78-1.94 (m, 4H).<br>Mass Spectrum (LCMS, ESI pos.) Calcd. for C$_{21}$H$_{18}$F$_3$N$_3$O$_2$: 402.1 (M + H), Found 402.1. |

Example 15

3-[5-(2-Chloro-phenyl)-7-trifluoromethyl-1H-benzimidazol-2-yl]-1-oxa-2-aza-spiro[4.5]dec-2-ene hydrochloride (Cpd 30)

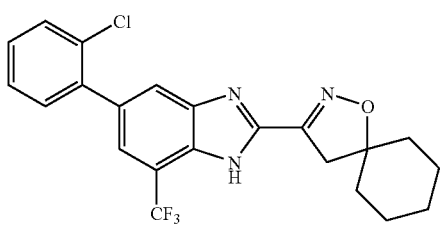

A. 2'-Chloro-5-nitro-3-trifluoromethyl-biphenyl-4-ylamine

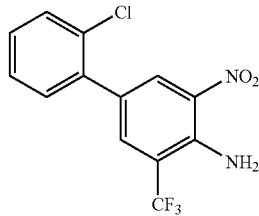

4-Bromo-2-nitro-6-trifluoromethyl-phenylamine (1.01 g, 3.55 mmol), 2-chlorophenylboronic acid (1.5 eq., 833 mg, 5.33 mmol), and (dppf)PdCl$_2$.DCM (0.05 eq., 145 mg, 0.178 mmol) were placed in a 40 mL vial equipped with a magnetic stir bar. The vial was evacuated and backflushed with Ar, and DME (15 mL) and 2M aq Na$_2$CO$_3$ (5 mL) were added via syringe. The vial was capped tightly and placed in a heating block where the reaction was stirred at 90° C. for 18 h. The mixture was cooled to rt, diluted with EtOAc, and washed with water. The aqueous layers were combined and extracted with EtOAc. The combined organic extracts were dried over anhydrous MgSO$_4$, filtered, and the solvent was removed under reduced pressure. The crude product was purified by column chromatography using a 24-g SiO$_2$ pre-packed column eluting with EtOAc/hexanes, 0 to 1:4, v/v over 20 min, yielding 1.05 g (94%) of the desired compound. $^1$H-NMR (400 MHz, CDCl$_3$) δ: 8.47 (d, J=2.0 Hz, 1H), 7.89 (d, J=2.0 Hz, 1H), 7.47-7.53 (m, 1H), 7.30-7.37 (m, 3H), 6.76 (br. s., 2H).

B. 3-[5-(2-Chloro-phenyl)-7-trifluoromethyl-1H-benzimidazol-2-yl]-1-oxa-2-aza-spiro[4.5]dec-2-ene

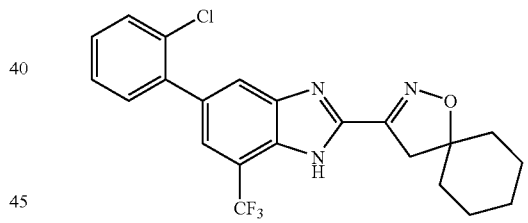

1-Oxa-2-aza-spiro[4.5]dec-2-ene-3-carboxylic acid (611 mg, 3.33 mmol, as prepared in Example 1, step B) was placed in a 40 mL vial equipped with a magnetic stir bar. DCM (6 mL) and DMF (1 drop) were added via syringe. To the stirred solution was added oxalyl chloride (1.3 eq., 0.367 mL, 4.33 mmol) dropwise via syringe. After completion of the addition, the reaction was stirred at rt for 1 h. The solvent was removed under reduced pressure, and the resulting residue was dissolved in dry THF (7 mL).

2'-Chloro-5-nitro-3-trifluoromethyl-biphenyl-4-ylamine (1 eq., 1.06 g, 3.33 mmol, as prepared in the previous step) was placed in a 40 mL vial equipped with a magnetic stir bar. The vial was evacuated and backflushed with Ar, and dry THF (10 mL) was added. The mixture was cooled to 0° C. in an ice bath, and NaH (3 eq., 400 mg, 9.99 mmol, 60% dispersion in oil) was added in small portions. The above-prepared acid chloride solution was added dropwise over a period of 10 min to the stirred reaction mixture. The resulting solution was stirred at 0° C. for 30 min then warmed to rt and stirred for 16 h. The mixture was quenched with water and brine, and extracted three times with EtOAc (20 mL). The combined organic extracts were dried over anhydrous MgSO$_4$ and concentrated under reduced pressure. The residue was dissolved in glacial acetic acid (20 mL) and placed in a 40 mL vial equipped with a stir bar. Fe powder (5 eq., 930 mg, 16.7 mmol) was added, the vial was capped, and the mixture was stirred at 80° C. for 1 h. The mixture was cooled to rt and poured into ice (100 mL). The precipitate was filtered, and the solid was washed with water, dissolved in EtOAc, dried over anhydrous MgSO$_4$, and concentrated under reduced pressure. The crude product was purified by column chromatography using a 40-g SiO$_2$ pre-packed column eluting with EtOAc/hexanes, 0:1 to 3:7, v/v over 30 min, yielding 1.14 g (79%) of the desired compound. $^1$H-NMR (400 MHz, d$_6$-DMSO) δ: 13.52 (br. s., 1H), 7.86 (d, J=7.6 Hz, 1H), 7.75 (t, J=7.5 Hz, 1H), 7.65 (t, J=7.6 Hz, 1H), 7.51 (d, J=7.6 Hz, 1H), 7.35 (s, 1H), 7.25 (s, 1H), 3.33 (s, 2H), 1.63-1.82 (m, 6H), 1.33-1.59 (m, 4H).

C. 3-[5-(2-Chloro-phenyl)-7-trifluoromethyl-1H-benzimidazol-2-yl]-1-oxa-2-aza-spiro[4.5]dec-2-ene hydrochloride 3-[5-(2-Chloro-phenyl)-7-trifluoromethyl-1H-benzimidazol-2-yl]-1-oxa-2-aza-spiro[4.5]dec-2-ene (1.14 g, 2.63 mmol, as prepared in the previous step) was placed in a 100 mL round-bottom flask, and EtOAc (10 mL) was added. HCl (1 eq., 2.60 mL, 2.63 mmol, 1 M solution in ether) was added via syringe. The solvent was removed under reduced pressure, and the solid was dried under high vacuum for 3 days, yielding 1.12 g (90%) of the desired compound. $^1$H-NMR (400 MHz, d$_6$-DMSO) δ: 7.80 (s, 1H), 7.60-7.66 (m, 1H), 7.59 (s, 1H), 7.52-7.58 (m, 1H), 7.43-7.51 (m, 2H), 1.61-1.82 (m, 6H), 1.32-1.59 (m, 4H). Mass Spectrum (LCMS, ESI pos.): Calcd. for C$_{22}$H$_{19}$ClF$_3$N$_3$O: 434.1 (M+H). found: 434.2.

Example 16

3-[5-(2-Fluoro-phenyl)-1H-benzimidazol-2-yl]-1,8-dioxa-2-aza-spiro[4.5]dec-2-ene

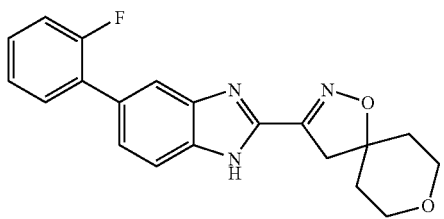

A. 2'-Fluoro-3-nitro-biphenyl-4-ylamine

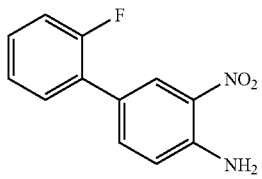

A solution of 4-bromo-2-nitro-phenylamine (2.17 g, 10.0 mmol) in dioxane (40 mL) was treated with 2-fluorophenylboronic acid (1.40 g, 10.0 mmol) and NaHCO$_3$ (40.0 mL, 80.0 mmol, 2M aqueous). The mixture was degassed via sonication and flushed with Ar. Pd(PPh$_3$)$_4$ (116 mg, 0.100 mmol) was added, and the mixture was heated to 80° C. for 12 h. The mixture was diluted with water (40 mL) and extracted twice with EtOAc (40 mL). The combined organic layers were dried over MgSO$_4$ and concentrated in vacuo. The residue was purified on silica (EtOAc/hexanes, 0:1 to 1:1, v/v) to obtain 1.80 g (78%) of the title compound. $^1$H-NMR (400 MHz, CDCl$_3$) δ: 8.36 (d, J=1.8 Hz, 1H), 7.64 (dt, J=8.6, 2.0 Hz, 1H), 7.45 (td, J=7.8, 1.8 Hz, 1H), 7.30-7.38 (m, 1H), 7.13-7.27 (m, 2H), 6.91 (d, J=8.6 Hz, 1H), 6.18 (br. s., 2H).

B. 1,8-Dioxa-2-aza-spiro[4.5]dec-2-ene-3-carboxylic acid ethyl ester

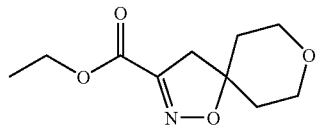

To a well-vented 500 mL three-necked round-bottom flask was added methyl triphenylphosphonium bromide/sodium amide mixture ("instant ylide", 22.9 g, 5.49 mmol) and dry ether (100 mL). The mixture was stirred at rt for 1 h and filtered through a glass-fritted funnel directly into a solution of tetrahydro-pyran-4-one (5.00 g, 4.99 mmol) in ether (20 mL). This mixture was stirred at rt for 4 h. Ethyl-2-chloro-2-(hydroxyamino)acetate (8.32 g, 5.49 mmol) in DCM (100 mL) was added dropwise via addition funnel over 3 h, and the mixture was stirred for 2.5 days. Water (100 mL) was added, and the mixture was extracted three times with DCM (200 mL, 100 mL, 100 mL). The combined organic extracts were dried over MgSO$_4$ and concentrated in vacuo. The residue was purified on a 200-g Sepra Si 50 SPE column (Isco system: Flow rate=30 mL/min; Eluent=EtOAc/heptane, 1:9 v/v for 10 min, then 1:9 to 2:3 v/v over 40 min) to afford the title compound (3.00 g, 28%) as a tan oil. $^1$H-NMR (400 MHz, CDCl$_3$) δ: 4.35 (q, J=7.2 Hz, 2H), 3.89 (ddd, J=11.8, 8.7, 3.3 Hz, 2H), 3.65-3.75 (m, 2H), 2.99 (s, 2H), 1.89-1.97 (m, 2H), 1.76-1.86 (m, 2H), 1.37 (t, J=7.2 Hz, 3H).

C. 1,8-Dioxa-2-aza-spiro[4.5]dec-2-ene-3-carboxylic acid

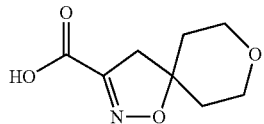

A solution of 1,8-dioxa-2-aza-spiro[4.5]dec-2-ene-3-carboxylic acid ethyl ester (3.00 g, 1.41 mmol, as prepared in the previous step) in MeOH (60 mL) and water (20 mL) was treated with LiOH (649 mg, 1.55 mmol) at rt for 2.5 h. MeOH was removed in vacuo. The resulting aqueous solution was acidified with 1 N aq HCl and extracted three times with EtOAc (100 mL, 100 mL, 50 mL). The combined organic extracts were dried over MgSO$_4$ and concentrated in vacuo to afford the title compound (2.50 g, 96%) as a white solid.

$^1$H-NMR (400 MHz, CDCl$_3$) δ: 3.86-3.95 (m, 2H), 3.74 (dt, J=11.8, 4.7 Hz, 2H), 3.01 (s, 2H), 1.91-1.99 (m, 2H), 1.80-1.89 (m, 2H).

D. 1,8-Dioxa-2-aza-spiro[4.5]dec-2-ene-3-carboxylic acid (2'-fluoro-3-nitro-biphenyl-4-yl)-amide

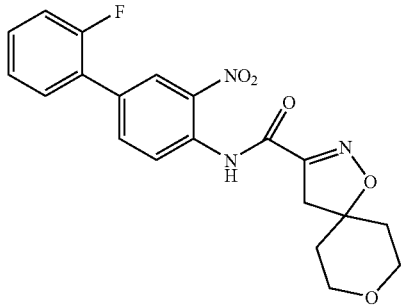

A solution of 1,8-dioxa-2-aza-spiro[4.5]dec-2-ene-3-carboxylic acid (87.7 mg, 0.474 mmol, as prepared in the previous step) in CH$_2$Cl$_2$ (10 mL) was treated with oxalyl chloride (41.3 μL, 0.474 mmol) and DMF (1 drop) at rt for 1 h. Simultaneously, a solution of 2'-fluoro-3-nitro-biphenyl-4-ylamine (100 mg, 0.431 mmol, as prepared in step A of this Example) in dry THF (10 mL) was treated with NaH (51.7 mg, 1.29 mmol, 60% dispersion in oil) at rt for 1 h. The acid chloride solution was concentrated in vacuo, taken up in dry THF (10 mL), and slowly added to the 2'-fluoro-3-nitro-biphenyl-4-ylamine solution. The mixture was allowed to stir for 20 min at rt, quenched with satd aq NH$_4$Cl, diluted with water, and extracted with EtOAc. The combined organic extracts were dried over MgSO$_4$ and concentrated in vacuo. The residue was purified on a 40-g Sepra Si 50 SPE column (Isco system: Flow rate=20 mL/min; Eluent=EtOAc/hexanes, 1:9 v/v for 10 min, then 1:9 to 2:3 v/v over 40 min) to afford the title compound (131 mg, 76%) as a yellow solid. $^1$H-NMR (400 MHz, CDCl$_3$) δ: 11.58 (s, 1H), 8.87 (d, J=8.8 Hz, 1H), 8.47 (d, J=2.0 Hz, 1H), 7.89 (dt, J=8.8, 1.6 Hz, 1H), 7.47 (td, J=7.7, 1.8 Hz, 1H), 7.35-7.44 (m, 1H), 7.24-7.31 (m, 1H), 7.20 (ddd, J=10.9, 8.3, 1.0 Hz, 1H), 3.92 (ddd, J=11.8, 8.8, 3.2 Hz, 2H), 3.71-3.82 (m, 2H), 3.10 (s, 2H), 1.94-2.03 (m, 2H), 1.83-1.93 (m, 2H). Mass Spectrum (LCMS, APCI pos.): Calcd. for C$_{20}$H$_{18}$FN$_3$O$_5$: 400.1 (M+H). found: 400.1.

E. 3-[5-(2-Fluoro-phenyl)-1H-benzimidazol-2-yl]-1,8-dioxa-2-aza-spiro[4.5]dec-2-ene

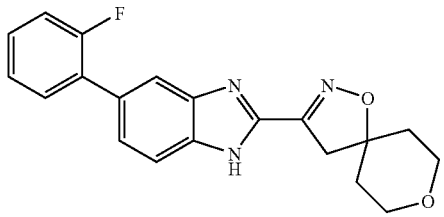

A solution of 1,8-dioxa-2-aza-spiro[4.5]dec-2-ene-3-carboxylic acid (2'-fluoro-3-nitro-biphenyl-4-yl)-amide (131 mg, 0.327 mmol, as prepared in the previous step) in glacial acetic acid (10 mL) was treated with Fe powder (91.2 mg, 1.36 mmol) and heated to 100° C. under a reflux condenser for 4 h. The pH of the mixture was adjusted to 7 with 6M aq NaOH. The resulting aqueous mixture was extracted three times with EtOAc (50 mL), and the combined organic layers were dried over MgSO$_4$ and concentrated in vacuo. The residue was purified on a 40-g Sepra Si 50 SPE column (Isco system: Flow rate=25 mL/min; Eluent=EtOAc/hexanes, 1:9 v/v for 10 min, then 1:9 to 2:3 v/v over 40 min) to afford the title compound (98.8 mg, 86%) as an off-white solid. $^1$H-NMR (400 MHz, CDCl$_3$) δ: 7.78-7.90 (m, 1H), 7.55-7.68 (m, 1H), 7.46-7.54 (m, 2H), 7.29-7.39 (m, 1H), 7.14-7.26 (m, 2H), 3.97 (ddd, J=11.7, 8.1, 3.4 Hz, 2H), 3.70-3.81 (m, 2H), 3.47 (s, 2H), 1.99-2.08 (m, 3H), 1.87-1.98 (m, 2H). Mass Spectrum (LCMS, ESI pos.): Calcd. for C$_{20}$H$_{18}$FN$_3$O$_2$: 352.1 (M+H). found: 352.2.

F. 3-[5-(2-Fluoro-phenyl)-1H-benzimidazol-2-yl]-1,8-dioxa-2-aza-spiro[4.5]dec-2-ene hydrochloride A solution of 3-[5-(2-fluoro-phenyl)-1H-benzimidazol-2-yl]-1,8-dioxa-2-aza-spiro[4.5]dec-2-ene (98.8 mg, 0.281 mmol, as prepared in the previous step) in EtOH (5 mL) was treated with HCl (56.2 μL, 0.281 mmol, 5 M in isopropanol) at rt for 2 h. The mixture was concentrated in vacuo and the residue was dissolved in a minimum amount of EtOH (2.5 mL) with sonication and heating. The solution was cooled to rt, and hexanes were added dropwise until the solution became cloudy. The solution was allowed to sit for 2 min then was treated with additional hexanes. The resulting precipitate was filtered, washed with hexanes, and air-dried to afford the title compound (63.7 mg, 58%) as a white solid. $^1$H-NMR (400 MHz, d$_4$-MeOH) δ: 7.85 (s, 1H), 7.77-7.83 (m, 1H), 7.70-7.77 (m, 1H), 7.46-7.53 (m, 1H), 7.32-7.41 (m, 1H), 7.21-7.27 (m, 1H), 7.13-7.21 (m, 1H), 3.78-3.88 (m, 2H), 3.63-3.73 (m, 2H), 3.32-3.36 (m, 2H), 1.85-1.98 (m, 4H). Mass Spectrum (LCMS, APCI pos.): Calcd. for C$_{20}$H$_{18}$FN$_3$O$_2$: 352.1 (M+H). found: 352.3.

Using the procedures described in Example 16, and reagents, starting materials and conditions known to those skilled in the art, the following compounds representative of the present invention were prepared:

| Cpd | Data |
| --- | --- |
| 32 | 3-[7-Methyl-5-(2-trifluoromethyl-phenyl)-1H-benzimidazol-2-yl]-1,8-dioxa-2-aza-spiro[4.5]dec-2-ene hydrochloride<br>$^1$H-NMR (400 MHz, d$_4$-MeOH) δ: 7.74 (d, J = 7.8 Hz, 1H), 7.61 (t, J = 7.6 Hz, 1H), 7.53 (t, J = 7.7 Hz, 1H), 7.45 (s, 1H), 7.35 (d, J = 7.6 Hz, 1H), 7.30 (s, 1H), 3.83 (ddd, J = 11.8, 7.3, 4.7 Hz, 2H), 3.68 (dt, J = 11.8, 4.8 Hz, 2H), 3.36 (s, 2H), 2.63 (s, 3H), 1.86-1.96 (m, 4H). |
| 33 | 3-[7-Bromo-5-(2-trifluoromethyl-phenyl)-1H-benzimidazol-2-yl]-1,8-dioxa-2-aza-spiro[4.5]dec-2-ene hydrochloride Ex 7, step A but brominated with NBS)<br>$^1$H-NMR (400 MHz, d$_4$-MeOH) δ: 7.75 (d, J = 7.8 Hz, 1H), 7.59-7.65<br>(m, 1H), 7.50-7.59 (m, 3H), 7.37 (d, J = 7.6 Hz, 1H), 3.77-3.88 (m, 2H), 3.62-3.72 (m, 2H), 3.36 (s, 2H), 1.84-1.93 (m, 4H). Mass Spectrum (LCMS, APCI pos.): Calcd. for C$_{21}$H$_{17}$BrF$_3$N$_3$O$_2$: 480.1 (M + H); found: 480.2. |
| 34 | 3-[7-Chloro-5-(2-trifluoromethyl-phenyl)-1H-benzimidazol-2-yl]-1,8-dioxa-2-aza-spiro[4.5]dec-2-ene hydrochloride<br>$^1$H-NMR (400 MHz, d$_4$-MeOH) δ: 7.74 (d, J = 7.6 Hz, 1H), 7.61 (t, J = 7.3 Hz, 1H), 7.53 (t, J = 7.6 Hz, 1H), 7.47 (br. s., 1H), 7.37 (d, J = 6.8 Hz, 1H), 3.78-3.87 (m, 2H), 3.67 (dt, J = 11.8, 4.8 Hz, 2H), 3.35 (s, 2H), 1.83-1.93 (m, 4H). Mass Spectrum (LCMS, APCI pos.): Calcd. for C$_{21}$H$_{17}$ClF$_3$N$_3$O$_2$: 436.1 (M + H); found: 436.3. |

| Cpd | Data |
|---|---|
| 35 | 2-(1,8-Dioxa-2-aza-spiro[4.5]dec-2-en-3-yl)-6-(2-trifluoromethyl-phenyl)-3H-benzimidazole-4-carbonitrile hydrochloride<br>¹H-NMR (400 MHz, d₄-MeOH) δ: 7.74 (d, J = 7.6 Hz, 1H), 7.67 (s, 1H), 7.57-7.65 (m, 1H), 7.49-7.56 (m, 2H), 7.37 (d, J = 7.6 Hz, 1H), 3.81 (dt, J = 11.8, 5.8 Hz, 2H), 3.63-3.72 (m, 2H), 3.36 (s, 2H), 1.85 (t, J = 5.4 Hz, 4H). Mass Spectrum (LCMS, APCI pos.): Calcd. for C₂₂H₁₇F₃N₄O₂: 427.1 (M + H); found: 427.2. |
| 36 | 8,8-Dimethyl-3-[5-(2-trifluoromethyl-phenyl)-1H-benzimidazol-2-yl]-1-oxa-2-aza-spiro[4.5]dec-2-ene hydrochloride<br>¹H-NMR (400 MHz, d₄-MeOH) δ: 7.71-7.77 (m, 2H), 7.58-7.65 (m, 2H), 7.50-7.57 (m, 1H), 7.46 (dd, J = 8.6, 1.0 Hz, 1H), 7.36 (d, J = 7.6 Hz, 1H), 3.24 (s, 2H), 1.82-1.93 (m, 2H), 1.71-1.81 (m, 2H), 1.55 (ddd, J = 13.5, 9.1, 4.2 Hz, 2H), 1.26-1.36 (m, 2H), 0.93 (d, J = 3.5 Hz, 6H). Mass Spectrum (LCMS, APCI pos.): Calcd. for C₂₄H₂₄F₃N₃O: 428.2 (M + H); found: 428.3. |
| 37 | 3-[5-(Chloro-phenyl)-1H-benzimidazol-2-yl]-8,8-dimethyl-1-oxa-2-aza-spiro[4.5]dec-2-ene hydrochloride<br>¹H-NMR (400 MHz, d₄-MeOH) δ: 7.78 (d, J = 8.6 Hz, 1H), 7.72 (s, 1H), 7.60 (d, J = 8.6 Hz, 1H), 7.45-7.49 (m, 1H), 7.30-7.39 (m, 3H), 3.25 (s, 2H), 1.84-1.92 (m, 2H), 1.72-1.81 (m, 2H), 1.56 (ddd, J = 13.5, 9.1, 4.2 Hz, 2H), 1.26-1.35 (m, 2H), 0.93 (d, J = 3.5 Hz, 6H). Mass Spectrum (LCMS, ESI pos.): Calcd. for C₂₃H₂₄ClN₃O: 393.2 (M + H); found: 393.3. |
| 38 | 3-[5-(2,6-Difluoro-phenyl)-1H-benzimidazol-2-yl]-1,8-dioxa-2-aza-spiro[4.5]dec-2-ene hydrochloride<br>¹H-NMR (400 MHz, d₄-MeOH) δ: 7.82 (dd, J = 8.6, 0.8 Hz, 1H), 7.79 (s, 1H), 7.63 (dd, J = 8.6, 1.5 Hz, 1H), 7.39 (tt, J = 8.5, 6.4 Hz, 1H), 7.06 (t, J = 8.2 Hz, 2H), 3.78-3.88 (m, 2H), 3.64-3.73 (m, 2H), 3.34 (s, 2H), 1.86-1.95 (m, 4H). |
| 39 | 8,8-Dimethyl-3-[7-trifluoromethyl-5-(2-trifluoromethyl-phenyl)-1H-benzimidazol-2-yl]-1-oxa-2-aza-spiro[4.5]dec-2-ene hydrochloride<br>¹H-NMR (400 MHz, d₄-MeOH) δ: 7.74 (d, J = 7.6 Hz, 1H), 7.65 (s, 1H), 7.57-7.64 (m, 1H), 7.49-7.55 (m, 1H), 7.41 (s, 1H), 7.37 (d, J = 7.6 Hz, 1H), 3.27 (s, 2H), 1.76-1.86 (m, 2H), 1.66-1.76 (m, 2H), 1.53 (ddd, J = 13.3, 8.9, 4.3 Hz, 2H), 1.25-1.35 (m, 2H), 0.92 (d, J = 2.5 Hz, 6H). Mass Spectrum (LCMS, APCI pos.): Calcd. for C₂₅H₂₃F₆N₃O: 496.2 (M + H); found: 496.3. |
| 40 | 3-[5-(2-Chloro-phenyl)-1H-benzimidazol-2-yl]-1,8-dioxa-2-aza-spiro[4.5]dec-2-ene hydrochloride<br>¹H-NMR (400 MHz, d₄-MeOH) δ: 7.76-7.82 (m, 1H), 7.72-7.75 (m, 1H), 7.61 (dd, J = 8.6, 1.5 Hz, 1H), 7.44-7.50 (m, 1H), 7.29-7.40 (m, 3H), 3.78-3.88 (m, 2H), 3.63-3.73 (m, 2H), 3.35 (s, 2H), 1.87-1.95 (m, 4H). Mass Spectrum (LCMS, ESI pos.): Calcd. for C₂₀H₁₈ClN₃O:<br>368.1 (M + H); found: 368.2. |
| 41 | 3-[7-Chloro-5-(2-trifluoromethyl-phenyl)-1H-benzimidazol-2-yl]-8,8-dimethyl-1-oxa-2-aza-spiro[4.5]dec-2-ene hydrochloride<br>¹H-NMR (400 MHz, d₄-MeOH) δ: 7.69-7.83 (m, 2H), 7.44-7.67 (m, 2H), 7.25-7.42 (m, 2H), 3.26 (s, 2H), 1.61-1.86 (m, 4H), 1.44-1.58 (m, 2H), 1.21-1.35 (m, 2H), 0.85-0.95 (m, 6H). Mass Spectrum (LCMS, ESI pos.): Calcd. for C₂₄H₂₃ClF₃N₃O: 462.2 (M + H); found: 462.3. |
| 42 | 3-[7-Trifluoromethyl-5-(2-trifluoromethyl-phenyl)-1H-benzimidazol-2-yl]-1,8-dioxa-2-aza-spiro[4.5]dec-2-ene hydrochloride<br>¹H-NMR (400 MHz, d₄-MeOH) δ: 7.76 (d, J = 7.6 Hz, 1H), 7.72 (s, 1H), 7.59-7.65 (m, 1H), 7.55 (d, J = 7.8 Hz, 1H), 7.52 (s, 1H), 7.39 (d, J = 7.6 Hz, 1H), 3.78-3.86 (m, 2H), 3.63-3.72 (m, 2H), 3.37 (s, 2H), 1.82-1.91 (m, 4H). Mass Spectrum (LCMS, ESI pos.): Calcd. for C₂₂H₁₇F₆N₃O₂: 470.1 (M + H); found: 470.2. |

Example 17

2-(1-Oxa-2-aza-spiro[4.5]dec-2-en-3-yl)-5-(2-trifluoromethyl-phenyl)-1H-imidazo[4,5-b]pyridine hydrochloride (Cpd 56)

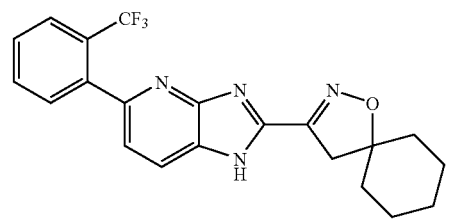

A. 3-Nitro-6-(2-trifluoromethyl-phenyl)-pyridin-2-ylamine

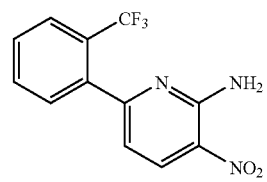

To a solution of 6-chloro-2-nitro-pyridin-3-ylamine (143 mg, 1.00 mmol), 2-trifluoromethylphenylboronic acid (285 mg, 1.50 mmol) and K₃PO₄ (424 mg, 2.00 mmol) in toluene (5 mL) were added S-Phos (16.4 mg, 0.040 mmol) and Pd(OAc)₂ (4.49 mg, 0.020 mmol). The resulting mixture was stirred at 90° C. under Ar for 4 h. The reaction mixture was allowed to cool to rt, diluted with EtOAc (20 mL) and filtered through a pad of Celite. The filtrate was concentrated, and the resulting residue was purified on silica (EtOAc/hexanes, 0:1 to 1:1 v/v) to obtain the title compound (130 mg, 46%). ¹H-NMR (400 MHz, CDCl₃) δ: 8.39 (d, J=8.3 Hz, 1H), 7.70 (d, J=7.8 Hz, 1H), 7.46-7.62 (m, 2H), 7.39 (d, J=7.6 Hz, 1H), 6.76 (d, J=8.6 Hz, 1H).

B. 6-(2-Trifluoromethyl-phenyl)-pyridine-2,3-diamine

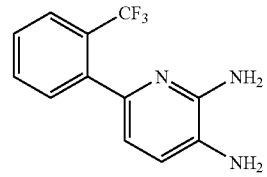

To a solution of 2-nitro-6-(2-trifluoromethyl-phenyl)-pyridin-3-ylamine (130 mg, 0.460 mmol, as prepared in the previous step) in EtOH (10 mL), 10% Pd/C (60 mg) was added. The resulting mixture was hydrogenated at 50 psi for 3 h. The reaction mixture was filtered through a pad of Celite, and the filtrate was concentrated in vacuo to obtain the title compound, which was directly used in the next step without further purification. ¹H-NMR (400 MHz, CDCl₃) δ: 7.62 (d, J=7.8 Hz, 1H), 7.41-7.49 (m, 1H), 7.29-7.41 (m, 2H), 6.81 (d, J=7.8 Hz, 1H), 6.64 (d, J=7.8 Hz, 1H), 4.31 (br. s., 2H), 3.34 (br. s., 2H).

C. 1-Oxa-2-aza-spiro[4.5]dec-2-ene-3-carboxylic acid [2-amino-6-(2-trifluoromethyl-phenyl)-pyridin-3-yl]-amide

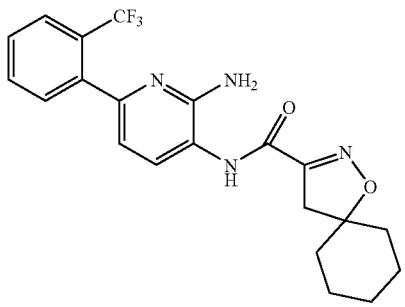

The title compound was prepared from 6-(2-trifluoromethyl-phenyl)-pyridine-2,3-diamine (as prepared in the previous step) according to the procedure described in Example 16, step D. $^1$H-NMR (400 MHz, CDCl$_3$) δ: 8.26 (s, 1H), 7.70-7.76 (m, 2H), 7.55-7.61 (m, 1H), 7.45-7.52 (m, 2H), 6.87 (d, J=7.8 Hz, 1H), 4.72 (s, 2H), 3.03 (s, 2H), 1.75-1.88 (m, 5H), 1.66-1.75 (m, 2H), 1.48 (br. s., 4H). Mass Spectrum (LCMS, ESI pos.): Calcd. for C$_{21}$H$_{21}$F$_3$N$_4$O$_2$: 419.2 (M+H). found: 419.2.

D. 2-(1-Oxa-2-aza-spiro[4.5]dec-2-en-3-yl)-5-(2-trifluoromethyl-phenyl)-1H-imidazo[4,5-b]pyridine hydrochloride The title compound was prepared from 1-oxa-2-aza-spiro[4.5]dec-2-ene-3-carboxylic acid [2-amino-6-(2-trifluoromethyl-phenyl)-pyridin-3-yl]-amide (as prepared in the previous step) according to the procedures described in Example 16, steps E and F, except that the iron powder in step E was omitted. $^1$H-NMR (400 MHz, d$_4$-MeOH) δ: 8.08 (d, J=8.3 Hz, 1H), 7.84 (d, J=7.8 Hz, 1H), 7.69-7.76 (m, 1H), 7.61-7.68 (m, 1H), 7.58 (d, J=7.6 Hz, 1H), 7.43 (d, J=8.3 Hz, 1H), 3.32 (s, 2H), 1.72-1.90 (m, 6H), 1.47-1.65 (m, 4H). Mass Spectrum (LCMS, ESI pos.): Calcd. for C$_{21}$H$_{19}$F$_3$N$_4$O: 401.2 (M+H). found: 401.2.

Example 18

2-(1-Oxa-2-aza-spiro[4.5]dec-2-en-3-yl)-6-(2-trifluoromethyl-phenyl)-3H-imidazo[4,5-c]pyridine hydrochloride (Cpd 57)

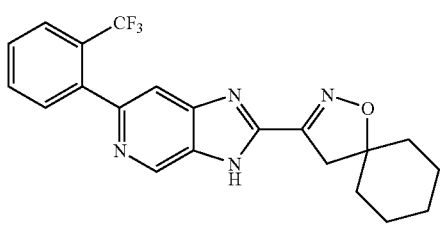

A. 4-Nitro-6-(2-trifluoromethyl-phenyl)-pyridin-3-ylamine

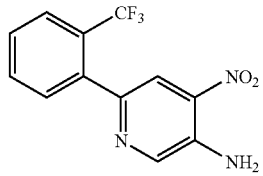

The title compound was prepared from 5-bromo-3-nitro-pyridin-2-ylamine (patent application WO 2005037197) and 2-trifluoromethylphenylboronic acid according to the procedure described in Example 17, step A. $^1$H-NMR (400 MHz, CDCl$_3$) δ: 9.26 (s, 1H), 7.77 (d, J=7.8 Hz, 1H), 7.59-7.66 (m, 1H), 7.52-7.59 (m, 1H), 7.48 (d, J=7.6 Hz, 1H), 6.79 (s, 1H).

B. 1-Oxa-2-aza-spiro[4.5]dec-2-ene-3-carboxylic acid [4-nitro-6-(2-trifluoromethyl-phenyl)-pyridin-3-yl]-amide

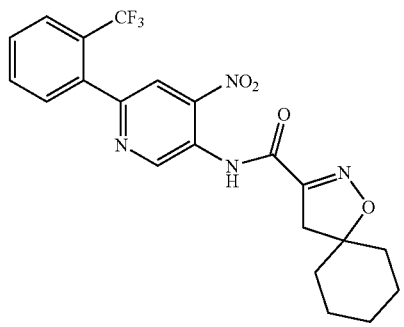

The title compound was prepared from 4-nitro-6-(2-trifluoromethyl-phenyl)-pyridin-3-ylamine (as prepared in the previous step) and 1-oxa-2-aza-spiro[4.5]dec-2-ene-3-carboxylic acid (as prepared in Example 1, step B) according to the procedure described in Example 16, step D. $^1$H-NMR (400 MHz, CDCl$_3$) δ: 9.45 (s, 1H), 8.93 (s, 1H), 7.80 (d, J=7.3 Hz, 1H), 7.65 (t, J=7.1 Hz, 1H), 7.59 (t, J=7.5 Hz, 1H), 7.51 (d, J=7.6 Hz, 1H), 2.97 (s, 2H), 1.73-1.90 (m, 5H), 1.62-1.73 (m, 3H), 1.40-1.54 (m, 2H). Mass Spectrum (LCMS, ESI pos.): Calcd. for C$_{21}$H$_{19}$F$_3$N$_4$O$_4$: 449.1 (M+H). found: 449.2.

C. 2-(1-Oxa-2-aza-spiro[4.5]dec-2-en-3-yl)-6-(2-trifluoromethyl-phenyl)-3H-imidazo[4,5-c]pyridine hydrochloride The title compound was prepared from 1-oxa-2-aza-spiro[4.5]dec-2-ene-3-carboxylic acid [4-nitro-6-(2-trifluoromethyl-phenyl)-pyridin-3-yl]-amide (as prepared in the previous step) according to the procedures described in Example 16, steps E and F. $^1$H-NMR (400 MHz, CDCl$_3$) δ: 8.94 (s, 1H), 7.84 (d, J=7.6 Hz, 1H), 7.69-7.76 (m, 1H), 7.60-7.68 (m, 2H), 7.56 (d, J=7.3 Hz, 1H), 4.56 (s, 2H), 1.73-1.90 (m, 6H), 1.48-1.66 (m, 4H). Mass Spectrum (LCMS, ESI pos.): Calcd. for C$_{21}$H$_{19}$F$_3$N$_4$O: 401.2 (M+H). found: 401.2.

Using the procedures described in Example 18, and reagents, starting materials and conditions known to those

| Cpd | Data |
|---|---|
| 58 | 2-(1-Oxa-2-aza-spiro[4.5]dec-2-en-3-yl)-6-(2-trifluoromethyl-phenyl)-3H-imidazo[4,5-b]pyridine hydrochloride<br>$^1$H-NMR (400 MHz, d$_4$-MeOH/CDCl$_3$) δ: 8.28 (br. s., 1H), 7.73 (d, J = 7.6 Hz, 1H), 7.58 (t, J = 7.2 Hz, 1H), 7.50 (t, J = 7.6 Hz, 1H), 7.39 (s, 1H), 7.33 (d, J = 7.6 Hz, 1H), 3.23 (s, 2H), 1.64-1.83 (m, 7H), 1.40-1.52 (m, 4H).<br>Mass Spectrum (LCMS, ESI pos.): Calcd. for C$_{21}$H$_{19}$F$_3$N$_4$O: 401.2 (M + H); found: 401.3. |

Example 19

3-[7-Methyl-5-(2,6-difluorophenyl)-1H-benzimidazol-2-yl]-1-oxa-2-aza-spiro[4.5]dec-2-ene hydrochloride (Cpd 48)

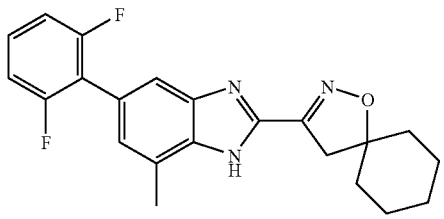

A.
3-Dimethoxymethyl-1-oxa-2-aza-spiro[4.5]dec-2-ene

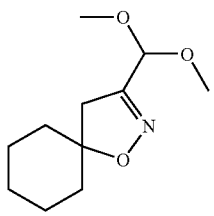

To a 40 mL vial equipped with a magnetic stir bar was added DMF (10 mL) and dimethoxy-acetaldehyde (1.50 mL, 10.0 mmol). Aqueous hydroxylamine (0.640 mL, 10.5 mmol) was added via syringe, and the mixture was stirred for 2 h at rt. NCS (1.40 g, 10.5 mmol) was added in small portions as a solid. The mixture was stirred an additional 1 h at rt, diluted with DCM (40 mL), dried over MgSO$_4$, and filtered. The solid was washed with DCM. The filtrate was diluted to a volume of 100 mL and transferred to two 60 mL syringes. Methylene-cyclohexane (2.40 mL, 20.0 mmol), DIPEA (1.92 mL, 11.0 mmol), and DCM (10 mL) were placed in a 200 mL round-bottom flask equipped with a magnetic stir bar. The above-prepared chlorooxime solution was added dropwise with a syringe pump at a rate of 0.0774 mL/min until the addition was complete. The mixture stirred at rt for 3 days, and the solvent was removed under reduced pressure. The residue was dissolved in water (50 mL) and extracted three times with hexanes (25 mL). The combined organic extracts were dried over MgSO$_4$ and concentrated in vacuo. The material was used in the next step without purification.

B. 1-Oxa-2-aza-spiro[4.5]dec-2-ene-3-carbaldehyde

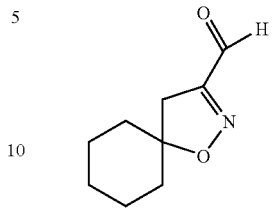

3-Dimethoxymethyl-1-oxa-2-aza-spiro[4.5]dec-2-ene (1.06 g, 4.97 mmol, as prepared in the previous step) was placed in a 50 mL round-bottom flask equipped with a stir bar. Acetone (20 mL), water (0.3 mL), and Amberlyst-15 resin (200 mg) were added. The mixture was stirred at rt for 24 h. The solids were removed by filtration and rinsed with acetone (20 mL), and the solvent was removed under reduced pressure. The residue was purified by column chromatography using a 40-g SiO$_2$ pre-packed column eluting with EtOAc/heptane, 0:1 to 3:2, v/v over 30 min, yielding 451 mg (54%) of the desired compound. $^1$H-NMR (400 MHz, CDCl$_3$) δ: 9.90 (s, 1H), 2.81 (s, 2H), 1.72-1.87 (m, 4H), 1.58-1.69 (m, 2H), 1.40-1.53 (m, 4H).

C. 2',6'-Difluoro-5-methyl-biphenyl-3,4-diamine

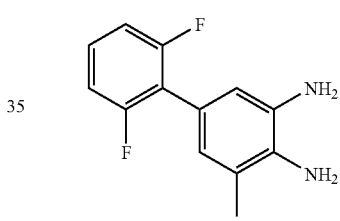

The title compound was prepared from 2-methyl-6-nitro-4-(4,4,5,5-tetramethyl-[1,3,2]dioxaborolan-2-yl)-phenylamine (as prepared in Example 8, step A) and 2-bromo-1,3-difluoro-benzene according to the procedures described in Example 4, step A and Example 1, step E. $^1$H-NMR (400 MHz, CDCl$_3$) δ: 7.17 (tt, J=8.3, 6.3 Hz, 1H), 6.87-6.97 (m, 2H), 6.76 (s, 1H), 6.72 (s, 1H), 3.44 (br. s., 4H), 2.21 (s, 3H).

D. 3-[7-Methyl-5-(2,6-difluorophenyl)-1H-benzimidazol-2-yl]-1-oxa-2-aza-spiro[4.5]dec-2-ene

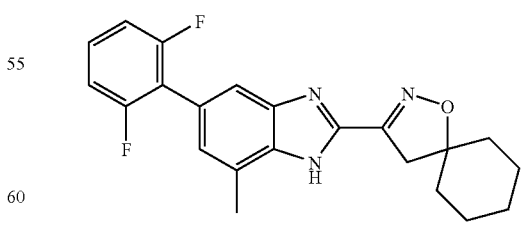

2',6'-Difluoro-5-methyl-biphenyl-3,4-diamine (186 mg, 0.792 mmol, as prepared in the previous step) was placed in an 8 mL vial equipped with a stir bar, and dry DMF (2 mL) was added. 1-Oxa-2-aza-spiro[4.5]dec-2-ene-3-carbaldehyde (122 mg, 0.730 mmol, as prepared in step B of this Example) was added as a solution in DMF (2 mL). Solid Na$_2$S$_2$O$_5$ (153 mg, 0.803 mmol) was added, and the mixture was heated to 100° C. for 4 h. The cooled mixture was poured into water (100 mL) and extracted three times with EtOAc (50 mL). The combined organic extracts were dried over MgSO$_4$, filtered, and the solvents were removed under reduced pressure. The residue was purified by column chromatography using a 4-g SiO$_2$ pre-packed column eluting with EtOAc/ hexanes, 0:1 to 3:17, v/v over 30 min, yielding 105 mg (38%) of the title compound. $^1$H-NMR (400 MHz, d$_6$-DMSO) δ: 7.43-7.55 (m, 2H), 7.15-7.30 (m, 3H), 3.35 (s, 2H), 2.61 (s, 3H), 1.63-1.83 (m, 6H), 1.34-1.57 (m, 4H). Mass Spectrum (LCMS, ESI pos.): Calcd. for C$_{22}$H$_{21}$F$_2$N$_3$O: 382.2 (M+H). found: 382.2.

E. 3-[7-Methyl-5-(2,6-difluorophenyl)-1H-benzimidazol-2-yl]-1-oxa-2-aza-spiro[4.5]dec-2-ene hydrochloride The title compound was prepared from 3-[7-methyl-5-(2, 6-difluorophenyl)-1H-benzimidazol-2-yl]-1-oxa-2-aza-spiro[4.5]dec-2-ene (as prepared in the previous step) according to the procedure described in Example 1, step H. $^1$H-NMR (400 MHz, CDCl$_3$) δ: $^1$H-NMR (400 MHz, d$_6$-DMSO) δ: 7.43-7.55 (m, 2H), 7.15-7.30 (m, 3H), 3.35 (s, 2H), 2.61 (s, 3H), 1.63-1.83 (m, 6H), 1.34-1.57 (m, 4H). Mass Spectrum (LCMS, ESI pos.): Calcd. for C$_{22}$H$_{21}$F$_2$N$_3$O: 382.2 (M+H). found: 382.2.

Example 20

3-[7-Methyl-5-(2-fluorophenyl)-1H-benzimidazol-2-yl]-1-oxa-2-aza-spiro[4.5]dec-2-ene hydrochloride (Cpd 47)

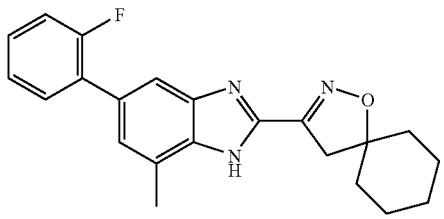

A. 2'-Fluoro-5-methyl-biphenyl-3,4-diamine

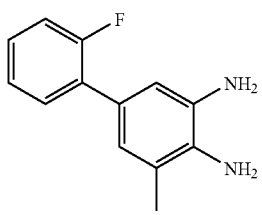

The title compound was prepared from 4-bromo-2-methyl-6-nitro-phenylamine and 2-(2-fluoro-phenyl)-4,4,5,5-tetramethyl-[1,3,2]dioxaborolane using the procedures described in Example 1, steps D and E. $^1$H-NMR (400 MHz, CDCl$_3$) δ: 7.36 (td, J=7.8, 1.9 Hz, 1H), 7.16-7.23 (m, 1H), 7.03-7.15 (m, 2H), 6.84 (s, 1H), 6.79-6.82 (m, 1H), 3.47 (br. s., 4H), 2.20 (s, 3H).

B. 3-[7-Methyl-5-(2-fluorophenyl)-1H-benzimidazol-2-yl]-1-oxa-2-aza-spiro[4.5]dec-2-ene

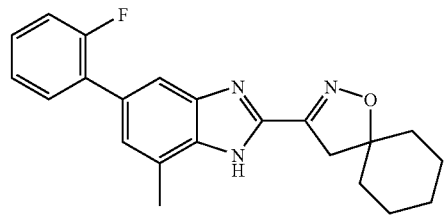

1-Oxa-2-aza-spiro[4.5]dec-2-ene-3-carbaldehyde (167 mg, 1.00 mmol, as prepared in Example 19, step B) was placed in a 25 mL round-bottom flask equipped with a magnetic stir bar. 2'-Fluoro-5-methyl-biphenyl-3,4-diamine (218 mg, 1.01 mmol, as prepared in the previous step) was added as a solution in EtOH (10 mL). The flask was fitted with a reflux condenser (top open to air), and the mixture was heated to 80° C. for 6 h. The cooled mixture was concentrated under reduced pressure. The residue was purified by column chromatography using a 40-g SiO$_2$ pre-packed column eluting with EtOAc/hexanes, 0:1 to 3:7, v/v over 30 min, yielding 159 mg (44%) of the title compound. $^1$H-NMR (400 MHz, CDCl$_3$) δ: 7.57 (br. s., 1H), 7.50 (td, J=7.8, 1.9 Hz, 1H), 7.31-7.37 (m, 1H), 7.08-7.28 (m, 4H), 2.64 (s, 3H), 2.31 (s, 2H), 1.69-1.89 (m, 6H), 1.47-1.64 (m, 4H).

C. 3-[7-Methyl-5-(2-fluorophenyl)-1H-benzimidazol-2-yl]-1-oxa-2-aza-spiro[4.5]dec-2-ene hydrochloride The title compound was prepared from 3-[7-methyl-5-(2-fluorophenyl)-1H-benzimidazol-2-yl]-1-oxa-2-aza-spiro [4.5]dec-2-ene (as prepared in the previous step) according to the procedure described in Example 1, step H. $^1$H-NMR (400 MHz, d$_6$-DMSO) δ: 7.54-7.65 (m, 2H), 7.39-7.49 (m, 1H), 7.28-7.38 (m, 3H), 3.36 (s, 2H), 2.63 (s, 3H), 1.65-1.82 (m, 6H), 1.32-1.57 (m, 4H). Mass Spectrum (LCMS, ESI pos.): Calcd. for C$_{22}$H$_{22}$FN$_3$O: 364.2 (M+H). found: 364.2.

Example 21

3-[7-Methyl-5-(2-trifluoromethylphenyl)-1H-benzimidazol-2-yl]-1-oxa-2-aza-spiro[4.5]dec-2-ene hydrochloride (Cpd 46)

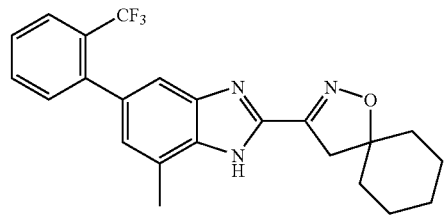

A. 5-Methyl-2'-trifluoromethyl-biphenyl-3,4-diamine

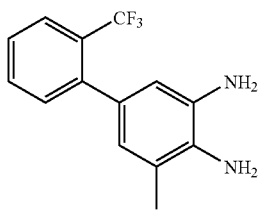

The title compound was prepared from 4-bromo-2-methyl-6-nitro-phenylamine and 4,4,5,5-tetramethyl-2-(2-trifluoromethyl-phenyl)-[1,3,2]dioxaborolane according to the procedures described in Example 1, steps D and E. $^1$H-NMR (400 MHz, CDCl$_3$) δ: 7.68 (d, J=7.8 Hz, 1H), 7.47 (t, J=7.3 Hz, 1H), 7.36 (t, J=7.6 Hz, 1H), 7.30 (d, J=7.6 Hz, 1H), 6.59 (s, 1H), 6.61 (s, 1H), 3.41 (br. s., 4H), 2.19 (s, 3H).

B. 3-[7-Methyl-5-(2-trifluoromethylphenyl)-1H-benzimidazol-2-yl]-1-oxa-2-aza-spiro[4.5]dec-2-ene

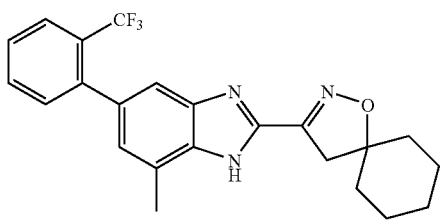

1-Oxa-2-aza-spiro[4.5]dec-2-ene-3-carbaldehyde (135 mg, 0.807 mmol, as prepared in Example 19, step B) was placed in a 4 mL vial equipped with a magnetic stir bar. 40% Aqueous NaHSO$_3$ (0.8 mL) was added via syringe, and the mixture stirred at rt for 2 h. 5-Methyl-2'-trifluoromethyl-biphenyl-3,4-diamine (246 mg, 0.923 mmol, as prepared in the previous step) was placed in an 8 mL vial equipped with a magnetic stir bar. EtOH (2 mL) was added. The 1-oxa-2-aza-spiro[4.5]dec-2-ene-3-carbaldehyde solution was added to the 5-methyl-2'-trifluoromethyl-biphenyl-3,4-diamine solution. The flask which had contained the 1-oxa-2-aza-spiro[4.5]dec-2-ene-3-carbaldehyde solution was rinsed with EtOH (0.5 mL) and water (0.25 mL), and this was also added to the 5-methyl-2'-trifluoromethyl-biphenyl-3,4-diamine solution. The mixture was heated to 90° C. for 2 h. The mixture was poured into water, and the precipitate was isolated by filtration. The solid was washed with water, dissolved in EtOAc, dried over MgSO$_4$, filtered, and the solvent was removed under reduced pressure. The residue was purified by column chromatography using a 40-g SiO$_2$ pre-packed column eluting with EtOAc/heptane, 0:1 to 3:7, v/v over 30 min, yielding 136 mg (41%) of the title compound. $^1$H-NMR (400 MHz, d$_4$-MeOH) δ: 7.76 (d, J=7.8 Hz, 1H), 7.61 (t, J=7.5 Hz, 1H), 7.52 (t, J=7.6 Hz, 1H), 7.26-7.49 (m, 2H), 7.03 (br. s., 1H), 2.63 (br. s., 3H), 1.69-1.88 (m, 6H), 1.45-1.63 (m, 4H).

C. 3-[7-Methyl-5-(2-trifluoromethylphenyl)-1H-benzimidazol-2-yl]-1-oxa-2-aza-spiro[4.5]dec-2-ene hydrochloride The title compound was prepared from 3-[7-methyl-5-(2-trifluoromethylphenyl)-1H-benzimidazol-2-yl]-1-oxa-2-aza-spiro[4.5]dec-2-ene (as prepared in the previous step) according to the procedure described in Example 1, step H. $^1$H-NMR (400 MHz, d$_6$-DMSO) δ: 7.85 (d, J=7.8 Hz, 1H), 7.73 (t, J=7.3 Hz, 1H), 7.63 (t, J=7.6 Hz, 1H), 7.47 (d, J=7.6 Hz, 1H), 7.36 (s, 1H), 7.10 (s, 1H), 3.34 (s, 2H), 2.60 (s, 3H), 1.64-1.84 (m, 6H), 1.33-1.57 (m, 4H). Mass Spectrum (LCMS, ESI pos.): Calcd. for C$_{23}$H$_{22}$F$_3$N$_3$O: 414.2 (M+H). found: 414.2.

Example 22

3-[5-(2-Chlorophenyl)-1H-benzimidazol-2-yl]-1-oxa-2-aza-spiro[4.5]dec-2-ene hydrochloride (Cpd 45)

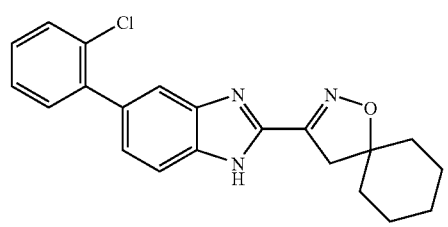

A. 3-(5-Bromo-1H-benzimidazol-2-yl)-1-oxa-2-aza-spiro[4.5]dec-2-ene

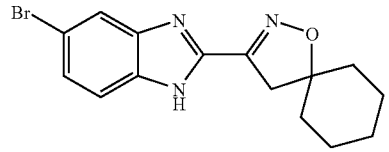

The title compound was prepared from 4-bromo-benzene-1,2-diamine and 1-oxa-2-aza-spiro[4.5]dec-2-ene-3-carboxylic acid (as prepared in Example 1, step B) according to the procedures described in Example 1, steps F and G. $^1$H-NMR (400 MHz, d$_4$-MeOH) δ: 7.74 (s, 1H), 7.51 (d, J=8.6 Hz, 1H), 7.40 (dd, J=8.6, 1.8 Hz, 1H), 3.25 (s, 2H), 1.69-1.87 (m, 6H), 1.45-1.63 (m, 4H).

B. 3-[5-(2-Chlorophenyl)-1H-benzimidazol-2-yl]-1-oxa-2-aza-spiro[4.5]dec-2-ene

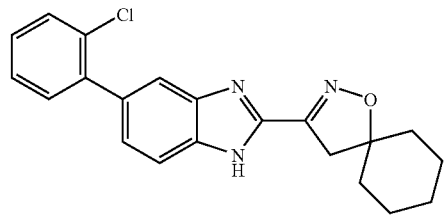

The title compound was prepared from 3-(5-bromo-1H-benzimidazol-2-yl)-1-oxa-2-aza-spiro[4.5]dec-2-ene (as prepared in the previous step) and 2-chloro-benzene-boronic acid according to the procedure described in Example 1, step D. $^1$H-NMR (400 MHz, d$_4$-MeOH) δ: 7.46-7.76 (m, 3H), 7.29-7.42 (m, 4H), 3.27 (s, 2H), 1.69-1.87 (m, 6H), 1.46-1.62 (m, 4H).

C. 3-[5-(2-Chlorophenyl)-1H-benzimidazol-2-yl]-1-oxa-2-aza-spiro[4.5]dec-2-ene hydrochloride The title compound was prepared from 3-[5-(2-chlorophenyl)-1H-benzimidazol-2-yl]-1-oxa-2-aza-spiro[4.5]dec-2-ene (as prepared in the previous step) according to the procedure described in Example 1, step H. $^1$H-NMR (400 MHz, d$_6$-DMSO) δ: 7.71 (d, J=8.6 Hz, 1H), 7.66 (s, 1H), 7.56-7.62 (m, 1H), 7.35-7.52 (m, 4H), 3.31 (s, 2H), 1.63-1.81 (m, 6H), 1.35-1.55 (m, 4H). Mass Spectrum (LCMS, ESI pos.): Calcd. for C$_{21}$H$_{20}$ClN$_3$O: 366.1 (M+H). found: 366.2.

Example 23

3-[7-(3-Methoxy-propyl)-5-(2-trifluoromethylphenyl)-1H-benzimidazol-2-yl]-1-oxa-2-aza-spiro[4.5]dec-2-ene hydrochloride (Cpd 52)

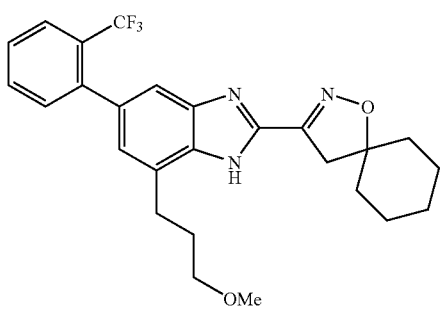

A. 5-(3-Methoxy-propyl)-2'-trifluoromethyl-biphenyl-3,4-diamine

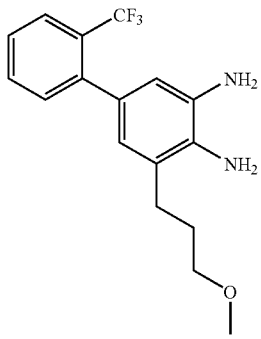

The title compound was prepared from 3-iodo-5-nitro-2'-trifluoromethyl-biphenyl-4-ylamine (as prepared in Example 9, step A) and 3-methoxy-propyne according to the procedures described in Example 10, steps A and B.

B. 3-[7-(3-Methoxy-propyl)-5-(2-trifluoromethylphenyl)-1H-benzimidazol-2-yl]-1-oxa-2-aza-spiro[4.5]dec-2-ene hydrochloride The title compound was prepared from 5-(3-methoxy-propyl)-2'-trifluoromethyl-biphenyl-3,4-diamine (as prepared in the previous step) and 1-oxa-2-aza-spiro[4.5]dec-2-ene-3-carboxylic acid (as prepared in Example 1, step B) according to the procedures described in Example 1, steps F through H. $^1$H-NMR (400 MHz, d$_6$-DMSO) δ: 7.86 (d, J=7.6 Hz, 1H), 7.74 (t, J=7.5 Hz, 1H), 7.64 (t, J=7.6 Hz, 1H), 7.48 (d, J=7.6 Hz, 1H), 7.41 (s, 1H), 7.11 (s, 1H), 3.31-3.41 (m, 2H), 3.36 (s, 2H), 3.22 (s, 3H), 3.03 (t, J=7.5 Hz, 2H), 1.86-1.98 (m, 2H), 1.63-1.83 (m, 6H), 1.32-1.59 (m, 4H). Mass Spectrum (LCMS, ESI pos.): Calcd. for C$_{26}$H$_{28}$F$_3$N$_3$O$_2$: 472.2 (M+H). found: 472.3.

Example 24

3-[7-Chloro-4-methyl-5-(2-trifluoromethylphenyl)-1H-benzimidazol-2-yl]-1-oxa-2-aza-spiro[4.5]dec-2-ene hydrochloride (Cpd 55)

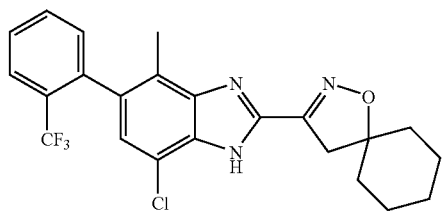

A. 5-Chloro-2-methyl-2'-trifluoromethyl-biphenyl-4-ylamine

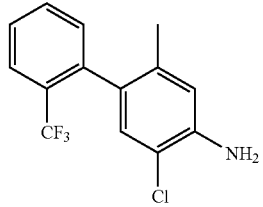

The title compound was prepared from 1-bromo-5-chloro-2-methyl-4-nitro-benzene and 2-trifluorophenylboronic acid according to the procedures described in Example 1, steps D and E. $^1$H-NMR (400 MHz, CDCl$_3$) δ: 7.72 (d, J=7.8 Hz, 1H), 7.51 (t, J=7.6 Hz, 1H), 7.43 (t, J=7.6 Hz, 1H), 7.20 (d, J=7.3 Hz, 1H), 7.03 (s, 1H), 6.64 (s, 1H), 4.01 (br. s., 2H), 1.90 (s, 3H).

B. N-(5-Chloro-2-methyl-3-nitro-2'-trifluoromethyl-biphenyl-4-yl)-acetamide

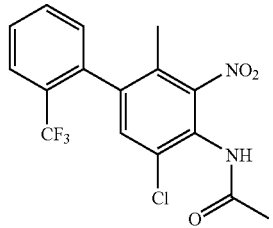

5-Chloro-2-methyl-2'-trifluoromethyl-biphenyl-4-ylamine (384 mg, 1.34 mmol, as prepared in the previous step) was placed in a 50 mL round-bottom flask equipped with a magnetic stir bar. Acetic anhydride (1.5 mL) was added. The mixture was stirred at rt for 1 h and then cooled to 0° C. To a 4 mL vial cooled at 0° C. was added AcOH (0.27 mL), acetic anhydride (0.31 mL), and nitric acid (0.45 mL). The nitrating mixture was added dropwise via pipette to the above-prepared solution, maintaining the temperature below 10° C. Upon completion of the addition, the mixture was stirred at 0° C. for 1 hour and poured onto ice. The resulting precipitate was isolated by filtration, washed with water, and dissolved in EtOAc. The solution was dried over $MgSO_4$ and filtered, and the solvent was removed under reduced pressure. The residue was purified by column chromatography using a 40-g $SiO_2$ pre-packed column eluting with EtOAc/hexanes, 0:1 to 3:7, v/v over 30 min, yielding 301 mg (60%) of the title compound. $^1$H-NMR (400 MHz, $CDCl_3$) δ: 7.80 (d, J=7.8 Hz, 1H), 7.54-7.68 (m, 2H), 7.50 (s, 1H), 7.43 (s, 1H), 7.25 (d, J=7.6 Hz, 1H), 2.21 (s, 3H), 1.98 (s, 3H).

C. 3-[7-Chloro-4-methyl-5-(2-trifluoromethylphenyl)-1H-benzimidazol-2-yl]-1-oxa-2-aza-spiro[4.5]dec-2-ene hydrochloride The title compound was prepared from N-(5-chloro-2-methyl-3-nitro-2'-trifluoromethyl-biphenyl-4-yl)-acetamide (as prepared in the previous step) and 1-oxa-2-aza-spiro[4.5]dec-2-ene-3-carboxylic acid (as prepared in Example 1, step B) according to the procedures described in Example 1, steps E through H. $^1$H-NMR (400 MHz, $d_6$-DMSO) δ: 7.87 (d, J=7.6 Hz, 1H), 7.75 (t, J=7.3 Hz, 1H), 7.66 (t, J=7.7 Hz, 1H), 7.40 (d, J=7.3 Hz, 1H), 7.07 (s, 1H), 3.34 (s, 2H), 2.16 (s, 3H), 1.62-1.83 (m, 6H), 1.31-1.61 (m, 4H). Mass Spectrum (LCMS, ESI pos.): Calcd. for $C_{23}H_{21}ClF_3N_3O$: 448.1 (M+H). found: 448.3.

Example 25

3-[7-Chloro-5-(2-trifluoromethoxyphenyl)-1H-benzimidazol-2-yl]-1-oxa-2-aza-spiro[4.5]dec-2-ene methanesulfonate (Cpd 50)

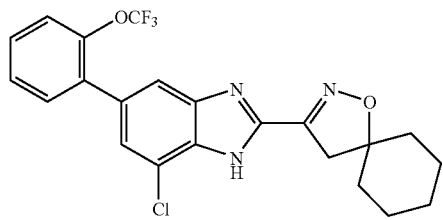

A. 3-[7-Chloro-5-(2-trifluoromethoxyphenyl)-1H-benzimidazol-2-yl]-1-oxa-2-aza-spiro[4.5]dec-2-ene

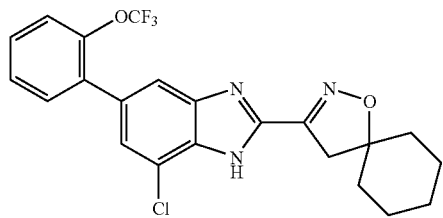

The title compound was prepared from 4-bromo-2-nitrophenylamine, 2-trifluoromethoxyphenylboronic acid, and 1-oxa-2-aza-spiro[4.5]dec-2-ene-3-carboxylic acid (as prepared in Example 1, step B) according to the procedures described in Example 6, steps A through C. $^1$H-NMR (400 MHz, $d_4$-MeOH) δ: 7.51-7.65 (m, 2H), 7.36-7.50 (m, 4H), 3.31 (br. s., 3H), 1.68-1.90 (m, 6H), 1.45-1.64 (m, 4H).

B. 3-[7-Chloro-5-(2-trifluoromethoxyphenyl)-1H-benzimidazol-2-yl]-1-oxa-2-aza-spiro[4.5]dec-2-ene methanesulfonate 3-[7-Chloro-5-(2-trifluoromethoxyphenyl)-1H-benzimidazol-2-yl]-1-oxa-2-aza-spiro[4.5]dec-2-ene (64.0 mg, 0.142 mmol, as prepared in the previous step) was placed in an 8 mL vial, and EtOAc (1 mL) was added. Methanesulfonic acid (9.22 μL, 0.142 mmol) was added via microsyringe. The solvent was removed under reduced pressure. The residue was triturated with ether (4 mL), and the solvent was removed via pipette. Trituration and solvent removal were repeated. The solid was dried under high vacuum to yield 72.3 mg (93%) of the title compound. $^1$H-NMR (400 MHz, $d_6$-DMSO) δ: 7.59-7.66 (m, 1H), 7.45-7.59 (m, 4H), 7.40 (s, 1H), 3.32 (s, 2H), 2.33 (s, 3H), 1.59-1.82 (m, 6H), 1.30-1.59 (m, 4H). Mass Spectrum (LCMS, ESI pos.): Calcd. for $C_{23}H_{19}ClF_3N_3O_2$: 450.1 (M+H). found: 450.2.

Example 26

3-[7-Chloro-5-(2-fluorophenyl)-1H-benzimidazol-2-yl]-1-oxa-2-aza-spiro[4.5]dec-2-ene methanesulfonate (Cpd 49)

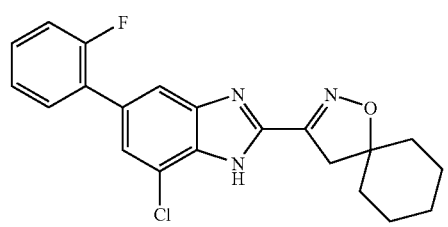

A. 3-Chloro-2'-fluoro-5-nitro-biphenyl-4-ylamine

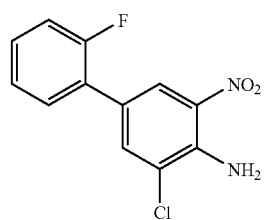

The title compound was prepared from 4-bromo-2-nitrophenylamine and 2-fluorophenylboronic acid according to the procedures described in Example 6, steps A and B. $^1$H-NMR (400 MHz, $CDCl_3$) δ: 8.32 (d, J=1.8 Hz, 1H), 7.81 (t, J=1.8 Hz, 1H), 7.42 (td, J=7.8, 1.8 Hz, 1H), 7.30-7.38 (m, 1H), 7.23 (dd, J=7.6, 1.3 Hz, 1H), 7.13-7.22 (m, 1H), 6.64 (br. s., 2H).

B. 3-[7-Chloro-5-(2-fluorophenyl)-1H-benzimidazol-2-yl]-1-oxa-2-aza-spiro[4.5]dec-2-ene

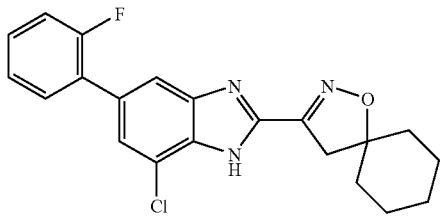

The title compound was prepared from 3-chloro-2'-fluoro-5-nitro-biphenyl-4-ylamine (as prepared in the previous step) and 1-oxa-2-aza-spiro[4.5]dec-2-ene-3-carboxylic acid (as prepared in Example 1, step B) according to the procedures described in Example 16, steps B and C. $^1$H-NMR (400 MHz, d$_4$-MeOH) δ: 7.64 (br. s., 1H), 7.52 (td, J=7.8, 1.8 Hz, 1H), 7.48 (s, 1H), 7.35-7.43 (m, 1H), 7.27 (td, J=7.5, 1.3 Hz, 1H), 7.21 (ddd, J=11.1, 8.2, 1.1 Hz, 1H), 1.71-1.88 (m, 6H), 1.48-1.66 (m, 4H).

C. 3-[7-Chloro-5-(2-fluorophenyl)-1H-benzimidazol-2-yl]-1-oxa-2-aza-spiro[4.5]dec-2-ene methanesulfonate The title compound was prepared from 3-[7-chloro-5-(2-fluorophenyl)-1H-benzimidazol-2-yl]-1-oxa-2-aza-spiro[4.5]dec-2-ene (as prepared in the previous step) according to the procedure described in Example 25, step B. $^1$H-NMR (400 MHz, d$_6$-DMSO) δ: 7.57-7.66 (m, 2H), 7.49 (s, 1H), 7.41-7.48 (m, 1H), 7.33-7.38 (m, 1H), 7.28-7.33 (m, 1H), 3.33 (s, 2H), 2.32 (s, 3H), 1.62-1.83 (m, 6H), 1.33-1.58 (m, 4H). Mass Spectrum (LCMS, ESI pos.): Calcd. for $C_{21}H_{19}ClFN_3O$: 384.1 (M+H). found: 384.3.

Using the procedures described in Example 26, and reagents, starting materials and conditions known to those skilled in the art, the following compounds representative of the present invention were prepared:

| Cpd | Data |
|---|---|
| 44 | 3-[7-Chloro-5-(2,6-difluorophenyl)-1H-benzimidazol-2-yl]-1-oxa-2-aza-spiro[4.5]dec-2-ene methanesulfonate<br>$^1$H-NMR (400 MHz, d$_6$-DMSO) δ: 7.46-7.57 (m, 1H), 7.55 (s, 1H), 7.41 (s, 1H), 7.20-7.31 (m, 2H), 3.34 (s, 2H), 2.37 (s, 3H), 1.62-1.81 (m, 6H), 1.30-1.58 (m, 4H). Mass Spectrum (LCMS, ESI pos.): Calcd. for $C_{21}H_{18}ClF_2N_3O$: 402.1 (M + H); found: 402.2. |

Example 27

2-Methyl-4-[2-(1-oxa-2-aza-spiro[4.5]dec-2-en-3-yl)-6-(2-trifluoromethylphenyl)-3H-benzimidazol-4-yl]-butan-2-ol (Cpd 43)

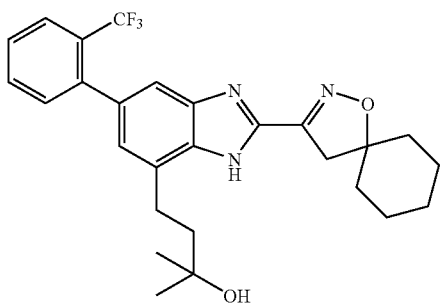

A. 4-(4,5-Diamino-2'-trifluoromethyl-biphenyl-3-yl)-2-methyl-butan-2-ol

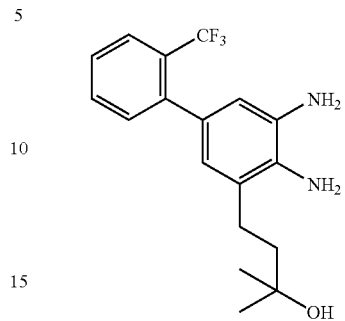

The title compound was prepared from 3-iodo-5-nitro-2'-trifluoromethyl-biphenyl-4-ylamine (as prepared in Example 9, step A) and 2-methyl-but-3-yn-2-ol according to the procedures described in Example 10, steps A and B.

B. 1-Oxa-2-aza-spiro[4.5]dec-2-ene-3-carboxylic acid [4-amino-5-(3-hydroxy-3-methyl-butyl)-2'-trifluoromethyl-biphenyl-3-yl]-amide

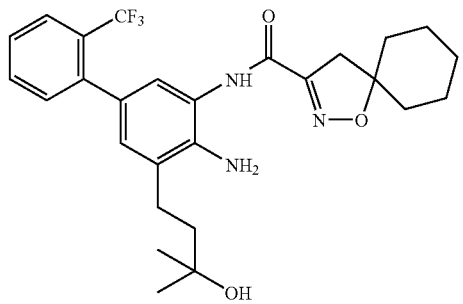

4-(4,5-Diamino-2'-trifluoromethyl-biphenyl-3-yl)-2-methyl-butan-2-ol (57.5 mg, 0.170 mmol, as prepared in the previous step) was placed in a 50 mL round-bottom flask equipped with a magnetic stir bar. DCM (15 mL), PyBrOP (95.0 mg, 0.204 mmol), and DIPEA (36.0 μL, 0.204 mmol) were added via syringe. 1-Oxa-2-aza-spiro[4.5]dec-2-ene-3-carboxylic acid (31.0 mg, 0.170 mmol, as prepared in Example 1, step B) in DCM (10 mL) was placed in an addition funnel and added dropwise over 2 h. After completion of the addition, the mixture was stirred at rt for 2 h. The solvent was removed under reduced pressure. The residue was chromatographed on a 40-g pre-packed SiO$_2$ column eluting with EtOAc/heptane, 0:1 to 3:7, v/v over 20 min, yielding 34.4 mg (40%) of the title compound. Mass Spectrum (LCMS, ESI pos.) Calcd. for $C_{27}H_{32}F_3N_3O_3$: 504.2 (M+H). Found 504.1.

C. 2-Methyl-4-[2-(1-oxa-2-aza-spiro[4.5]dec-2-en-3-yl)-6-(2-trifluoromethylphenyl)-3H-benzimidazol-4-yl]-butan-2-ol The title compound was prepared from 1-oxa-2-aza-spiro[4.5]dec-2-ene-3-carboxylic acid {4-amino-5-[3-(tert-butyl-dimethyl-silanyloxy)-3-methyl-butyl]-2'-trifluoromethyl-biphenyl-3-yl}-amide (as prepared in the previous step) according to the procedure described in Example 1, step G. $^1$H-NMR (400 MHz, d$_6$-DMSO+d$_1$-TFA) δ: 7.85 (d, J=7.8 Hz, 1H), 7.73 (t, J=7.3 Hz, 1H), 7.63 (t, J=7.7 Hz, 1H), 7.48

(d, J=7.6 Hz, 1H), 7.37 (s, 1H), 7.08 (s, 1H), 3.33 (s, 2H), 2.97-3.10 (m, 2H), 1.63-1.83 (m, 8H), 1.35-1.57 (m, 4H), 1.18 (s, 6H). Mass Spectrum (LCMS, ESI pos.): Calcd. for $C_{27}H_{30}F_3N_3O_2$: 486.2 (M+H). found: 486.1.

The following compounds of Formula (I) were prepared by the schemes and examples described herein.

| Cpd No. | Cpd Name |
|---|---|
| 1 | 3-[6-(2-Trifluoromethyl-phenyl)-1H-benzimidazol-2-yl]-1-oxa-2-aza-spiro[4.5]dec-2-ene; |
| 2 | 2-[6-(2-Trifluoromethoxy-phenyl)-1H-benzimidazol-2-yl]-3-oxa-1-aza-spiro[4.5]dec-1-ene; |
| 3 | 2-[6-(2-Trifluoromethoxy-phenyl)-1H-benzimidazol-2-yl]-1-oxa-3-aza-spiro[4.5]dec-2-ene; |
| 4 | 2-[6-(2-Trifluoromethyl-phenyl)-1H-benzimidazol-2-yl]-1-oxa-3-aza-spiro[4.5]dec-2-ene; |
| 5 | 2-[6-(2-Trifluoromethyl-phenyl)-1H-benzimidazol-2-yl]-3-oxa-1-aza-spiro[4.5]dec-1-ene; |
| 6 | 3-[5-(2-Fluoro-6-trifluoromethyl-phenyl)-1H-benzimidazol-2-yl]-1-oxa-2-aza-spiro[4.5]dec-2-ene; |
| 7 | 3-[5-(2-Trifluoromethoxy-phenyl)-1H-benzimidazol-2-yl]-1-oxa-2-aza-spiro[4.5]dec-2-ene; |
| 8 | 3-[5-(2-Fluoro-6-trifluoromethoxy-phenyl)-1H-benzimidazol-2-yl]-1-oxa-2-aza-spiro[4.5]dec-2-ene; |
| 9 | 3-[5-(2-Trifluoromethylphenyl)-1H-benzimidazol-2-yl]-1,8-dioxa-2-aza-spiro[4.5]dec-2-ene; |
| 10 | 8,8-Difluoro-3-[5-(2-trifluoromethylphenyl)-1H-benzimidazol-2-yl]-1-oxa-2-aza-spiro[4.5]dec-2-ene; |
| 11 | 3-{5-[2-(2,2,2-Trifluoroethyl)-phenyl]-1H-benzimidazol-2-yl}-1-oxa-2-aza-spiro[4.5]dec-2-ene; |
| 12 | 3-[5-(2,2-Difluoro-benzo[1,3]dioxol-4-yl)-1H-benzimidazol-2-yl]-1-oxa-2-aza-spiro[4.5]dec-2-ene hydrochloride; |
| 13 | 3-[5-(2-Difluoromethoxyphenyl)-1H-benzimidazol-2-yl]-1-oxa-2-aza-spiro[4.5]dec-2-ene hydrochloride; |
| 14 | 3-[7-Fluoro-5-(2-trifluoromethylphenyl)-1H-benzimidazol-2-yl]-1-oxa-2-aza-spiro[4.5]dec-2-ene hydrochloride; |
| 15 | 4-Methyl-3-[5-(2-trifluoromethylphenyl)-1H-benzimidazol-2-yl]-1-oxa-2-aza-spiro[4.5]dec-2-ene hydrochloride; |
| 16 | 3-[7-Chloro-5-(2-trifluoromethylphenyl)-1H-benzimidazol-2-yl]-1-oxa-2-aza-spiro[4.5]dec-2-ene hydrochloride; |
| 17 | 3-[7-Bromo-5-(2-trifluoromethylphenyl)-1H-benzimidazol-2-yl]-1-oxa-2-aza-spiro[4.5]dec-2-ene hydrochloride; |
| 18 | 2-{2-[2-(1-Oxa-2-aza-spiro[4.5]dec-2-en-3-yl)-1H-benzimidazol-5-yl]-phenyl}-propan-2-ol; |
| 19 | 2-(1,3-Diaza-spiro[4.5]dec-2-en-2-yl)-5-(2-trifluoromethyl-phenyl)-1H-benzimidazole hydrochloride; |
| 20 | 3-[5-(2-Difluoromethoxyphenyl)-7-methyl-1H-benzimidazol-2-yl]-1-oxa-2-aza-spiro[4.5]dec-2-ene hydrochloride; |
| 21 | 2-(1-Oxa-2-aza-spiro[4.5]dec-2-en-3-yl)-6-(2-trifluoromethyl-phenyl)-3H-benzimidazole-4-carbonitrile hydrochloride; |
| 22 | 3-[2-(1-Oxa-2-aza-spiro[4.5]dec-2-en-3-yl)-6-(2-trifluoromethylphenyl)-3H-benzimidazol-4-yl]-propan-1-ol hydrochloride; |
| 23 | 3-[5-(2-Fluorophenyl)-1H-benzimidazol-2-yl]-1-oxa-2-aza-spiro[4.5]dec-2-ene, trifluoroacetic acid salt; |
| 24 | 3-[4-Methyl-5-(2-trifluoromethyl-phenyl)-1H-benzimidazol-2-yl]-1-oxa-2-aza-spiro[4.5]dec-2-ene hydrochloride; |
| 25 | 3-[2-(1-Oxa-2-aza-spiro[4.5]dec-2-en-3-yl)-6-(2-trifluoromethyl-phenyl)-3H-benzimidazol-4-yl]-prop-2-en-1-ol; |
| 26 | 3-[5-(2,6-Difluorophenyl)-1H-benzimidazol-2-yl]-1-oxa-2-aza-spiro[4.5]dec-2-ene, trifluoroacetic acid salt; |
| 27 | 3-[7-Trifluoromethyl-5-(2-trifluoromethylphenyl)-1H-benzimidazol-2-yl]-1-oxa-2-aza-spiro[4.5]dec-2-ene hydrochloride; |
| 28 | 4-Methyl-3-[7-trifluoromethyl-5-(2-trifluoromethylphenyl)-1H-benzimidazol-2-yl]-1-oxa-2-aza-spiro[4.5]dec-2-ene hydrochloride; |
| 29 | 2-[5-(2-Trifluoromethyl-phenyl)-1H-benzimidazol-2-yl]-3,8-dioxa-1-aza-spiro[4.5]dec-1-ene; |
| 30 | 3-[5-(2-Chloro-phenyl)-7-trifluoromethyl-1H-benzimidazol-2-yl]-1-oxa-2-aza-spiro[4.5]dec-2-ene hydrochloride; |
| 31 | 3-[5-(2-Fluoro-phenyl)-1H-benzimidazol-2-yl]-1,8-dioxa-2-aza-spiro[4.5]dec-2-ene hydrochloride; |
| 32 | 3-[7-Methyl-5-(2-trifluoromethyl-phenyl)-1H-benzimidazol-2-yl]-1,8-dioxa-2-aza-spiro[4.5]dec-2-ene hydrochloride; |
| 33 | 3-[7-Bromo-5-(2-trifluoromethyl-phenyl)-1H-benzimidazol-2-yl]-1,8-dioxa-2-aza-spiro[4.5]dec-2-ene hydrochloride; |
| 34 | 3-[7-Chloro-5-(2-trifluoromethyl-phenyl)-1H-benzimidazol-2-yl]-1,8-dioxa-2-aza-spiro[4.5]dec-2-ene hydrochloride; |
| 35 | 2-(1,8-Dioxa-2-aza-spiro[4.5]dec-2-en-3-yl)-6-(2-trifluoromethyl-phenyl)-3H-benzimidazole-4-carbonitrile hydrochloride; |
| 36 | 8,8-Dimethyl-3-[5-(2-trifluoromethyl-phenyl)-1H-benzimidazol-2-yl]-1-oxa-2-aza-spiro[4.5]dec-2-ene hydrochloride; |
| 37 | 3-[5-(Chloro-phenyl)-1H-benzimidazol-2-yl]-8,8-dimethyl-1-oxa-2-aza-spiro[4.5]dec-2-ene hydrochloride; |
| 38 | 3-[5-(2,6-Difluoro-phenyl)-1H-benzimidazol-2-yl]-1,8-dioxa-2-aza-spiro[4.5]dec-2-ene hydrochloride; |
| 39 | 8,8-Dimethyl-3-[7-trifluoromethyl-5-(2-trifluoromethyl-phenyl)-1H-benzimidazol-2-yl]-1-oxa-2-aza-spiro[4.5]dec-2-ene hydrochloride; |
| 40 | 3-[5-(2-Chloro-phenyl)-1H-benzimidazol-2-yl]-1,8-dioxa-2-aza-spiro[4.5]dec-2-ene hydrochloride; |
| 41 | 3-[7-Chloro-5-(2-trifluoromethyl-phenyl)-1H-benzimidazol-2-yl]-8,8-dimethyl-1-oxa-2-aza-spiro[4.5]dec-2-ene hydrochloride; |
| 42 | 3-[7-Trifluoromethyl-5-(2-trifluoromethyl-phenyl)-1H-benzimidazol-2-yl]-1,8-dioxa-2-aza-spiro[4.5]dec-2-ene |
| 43 | 2-Methyl-4-[2-(1-oxa-2-aza-spiro[4.5]dec-2-en-3-yl)-6-(2-trifluoromethylphenyl)-3H-benzimidazol-4-yl]-butan-2-ol; |
| 44 | 3-[7-Chloro-5-(2,6-difluorophenyl)-1H-benzimidazol-2-yl]-1-oxa-2-aza-spiro[4.5]dec-2-ene methanesulfonate; |
| 45 | 3-[5-(2-Chlorophenyl)-1H-benzimidazol-2-yl]-1-oxa-2-aza-spiro[4.5]dec-2-ene hydrochloride; |
| 46 | 3-[7-Methyl-5-(2-trifluoromethylphenyl)-1H-benzimidazol-2-yl]-1-oxa-2-aza-spiro[4.5]dec-2-ene hydrochloride; |
| 47 | 3-[7-Methyl-5-(2-fluorophenyl)-1H-benzimidazol-2-yl]-1-oxa-2-aza-spiro[4.5]dec-2-ene hydrochloride; |
| 48 | 3-[7-Methyl-5-(2,6-difluorophenyl)-1H-benzimidazol-2-yl]-1-oxa-2-aza-spiro[4.5]dec-2-ene hydrochloride; |
| 49 | 3-[7-Chloro-5-(2-fluorophenyl)-1H-benzimidazol-2-yl]-1-oxa-2-aza-spiro[4.5]dec-2-ene methanesulfonate; |
| 50 | 3-[7-Chloro-5-(2-trifluoromethoxyphenyl)-1H-benzimidazol-2-yl]-1-oxa-2-aza-spiro[4.5]dec-2-ene methanesulfonate; |
| 51 | 3-[5-(2-Trifluoromethoxyphenyl)-7-trifluoromethyl-1H-benzimidazol-2-yl]-1-oxa-2-aza-spiro[4.5]dec-2-ene hydrochloride; |
| 52 | 3-[7-(3-Methoxy-propyl)-5-(2-trifluoromethylphenyl)-1H-benzimidazol-2-yl]-1-oxa-2-aza-spiro[4.5]dec-2-ene hydrochloride; |
| 53 | 3-[5-(2-Fluorophenyl)-7-trifluoromethyl-1H-benzimidazol-2-yl]-1-oxa-2-aza-spiro[4.5]dec-2-ene hydrochloride; |
| 54 | 3-[4,7-Dimethyl-5-(2-trifluoromethylphenyl)-1H-benzimidazol-2-yl]-1-oxa-2-aza-spiro[4.5]dec-2-ene hydrochloride; |
| 55 | 3-[7-Chloro-4-methyl-5-(2-trifluoromethylphenyl)-1H-benzimidazol-2-yl]-1-oxa-2-aza-spiro[4.5]dec-2-ene hydrochloride; |
| 56 | 2-(1-Oxa-2-aza-spiro[4.5]dec-2-en-3-yl)-5-(2-trifluoromethyl-phenyl)-1H-imidazo[4,5-b]pyridine hydrochloride; |
| 57 | 2-(1-Oxa-2-aza-spiro[4.5]dec-2-en-3-yl)-6-(2-trifluoromethyl-phenyl)-3H-imidazo[4,5-c]pyridine hydrochloride; and |
| 58 | 2-(1-Oxa-2-aza-spiro[4.5]dec-2-en-3-yl)-6-(2-trifluoromethyl-phenyl)-3H-imidazo[4,5-b]pyridine hydrochloride; | and pharmaceutically acceptable salts thereof.

BIOLOGICAL EXAMPLES

In Vitro Models

Example 1a

In Vitro Canine TRPM8 Functional Assay

The functional activity of compounds of the Formula (I) was determined by measuring changes in intracellular calcium concentration using a $Ca^{2+}$-sensitive fluorescent dye. The changes in fluorescent signal were monitored by a fluorescence plate reader, either a FLIPR™ (Molecular Devices) or FDSS (Hamamatsu). Increases in intracellular $Ca^{2+}$ concentration were readily detected upon activation with icilin.

At 24 hrs prior to assay, HEK293 cells stably expressing canine TRPM8 were seeded in culture medium in black wall, clear-base poly-D-lysine coated 384-well plates (BD Biosciences, NJ, USA) and grown overnight in 5% $CO_2$ at 37° C. On assay day, growth media was removed and cells were loaded with Calcium 3 Dye (Molecular Devices) for 35 min at 37° C., under 5% $CO_2$ and then for 25 min at room temperature and atmosphere. Subsequently, cells were tested for agonist-induced increases in intracellular $Ca^{2+}$ levels using FLIPR™ or FDSS. Cells were challenged with a compound of the Formula (I) (at varying concentrations) and intracellular $Ca^{2+}$ was measured for 5 min prior to the addition of icilin to all wells to achieve a final concentration that produces approximately an 80% maximal response. $EC_{50}$ or $IC_{50}$ values for compounds of the present invention were determined from eight-point dose-response studies. Curves were generated using the average of quadruplicate wells for each data point. The resultant data are displayed in Table 2.

TABLE 2

| Cpd | % Inh. @ 0.200 µM | $IC_{50}$ (nM) |
|---|---|---|
| 1 | 99.5 | 3.1 |
| 2 | 106 | 7.0 |
| 3 | 60 | n.d. |
| 4 | 84 | 61 |
| 5 | 94 | 6.0 |
| 6 | 102 | 0.6 |
| 7 | 102 | 1.1 |
| 8 | 102 | 0.8 |
| 9 | 101 | 6.7 |
| 10 | 102 | 0.9 |
| 11 | 102 | 1.5 |
| 12 | 87 | 91 |
| 13 | 102 | 2.5 |
| 14 | 102 | 2.2 |
| 15 | 102 | 3.9 |
| 16 | 102 | 3.3 |
| 17 | 102 | 2.7 |
| 18 | 102 | 7.9 |
| 19 | 50 | n.d. |
| 20 | 103 | 1.8 |
| 21 | 103 | 0.7 |
| 22 | 103 | 0.2 |
| 23 | 103 | 2.9 |
| 24 | 103 | 5.6 |
| 25 | 100 | 0.8 |
| 26 | 100 | 2.3 |
| 27 | 100 | 0.8 |
| 28 | 101 | 1.1 |
| 29 | 71 | 100 |
| 30 | 97 | 1.0 |
| 31 | 99 | 13.4 |
| 32 | 100 | 4.9 |
| 33 | 100 | 1.7 |
| 34 | 100 | 4.0 |
| 35 | 100 | 5.2 |
| 36 | 99 | 12.5 |
| 37 | 99 | 5.2 |
| 38 | 99 | 8.3 |
| 39 | 99 | 6.3 |
| 40 | 98 | 11.0 |
| 41 | 92 | 50.2 |
| 42 | 100 | 1.4 |
| 43 | 99 | 1.7 |
| 44 | 100 | 2.1 |
| 45 | 97 | 2.4 |
| 46 | 97 | 1.8 |
| 47 | 97 | 6.9 |
| 48 | 97 | 3.9 |
| 49 | 101 | 6.1 |
| 50 | 101 | 1.9 |
| 51 | 97 | 1.2 |
| 52 | 97 | 1.0 |
| 53 | 97 | 1.7 |
| 54 | 97 | 5.8 |
| 55 | 97 | 4.7 |
| 56 | 101 | 4.6 |
| 57 | 102 | 2.7 |
| 58 | 101 | 2.0 |

Example 1b

In Vitro Rat and Human TRPM8 Functional Assay

HEK293 cells are routinely grown as monolayer in Dulbecco's minimum essential medium supplemented with 10% FBS, 1 mM L-glutamine, 100 units/mL penicillin and 100 ug/mL streptomycin. Cells are maintained in 5% CO2 at 37° C.

For functional expression of TRPM8, the full-length cDNA encoding human and rat TRPM8 are subcloned into pCI-NEO mammalian expression vectors. The expression constructs are transiently transfected into HEK293 cells according to the FuGENE 6 Transfection Reagent® (ROCHE) instructions. Within twenty-four hours, transiently transfected cells are harvested and either seeded directly into assay plate or cryopreserved for future usage.

Transfected cells may be either cryopreserved or freshly transfected and plated into clearbase poly-D-lysine coated 384-well plates (BD Biosciences, NJ, USA) at a density of 10,000 cells per well in culture medium and grown overnight. The following day, all medium is removed and the cells are incubated with 52 L of 0.5× calcium 3 dye (Molecular Devices) prepared in complete assay buffer containing 20 mM HEPES, 0.1% BSA, and 2.5 mM probenecid at 37° C. for thirty five minutes. The cells are then incubated for an additional fifteen minutes at room temperature before initiating experiments. Following incubation, plates are inserted into a FDSS instrument, where cells were challenged with compounds of the Formula (I) (at varying concentrations) and intracellular $Ca^{2+}$ are measured for 5 min prior to the addition of icilin at the $EC_{80}$ concentration. IC50 values for compounds of the Formula (I) are determined from eight point dose-response studies.

Maximal fluorescence intensity (FI) achieved upon addition of icilin is exported from the FDSS and further analyzed using GraphPad Prism 3.02 (Graph Pad Software Inc., CA, U.S.A.) where data is normalized to percent of maximal response. The dose response curves from the average of quadruplicate wells for each data point are analyzed by using nonlinear regression of either sigmoidal dose response or sigmoidal dose response (variable slope). Finally, the $IC_{50}$ values are calculated with the best-fit dose curve determined by Prism.

Example 2

TRPM8 Patch Clamp Assays

For patch clamp experiments, HEK293 cells are stably transfected with canine TRPM8 and cultured in DMEM supplemented with 10% fetal bovine serum, 100 units/ml penicillin, 100 µg/ml streptomycin and 1 mg/ml G418. Cells are maintained at 37° C. and in 5% $CO_2$.

The extracellular solution contains (in mM): NaCl, 132; EGTA, 1; KCl, 5.4; $MgCl_2$, 0.8; HEPES, 10; glucose, 10; pH=7.4. Recordings are performed using the conventional whole-cell patch clamp technique, 1-2 days after plating cells onto glass coverslips at densities appropriate for single cell recording. Currents are amplified by a patch clamp amplifier and filtered at 2 kHz (Axopatch 200B, Molecular Devices, Union City, Calif.). Menthol (100 µM) is applied to the cell at 0.5 ml/min via a gravity-fed perfusion system. Recordings involving menthol activation are performed at 22° C.

In experiments where temperatures are varied, temperature ramps are generated by cooling the perfusate in an in-line cooler (Model SC-20, Warner Instruments, Hamden, Conn.)

controlled by a temperature controller (Model CL-100, Warner Instruments). The temperature in the vicinity of the recorded cell is measured with a custom-made miniature thermo-microprobe connected to a monitoring thermometer (Model TH-8, Physitemp, Clifton, N.J.), and sampled using Digidata 1322A and pClamp 9.0 (Molecular Devices), as are the currents concurrently measured in the whole-cell patch clamp mode. The current is continuously sampled (at 100 Hz) at a holding potential of −60 mV.

Compounds of the Formula (I) are diluted from 10 mM DMSO stocks (stored at −20° C.) into an extracellular solution either containing 100 M menthol or subjected to cooling. Increasing concentrations of a compound are applied to a cell in a cumulative manner and concentration-dependent responses are measured after steady-state activation is achieved by either 100 µM menthol or cooling to 10° C. A saturating concentration of a reference antagonist is applied at the end of an experiment (either in the presence of 100 µM menthol or 10° C. temperature) to establish the baseline from which all the other measurements are subtracted.

Percentage inhibition by a compound is calculated as follows: $100\times(1-I_{comp}/I_0)$; where $I_{comp}$ and $I_0$ are steady-state current amplitudes in either the presence or absence of a concentration of compounds of the Formula (I). Concentration-response data are fitted to a logistic function as follows: $R=100/(1+c/IC_{50})^p$; where, R is the percentage inhibition, p is the Hill coefficient and c is the concentration of compounds of the Formula (I).

In Vivo Models

Example 3

Inhibition of Icilin-Induced Behaviors in Rodents

Icilin was initially developed as a "super-cooling" compound by Delmar Chemicals Ltd. Subsequently it was shown to be one of the most potent known agonists of TRPM8 (McKemy, D. D. et al. *Nature* 2002, 416(6876), 52-8), having an $EC_{50}=0.2$ µM in stimulating calcium ion influx into TRPM8 transfected cells (Behrendt, H. J. et al. *Brit. J. Pharmacol.* 2004, 141(4), 737-45). Initial in vivo testing of icilin showed it to cause "wet-dog" shakes in rats. Similar shaking or jumping behavior was also evident in mice, rabbits, cats, dogs and monkeys. In humans, icilin produced a sensation of coolness on contact with mucous membranes, cold prickling when 0.1 mg was dropped on the tongue and coldness in the mouth, pharynx and chest lasting 30-60 minutes when 5-10 mg was ingested orally (Wei, E. T.; Seid, D. A. *J. Pharm. Pharmacol.* 1983, 35, 110). The inhibition or reversal of icilin-induced shaking behaviors in rodents provides evidence for the utility of TRPM8 antagonists of the Formula (I) in treating or preventing a disease, syndrome, disorder, or condition in a subject in which the disease, syndrome, disorder or condition is affected by the modulation of TRPM8 receptors.

Example 3a

Inhibition of Icilin-Induced "Wet-Dog" Shakes in Rats

Male Sprague Dawley rats (220-450 g, Charles River Labs, n=6-9/treatment) were used to evaluate the ability of selected compounds of the Formula (I) to block icilin-induced "wet-dog" shakes (WDS). Compounds of the Formula (I) were administered in an appropriate vehicle, such as hydroxypropyl-β-cyclodextrin (HPβCD), methocellulose, 10% Solutol, or $H_2O$, or the like, by the appropriate route, i.p. or p.o., 30-120 minutes before icilin. Icilin was administered in PEG-400 or 10% solutol/$H_2O$, at 1.0 or 3.0 mg/kg, i.p. and spontaneous "wet-dog" shakes were counted 10-20 minutes post-icilin. Results are presented as a percent inhibition of shakes, which was calculated as [1−(test compound WDS count/vehicle WDS count)]×100.

Example 3b

Reversal of Icilin-Induced Behaviors in Rats

Male Sprague Dawley rats (225-450 g, Charles River Labs, n=4-6/treatment) were used to evaluate the ability of selected compounds of the Formula (I) to reverse icilin-induced "wet-dog" shakes. Icilin was administered in PEG-400 or 10% solutol/$H_2O$, at 1.0 or 3.0 mg/kg, i.p. and spontaneous "wet-dog" shakes (WDS) were counted 10-20 minutes post-icilin. Animals that exhibited 10 or more shakes were randomized into treatment groups and immediately administered compounds of the Formula (I) in an appropriate vehicle, such as hydroxypropyl-β-cyclodextrin (HP β CD), methocellulose, 10% Solutol, or $H_2O$, or the like, and by the appropriate route, such as i.p. or p.o. Spontaneous "wet-dog" shakes were counted 60-70 minutes after compound administration. Results are presented as a percent inhibition of shakes, which was calculated as [1−(test compound WDS count/vehicle WDS count)]×100. Resultant data is shown in Table 3.

TABLE 3

| Cpd No. | Dose (mg/kg) | Route | Post-icilin | % Inhibition |
|---|---|---|---|---|
| 1 | 30 | p.o. | 1 h | 100 |
| 7 | 10 | p.o. | 1 h | >96 |
| 8 | 10 | p.o. | 1 h | >96 |
| 16 | 10 | p.o. | 1 h | >99 |
| 27 | 10 | p.o. | 1 h | >99 |
| 28 | 10 | p.o. | 1 h | 30 |
| 30 | 10 | p.o. | 1 h | >98 |
| 51 | 10 | p.o. | 1 h | >98 |
| 53 | 10 | p.o. | 1 h | >98 |

Example 3c

Rightward Shift of Icilin Dose Effect Curve in Rats

Male Sprague Dawley rats (200-400 g, Charles River Labs, n=6-9/treatment) were administered icilin in a suitable vehicle (e.g. PEG-400, 10% Solutol) at 0.1-30 mg/kg, i.p. Spontaneous "wet-dog" shakes were counted 10-20 minutes post-icilin in order to generate an icilin dose-effect curve. A compound of the present invention was administered orally in hydroxypropyl-β-cyclodextrin 60 minutes before icilin challenge to assess the compound's ability to inhibit spontaneous "wet-dog" shakes (WDS) produced by a range of icilin doses. The $ED_{50}$ of the icilin dose-effect curve generated in the presence of TRPM8 antagonist may be compared to that generated in the presence of vehicle to determine the magnitude of rightward shift.

Example 4

In Vivo Model of Subacute Inflammatory Pain: Carrageenan-Induced Hyperalgesia

Intraplantar injection of carrageenan into the hind paw of rats causes a robust acute inflammatory response characterized by reddening, swelling and hypersensitivity of the paw to thermal and mechanical stimuli typically peaking 3-6 hours following application and subsiding over the 12-24 hours.

Example 4a

Rat Carrageenan-Induced Radiant Heat Hypersensitivity

To assess the effect of test compounds of the Formula (I) on inflammatory hyperalgesia radiant heat response latencies were evaluated 3 hours following intraplantar carrageenan (Lambda, Type IV, 200 uL) injection into a single hind paw in male Sprague-Dawley rats. The test compound was administered either 2 hours prior to or 1 hour following carrageenan injection. The intent was to determine whether the compound would prevent or retard the hypersensitivity associated with this inflammogen. Baseline thermal response latencies were determined prior to any treatment and again 3 hours after carrageenan injection. Percent reversal of hyperalgesia relative to vehicle treatment (% R) was calculated for both compound treatment paradigms according to the following formula.

% R=(Post compound latency−Post vehicle latency)/
((Baseline latency−Post vehicle latency)×100%

Example 5

In Vivo Model for of Chronic Inflammatory Pain: Complete Freund's Adjuvant (CFA)-Induced Hyperalgesia Intraplantar injection of complete Freund's adjuvant (CFA) in rodents results in a long-lasting inflammatory reaction, characterized by a pronounced hypersensitivity to both thermal and mechanical stimuli. This hypersensitivity peaks between 24-72 hours following injection and can last for several weeks. To assess whether test compounds of the Formula (I) reverse established hypersensitivity, a 100 μL intraplantar injection of CFA (suspended in a 1:1 emulsion of saline and heat-killed *Mycobacterium tuberculosis* in mineral oil) can be injected into a single hind paw of Sprague-Dawley rats (typically males ranging from 150-350 g). This paradigm also may be conducted with a multiple dosing or a prophylactic dosing regime designed to alter the course of hyperalgesia development. This test predicts the analgesic, anti-allodynic and antihyperalgesic effect of numerous effective clinical agents, including acetaminophen, NSAIDS such as aspirin and ibuprofen, and opioids, such as morphine.

Example 5a

CFA-Induced Paw Radiant Heat Hypersensitivity

Each rat is placed in a test chamber on a warm glass surface and allowed to acclimate for approximately 10 minutes. A radiant thermal stimulus (beam of light) is then focused through the glass onto the plantar surface of each hind paw in turn. The thermal stimulus is automatically shut off by a photoelectric relay when the paw is moved or when the cut-off time is reached (20 seconds for radiant heat at ~5 Amps). An initial (baseline) response latency to the thermal stimulus is recorded for each animal prior to the injection of CFA. Twenty-four hours following intraplantar CFA injection, the response latency of the animal to the thermal stimulus is then re-evaluated and compared to the animal's baseline response time. Only rats that exhibit at least a 25% reduction in response latency (i.e. hyperalgesia) are included in further analysis. Immediately following the post-CFA latency assessment, test compound or vehicle (usually Solutol, hydroxypropyl methylcellulose, hydroxypropyl beta-cyclodextrin or PEG-400) is administered i.p. or p.o. to rats. Post-compound treatment withdrawal latencies are assessed at fixed time intervals, typically 30, 60 and 120 minutes. The percent reversal (% R) of hypersensitivity is calculated according to the following formula:

% Reversal=(Treatment Response−CFA Response)/
(Baseline Response−CFA Response)×100.

Example 5b

CFA-Induced Paw Cold Hypersensitivity

Prior to intraplantar CFA injection, mice or rats are placed individually in elevated observation chambers having wire mesh floors. Through the mesh floor a series of three applications of acetone (0.04-0.10 mL/application) is sprayed onto the bottom of the paw using a multidose syringe device. A positive response takes the form of an abrupt withdrawal and licking of the paw. The cumulative duration of licking is recorded for each of the three trials, which are then averaged to give the individual's response. Twenty-four hours following CFA injection, acetone licking durations are markedly elevated, implying a hypersensitivity to cooling. Test compounds of the Formula (I) can be assessed for their ability to return acetone-evoked paw licking durations to pre-CFA levels (typically near zero) following systemic administration. Percent inhibition is calculated as follows % Inhibition=[1−(treatment licking duration/vehicle
licking duration)]×100.

Example 6

Chemically-Induced Abdominal Irritant Models of Visceral Pain

A chemical irritant (such as acetic acid, kaolin, bradykinin, phenyl-p-(benzo) quinine, bromo-acetylcholine, or zymosan) is injected in mice intraperitoneally, causing a contraction of the abdominal musculature, which is characterized by an elongation of the body extending through to the hind limbs. The number of such responses is quantitated and is reduced by pretreatment of analgesic agents, thus forming the basis for a screening test (Collier, H. O. et al. *Brit. J. Pharmacol. Chemother.* 1968, 32(2): 295-310). This type of abdominal irritant test has been used to predict the analgesic effect of numerous clinically effective agents, the potency of which in the abdominal irritant test parallels the magnitude of the dose needed in the relief of clinical pain. Such agents include acetaminophen, NSAIDS such as aspirin and ibuprofen, opioids, such as morphine and codeine, and other centrally acting analgesics, such as tramadol.

One modification of the chemically-induced abdominal irritant model of visceral pain is to pretreat animals with agents known to induce inflammatory responses following intraperitoneal injection (such as LPS, zymosan, or thioglycolate). A small intraperitoneal dose of such an inflammogen, administered hours or days before the acute chemical irritant challenge, has been shown to increase the number of abdominal contractions observed (Ribeiro, R. A. et al. *Eur. J. Pharmacol.* 2000, 387(1), 111-8). While some analgesic agents are effective at mitigating acute viscerochemical nociception, others, particularly those dependent upon receptor induction, are more effective at preventing or reversing the enhancement of behavioral responses caused by a preconditioning inflammatory stimulus. Because of the up-regulation of the TRPM8 receptor in inflammation, TRPM8 antagonists that are effective at reducing the mean number of contractions are predicted to provide analgesic action in human clinical use.

The ability of compounds of the Formula (I) to mitigate chemical irritant-induced abdominal contractions following a pre-conditioning inflammatory stimulus can be studied as follows. Thioglycolate (3%, w/v, 2-3 mL i.p.) is injected into male CD1 mice (20-40 g, Charles River Labs), at a maximum dosage volume of 80 mL/kg, to induce peritoneal inflammation. Following a twenty-four hour pre-inflammation period these mice are dosed orally with compounds of the Formula (I) (30 mg/kg; n=10) or vehicle (HPMC with 2% Tween80; n=9) and then one hour later subjected to an abdominal irritant challenge of acetic acid (1%, 10 mL/kg, i.p.). Immediately following injection of acetic acid, mice are placed individually in glass bell jars (approximately 15 cm in diameter) for counting of abdominal contractions over the next 15 minutes. The total number of abdominal contractions is summed for each treatment group and employed in the following formula to calculate Percent Inhibition (% I):

% I=[1−(test compound contractions/vehicle contractions)]×100.

Example 7

In Vivo Models of Neuropathic Pain

The sciatic nerve is the major sensorimotor innervation of the (hind) leg and foot. Injury to the sciatic nerve or its constituent spinal nerves often results in pain-related behaviors. In rats and mice, tight ligation of the L5 spinal nerve with silk suture, partial tight ligation of the sciatic nerve with silk suture or loose ligation of the sciatic nerve with chromic gut suture each result in behaviors reminiscent of neuropathic pain in humans. These lesions (one per animal) are performed surgically in anesthetized rodents. Both the spinal nerve and sciatic nerve lesions result in allodynia, a painful response to normally innocuous stimuli, and hyperalgesia, an exaggerated response to normally noxious stimuli. It is important to note that both of these pain-related behaviors are evoked by the testing procedures and that normal use of the paw (e.g., walking) is relatively uncompromised, apart from occasional "guarding" of the paw. Subsequent to the surgery, the subjects' behaviors, such as grooming, feeding, and weight gain, are normal, except for hypersensitivity (as defined above) of the affected paw.

In addition to induction by nerve damage resulting from accidental trauma or surgical procedures, neuropathic pain can also be induced by diabetes (Fox, A. et al. *Pain* 1999, 81, 307-316) or by treatment with chemotherapeutic agents, such as paclitaxel or vincristine (Yaksh, T. L. et al. *Pain* 2001, 93, 69-76).

Agents that attenuate neuropathic pain in the clinic also are effective in rodent neuropathic pain models. These agents include the recently approved Cymbalta (Duloxetine, Iyengar, S. et al. *J. Pharmacol. Exp. Ther.* 2004, 311, 576-584), morphine (Suzuki, R. et al. *Pain* 1999, 80, 215-228), and gabapentin (Hunter, J. C. et al. *Eur. J. Pharmacol.* 1997, 324, 153-160). The dual TRPV1/TRPM8 receptor antagonist BCTC reduced mechanical hyperalgesia and tactile allodynia in the chronic constriction injury rodent neuropathic pain model (Pomonis, J. D. et al. *Pharmacol. Exp. Ther.* 2003, 306, 387-393; Behrendt, H. et al. *Brit. J. Pharm.* 2004, 141, 737). Cold allodynia is a particularly debilitating symptom of neuropathic pain conditions (Jorum, E. et al. *Pain* 2003, 101, 229-235). The antiallodynic effect of compounds of the Formula (I) in this rodent model is predictive of clinical effect for these novel agents.

Example 7a

Chronic Constriction Injury (CCI)-Induced Model of Neuropathic Pain-Acetone-Induced Hypersensitivity Male Sprague Dawley rats (225-450 g; n=5-8/treatment) were used to evaluate the ability of selected compounds of the Formula (I) to reverse CCI-induced cold hypersensitivity. Four loose ligatures of 4-0 chromic gut were surgically placed around the left sciatic nerve under inhalation anesthesia as described by Bennett et al. (Bennett, G. J.; Xie, Y. K. *Pain* 1988, 33(1), 87-107). Fourteen to 35 days following CCI surgery, subjects were placed in elevated observation chambers containing wire mesh floors and five applications of acetone (0.05 mL/application separated by approximately 5 minutes) were spritzed onto the plantar surface of the paw using a multidose syringe. An abrupt withdrawal or lifting of the paw was considered a positive response. The number of positive responses was recorded for each rat over the five trials. Following baseline withdrawal determinations, compounds of Formula (I) are administered in an appropriate vehicle, such as hydroxypropyl-β-cyclodextrin (HP α CD), methylcellulose, Methocel, 10% Solutol, or $H_2O$, or the like, by the appropriate route, i.p. or p.o. The number of withdrawals were redetermined 1 to 3 h after compound administration. Results are presented as a percent inhibition of shakes, which was calculated for each subject as [1−(test compound withdrawals/pre-test withdrawals)]×100 and then averaged by treatment. Resultant data is shown in Table 4.

TABLE 4

| Cpd No. | Dose (mg/kg) | Route | Post-dose | % Inhibition |
|---|---|---|---|---|
| 1 | 10 | p.o. | 3 h | 65 |
| 7 | 10 | p.o. | 3 h | 83 |
| 16 | 10 | p.o. | 3 h | 82.5 |
| 17 | 10 | p.o. | 3 h | 97 |
| 27 | 10 | p.o. | 3 h | 83 |
| 30 | 10 | p.o. | 3 h | 62.9 |
| 51 | 10 | p.o. | 3 h | 57.1 |
| 53 | 10 | p.o. | 3 h | 42.9 |

Example 7b

Chronic Constriction Injury (CCI)-Induced Model of Neuropathic Pain-Cold Plate-Induced Hypersensitivity In male SD rats (175-325 g), four loose ligatures of 4-0 chromic gut are surgically placed around the left sciatic nerve under inhalation anesthesia as described by Bennet et al. (Bennett, G. J.; Xie, Y. K. *Pain* 1988, 33(1), 87-107). Seven to 21 days following sciatic chronic constriction injury (CCI) surgery, the subjects can be placed onto a commercial cold plate device cooled by peltier elements such that the surface temperature is held at 1° C. Each subject can undergo a 6 minute conditioning period followed by a 3 minute assessment period during which the total duration of hind paw lifting is recorded. This procedure is repeated at several intervals prior to and following systemic drug administration. Compounds of the Formula (I) can be assessed for their ability to return duration of paw lifting back to pre-lesion levels. The duration of paw lifting during the 3 minute test period following administration of test compound is taken as a percentage of the duration of paw lifting during the 3 minute test period prior to test compound treatment.

Example 7c

Chronic Constriction Injury (CCI)-Induced Model of Neuropathic Pain-Mechanical Allodynia (von Frey Test)

In male SD rats (175-325 g), four loose ligatures of 4-0 chromic gut are surgically placed around the left sciatic nerve under inhalation anesthesia as described by Bennet et al. (Bennett, G. J.; Xie, Y. K. *Pain* 1988, 33(1), 87-107). Seven to 21 days following sciatic chronic constriction injury (CCI) surgery, the subjects can be placed onto an elevated rack of plexigas chambers having wire mesh or another type of perforated flooring. The measurement of mechanical allodynia can be performed using the von Frey hairs (Semmes-Weinstein Monofilaments, Stoelting Co., IL) wherein the rats can be habituated to the wire mesh bottom cages before the start of the experiment. Static allodynia can be tested in the unrestrained rats by touching the plantar surface of the hind paw with von Frey hairs in ascending order of force (1.2, 1.5, 2.0, 3.6, 5.5, 8.5, 12, 15, 29, and 76 g) for up to 6 s or until a paw withdrawal response can be elicited. The lowest amount of force required to elicit a response can be recorded as the withdrawal threshold in log g. This procedure is repeated at several intervals prior to and following systemic drug administration. Compounds of the Formula (I) can be assessed for their ability to return the threshold force, which elicits paw lifting back to pre-lesion levels.

Example 8

Inflammatory Agent-Induced Models of Pyresis/Antipyresis

Compounds of the Formula (I) can be tested in animal models of pyresis, according to previously documented and validated methods, such as those described by Kozak et al. (Kozak, W.; Fraifeld, V. *Front. Biosci.* 2004, 9, 3339-55). Fever is a frequent accompaniment of inflammatory disease. Animal models make use of the pyretic properties of yeast and other inflammatory agents, injecting a yeast suspension or other agent subcutaneously (Tomazetti, J. et al. *J. Neurosci. Methods* 2005, 147(1), 29-35); Van Miert, A. S.; Van Duin, C. T. *Eur. J. Pharmacol.* 1977, 44(3), 197-204). For example, Male Wistar rats (75-100 g) can be housed in groups of four to a cage at controlled temperature (23±1° C.) with a 12 h light: 12 h dark cycle (lights on at 07:00 h) and with standard lab chow and tap water ad libitum. All measured temperatures can be taken between 08:00 and 19:00 h. Each animal can be used in only one study. Rectal temperature (TR) can be measured by inserting a lubricated thermistor probe (external diameter: 3 mm) 2.8 cm into the rectum of the animal. The probe can be linked to a digital device, which displayed the temperature at the tip of the probe with a 0.1° C. precision and logs the values over time. Immediately after measuring the initial basal rectal temperature, the animals can be injected with commercially available dried baker yeast (*Saccharomyces cerevisiae*) suspended in pyrogen-free 0.9% NaCl (0.05-0.25 g/kg, i.p.) or 0.9% NaCl (10 ml/kg). TR changes can be recorded every hour up to 12 h, and expressed as the difference from the basal value. Since it has been previously reported that handling and temperature measuring-related stress alter rectal temperature, these animals can be habituated to the injection and measuring procedure for 2 days before experiments are carried out. In these sessions, the animals can be subjected to the same temperature measuring procedure described above, and can be injected intraperitoneally (i.p.) with 0.9% NaCl (10 ml/kg).

To assess the effect of potential antipyretic compounds on basal rectal temperature study animals can have their TR measured for 4 h, and after the fourth TR measurement they can be subcutaneously (s.c.) injected with vehicle (such as 10% Solutol in sterile water 5 ml/kg) or compounds of the Formula (I) prepared in vehicle. TR can then be recorded every hour up to 8 h after the compound injections. To assess the effect of compounds of the Formula (I) on baker yeast-induced hyperthermia, study animals can have their basal TR measured and then be injected with a pyrogenic dose of baker yeast (for example, 0.135 g/kg). TR changes can be recorded every hour up to 4 h, when potential antipyretics agents such as those compounds of the Formula (I) are administered. Rectal temperature can then be monitored over the following 8 h. Basal rectal temperature and changes in rectal temperature can be expressed as means±S.E.M. of the differences from TR at 07:00 h. Data can be analyzed by two-way analysis of variance (ANOVA), with time of measures treated as within subject factor, depending on the experimental design. Post hoc analysis can be carried out by the F-test for simple effect and the Student-Newman-Keuls test, when appropriate. A value of $P<0.05$ would be considered statistically significant.

The modification of the subsequent pyretic response by therapeutic agents can also be monitored by rectal telemetry or other measurements of body temperature. Several clinically relevant agents such as acetaminophen, aspirin and ibuprofen, reduce fever in these models. The antipyretic effect of TRPM8 antagonists, such as compounds of the Formula (I), in these tests would also be predictive of their clinical effect.

Example 9

CFA-Induced Model of Rheumatoid Arthritis

Compounds of the Formula (I) can be tested in animal models of rheumatoid arthritis, according to previously documented and validated methods, such as those described by Nagakura et al (Nagakura, Y. et al. *J. Pharmacol. Exp. Ther.* 2003, 306(2), 490-7). For example, arthritis can be induced by the CFA inoculation in the rats (Male Lewis rats 150-225 g; Charles River). Briefly, 100 mg of *Mycobacterium Butyricum* (Difco, Detroit, Mich.) can be thoroughly mixed with 20 mL of paraffin oil. Then mixture can be autoclaved for 20 min at 120° C. Each rat can be injected in the right footpad (hind paw) with the mixture in a 0.1-mL volume under inhalation anesthesia. The rats serving as controls can be injected with 0.1 mL of saline. Pain and other disease development parameters can be measured in the CFA- or saline-treated rats just before inoculation and up to 28 days post-inoculation. The measurement for pain parameters can be conducted for both mechanical and thermal (hot or cold) endpoints. The measurement of mechanical allodynia can be performed using the von Frey hairs (Semmes-Weinstein Monofilaments, Stoelting Co., Ill.) wherein the rats can be habituated to wire mesh bottom cages before the start of the experiment. Static allodynia can be tested in the unrestrained rats by touching the plantar surface of the hind paw with von Frey hairs in ascending order of force (1.2, 1.5, 2.0, 3.6, 5.5, 8.5, 12, 15, 29, and 76 g) for up to 6 s or until a paw withdrawal response can be elicited. The lowest amount of force required to elicit a response can be recorded as the withdrawal threshold in log g. Thermal hyperalgesia can be assessed using the radiant heat test wherein a mobile radiant heat source can be located under a glass surface upon which the rat is placed. The beam of light can be focused on the hind paw, and the paw withdrawal latencies are defined as the time taken by the rat to remove its hind paw from the heat source. The measurement of joint hyperalgesia can be performed by a modification of the previously reported method (Rupniak, N. M. J. et al. *Pain* 1997, 71, 89-97). The torso of each rat can be held from the back with the left palm, and the bending and extension (one after the other and five times in each direction) of the ankle within its limits of range of motion can be performed with the right fingers. The total number of vocalizations emitted after the manipulation (the bending and extension, five times in each direction) can be recorded for each paw (the maximum score is 10 for each paw).

The scoring of mobility can be performed by modifying the evaluation scale reported by Butler et al. (Butler, S. H. et al. *Pain* 1992, 48, 73-81): score 6, walks normally; score 5, walks being protective toward the ipsilateral hind paw (touches the ipsilateral hind paw fully on the floor); score 4, walks being protective toward the ipsilateral hind paw (touches only the toe of the ipsilateral hind paw on the floor); score 3, walks being protective toward both hind paws (touches the contralateral hind paw fully on the floor); score 2, walks being protective toward both hind paws (touches only the toe of the contralateral hind paw on the floor); score 1, crawls only using the fore paws; and score 0, does not move. Paw volumes can be measured by volume displacement of electrolyte solution in a commercially available plethysmometer device. The hind paw can be immersed to the junction of the hairy skin, and the volumes can be read on a digital display. The scoring of joint stiffness can be performed as follows: the body of rats can be held from the back with the left palm, and the bending and extension (once in each direction) of the ankle within its limits of range of motion can be performed with the right fingers. It can be confirmed beforehand that there is no restriction of ankle joint movement in the bending and extension manipulations in naive rats, and the scoring can be performed according to the evaluation scale reported by Butler (Butler, S. H. et al. *Pain* 1992, 48, 73-81): score 2, there are restrictions of full range of movement of the ankle in both bending and extension; score 1, there is a restriction of full range of movement of the ankle in bending or extension; and score 0, no restriction. The measurements for paw volume and joint stiffness can be conducted for both hind paws.

Compounds of the Formula (I) can be assessed for antihyperalgesic efficacy as follows: thirty-two rats (8 rats per dose and four doses per compound) that are to be treated with the CFA and another eight rats as naive controls can be used for each drug evaluation. The analgesic effects can be evaluated on post-inoculation day 9, when mechanical allodynia, thermal hyperalgesia, joint hyperalgesia, and joint stiffness in the ipsilateral paw reached almost the maximum, although those parameters in the contralateral paw changed only slightly and the systemic disturbance shown by the change of mobility score is small. On the day before evaluation, body weight, mechanical allodynia, thermal hyperalgesia, and joint hyperalgesia can be measured for the 32 rats that are to be used for compound evaluation. The rats are allocated to four groups (eight rats per group) such that the differences in the averages of those parameters among the groups became small. All the analgesic effect evaluations and behavioral observations can be carried out by the observer who is blind to the drug treatment.

Data can be expressed as the mean+/−S.E.M. The time-course curves for mechanical allodynia, thermal hyperalgesia, joint hyperalgesia, body weight, and paw volume can be subjected to two-way repeated measures analysis of variance with post hoc t test. In experiments for evaluation of compounds of Formula (I), the difference in scores between the vehicle-treated and naive control groups can be analyzed by Student's t test to confirm significant changes in the pain parameters in the ipsilateral paw. The analgesic effects can be analyzed by Dunnett's t test, and in each case the drug-treated groups can be compared with the vehicle-treated group. In each statistical analysis, the comparison can be conducted for paws on the corresponding side. $P<0.05$ is considered statistically significant. In this model, the centrally acting analgesics morphine and tramadol fully relieved pain, whereas the NSAIDs, indomethacin and diclofenac are partially effective, evidencing the model's clinical predictability. The analgesic effect of compounds of the Formula (I) in this test would predict their clinical usefulness in treating arthritis.

Example 10

In Vivo Model for Arthritis: Inflammogen-Induced Hyperalgesia of the Knee Joint

Compounds of the Formula (I) can be tested in animal models of osteoarthritis, according to previously documented and validated methods, such as those described by Sluka et al. (Sluka, K. A.; Westlund, K. N. *Pain* 1993, 55(3), 367-77). For example, male Sprague-Dawley rats (Harlan, Indianapolis, Ind.) weighing 225 to 350 g can be briefly anesthetized with vaporized halothane and then injected with a mixture of 3% carrageenan and 3% kaolin (100 µL in 0.9% sterile saline) into the joint cavity of one knee. After the injection, the animals can be returned to their cages until the time of testing. For behavioral testing, animals can be placed in individual clear plastic cages on top of an elevated wire mesh surface that restricted movement. The animals should be allowed to acclimate for approximately 1 hour before testing. Von Frey filaments, as described above, can then be used to test for enhanced responses to mechanical stimuli. The filaments can be successively applied through the wire mesh perpendicularly to the plantar surface in between the pads of the third and fourth phalanges. The response threshold to mechanical stimuli can be determined before inflammation of the knee joint; 4 hours after inflammation to confirm the development of hyperalgesia; immediately after the administration of test compound such as those of Formula (I) i.e. 5 hours after inflammation; and at 8, 12, and 24 hours after inflammation.

The Kruskal-Wallis test, a nonparametric test, can be used to analyze the effects for frequency, intensity, and group for response to mechanical stimuli at baseline, 4 hours after inflammation, and after compound treatment (5 hours, 8 hours, 12 hours, and 24 hours after inflammation). Further post hoc testing between groups can be executed by using the Mann-Whitney signed rank test. The data can be presented as median with 25th and 75th percentiles. Significance is $P \leq 0.05$.

Additionally, the gait of the animal or other pain-related behavior can be scored as the dependent measure of the painful effect of the arthritis on the animal's activity (Hallas, B.; Lehman, S.; Bosak, A. et al. *J. Am. Osteopath. Assoc.* 1997, 97(4), 207-14). The effect of test drug on the animal's normal behavior can be quantified from zero, meaning no response, to three for incapacitating impairment. Effective analgesic treatment includes the clinically used indomethacin (Motta, A. F. et al. *Life Sci.* 2003, 73(15), 1995-2004). Thus the benefit of compounds of the Formula (I) in this model would predict their clinical relevance.

Example 11

Sarcoma Cell-Induced Models of Bone Cancer Pain

Compounds of the Formula (I) can be tested in animal models of bone cancer pain, according to previously documented and validated methods, such as those described in the scientific literature (El Mouedden, M.; Meert, T. F. *Pharmacol. Biochem. Behav.* 2005, 82(1), 109-19; Ghilardi, J. R. et al. *J. Neurosci.* 2005, 25(12), 3126-31). In preparation for cell inoculation and tumor induction, osteolytic murine sarcoma cells (NCTC 2472, American Type Culture Collection (ATCC), Rockville, Md., USA) can be cultured in NCTC 135 medium (Invitrogen) containing 10% horse serum (Gibco) and passaged 2 times weekly according to ATCC guidelines. For their administration, cells can be detached by scraping and then centrifuged at 1000×g. The pellet can be suspended in fresh NCTC 135 medium ($2.5 \times 10^6$ cells/20 µL) and then used for intramedullary femur inoculation. Male C3H/HeN-Crl mice (25-30 g, Charles River Labs) can be used in such experiments. After induction of general anesthesia with xylazine (10 mg/kg i.p.) and ketamine (100 mg/kg i.p.) the left hind paw can be shaved and disinfected with povidone-iodine followed by 70% ethanol. A superficial incision of 1 cm can then be made over the knee overlaying the patella. The patellar ligament can then be cut, exposing the condyles of the distal femur. A 23-gauge needle can be inserted at the level of the intercondylar notch and the intramedullary canal of the femur to create a cavity for injection of the cells. Twenty microliters of media (sham animals) or media containing tumor cells (approximately $2.5 \times 10^6$ cells) can then be injected into the bone cavity using a syringe. To prevent leakage of cells outside the bone, the injection site can be sealed with dental acrylic and the wound closed with skin stitches.

Pain behaviors can be evaluated in separate groups (n=6) of sham and bone tumor mice with confirmed hyperalgesia as assessed by spontaneous lifting behavior. Animals can be behaviorally tested during a 3-week period prior to and after tumor inoculation. Body weight of the mice can be recorded throughout the experimental period to help monitor general health status. To measure the spontaneous lifting, the animals can be habituated in a transparent acrylic cylinder of 20 cm diameter put on an horizontal surface and thereafter observed during 4 min for spontaneous lifting behavior of the left hind paw. After spontaneous lifting behavior assessment, animals can be immediately placed on a mouse rotarod (e.g. ENV-575M\, Med Associates Inc., GA, USA) at a speed of 16 rpm for 2 min wherein limb-use during forced ambulation is scored: 4=normal; 3=limping; 2=partial non-use of left hind paw; 1=substantial non-use of left hind paw; 0=non-use of left hind paw. Assessment of cold allodynia may be made by exposing the ipsilateral hind paw of the mouse to 5 repeated applications of acetone (20 µL) and quantifying the lift/licking frequency and/or duration. Post-mortem evaluation of bone destruction can be assessed by ACT processing followed by scanning using a system such as the Skyscan 1076 microtomograph system for small animal imaging (Skyscan 1076\, Skyscan, Aartselaar, Belgium). Measured histomorphometry parameters of bone destruction can be subsequently correlated with behavioral endpoints.

The antihyperalgesic, antiallodynic and disease modifying effects of compounds of the Formula (I) can be tested in this murine model of bone cancer pain in separate groups (n=6 per dose group). Animals with confirmed hyperalgesia, as assessed by spontaneous or acetone-evoked lifting, can be behaviorally tested, for example, on days and 22 after distal femur tumor inoculation before and 1 h after systemic administration of vehicle (e.g. 20% HPbCD in sterile water) or compounds of the Formula (I). The statistical analysis can be performed by one-way ANOVA to compare behavioral measurements and bone parameters among the experimental groups. To compare behavioral measurements and bone parameters between sham and tumor-bearing animals, a Mann-Whitney U test can be used. Results are considered statistically significant at $P<0.05$ (two-tailed). Data are expressed as mean+/−S.E.M.

Bone cancer causes intense pain in humans, mimicked in animal models of bone cancer pain in rodents such as that described above. Analgesic treatments that are effective in this model include COX-2 inhibitors (Sabino, M. A.; Ghilardi, J. R.; Jongen, J. L. et al. *Cancer Res.* 2002, 62(24), 7343-9) and high doses of morphine (Luger, N. M. et al. *Pain* 2002, 99(3), 397-406), agents used clinically for pain relief in patients experiencing bone cancer pain. Because this model so closely mimics the human disease state, the finding that cold allodynia is a prominent symptom (Lee, Seong et al. *Yonsei Med. J.* 2005, 46(2), 252-9) strongly supports the concept that TRPM8 antagonists of the present invention will provide relief of pain associated with human bone cancer.

Example 12

Respiratory Irritant-Induced Models of Cough

Compounds of the Formula (I) can be tested in animal models of antitussive activity, according to previously documented and validated methods, such as those described by: Tanaka, M. and Maruyama, K. *J. Pharmacol. Sci.* 2005, 99(1), 77-82; Trevisani, M. et al. *Throax* 2004, 59(9), 769-72; and Hall, E. et al. *J. Med. Microbiol.* 1999, 48, 95-98. Testing is conducted in transparent ventilated chambers with a constant airflow of 400 mL/min. The tussive agent (citric acid 0.25 M or capsaicin 30 mM) can be nebulized via a miniultrasonic nebulizer with an output of 0.4 mL/min. The appearance of cough can be detected by means of a tie clip microphone and confirmed by the characteristic posture of the animal. The cough sounds can be recorded and digitally stored. A blinded observer subsequently counts the number of elicited cough efforts. In some cases, animals can be sensitized by pre-exposure to certain agents such as ovalbumin. A test compound can be administered to at the peak of irritant-induced cough to evaluate the antitussive effects of the compound. In addition, prophylactic or multiple dosing regimes can be utilized to evaluate the test compound for modulation of the onset and duration of irritant-induced cough. Variations of these tests predict the antitussive effects of effective clinical agents, including NMDA antagonists such as dextrorphan and dextromethorphan, opioids such as codeine, beta 2 agonists such as salbutamol and antimuscarinics such as ipratropium (Bolser, D. C. et al. *Eur. J. Pharmacol.* 1995, 277(2-3), 159-64; Braga, P. C. *Drugs Exper. Clin. Res.* 1994, 20, 199-203). The antitussive action of menthol in both guinea pig and humans (Eccles, R. *Curr. Allergy Asthma Rep.* 2003, 3(3), 210-4; Laude, E. A. et al. *Pulm. Pharmacol.* 1994, 7(3), 179-84; Morice, A. H. et al. *Thorax* 1994, 49(10), 1024-6) is predictive of the clinical utility of compounds of the Formula (I) as antitussive agents.

Example 13

Chemical Irritant-Induced Models of Itch, Contact Dermatitis, Eczema and Other Manifestations of Dermal Allergy, Hypersensitivity and/or Inflammation Compounds of the Formula (I) can be tested in animal models of contact dermatitis or itch, according to previously documented and validated methods, such as those described in the scientific literature (Saint-Mezard, P. et al. *Eur. J. Dermatol.* 2004, 14(5), 284-95; Thomsen, J. S. et al. *J. Exp. Dermatol.* 2002, 11(4), 370-5; Weisshaar, E. et al. *Arch. Dermatol. Res.* 1998, 290(6), 306-11; Wille, J. J. et al. *Skin Pharmacol. Appl. Skin Physiol.* 1999, 12(1-2), 18-27). Mice (or species such as guinea pig or rat) can be sensitized with 25 mL of 0.5% dinitrofluorobenzene solution (DNFB diluted 4:1 in acetone:olive oil immediately before application or other haptens, such as 12-myristate-13 acetate, picryl chloride, oxazolone, capsaicin, arachidonic acid, lactic acid, trans-retinoic acid or sodium lauryl sulfate) painted to the shaved dorsal skin or untreated (controls). Five days later, 10 mL of 0.2% DNFB a nonirritant dose) can be applied onto both sides of the right ear and the same amount of solvent alone onto the left ear. Ear thickness can be monitored daily using a caliper. Compounds of the Formula (I) can be administered at the peak of inflammation to evaluate the anti-allergy activity of compounds. In addition, prophylactic or multiple dosing regimes can be utilized to evaluate the test compound for modulation of the onset and duration of anti-allergy activity. Variations of these tests can predict the anti-allergy and itch activity of effective clinical agents. The ability of these models to predict the therapeutic effect of compounds in human dermal conditions is supported by the cross-species ability of serotonin to induce itch (Weisshaar, E.; Gollnick, H. *Skin Therapy Lett.* 2000, 5(5), 1-2, 5). Additionally, the contact sensitizing property of commercially important drugs and the ability of ion channel modulators to prevent and treat skin sensitization in these models (Kydonieus, A. et al. *Proceedings of the International Symposium on Controlled Release of Bioactive Materials* 24th: 23-24, 1997) demonstrate the therapeutic utility of compounds of the Formula (I) in dermal sensitization.

Example 14

Chemical Irritant-Induced Models of Rhinitis and Other Manifestations of Nasal Hypersensitivity and/or Inflammation Compounds of the Formula (I) can be tested in animal models of rhinitis, according to previously documented and validated methods, such as those described in the scientific literature (Hirayama, Y. et al. *Eur. J. Pharmacol.* 2003, 467 (1-3), 197-203; Magyar, T. et al. *Vaccine* 2002, 20(13-14), 1797-802; Tiniakov, R. L. et al. *J. Appl. Physiol.* 2003, 94(5), 1821-8). Testing can be conducted in mouse, guinea pig, dog or human in response to intranasal challenge with one or more irritants such as cold air, capsaicin, bradykinin, histamine, pollens, dextran sulfate, 2,4-tolylene diisocyanate, *Bordetella bronchiseptica*, *Pasteurella multodica* or acetic acid. In some cases, animals can be sensitized by pre-exposure to certain agents including, but not limited to, ragweed or ovalbumin. Prior to or following irritant administration, the test subject can receive, respectively, the prophylactic or therapeutic administration one or more times of compounds of the Formula (I), or vehicle control, by the enteral or parenteral route. Significant differences indicative of nasal rhinitis or sensitization for the test compound-treated subjects compared with vehicle-treated subjects can be taken as evidence of antirhinitis activity. Independent variables include dose, frequency and route of administration, time interval between prophylactic or therapeutic test compound administration and irritant challenge as well as sex and non-sex genotype of the test subject. The intimate role of neurogenic inflammation in these hypersensitivity states demonstrates that compounds of the Formula (I) desensitize or block the sensitization underlying these disease states.

Example 15

Conflict-Induced Models of Anxiety, Panic Disorder and Other Non-Adaptive Stressful or Phobic Responses Compounds of the Formula (I) can be tested in animal models of anxiety, panic disorders and other non-adaptive responses, according to previously documented and validated methods, such as those described by Cryan and Holmes (Cryan, J. F.; Holmes, A. *Nat. Rev. Drug Discov.* 2005, 4(9), 775-90) or Braw et al. (Braw, Y. et al. *Behav. Brain Res.* 2006, 167, 261-269). Specifically, for studies in rats, the following apparati may be utilized: an open-field arena (62 cm×62 cm) enclosed by opaque walls (30 cm high) and plus-maze consists of two open arms, 50 cm×10 cm, and two enclosed arms, 50 cm×10 cm×40 cm with an open roof, arranged such that the two arms of each type are opposite each other. The maze is elevated to a height of 70 cm. The walls of the enclosed arms are made from black Plexiglas, while the floors from white Plexiglas. Videotape recordings can be analyzed using the 'Observer' system (Noldus Information Technology). A subject rat can be removed from its home cage, weighed and placed gently in the center of the open-field arena. The rat can be allowed to explore the open-field freely while its behavior is videotaped for 5 min. Afterwards, it can be transferred to the plus-maze and placed at the center, facing a closed arm. The rat's behavior can again be videotaped for 5 min, after which it can be returned to its home cage. The apparatus can be cleaned using a 70% ethanol solution between rats.

Open-field and plus-maze measures can be grouped into two behavioral classes, namely 'anxiety-like behaviors' and 'activity'. Open-field behavioral measures may include 1) Anxiety measures: % time in center square, % number of entries to center square (from total squares entered), % time freezing, latency to first freezing (freezing is scored when the subject is in an immobile state for at least 3 seconds; and 2) Activity measures: Total squares entered, number of rearings (standing on two hind legs), latency for first rearing. Plus-maze measures may include 1) Anxiety: % time in open arms, % number of entries to open arms (from total entries), number of unprotected head dips, latency to enter open arm; and 2) Activity: Total entries to all arms. Anxiety-like behaviors and activity can be analyzed by one-way ANOVA's on each of the measures, for each the between-subject comparisons. Plus-maze analyses can be conducted in a similar fashion.

Testing may also be conducted in mouse or rat in this fashion in order to measure avoidance of other aversive environmental stimuli such as Geller or Vogel anticonflict tests, the light/dark test and the hole-board test (see Cryan, J. F.; Holmes, A. *Nat. Rev. Drug Discov.* 2005, 4(9), 775-90). Prior to environmental exposure, the test subject can receive the prophylactic administration one or more times of compounds of the Formula (I), or vehicle control (e.g. 10% Solutol in sterile water), by the enteral or parenteral route. The cumulative time or number of times spent engaged in the aversive behavior can be measured. Significant differences in one or more of these measures for the test compound-treated subjects compared with vehicle-treated subjects can be taken as evidence of anxiolytic activity. Because these models are pharmacologically validated by the effectiveness of clinically useful anxiolytics (Cryan, J. F.; Holmes, A. *Nat. Rev. Drug Discov.* 2005, 4(9), 775-90), they will be useful for the detection of anxiolytic compounds of the Formula (I).

Example 16

Bladder Pressure- and Hypertrophy-Induced Models of Urinary Incontinence

Compounds of the Formula (I) can be tested in animal models of urinary incontinence according to previously documented and validated methods, such as those described by in the scientific literature (Kaiser, S.; Plath, T. (Metagen Pharmaceuticals GmbH, Germany DE Patent 10215321); McMurray, G. et al. *Brit. J. Pharmacol.* 2006, 147 Suppl 2, S62-79). TRPM8 is expressed in human prostate, testicle, seminiferous tubules, scrotal skin and inflamed bladder (Stein, R. J. et al. *J. Urol.* 2004, 172(3), 1175-8; Stein, R. J. et al. *J. Urol.* 2004, 172(3), 1175-8; Mukerji et al. *BMC Urology* 2006, 6, 6). Excitation of TRPM8 receptors through cooling or application of menthol causes contraction in the bladder and a decrease in micturation threshold volume (Tsukimi, Y.; Mizuyachi, K. et al. *Urology* 2005, 65(2), 406-10). To assess compounds of the Formula (I) for potential urinary incontinence activity, Sprague-Dawley rats are surgically implanted with bladder catheters allowing for the delivery of fluid (typically saline) and the monitoring of pressure (using a pressure transducer). Cystometry recordings can be monitored with a polygraph to evaluate voiding interval, threshold pressure, bladder capacity, bladder compliance, and the number of spontaneous bladder contractions. For example, the bladder catheter can be connected to a Harvard infusion pump, and bladders perfused overnight with saline at 2 mL/h. The next morning the bladder catheter can be attached (using a "T" connector) to a Statham pressure transducer (Model P23 Db) and to a Harvard infusion pump. A plastic beaker attached to a force displacement transducer (Grass FTO3) can be placed under the rat's cage to collect and record urine volume. The cystometric evaluation of bladder function can be started by infusing saline (20 mL/h) and after the first micturition the infusion is maintained for 20 min. Two hours after the first cystometry period, the rats can be dosed orally with compounds of the Formula (I) and a second cystometry is performed between 30 min and 4 h after administration of test compound. The appropriate vehicle (e.g. 10% Solutol in sterile water) can be similarly administered to groups of rats that served as controls and the cystometry can be performed at the same respective time points.

Compounds of the Formula (I) can also be evaluated under conditions of bladder hypertrophy and instability. Under anesthesia, a silk ligature is tied around the proximal urethra of rodents producing a partial outlet obstruction and subsequent hypertrophied bladder development within 6-9 weeks (Woods, M. et al. *J. Urology* 2001, 166, 1142-47). Cystometry recordings can then be evaluated as described above. Such preclinical procedures are sensitive to compounds having clinical utility for the treatment of urinary incontinence (Soulard, C. et al. *J. Pharmacol. Exp. Ther.* 1992, 260(3), 1152-8), and the activity of compounds of the Formula (I) in this model would be predictive of clinical utility.

Example 17

In Vivo Model for Cold-Enhanced Central Pain States

Injury to the brain or spinal cord, such as that caused by trauma, interrupted blood flow or neurodegenerative diseases, often precipitates a central pain condition. Examples of such injuries characterized, in part by, a hypersensitivity to cold stimuli include multiple sclerosis (Morin, C. et al. *Clin. J. Pain* 2002, 18(3), 191-5; Svendsen, K. B. et al. *Pain* 2005, 114(3), 473-81), stroke or cerebral ischemia (Greenspan, J. D. et al. *Pain* 2004, 109(3), 357-66) and spinal cord injury (Defrin, R.; Ohry, A.; Blumen, N.; Urca, G. *Pain* 2001, 89(2-3), 253-63; Defrin, R. et al. *Brain* 2002, 125(Pt 3), 501-10; Finnerup, N. B. et al. *Anesthesiology* 2005, 102(5), 1023-30). Each of these conditions may be readily modeled in animals for assessment of the ability of compounds of the Formula (I) to mollify the hypersensitive state. For example, a spinal cord injury (SCI) can be performed in adult Sprague-Dawley rats having a body weight of 150-200 g at time of surgery (Erichsen et al. *Pain* 2005, 116, 347-358). The rats can be anaesthetized with chloral hydrate (300 mg/kg, i.p., Sigma, USA) and a catheter can be inserted into the jugular vein. A midline skin incision can then be made along the back to expose the T11-L2 vertebrae. The animals can be positioned beneath a tunable argon ion laser (Innova model 70, Coherent Laser Products Division, CA, USA) operating at a wavelength of 514 nm with an average power of 0.17 W. The laser light can be focused into a thin beam covering the single T13 vertebra, which can be irradiated for 10 min. Immediately before the irradiation, erythrosin B (Aldrich, 32.5 mg/kg dissolved in 0.9% saline) can be injected intravenously via the jugular catheter. Due to rapid metabolism of erythrosin B, the injection can be repeated after 5 min in order to maintain adequate blood concentrations. During irradiation, the body core temperature can be maintained at 37-38° C. by a heating pad. After irradiation the wound can be closed in layers and the skin sutured together.

SCI rats can be routinely tested for the presence of pain-like behaviors from 3-4 weeks after surgery. The fur of the animals can be shaved at least a day prior to examination of the cutaneous pain threshold to avoid sensitization of the skin receptors. During testing, the rats can be gently held in a standing position by the experimenter and the flank area and hind limbs can be examined for hypersensitivity to sensory stimulation. On the day of drug testing, SCI rats can be administered drug according to the experimental schedule and the time course of pain-like behaviors can be measured. To test for the presence of cold allodynia, ethyl chloride or acetone can be sprayed onto the skin of the animals, often that which has been previously determined to be sensitive to mechanical stimulation by von Frey filament testing. The subsequent response to cold stimulation can be observed and classified according to the following scale: 0, no visible response; 1, localized response (skin twitch) without vocalization; 2, transient vocalization; 3, sustained vocalization. Kruskal Wallis ANOVA on ranks can be used to analyze the overall effects of non-parametric data obtained in response to cold stimulation following pretreatment with either compounds of the Formula (I) or vehicle.

Example 18

In Vivo Model for Post-Anesthetic Shivering

Spontaneous post-anesthetic tremor that resembles shivering is common during recovery from anesthesia. Risks to postoperative patients include an increase in metabolic rate of up to 400%, hypoxemia, wound dehiscence, dental damage, and disruption of delicate surgical repairs. The etiology of spontaneous post-anesthetic tremor is most commonly attributed to normal thermoregulatory shivering in response to intraoperative hypothermia. In most operating and recovery rooms, shivering is controlled by the use of humidifiers, warming blankets, and inhalation of humidified heated oxygen. However, pharmacological control is an effective alternate treatment modality (Bhatnagar, S. et al. *Anesth. Intensive Care* 2001, 29(2), 149-54; Tsai, Y. C.; Chu, K. S. *Anesth. Analg.* 2001, 93(5), 1288-92). Compounds of the Formula (I) may be assessed for their ability to mitigate post-anesthetic induced-shaking by using animal models such as that described by Nikki et al. (Nikki, P.; Tammisto, T. *Acta Anaesth. Scand.* 1968, 12(3), 125-34) and Grahn (Grahn, D. A. et al. *J. Applied Physiology* 1996, 81, 2547-2554). For example, Wistar rats (males, weighing 250-450 g) may be surgically implanted with an EEG/EMG recording array to assess post anesthetic tremor activity. The EEG electrodes are located bilaterally 2 mm off midline and adjacent to bregma and lamda. Following a one-week recovery period, frontal-occipital EEG, raw EMG, and integrated EMG activities, as well as three temperatures (skin, rectal, and water blanket temperatures during anesthesia), and ambient temperature post-anesthesia can be monitored throughout the experiment using copper-constantin thermocouples. The EEG and EMG signals can be recorded on polygraph paper (5 mm/s, Grass model 7E polygraph) and, during recovery from anesthesia, the EEG is computer scored in 10 second epochs as either synchronized: high amplitude ($0.100\,\mu V$), low frequency (1-4 Hz dominated) activity characteristic of slow-wave sleep (SWS-like) or desynchronized: low amplitude ($75\,\mu V$), high frequency (5-15 Hz dominated), characteristic of waking and rapid-eye-movement sleep (W-like). The EMG activity can be quantified as the averaged summed voltage/time interval by processing the raw EMG signal through an integrator (Grass model 7P3, 0.5 s time constant). On the day of an experiment, the animal can be placed in a small acrylic box (15×15×15 cm) and exposed to a halothane vapor-air mixture (4% halothane). Immediately after the induction of anesthesia, the animal can be removed from the enclosure and subsequently anesthetized through a nose cone. Following cessation of anesthesia, two stages of recovery can be judged: emergence from anesthesia and restoration of behavioral activity (behavioral recovery). Emergence from anesthesia may be defined as an increase in tonic EMG activity and a change in the EEG from a SWS-like pattern to a W-like pattern. Behaviorally, recovery has occurred when the animal rises from a prone position and initiated coordinated movements. The time intervals from termination of anesthesia to emergence and behavioral recovery can be measured in all animals. Time interval data can be subjected to a repeated measure analysis of variance, and the Scheffe's method can be employed for testing differences between pairs of means.

Example 19

Cold-Evoked Cardiovascular Pressor Responses

Compounds of the Formula (I) can be tested in animals and humans for their ability to mitigate cardiovascular pressor responses evoked by cold exposure. Seasonal environmental cooling is directly associated with elevated blood pressure and an increased incidence of coronary events in human populations worldwide (Barnett, A. G. et al. *J. Epidemiol. Community Heath* 2005, 59, 551-557). Cold-evoked pulmonary hypertension and cold aggravation of chronic obstructive pulmonary disease are clinical indications susceptible to heightened cardiopulmonary sensitivity to cold (Marno, P. et al. *Eur. Respiratory Review* 2006, 15(101), 185; Acikel, M. et al. *Int. J. of Cardiol.* 2004, 97, 187-192). The clinical cold pressor test assesses changes in blood pressure (BP) and cold pain perception during a 2-3 minute immersion of one hand into ice water. This test may be utilized to characterize analgesic compounds (Koltzenberg, M. et al. *Pain* 2006, 126(1-3), 165-74) and to assess cold hypersensitivity (Desmeules, J. A. et al. *Arthritis and Rheumatism* 2003, 48(5), 1420-9). Compounds of the Formula (I) can be studied in an anesthetized rat cold pressor paradigm to determine whether TRPM8 antagonism would interfere with the blood pressure pressor response to cold stimulation of the forepaws. Male Sprague-Dawley rats (300-450 g) anesthetized with sodium pentobarbital are instrumented with a jugular catheter and an indwelling carotid artery cannula connected to a pressure transducer. Vehicle (e.g. 20% HPbCD in sterile water) or test compound is infused (1 mL/kg) over one minute through the intravenous catheter. Ten minutes later both forelimbs are packed in crushed ice for 5 minutes. Alternatively, the test compound and vehicle treatments may be administered orally at an appropriated time prior to the surgical cannulations and cold challenge. Percent changes in mean arterial pressure in response to this cold stimulus are calculated for vehicle and test compound pretreatments. Percent inhibition attributed to treatment with test compound is then determined using the following formula: % Inhibition=[1−(cold evoked % change in BP post-test compound/cold evoked % change in BP post-vehicle)]×100.

Example 20

Cold-Induced Vasoconstriction: Ramifications for Tissue Perfusion

Damage may occur to a bodily tissue when blood flow is compromised or interrupted. Reasons for vascular compromise include peripheral vascular disease (Lamah, M. et al. *European Journal of Vascular and Endovascular Surgery* 1999, 18(1), 48-51), prior traumatic or frostbite injury, Raynaud's syndrome (Lutolf, O. et al. *Microvascular Research* 1993, 46(3), 374-82), diabetic neuropathy (Forst, T. et al. *Clinical Science* 1998, 94(3), 255-61), surgical intervention and autonomic dysregulation (Gherghel, D. et al. *Investigative Opthalmology and Visual Science* 2004, 45(10), 3546-54). In the case of marginal resting perfusion, vasoconstriction as enhanced by cool temperature may aggravate symptoms and potentiate tissue injury (Cankar, K. et al. *Journal of Hand Surgery* 2000, 25(3), 552-8; Lutolf, O. et al. *Microvascular Research* 1993, 46(3), 374-82.). Several of these conditions may be readily modeled in animals to assess the ability of TRPM8 antagonists such as compounds of the Formula (I) to preserve tissue perfusion in the face of local cooling. For example, laser Doppler assessment of skin blood flow may be studied in the paws of anesthetized rats (Hord, A. H. et al. *Anesthesia and Analgesia* 1999, 88(1), 103-8), wherein the paw is subject to a series of decreasing temperature steps as applied by physical contact with a Peltier cooling element under computer control. The laser Doppler measures skin perfusion in the face of cooling-induced vasoconstriction thereby generating a temperature×perfusion relationship. Systemic administration of a TRPM8 antagonist is anticipated to shift this curve toward preserving perfusion at reduced temperatures relative to vehicle pretreatment. This activity is envisioned to be therapeutic in protecting tissue from hypo-perfusion and ischemia thereby minimizing the associated symptoms (e.g. pain) and potential tissue damage.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:
1. A compound of the formula (I)

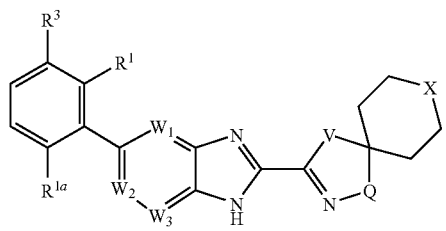

Formula (I)

wherein
$W_1$ is $C(R^{2a})$ or N;
$W_2$ is CH or N;
$W_3$ is $C(R^2)$ or N;
  such that no more than one of $W_1$, $W_2$, and $W_3$ is N; and when one of $W_1$, $W_2$, and $W_3$ is N, then $R^2$ and $R^{2a}$ are hydrogen;
$R^1$ is fluoro, chloro, trifluoromethyl, (1-hydroxy-1-methyl)ethyl, 2,2,2trifluoroethyl, trifluoromethoxy, or difluoromethoxy; or $R^1$ and $R^3$ are taken together to form a single fused —$OCF_2O$— moiety;
$R^{1a}$ is hydrogen, fluoro, chloro, or bromo;
$R^2$ is hydrogen, $C_{1-4}$alkyl, fluoro, chloro, bromo, cyano, trifluoromethyl, hydroxy($C_{1-6}$)alkyl, $C_{1-3}$alkoxy($C_{1-6}$) alkyl, cyclopropyl, —CH=CHCH$_2$OH, or $C_{2-4}$alkenyl bound via an unsaturated carbon atom;
$R^{2a}$ is hydrogen or methyl;
$R^3$ is hydrogen, fluoro, or taken with $R^1$ to form —$OCF_2O$—;
V and Q are selected from the group consisting of
  V is CH($R^4$) and Q is O;
  V is NH and Q is CH$_2$; and
  V is O and Q is CH$_2$;
$R^4$ is hydrogen or $C_{1-4}$alkyl;
X is CH$_2$, C(CH$_3$)$_2$, CF$_2$, or O;
  with the proviso that when V is NH, X is other than O;
or enantiomers, diastereomers, or pharmaceutically acceptable salts thereof.

2. The compound of claim 1 wherein $R^1$ is fluoro, trifluoromethyl, (1-hydroxy-1-methyl)ethyl, 2,2,2-trifluoroethyl, trifluoromethoxy, or difluoromethoxy; or $R^1$ and $R^3$ are taken together to form a single fused —$OCF_2O$— moiety.

3. The compound of claim 2 wherein $R^1$ is fluoro, trifluoromethyl, (1-hydroxy-1-methyl)ethyl, 2,2,2-trifluoroethyl, trifluoromethoxy, or difluoromethoxy.

4. The compound of claim 1 wherein $R^{1a}$ is hydrogen or fluoro.

5. The compound of claim 1 wherein $R^2$ is hydrogen, $C_{1-4}$alkyl, fluoro, chloro, bromo, cyano, trifluoromethyl, hydroxy$C_{1-6}$alkyl, $C_{1-3}$alkoxy ($C_{1-6}$alkyl) or —CH=CHCH$_2$OH.

6. The compound of claim 5 wherein $R^2$ is $C_{1-4}$alkyl, fluoro, chloro, bromo, cyano, trifluoromethyl, hydroxy($C_{1-6}$) alkyl, or —CH=CHCH$_2$OH.

7. The compound of claim 6 wherein $R^2$ is methyl, fluoro, chloro, bromo, trifluoromethyl, or hydroxy($C_{1-6}$)alkyl.

8. The compound of claim 1 wherein $R^{2a}$ is hydrogen or methyl.

9. The compound of claim 1 wherein $R^3$ is hydrogen or taken with $R^1$ to form —$OCF_2O$—.

10. The compound of claim 1 wherein $R^3$ is hydrogen.

11. The compound of claim 1 wherein V and Q are selected from the group consisting of
  V is CH($R^4$) and Q is O; and V is O and Q is CH$_2$.

12. The compound of claim 1 wherein $R^4$ is hydrogen or methyl.

13. The compound of claim 1 wherein X is CH$_2$, CF$_2$, or O.

14. The compound of claim 1 wherein X is CH$_2$ or O.

15. A compound of Formula (I)

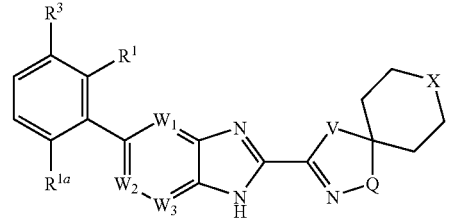

Formula (I)

wherein
$W_1$ is $C(R^{2a})$ or N;
$W_2$ is CH or N;
$W_3$ is $C(R^2)$ or N;
  such that no more than one of $W_1$, $W_2$, and $W_3$ is N; and when one of $W_1$, $W_2$, and $W_3$ is N, then $R^2$ and $R^{2a}$ are hydrogen;
R is fluoro, trifluoromethyl, (1-hydroxy-1-methyl)ethyl, 2,2,2-trifluoroethyl, trifluoromethoxy, or difluoromethoxy; or $R^1$ and $R^3$ are taken together to form a single fused —$OCF_2O$— moiety;
$R^{1a}$ is hydrogen or fluoro;
$R^2$ is hydrogen, $C_{1-4}$alkyl, fluoro, chloro, bromo, cyano, trifluoromethyl, hydroxy($C_{1-6}$)alkyl, $C_{1-3}$alkoxy($C_{1-6}$) alkyl, or —CH=CHCH$_2$OH;
$R^{2a}$ is hydrogen or methyl;
$R^3$ is hydrogen or taken with $R^1$ to form —$OCF_2O$—;
  V and Q are selected from the group consisting of
  V is CH($R^4$) and Q is O;
  V is NH and Q is CH$_2$; and
  V is O and Q is CH$_2$;
$R^4$ is hydrogen or methyl;
X is CH$_2$, CF$_2$, or O;
  with the proviso that when V is NH, X is other than O;
or enantiomers, diastereomers, or pharmaceutically acceptable salts thereof.

16. A compound of Formula (I)

Formula (I)

wherein
$W_1$ is $C(R^{2a})$ or N;
$W_2$ is CH or N;
$W_3$ is $C(R^2)$ or N;
such that no more than one of $W_1$, $W_2$, and $W_3$ is N; and when one of $W_1$, $W_2$, and $W_3$ is N, then $R^2$ and $R^{2a}$ are hydrogen;
$R^1$ is fluoro, trifluoromethyl, (1-hydroxy-1-methyl)ethyl, 2,2,2-trifluoroethyl, trifluoromethoxy, or difluoromethoxy;
$R^{1a}$ is hydrogen or fluoro;
$R^2$ is hydrogen, $C_{1-4}$alkyl, fluoro, chloro, bromo, cyano, trifluoromethyl, hydroxy($C_{1-6}$)alkyl, $C_{1-3}$alkoxy($C_{1-6}$)alkyl, or —CH=CHCH$_2$OH;
$R^{2a}$ is hydrogen or methyl;
$R^3$ is hydrogen;
V and Q are selected from the group consisting of
V is CH($R^4$) and Q is O; and V is O and Q is CH$_2$;
$R^4$ is hydrogen or methyl;
X is CH$_2$, CF$_2$, or O;
or enantiomers, diastereomers, or pharmaceutically acceptable salts thereof.

17. A compound of Formula (I)

Formula (I)

wherein
$W_1$ is $C(R^{2a})$ or N;
$W_2$ is CH or N;
$W_3$ is $C(R^2)$ or N;
such that no more than one of $W_1$, $W_2$, and $W_3$ is N; and when one of $W_1$, $W_2$, and $W_3$ is N, then $R^2$ and $R^{2a}$ are hydrogen;
$R^1$ is fluoro, trifluoromethyl, (1-hydroxy-1-methyl)ethyl, 2,2,2-trifluoroethyl, trifluoromethoxy, or difluoromethoxy;
$R^{1a}$ is hydrogen or fluoro;
$R^2$ is hydrogen, $C_{1-4}$alkyl, fluoro, chloro, bromo, cyano, trifluoromethyl, hydroxy($C_{1-6}$)alkyl, $C_{1-3}$alkoxy($C_{1-6}$)alkyl, or —CH=CHCH$_2$OH;
$R^{2a}$ is hydrogen or methyl;
$R^3$ is hydrogen;
V and Q are selected from the group consisting of
V is CH($R^4$) and Q is O; and V is O and Q is CH$_2$;
$R^4$ is hydrogen or methyl;
X is CH$_2$, CF$_2$, or O;
or enantiomers, diastereomers, or pharmaceutically acceptable salts thereof.

18. A compound of Formula (I)

Formula (I)

wherein
$W_1$ is $C(R^{2a})$ or N;
$W_2$ is CH or N;
$W_3$ is $C(R^2)$ or N;
such that no more than one of $W_1$, $W_2$, and $W_3$ is N; and when one of $W_1$, $W_2$, and $W_3$ is N, then $R^2$ and $R^{2a}$ are hydrogen;
$R^1$ is fluoro, trifluoromethyl, (1-hydroxy-1-methyl)ethyl, 2,2,2-trifluoroethyl, trifluoromethoxy, or difluoromethoxy;
$R^{1a}$ is hydrogen or fluoro;
$R^2$ is hydrogen, methyl, fluoro, chloro, bromo, cyano, trifluoromethyl, hydroxy($C_{1-6}$)alkyl, $C_{1-3}$alkoxy($C_{1-6}$)alkyl, or —CH=CHCH$_2$OH;
$R^{2a}$ is hydrogen or methyl;
$R^3$ is hydrogen;
V and Q are selected from the group consisting of
V is CH($R^4$) and Q is O; and V is O and Q is CH$_2$;
$R^4$ is hydrogen or methyl;
X is CH$_2$ or O;
or enantiomers, diastereomers, or pharmaceutically acceptable salts thereof.

19. A compound of Formula (I)

Formula (I)

selected from the group consisting of:
a compound wherein $W_1$ is $C(R^{2a})$, $W_2$ is CH, $W_3$ is $C(R^2)$, $R^1$ is trifluoromethyl, $R^{1a}$, $R^2$, $R^{2a}$, and $R^3$ are hydrogen, V is CH($R^4$), Q is O, $R^4$ is hydrogen, and X is CH$_2$;
a compound wherein $W_1$ is $C(R^{2a})$, $W_2$ is CH, $W_3$ is $C(R^2)$, $R^1$ is trifluoromethoxy, $R^{1a}$, $R^2$, $R^{2a}$, and $R^3$ are hydrogen, V is O, Q is CH$_2$, and X is CH$_2$;
a compound wherein $W_1$ is $C(R^{2a})$, $W_2$ is CH, $W_3$ is $C(R^2)$, $R^1$ is trifluoromethoxy, $R^{1a}$, $R^2$, $R^{2a}$, and $R^3$ are hydrogen, V is O, Q is CH$_2$, and X is CH$_2$;

a compound wherein $W_1$ is $C(R^{2a})$, $W_2$ is CH, $W_3$ is $C(R^2)$, $R^1$ is trifluoromethyl, $R^{1a}$, $R^2$, $R^{2a}$, and $R^3$ are hydrogen, V is O, Q is $CH_2$, and X is $CH_2$;

a compound wherein $W_1$ is $C(R^{2a})$, $W_2$ is CH, $W_3$ is $C(R^2)$, $R^1$ is trifluoromethyl, $R^{1a}$, $R^2$, $R^{2a}$, and $R^3$ are hydrogen, V is O, Q is $CH_2$, and X is $CH_2$;

a compound wherein $W_1$ is $C(R^{2a})$, $W_2$ is CH, $W_3$ is $C(R^2)$, $R^1$ is trifluoromethyl, $R^{1a}$ is fluoro, $R^2$, $R^{2a}$, and $R^3$ are hydrogen, V is $CH(R^4)$, Q is O, $R^4$ is hydrogen, and X is $CH_2$;

a compound wherein $W_1$ is $C(R^{2a})$, $W_2$ is CH, $W_3$ is $C(R^2)$, $R^1$ is trifluoromethoxy, $R^{1a}$, $R^2$, $R^{2a}$, and $R^3$ are hydrogen, V is $CH(R^4)$, Q is O, $R^4$ is hydrogen, and X is $CH_2$;

a compound wherein $W_1$ is $C(R^{2a})$, $W_2$ is CH, $W_3$ is $C(R^2)$, $R^1$ is trifluoromethoxy, $R^{1a}$ is fluoro, $R^2$, $R^{2a}$, and $R^3$ are hydrogen, V is $CH(R^4)$, Q is O, $R^4$ is hydrogen, and X is $CH_2$;

a compound wherein $W_1$ is $C(R^{2a})$, $W_2$ is CH, $W_3$ is $C(R^2)$, $R^1$ is trifluoromethyl, $R^{1a}$, $R^2$, $R^{2a}$, and $R^3$ are hydrogen, V is $CH(R^4)$, Q is O, $R^4$ is hydrogen, and X is O;

a compound wherein $W_1$ is $C(R^{2a})$, $W_2$ is CH, $W_3$ is $C(R^2)$, $R^1$ is trifluoromethyl, $R^{1a}$, $R^2$, $R^{2a}$, and $R^3$ are hydrogen, V is $CH(R^4)$, Q is O, $R^4$ is hydrogen, and X is $CF_2$;

a compound wherein $W_1$ is $C(R^{2a})$, $W_2$ is CH, $W_3$ is $C(R^2)$, $R^1$ is 2,2,2-trifluoroethyl, $R^{1a}$, $R^2$, $R^{2a}$, and $R^3$ are hydrogen, V is $CH(R^4)$, Q is O, $R^4$ is hydrogen, and X is $CH_2$;

a compound wherein $W_1$ is $C(R^{2a})$, $W_2$ is CH, $W_3$ is $C(R^2)$, $R^1$ is taken with $R^3$ to form —$OCF_2O$—, $R^{1a}$, $R^2$, and $R^{2a}$ are hydrogen, V is $CH(R^4)$, Q is O, $R^4$ is hydrogen, and X is $CH_2$;

a compound wherein $W_1$ is $C(R^{2a})$, $W_2$ is CH, $W_3$ is $C(R^2)$, $R^1$ is difluoromethoxy, $R^{1a}$, $R^2$, $R^{2a}$, and $R^3$ are hydrogen, V is $CH(R^4)$, Q is O, $R^4$ is hydrogen, and X is $CH_2$;

a compound wherein $W_1$ is $C(R^{2a})$, $W_2$ is CH, $W_3$ is $C(R^2)$, $R^1$ is trifluoromethyl, $R^{1a}$ is hydrogen, $R^2$ is fluoro, $R^{2a}$ is hydrogen, $R^3$ is hydrogen, V is $CH(R^4)$, Q is O, $R^4$ is hydrogen, and X is $CH_2$;

a compound wherein $W_1$ is $C(R^{2a})$, $W_2$ is CH, $W_3$ is $C(R^2)$, $R^1$ is trifluoromethyl, $R^{1a}$, $R^2$, $R^{2a}$, and $R^3$ are hydrogen, V is $CH(R^4)$, Q is O, $R^4$ is methyl, and X is $CH_2$;

a compound wherein $W_1$ is $C(R^{2a})$, $W_2$ is CH, $W_3$ is $C(R^2)$, $R^1$ is trifluoromethyl, $R^{1a}$ is hydrogen, $R^2$ is chloro, $R^{2a}$ is hydrogen, $R^3$ is hydrogen, V is $CH(R^4)$, Q is O, $R^4$ is hydrogen, and X is $CH_2$;

a compound wherein $W_1$ is $C(R^{2a})$, $W_2$ is CH, $W_3$ is $C(R^2)$, $R^1$ is trifluoromethyl, $R^{1a}$ is hydrogen, $R^2$ is bromo, $R^{2a}$ is hydrogen, $R^3$ is hydrogen, V is $CH(R^4)$, Q is O, $R^4$ is hydrogen, and X is $CH_2$;

a compound wherein $W_1$ is $C(R^{2a})$, $W_2$ is CH, $W_3$ is $C(R^2)$, $R^1$ is (1-hydroxy-1-methyl)ethyl, $R^{1a}$, $R^2$, $R^{2a}$, and $R^3$ are hydrogen, V is $CH(R^4)$, Q is O, $R^4$ is hydrogen, and X is $CH_2$;

a compound wherein $W_1$ is $C(R^{2a})$, $W_2$ is CH, $W_3$ is $C(R^2)$, $R^1$ is trifluoromethyl, $R^{1a}$, $R^2$, $R^{2a}$, and $R^3$ are hydrogen, V is NH, Q is $CH_2$, and X is $CH_2$;

a compound wherein $W_1$ is $C(R^{2a})$, $W_2$ is CH, $W_3$ is $C(R^2)$, $R^1$ is difluoromethoxy, $R^{1a}$ is hydrogen, $R^2$ is methyl, $R^{2a}$ is hydrogen, $R^3$ is hydrogen, V is $CH(R^4)$, Q is O, $R^4$ is hydrogen, and X is $CH_2$;

a compound wherein $W_1$ is $C(R^{2a})$, $W_2$ is CH, $W_3$ is $C(R^2)$, $R^1$ is trifluoromethyl, $R^{1a}$ is hydrogen, $R^2$ is cyano, $R^{2a}$ is hydrogen, $R^3$ is hydrogen, V is $CH(R^4)$, Q is O, $R^4$ is hydrogen, and X is $CH_2$;

a compound wherein $W_1$ is $C(R^{2a})$, $W_2$ is CH, $W_3$ is $C(R^2)$, $R^1$ is trifluoromethyl, $R^{1a}$ is hydrogen, $R^2$ is 3-hydroxypropyl, $R^{2a}$ is hydrogen, $R^3$ is hydrogen, V is $CH(R^4)$, Q is O, $R^4$ is hydrogen, and X is $CH_2$;

a compound wherein $W_1$ is $C(R^{2a})$, $W_2$ is CH, $W_3$ is $C(R^2)$, $R^1$ is fluoro, $R^{1a}$, $R^2$, $R^{2a}$, and $R^3$ are hydrogen, V is $CH(R^4)$, Q is O, $R^4$ is hydrogen, and X is $CH_2$;

a compound wherein $W_1$ is $C(R^{2a})$, $W_2$ is CH, $W_3$ is $C(R^2)$, $R^1$ is trifluoromethyl, $R^{1a}$ is hydrogen, $R^2$ is hydrogen, $R^{2a}$ is methyl, $R^3$ is hydrogen, V is $CH(R^4)$, Q is O, $R^4$ is hydrogen, and X is $CH_2$;

a compound wherein $W_1$ is $C(R^{2a})$, $W_2$ is CH, $W_3$ is $C(R^2)$, $R^1$ is trifluoromethyl, $R^{1a}$ is hydrogen, $R^2$ is 1-hydroxyprop-2-en-3-yl, $R^{2a}$ is hydrogen, $R^3$ is hydrogen, V is $CH(R^4)$, Q is O, $R^4$ is hydrogen, and X is $CH_2$;

a compound wherein $W_1$ is $C(R^{2a})$, $W_2$ is CH, $W_3$ is $C(R^2)$, $R^1$ is fluoro, $R^{1a}$ is fluoro, $R^2$, $R^{2a}$, and $R^3$ are hydrogen, V is $CH(R^4)$, Q is O, $R^4$ is hydrogen, and X is $CH_2$;

a compound wherein $W_1$ is $C(R^{2a})$, $W_2$ is CH, $W_3$ is $C(R^2)$, $R^1$ is trifluoromethyl, $R^{1a}$ is hydrogen, $R^2$ is trifluoromethyl, $R^{2a}$ is hydrogen, $R^3$ is hydrogen, V is $CH(R^4)$, Q is O, $R^4$ is hydrogen, and X is $CH_2$;

a compound wherein $W_1$ is $C(R^{2a})$, $W_2$ is CH, $W_3$ is $C(R^2)$, $R^1$ is trifluoromethyl, $R^{1a}$ is hydrogen, $R^2$ is trifluoromethyl, $R^{2a}$ is hydrogen, $R^3$ is hydrogen, V is $CH(R^4)$, Q is O, $R^4$ is methyl, and X is $CH_2$;

a compound wherein $W_1$ is $C(R^{2a})$, $W_2$ is CH, $W_3$ is $C(R^2)$, $R^1$ is trifluoromethyl, $R^{1a}$, $R^2$, $R^{2a}$, and $R^3$ are hydrogen, V is O, Q is $CH_2$, and X is O;

a compound wherein $W_1$ is $C(R^{2a})$, $W_2$ is CH, $W_3$ is $C(R^2)$, $R^1$ is chloro, $R^{1a}$ is hydrogen, $R^2$ is trifluoromethyl, $R^{2a}$ is hydrogen, $R^3$ is hydrogen, V is $CH(R^4)$, Q is O, $R^4$ is hydrogen, and X is $CH_2$;

a compound wherein $W_1$ is $C(R^{2a})$, $W_2$ is CH, $W_3$ is $C(R^2)$, $R^1$ is fluoro, $R^{1a}$, $R^2$, $R^{2a}$, and $R^3$ are hydrogen, V is $CH(R^4)$, Q is O, $R^4$ is hydrogen, and X is O;

a compound wherein $W_1$ is $C(R^{2a})$, $W_2$ is CH, $W_3$ is $C(R^2)$, $R^1$ is trifluoromethyl, $R^{1a}$ is hydrogen, $R^2$ is methyl, $R^{2a}$ is hydrogen, $R^3$ is hydrogen, V is $CH(R^4)$, Q is O, $R^4$ is hydrogen, and X is O;

a compound wherein $W_1$ is $C(R^{2a})$, $W_2$ is CH, $W_3$ is $C(R^2)$, $R^1$ is trifluoromethyl, $R^{1a}$ is hydrogen, $R^2$ is bromo, $R^{2a}$ is hydrogen, $R^3$ is hydrogen, V is $CH(R^4)$, Q is O, $R^4$ is hydrogen, and X is O;

a compound wherein $W_1$ is $C(R^{2a})$, $W_2$ is CH, $W_3$ is $C(R^2)$, $R^1$ is trifluoromethyl, $R^{1a}$ is hydrogen, $R^2$ is chloro, $R^{2a}$ is hydrogen, $R^3$ is hydrogen, V is $CH(R^4)$, Q is O, $R^4$ is hydrogen, and X is O;

a compound wherein $W_1$ is $C(R^{2a})$, $W_2$ is CH, $W_3$ is $C(R^2)$, $R^1$ is trifluoromethyl, $R^{1a}$ is hydrogen, $R^2$ is cyano, $R^2$ is hydrogen, $R^3$ is hydrogen, V is $CH(R^4)$, Q is O, $R^4$ is hydrogen, and X is O;

a compound wherein $W_1$ is $C(R^{2a})$, $W_2$ is CH, $W_3$ is $C(R^2)$, $R^1$ is trifluoromethyl, $R^{1a}$, $R^2$, $R^{2a}$, and $R^3$ are hydrogen, V is $CH(R^4)$, Q is O, $R^4$ is hydrogen, and X is $C(CH_3)_2$;

a compound wherein $W_1$ is $C(R^{2a})$, $W_2$ is CH, $W_3$ is $C(R^2)$, $R^1$ is chloro, $R^{1a}$, $R^2$, $R^{2a}$, and $R^3$ are hydrogen, V is $CH(R^4)$, Q is O, $R^4$ is hydrogen, and X is $C(CH_3)_2$;

a compound wherein $W_1$ is $C(R^{2a})$, $W_2$ is CH, $W_3$ is $C(R^2)$, $R^1$ is fluoro, $R^{1a}$ is fluoro, $R^2$ is hydrogen, $R^{2a}$ is hydrogen, $R^3$ is hydrogen, V is $CH(R^4)$, Q is O, $R^4$ is hydrogen, and X is O;

a compound wherein $W_1$ is $C(R^{2a})$, $W_2$ is CH, $W_3$ is $C(R^2)$, $R^1$ is trifluoromethyl, $R^{1a}$ is hydrogen, $R^2$ is trifluoromethyl, $R^{2a}$ is hydrogen, $R^3$ is hydrogen, V is $CH(R^4)$, Q is O, $R^4$ is hydrogen, and X is $C(CH_3)_2$;

a compound wherein $W_1$ is $C(R^{2a})$, $W_2$ is CH, $W_3$ is $C(R^2)$, $R^1$ is chloro, $R^{1a}$, $R^2$, $R^{2a}$, and $R^3$ are hydrogen, V is $CH(R^4)$, Q is O, $R^4$ is hydrogen, and X is O;

a compound wherein $W_1$ is $C(R^{2a})$, $W_2$ is CH, $W_3$ is $C(R^2)$, $R^1$ is trifluoromethyl, $R^{1a}$ is hydrogen, $R^2$ is chloro, $R^{2a}$ is hydrogen, $R^3$ is hydrogen, V is CH($R^4$), Q is O, $R^4$ is hydrogen, and X is C(CH$_3$)$_2$;

a compound wherein $W_1$ is C($R^{2a}$), $W_2$ is CH, $W_3$ is C($R^2$), $R^1$ is trifluoromethyl, $R^{1a}$ is hydrogen, $R^2$ is trifluoromethyl, $R^{2a}$ is hydrogen, $R^3$ is hydrogen, V is CH($R^4$), Q is O, $R^4$ is hydrogen, and X is O;

a compound wherein $W_1$ is C($R^{2a}$), $W_2$ is CH, $W_3$ is C($R^2$), $R^1$ is trifluoromethyl, $R^{1a}$ is hydrogen, $R^2$ is CH$_2$CH$_2$C(CH$_3$)$_2$OH, $R^{2a}$ is hydrogen, $R^3$ is hydrogen, V is CH($R^4$), Q is O, $R^4$ is hydrogen, and X is CH$_2$;

a compound wherein $W_1$ is C($R^{2a}$), $W_2$ is CH, $W_3$ is C($R^2$), $R^1$ is fluoro, $R^{1a}$ is fluoro, $R^2$ is chloro, $R^{2a}$ is hydrogen, $R^3$ is hydrogen, V is CH($R^4$), Q is O, $R^4$ is hydrogen, and X is CH$_2$;

a compound wherein $W_1$ is C($R^{2a}$), $W_2$ is CH, $W_3$ is C($R^2$), $R^1$ is chloro, $R^{1a}$, $R^2$, $R^{2a}$, and $R^3$ are hydrogen, V is CH($R^4$), Q is O, $R^4$ is hydrogen, and X is CH$_2$;

a compound wherein $W_1$ is C($R^{2a}$), $W_2$ is CH, $W_3$ is C($R^2$), $R^1$ is trifluoromethyl, $R^{1a}$ is hydrogen, $R^2$ is methyl, $R^{2a}$ is hydrogen, $R^3$ is hydrogen, V is CH($R^4$), Q is O, $R^4$ is hydrogen, and X is CH$_2$;

a compound wherein $W_1$ is C($R^{2a}$), $W_2$ is CH, $W_3$ is C($R^2$), $R^1$ is fluoro, $R^{1a}$ is hydrogen, $R^2$ is methyl, $R^{2a}$ is hydrogen, $R^3$ is hydrogen, V is CH($R^4$), Q is O, $R^4$ is hydrogen, and X is CH$_2$;

a compound wherein $W_1$ is C($R^{2a}$), $W_2$ is CH, $W_3$ is C($R^2$), $R^1$ is fluoro, $R^{1a}$ is fluoro, $R^2$ is methyl, $R^{2a}$ is hydrogen, $R^3$ is hydrogen, V is CH($R^4$), Q is O, $R^4$ is hydrogen, and X is CH$_2$;

a compound wherein $W_1$ is C($R^{2a}$), $W_2$ is CH, $W_3$ is C($R^2$), $R^1$ is fluoro, $R^{1a}$ is hydrogen, $R^2$ is chloro, $R^{2a}$ is hydrogen, $R^3$ is hydrogen, V is CH($R^4$), Q is O, $R^4$ is hydrogen, and X is CH$_2$;

a compound wherein $W_1$ is C($R^{2a}$), $W_2$ is CH, $W_3$ is C($R^2$), $R^1$ is trifluoromethoxy, $R^{1a}$ is hydrogen, $R^2$ is chloro, $R^{2a}$ is hydrogen, $R^3$ is hydrogen, V is CH($R^4$), Q is O, $R^4$ is hydrogen, and X is CH$_2$;

a compound wherein $W_1$ is C($R^{2a}$), $W_2$ is CH, $W_3$ is C($R^2$), $R^1$ is trifluoromethoxy, $R^{1a}$ is hydrogen, $R^2$ is trifluoromethyl, $R^{2a}$ is hydrogen, $R^3$ is hydrogen, V is CH($R^4$), Q is O, $R^4$ is hydrogen, and X is CH$_2$;

a compound wherein $W_1$ is C($R^{2a}$), $W_2$ is CH, $W_3$ is C($R^2$), $R^1$ is trifluoromethyl, $R^{1a}$ is hydrogen, $R^2$ is CH$_2$CH$_2$OCH$_3$, $R^{2a}$ is hydrogen, $R^3$ is hydrogen, V is CH($R^4$), Q is O, $R^4$ is hydrogen, and X is CH$_2$;

a compound wherein $W_1$ is C($R^{2a}$), $W_2$ is CH, $W_3$ is C($R^2$), $R^1$ is fluoro, $R^{1a}$ is hydrogen, $R^2$ is trifluoromethyl, $R^{2a}$ is hydrogen, $R^3$ is hydrogen, V is CH($R^4$), Q is O, $R^4$ is hydrogen, and X is CH$_2$;

a compound wherein $W_1$ is C($R^{2a}$), $W_2$ is CH, $W_3$ is C($R^2$), $R^1$ is trifluoromethyl, $R^{1a}$ is hydrogen, $R^2$ is methyl, $R^{2a}$ is methyl, $R^3$ is hydrogen, V is CH($R^4$), Q is O, $R^4$ is hydrogen, and X is CH$_2$;

a compound wherein $W_1$ is C($R^{2a}$), $W_2$ is CH, $W_3$ is C($R^2$), $R^1$ is trifluoromethyl, $R^{1a}$ is hydrogen, $R^2$ is chloro, $R^{2a}$ is methyl, $R^3$ is hydrogen, V is CH($R^4$), Q is O, $R^4$ is hydrogen, and X is CH$_2$;

a compound wherein $W_1$ is N, $W_2$ is CH, $W_3$ is C($R^2$), $R^1$ is trifluoromethyl, $R^{1a}$ is hydrogen, $R^2$ is hydrogen, $R^3$ is hydrogen, V is CH($R^4$), Q is O, $R^4$ is hydrogen, and X is CH$_2$;

a compound wherein $W_1$ is C($R^{2a}$), $W_2$ is N, $W_3$ is C($R^2$), $R^1$ is trifluoromethyl, $R^{1a}$, $R^2$, $R^{2a}$, and $R^3$ are hydrogen, V is CH($R^4$), Q is O, $R^4$ is hydrogen, and X is CH$_2$;

a compound wherein $W_1$ is C($R^{2a}$), $W_2$ is CH, $W_3$ is N, $R^1$ is trifluoromethyl, $R^{1a}$, and $R^{2a}$, and $R^3$ are hydrogen, V is CH($R^4$), Q is O, $R^4$ is hydrogen, and X is CH$_2$;

or enantiomers, diastereomers, or pharmaceutically acceptable salts thereof.

20. A compound of formula (I) wherein the compounds are of the formula selected from the group consisting of a) Cpd 27

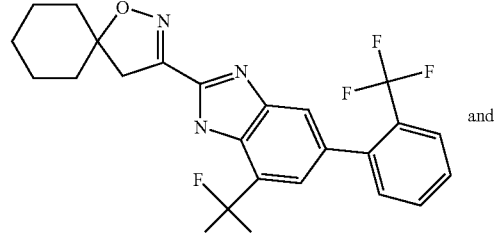

and b) Cpd 16

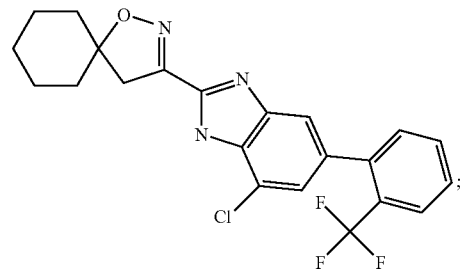

;

or a pharmaceutically acceptable salt form thereof.

21. A pharmaceutical composition comprising a compound of claim 1 and at least one of a pharmaceutically acceptable carrier, pharmaceutically acceptable excipient, and a pharmaceutically acceptable diluent.

22. The pharmaceutical composition of claim 21, wherein the composition is a solid oral dosage form.

23. The pharmaceutical composition of claim 21, wherein the composition is a syrup, an elixir, or a suspension.

24. A method for treating inflammatory pain, inflammatory hypersensitivity condition, neuropathic pain, anxiety and depression in a subject in need thereof comprising administering to the subject a therapeutically effective amount of a compound of claim 1.

25. The method of claim 24 wherein the inflammatory pain is due to inflammatory bowel disease, visceral pain, migraine, post operative pain, osteoarthritis, rheumatoid arthritis, back pain, lower back pain, joint pain, abdominal pain, chest pain, labor, musculoskeletal diseases, skin diseases, toothache, pyresis, burn, sunburn, snake bite, venomous snake bite, spider bite, insect sting, neurogenic bladder, interstitial cystitis, urinary tract infection, rhinitis, contact dermatitis/hypersensitivity, itch, eczema, pharyngitis, mucositis, enteritis, irritable bowel syndrome, cholecystitis, pancreatitis, postmastectomy pain syndrome, menstrual pain, endometriosis, sinus headache, tension headache, or arachnoiditis.

26. The method of claim 24 wherein the inflammatory pain is inflammatory hyperalgesia.

27. The method of claim 26 wherein the inflammatory hyperalgesia is inflammatory somatic hyperalgesia or inflammatory visceral hyperalgesia.

28. The method of claim 27 wherein the inflammatory hyperalgesia is due to inflammation, osteoarthritis, rheumatoid arthritis, back pain, joint pain, abdominal pain, musculoskeletal diseases, skin diseases, post operative pain, headaches, fibromyalgia, toothache, burn, sunburn, insect sting, neurogenic bladder, urinary incontinence, interstitial cystitis, urinary tract infection, cough, asthma, chronic obstructive pulmonary disease, rhinitis, contact dermatitis/hypersensitivity, itch, eczema, pharyngitis, enteritis, irritable bowel syndrome, Crohn's Disease, or ulcerative colitis.

29. The method of claim 24 wherein said inflammatory hypersensitivity condition is urinary incontinence, benign prostatic hypertrophy, cough, asthma, rhinitis, nasal hypersensitivity, itch, contact dermatitis, dermal allergy, or chronic obstructive pulmonary disease.

30. The method of claim 24 wherein said neuropathic pain is due to cancer, a neurological disorder, spine or peripheral nerve surgery, a brain tumor, traumatic brain injury (TBI), spinal cord trauma, a chronic pain syndrome, fibromyalgia, chronic fatigue syndrome, a neuralgia, lupus, sarcoidosis, peripheral neuropathy, bilateral peripheral neuropathy, diabetic neuropathy, central pain, neuropathies associated with spinal cord injury, stroke, ALS, Parkinson's disease, multiple sclerosis, sciatic neuritis, mandibular joint neuralgia, peripheral neuritis, polyneuritis, stump pain, phantom limb pain, a bony fracture, oral neuropathic pain, Charcot's pain, complex regional pain syndrome I and II (CRPS I/II), radiculopathy, Guillain-barre syndrome, meralgia paresthetica, burningmouth syndrome, optic neuritis, postfebrile neuritis, migrating neuritis, segmental neuritis, Gombault's neuritis, neuronitis, cervicobrachial neuralgia, cranial neuralgia, geniculate neuralgia, glossopharyngial neuralgia, migrainous neuralgia, idiopathic neuralgia, intercostals neuralgia, mammary neuralgia, Morton's neuralgia, nasociliary neuralgia, occipital neuralgia, red neuralgia, Sluder's neuralgia, splenopalatine neuralgia, supraorbital neuralgia, vulvodynia or vidian neuralgia.

31. The method of claim 30 wherein the neuralgia is trigeminal neuralgia, glossopharyngeal neuralgia, postherpetic neuralgia, or causalgia.

32. The method of claim 24 wherein the neuropathic pain is neuropathic cold allodynia.

33. The method of claim 32 wherein the neuropathic cold allodynia is pain arising from spine and peripheral nerve surgery or trauma, traumatic brain injury (TBI), trigeminal neuralgia, postherpetic neuralgia, causalgia, peripheral neuropathy, diabetic neuropathy, central pain, stroke, peripheral neuritis, polyneuritis, complex regional pain syndrome I and II (CRPS I/II), or radiculopathy.

34. The method of claim 24 wherein the anxiety is social anxiety, post traumatic stress disorder, phobias, social phobia, special phobias, panic disorder, obsessive compulsive disorder, acute stress disorder, separation anxiety disorder, or generalized anxiety disorder.

35. The method of claim 24 wherein the depression is major depression, bipolar disorder, seasonal affective disorder, post natal depression, manic depression, or bipolar depression.

36. A method for treating inflammatory somatic hyperalgesia in which a hypersensitivity to thermal stimuli exists, comprising administering to the subject a therapeutically effective amount of a compound of claim 1.

37. A method for treating inflammatory visceral hyperalgesia in which a enhanced visceral irritability exists, comprising administering to the subject a therapeutically effective amount of a compound claim 1.

38. A method for treating neuropathic cold allodynia in which a hypersensitivity to cooling stimuli exists, comprising administering to the subject a therapeutically effective amount of a compound of claim 1.

39. A method for treating cardiovascular disease aggravated by cold in a subject in need thereof which comprises administering to the subject a therapeutically effective amount of a compound of claim 1.

40. The method of claim 39 wherein the cardiovascular disease is selected from the group consisting of peripheral vascular disease, vascular hypertension, pulmonary hypertension, Raynaud's disease, and coronary artery disease.

* * * * *